A United States Patent [19]

Ohno et al.

[11] Patent Number: 5,401,768
[45] Date of Patent: Mar. 28, 1995

[54] 2,5,6,7-TETRANOR-4,8-INTER-M-PHENY-LENE PGI₂, DERIVATIVE, MANUFACTURING PROCESS THEREOF AND ITS USE

[75] Inventors: Kiyotaka Ohno, Fujisawa; Toshiya Takahashi, Kamakura; Atsushi Ohtake, Kamakura; Hisanori Wakita, Kamakura; Shintaro Nishio, Ebina, all of Japan

[73] Assignee: Toray Industries, Inc., Japan

[21] Appl. No.: 90,995

[22] PCT Filed: Oct. 14, 1988

[86] PCT No.: PCT/JP88/01048

§ 371 Date: Aug. 14, 1989

§ 102(e) Date: Aug. 14, 1989

[87] PCT Pub. No.: WO89/03387

PCT Pub. Date: Apr. 20, 1989

Related U.S. Application Data

[60] Continuation of Ser. No. 667,245, Mar. 8, 1991, abandoned, which is a division of Ser. No. 377,827, Aug. 14, 1989, abandoned.

[30] Foreign Application Priority Data

Oct. 16, 1987 [JP] Japan ................. 62-262021

[51] Int. Cl.⁶ ............... C07D 307/93; A61K 31/34
[52] U.S. Cl. ............................ 514/408; 549/458
[58] Field of Search ............... 549/458; 514/468

[56] References Cited

U.S. PATENT DOCUMENTS 4,564,620  1/1986  Ohno ................... 549/458
4,822,804  4/1989  Ohno ................... 549/458

FOREIGN PATENT DOCUMENTS 274004   7/1988  European Pat. Off. ......... 549/458
0274064  7/1988  European Pat. Off. ......... 549/458
32277    2/1982  Japan ...................... 549/458

Primary Examiner—Robert Gerstl
Attorney, Agent, or Firm—Austin R. Miller

[57] ABSTRACT

Disclosed are 2,5,6,7-tetranor-4,8-inter-m-phemylene PGI₂ derivatives such as 16-methyl-2,5,6,7-tetranor-4,8-inter-m-phenylene PGI₂ and methyl ester thereof, 17-methyl-2,5,6,7-tetranor-4,8-inter-m-phenylene PGI₂ and methyl ester thereof, 15-phenyl-2,5,6,7,16,17,18,19,20-nonanor-4,8-inter-m-phenylene PGI₂, 16-methyl-17-phenyl-2,5,6,7,18,19,20-heptanor-4,8-inter-m-phenylene PGI₂, 16,16-dimethyl-17-phenyl-2,5,6,7,18,19,20-heptanor-4,8-inter-m-phenylene PGI₂, 16-methyl-16-phenoxy-2,5,6,7,17,18,19,20-octanor-4,8-inter-m-phenylene PGI₂, 16-methyl-16-phenoxy-2,5,6,7,18,19,20-heptanor-4,8-inter-m-phenylene PGI₂ and methyl ester thereof, and 3-decarboxy-3-hydroxymethyl-16-methyl-16-phenoxy-2,5,6,7,18,19,20-heptanor-4,8-inter-m-phenylene PGI₂, which are useful as pharmaceuticals.

These compounds are useful as an antiulcer drug, antihypertensive drug, antithrombus drug or the like.

12 Claims, No Drawings

2,5,6,7-TETRANOR-4,8-INTER-M-PHENYLENE PGI₂, DERIVATIVE, MANUFACTURING PROCESS THEREOF AND ITS USE

This application is a continuation of application Ser. No. 07/667,245, filed Mar. 8, 1991, now abandoned, which is a continuation of application Ser. No. 07/377,827, filed on Aug. 14, 1989, now abandoned.

TECHNICAL FIELD

This invention relates to a prostaglandin I derivative which is excellent in the stability and which exhibits sustained activity in vivo, as well as manufacturing process thereof and its use. Further, this invention relates to a compound which may be used as a starting material or an intermediate for producing the derivative.

BACKGROUND ART

Prostaglandin $I_2$ ($PGI_2$, prostacyclin) was found by J. R. Vane et al. in 1976. Prostaglendin $I_2$ is synthesized from arachidonic acid via endoperoxide ($PGH_2$ or $PGG_2$) on vascular wall and is drawing attention as a compound having strong platelet aggregation inhibiting action, gastric acid secretion inhibiting action and vasodilation action of peripheral vessels [see C and EN, Dec. 20, 1976, P17 and S. Moncada, R. Gryglewski, S. Bunting, J. R. Vane, Nature, 263, 633 (1976)].

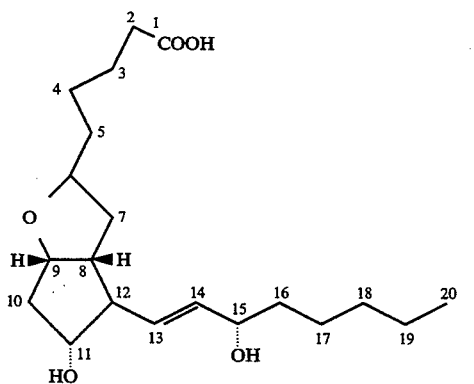

PGI₂

$PGI_2$ has unstable exoenol structure, so that it is very unstable even in neutral aqueous solution and readily converted to 6-oxo $PGF_{1\alpha}$ which has little physiological activity. It is a big drawback that $PGI_2$ has the unstability as descrived above when used as a medicine. Further, $PGI_2$ has drawbacks in that it is unstable in vivo and its physiological activity does not last.

A variety of derivatives which have been studied to improve the chamical stability and to promote the durability in vivo are not satisfactory.

Especially, as to the durablity of the drug, it was found to be a big drawback that β-oxidation which is a metabolic pathway of fatty acid is easy to occur.

The present inventors intebsively studied based on this finding to find a very stable structure which inhibits the metabolism by β-oxidation to accomplish this invention.

That is, the object of the present invention is to provide a novel PIG₂ derivative having excellent stability and sustained activity in vivo.

DISCLOSURE OF THE INVENTION

This invention relates to 2,5,6,7-tetranor-4,8-inter-m-phenylene $PGI_2$ derivative represented by the formula:

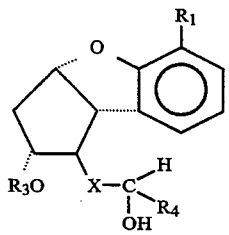

(wherein R₁ represents
 (i) $CH_2CH_2COOR_2$ or
 (ii) $CH_2CH_2CH_2OH$
(wherein R₂ represents hydrogen atom or pharmaceutically acceptable cation or ester residue); R₃ represents hydrogen atom, an acyl group having 1 to 12 carbon atoms or an aroyl group having 6 to 15 carbon atoms; X represents
 (i) $-CH_2-CH_2-$ or
 (ii) $-CH=CH-$; R₄ represents
 (i) a normal alkyl group having 1 to 12 carbon atoms or a branched alkyl group having 3 to 12 carbon atoms, or
 (ii) $-Z-Ar$ (wherein Z represents a valence bond or a normal or branched alkylene group defined as the formula $C_tH_{2t}$ (t is an integer of 1 to 5); Ar represents a phenyl group unsubstituted or substituted by 1 to 4 substituents selected from the class consisting of alkyl, methoxy, chloro, bromo, fluoro, iodo, trifluoromethyl, nitro, cyano, phenyl and phenoxy),
 (iii) $-Z-R_5$ (wherein Z has the same meaning as in (ii); R₅ represents a cycloalkyl group with 3 to 12 ring members which is unsubstituted or substituted by 1 to 4 normal alkyl substituents containing 1 to 4 carbon atoms), or
 (iv) $-C_tH_{2t}-O-R_6$ (wherein $C_tH_{2t}$ has the same meaning as in (ii); R₆ represents (1) a normal alkyl group having 1 to 6 carbon atoms or a branched alkyl group having 3 to 6 carbon atoms, (2) a cyclopentyl or cyclohexyl group unsubstituted or substituted by 1 to 4 normal alkyl substituents containing 1 to 4 carbon atoms, or (3) Ar (wherein Ar has the same meaning as in (ii)).

The novel compound of the present invention represented by the said formula is characterized in that the drawbacks of $PGI_2$ are largely improved. That is, since the compound of the present invention which is represented by the formula has an inter-m-phenylene structure in place of an exoenol structure which is characteristic to $PGI_2$, it is very stable even in aqueous solution. Further, β-oxidation of the compound of the present invention, which is a main metabolic pathway of prostaglandin, is conducted very slowly,so that physiological activity thereof lasts very long. Still further, since the compound of the present invention has various physiological activities of $PGI_2$ in selected forms, it is excellent in application as medicine.

BEST MODE FOR CARRYING OUT THE INVENTION

The formula will now be described in more detail. When $R_2$ represents an ester residue, $R_2$ may be (i) a normal alkyl group having 1 to 12 carbon atoms or a branched alkyl group having 3 to 12 carbon atoms;

(ii) —Z—$R_5$ (wherein Z and $R_5$ has the same meaning as in the above-described formula, wherein $R_2$ and $R_4$ represented by the same formula may be the same or different);

(iii) —Z—Ar (wherein Z and Ar have the same meaning as in the formula);

(iv) —(CH$_2$CH$_2$O)$_n$—CH$_3$ (wherein n is an integer of 1 to 5);

(v) —Z—$R_7$ (wherein Z has the same meaning as in the formula, $R_7$ represents α-naphthyl group, β-naphthyl group, 2-pyridyl group, 3-pyridyl group, 4-pyridyl group, α-furyl group, β-furyl group, α-thienyl group or μ-thienyl group);

(vi) —C$_t$H$_{2t}$COOR$_8$ (wherein C$_t$H$_{2t}$ has the same meaning as in the formula; $R_8$ represents methyl group, ethyl group or propyl group) or

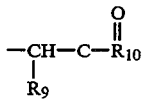
(vii)

(wherein $R_9$ represnts hydrogen atom or bezoyl group; $R_{10}$ represnts phenyl group, p-bromophenyl group, p-chlorophenyl group, p-biphenyl group, p-nitrophenyl group, p-benzamidophenyl group or 2-naphthyl group).

When $R_2$ represents a pharmaceutically acceptable cation, it may be a metal cation, ammonium, amine cation or tertiary ammonium cation, more preferably a metal cation derived from an alkaline metal such as lithium, sodium and potassium, or an alkali earth metal such as magnesium and calcium. Needless to say, other derived from other metals, such as aluminium, zinc or iron may be included in the present invention.

Pharmaceutically acceptable amine cations may be derived from primary, secondary or tertiary amine. Illustrative examples of the suitable amine may include aliphatic, alicyclic, aromatic amine containing up to about 18 carbon atoms and heterocyclic amine, such as methylamine, dimethylamine, triethylamine, ethylamine, dibutylamine, triisopropylamine, N-methylhexylamine, decylamine, dodecylamine, arylamine, crotylamine, cyclopentylamine, dicyclohexylamine, benzylamine, α-phenylethylamine, β-phenylethylamine, ethyldiamine, diethylenetriamine, 1-methylpiperidine, 4-ethylmorpholine, 1-isopropylpirrolidine, 2-methylpirrolidine, 4-dimethylpiperazine and 2-methylpiperidine; water-soluble amines and amines with hydrophilic group such as ethanolamine, diethanolamine, triethanolamine, ethylethanolamine, N-butylethanolamine, 2-amino-1-butanol, 2-amino-2-ethyl-1,3-propanediol, tris(hydroxymethyl)aminomethane, N-phenylethanolamine, N-(p-tert-amylphenyl)diethanolamine, galactamine, N-methylglutamine, N-methylgulcosamine, ephedrine, phenylephrine, epinephrine and procaine; and basic amino acids such as lysine and arginine. The examples of $R_2$ or $R_4$ which is a normal alkyl group having 1 to 12 carbon atoms may include methyl, ethyl, propyl, butyl, pentyl, hexyl, heptyl, octyl and dodecyl. Further, the examples of $R_2$ or $R_4$ which is a branched alkyl group having 3 to 12 carbons may include isopropyl, sec-butyl, t-butyl, iso-butyl, 2-methylpentyl, 3-methylpentyl, 4-methylpentyl, 1-methylpentyl, 1-methylhexyl, 2-methylhexyl, 3-methylhexyl, 4-methylhexyl, 5-methylhexyl, 1-methylheptyl, 2-methylheptyl, 3-methylheptyl, 4-methylheptyl, 5-methylheptyl, 6-methylheptyl, 1-methyloctyl, 2-methyloctyl, 3-methyloctyl, 4-methyloctyl, 5-methyloctyl, 6-methyloctyl, 7-methyloctyl, 1-methylnonyl, 1-methyldecanyl, 2-methylnonyl, 2-methyldecanyl, 1,1-dimethylbutyl, 2,2-dimethylbutyl, 1,1-dimethylpentyl, 2,2-dimethylpentyl, 3,3-dimethylpentyl, 4,4-dimethylpentyl, 1,1-dimethylhexyl, 2,2-dimethylhexyl, 3,3-dimethylhexyl, 4,4-dimethylhexyl, 5,5-dimethylhexyl, 6,6-dimethylhexyl, 1,1-dimethylheptyl, 2,2-dimethylheptyl, 3,3-dimethylheptyl, 4,4-dimethylheptyl, 5,5-dimethylheptyl, 6,6-dimethylheptyl, 7,7-dimethylheptyl, 1,1-dimethyloctyl, 2,2-dimethyloctyl, 3,3-dimethyloctyl, 1,1-dimethylnonyl, 2,2-dimethylnonyl, 3,3-dimethylnonyl, 1,1-dimethyldecanyl, 2,2-dimethyldecanyl, 3,3-dimethyldecanyl, 1,1,2,2-tetramethylpentyl, 1,1,3,3-tetramethylpentyl, 1,1,2,2-tetramethylhexyl, 1,1,3,3-tetramethylhexyl, 2,2,3,3-tetramethylhexyl.

The examples of $R_2$ or $R_4$ which is —Z—Ar may include phenyl, p-chlorophenyl, p-bromophenyl, p-fluorophenyl, 3,4-dichloropheny, m-fluorophenyl, m-trifluoromethylphenyl, p-trifluoromethylphenyl, p-nitrophenyl, p-anisyl, 3,4-dimethoxyphenyl, p-tolyl, m-tolyl, o-tolyl, p-ethylphenyl, p-propylphenyl, p-butylphenyl, 3,4-dimethylpehenyl, 2,4-dimethylphenyl, 3-chloro-4-methylphenyl, 3-fluoro-4-methylphenyl, 4-biphenyl, p-phenoxyphenyl, 3-chloro-4-phenoxyphenyl, benzyl, p-chlorobenzyl, m-chlorobenzyl, p-methoxybenzyl, o-methoxybenzyl, p-methylbenzyl, p-ethylbenzyl, p-propylbenzyl, p-nitrobenzyl, 3,4-dichlorobenzyl, α-methylbenzyl, α,α′-dimethylbenzyl, phenethyl, p-chlorophenetyl, p-bromophenetyl, p-fluorophenetyl, m-chlorophenetyl, m-fluorophenetyl, o-chlorophenetyl, p-methylphenetyl, p-methoxyphenetyl, 3,4-dimethoxyphenetyl, p-ethylphenetyl, α-methylphenetyl, β-methylphenetyl, α,α′-dimethylphenetyl, β,β′-dimethylphenetyl, 3-phenylpropyl, 3-(p-chlorophenyl)propyl, 3-(p-fluorophenyl)propyl, 3-(p-bromophenyl)propyl, 3-(m-chlorophenyl)propyl, 3-(3,4-dichlorophenyl)propyl, 3-(p-tolyl)propyl, 3-(p-ethylphenyl)propyl, 4-phenylbutyl, 4-(p-chlorophenyl)butyl, 4-(3,4-dichlorophenyl)butyl, 4-(p-tolyl)butyl, 5-phenylpentyl, α,α′-dimethyl-p-chlorophenethyl, α,α′-dimethyl-p-bromophenethyl, α,α′-dimethyl-p-fluorophenethyl, α,α′-dimethyl-m-chlorophenethyl, α,α′-dimethyl-m-bromophenethyl, α,α′-dimethyl-m-fluorophenethyl, α,α′-dimethyl-p-trifluoromethylphenethyl, α,α′-dimethyl-m-trifluoromethylphenethyl, α,α′-dimethyl-p-methylphenethyl, α,α′-dimethyl-p-methoxyphenethyl, α,α′-dimethyl-p-cyanophenethyl, 1,1-dimethyl-3-phenylpropyl, 1,1-dimethyl-4-phenylbutyl.

The examples of $R_2$ or $R_4$ which is —Z—$R_5$ may include cyclodecyl, cyclohexyl, cycloheptyl, cyclooctyl, cyclododecyl, cyclopentylmethyl, cyclohexylmethyl, cycloheptylmethyl, cyclododecylmethyl, cyclopentylethyl, cyclohexylethyl, cycloheptylethyl, cyclopentylpropyl, cyclohexylpropyl, cyclopentylbutyl, cyclohexylbutyl, cyclohexylpentyl, 2-methylcyclopentyl, 3-methylcyclopentyl, 2-methylcyclohexyl, 3-methylcyclohexyl, 4-methylcyclohexyl, 2-methylcycloheptyl, 3-methylcycloheptyl, 4-methylcycloheptyl, 4-methylcyclooctyl, 2-ethylcyclopentyl, 3-ethylcyclopentyl, 2-ethylcyclohexyl, 3-ethylcyclohecyl, 4-ethylcyclohexyl, 2-ethylcycloheptyl, 2-ethylcyclooctyl, 3-ethylcyclooctyl, 2-methylcyclopentylmethyl, 3-methylcyclopentylmethyl, 2-methylcyclohexylmethyl, 3-methylcyclohexylmethyl, 4-methylcyclohexylmethyl, 2-methylcycloheptylmethyl, 3-methylcycloheptylmethyl, 2-methylcyclooctylmethyl, 2-(2-methylcyclopentyl)ethyl, 2-(3-methylcyclopentyl)ethyl, 2-(2-methylcyclohexyl)ethyl, 2-(3-methylcyclohexyl)ethyl, 2-(4-methylcyclohexyl)ethyl, 2-(2-methylcycloheptyl)ethyl, 2-(2-methylcyclooctyl)ethyl, 3-(2-methylcyclopentyl)propyl, 3-(3-methylcyclopentyl)propyl, 3-(2-methylcyclohexyl)propyl, 3-(3-methylcyclohexyl)propyl, 3-(4-methylcyclohexyl)propyl, 5-(2-methylcyclopentyl)pentyl, 2-ethylcyclopentylmethyl, 3-ethylcyclopentylmethyl, 2-ethylcyclohexylmethyl, 3-ethylcyclohexylmethyl, 4-ethylcyclohexylmethyl, 2-ethylcycloheptylmethyl, 3-ethylcycloheptylmethyl, 2-ethylcyclooctylmethyl, 2-(2-ethylcyclopentyl)ethyl, 2-(3-ethylcyclopentyl)ethyl, 2-(4-ethylcyclohexyl)ethyl, 2-(2-ethylcycloheptyl)ethyl, 2-(2-ethylcyclooctyl)ethyl, 3-(2-ethylcyclopentyl)propyl, 3-(3-ethylcyclopentyl)propyl, 3-(2-ethylcyclohexyl)propyl, 3-(3-ethylcyclohexyl)propyl, 3-(4-ethylcyclohexyl)propyl, 5-(2-ethylcyclopentyl)pentyl, 5-(2-ethylcyclopentyl)pentyl, cyclopropyl, cyclobutyl, 2,3-dimethylcyclopropyl, 2,4-dimethylcyclobutyl, 3,3-dimethylcyclobutyl, cyclopentyldimethylmethyl, cyclohexyldimethylmethyl, cyclooctyldimethylmethyl, 2-cyclopentyl-1,1-dimethylethyl, 2-cyclohexyl-1,1-dimethylethyl, 2-cyclooctyl-1,1-dimethylethyl, 2-cyclododecyl-1,1-dimethylethyl, 3-cyclopentyl-1,1-dimethylpropyl, 3-cyclohexyl-1,1-dimethylpropyl, 3-cyclooctyl-1,1dimethylpropyl, 4-cyclopentyl-1,1-dimethylbutyl, 4-cyclohexyl-1,1-dimethylbutyl, 4-cyclooctyl-1,1-dimethylbutyl, 2-cyclopentyl-2,2-dimethylethyl, 2-cyclohexy-2,2-dimethylethyl, 2-cyclooctyl-2,2-dimethylethyl, 2-cyclopentyl-1-methylethyl, 2-cyclohexyl-1-methylethyl.

The examples of $R_4$ which is $-C_lH_{2l}-O-R_6$ may include methoxymethyl, ethoxymethyl, propoxymethyl, butoxymethyl, n-pentyloxymethyl, n-hexyloxymethyl, dimethylmethoxymethyl, dimethylethoxymethyl, dimethylpropoxymethyl, dimethylbutoxymethyl, dimethyl-n-pentyloxymethyl, dimethyl-n-hexyloxymethyl, isopropoxymethyl, sec-butoxymethyl, iso-butoxymethyl, t-butoxymethyl, (1,1-dimethylbutoxy)methyl, (1,1-dimethyl-n-pentyloxy)methyl, (1,1-dimethyl-n-hexyloxy)methyl, 2-methoxyethyl, 2-ethoxyethyl, 2-propoxyethyl, 2-butoxyethyl, 2-n-pentyloxyethyl, 2-n-hexyloxyethyl, 1,1-dimethyl-2-methoxyethyl, 1,1-dimethyl-2-propoxyethyl, 1,1-dimethyl-2-butoxyethyl, 1,1-dimethyl-2-n-pentyloxyethyl, 1,1-dimethyl-2-n-hexyloxyethyl, 3-methoxypropyl, 3-ethoxypropyl, 3-propoxypropyl, 3-butoxypropyl, 3-pentyloxypropyl, 3-n-hexyloxypropyl, 1,1-dimethyl-3-methoxypropyl, 1,1-dimethyl-3-ethoxypropyl, 1,1-dimethyl-3-propoxypropyl, 1,1-dimethyl-3-butoxypropyl, 1,1-dimethyl-3-n-pentyloxypropyl, 2-isopropoxyethyl, 2-sec-butoxyethyl, 2-t-butoxyethyl, 1-methyl-2-methoxyethyl, 1-methyl-2-ethoxyethyl, 1-methyl-2-propoxyethyl, 1-methyl-2-butoxyethyl, cyclopentyloxymethyl, cyclohexyloxymethyl, cyclopentyloxydimethymethyl, cyclohexyloxydimethylmethyl, (2,5-dimethylcyclopentyloxy)methyl, (3,4-dimethylcyclopentyloxy)methyl, (4-methylcyclohexyloxy)methyl, (2,6-dimethylcyclohexyloxy)methyl, (2,2,6,6-tetramethylcyclohexyloxy)methyl, dimethyl(3,4-dimethylcyclopentyloxy)methyl, dimethyl(4-methylcyclohexyloxy)methyl, 2-(cyclopentyloxy)ethyl, 2-(cyclohexyloxy)ethyl, 1,1-dimethyl-2-(cyclopentyloxy)ethyl, 1,1-dimethyl-2-(cyclohexyloxy)ethyl, 3-cyclopentyloxypropyl, 3-cyclohexyloxypropyl, 1,1-dimethyl-3-cyclopentyloxypropyl, 1,1-dimethyl-3-cyclohexyloxypropyl, phenoxymethyl, p-chlorophenoxymethyl, m-chlorophenoxymethyl, 2,4-dichlorophenoxymethyl, 3,4-dichlorophenoxymethyl, p-bromophenoxymethyl, m-bromophenoxymethyl, 2,4-dibromophenoxymethyl, 3,4-dibromophenoxymethyl, p-fluorophenoxymethyl, m-fluorophenoxymethyl, o-fluorophenoxymethyl, p-trifluoromethylphenoxymethyl, m-trifluoromethylphenoxymethyl, o-trifluoromethylphenoxymethyl, p-nitrophenoxymethyl, p-cyanophenoxymethyl, p-phenylphenoxymethyl, p-methylphenoxymethyl, m-methylphenoxymethyl, o-methylphenoxymethyl, p-methoxyphenoxymethyl, m-methoxyphenoxymethyl, o-methoxyphenoxymethyl, dimethylphenoxymethyl, dimethyl(p-chlorophenoxy)methyl, dimethyl(m-chlorophenoxy)methyl, dimethyl(2,4-dichlorophenoxy)methyl, dimethyl(3,4-dichlorophenoxy)methyl, dimethyl(p-bromophenoxy)methyl, dimethyl(m-bromophenoxy)methyl, dimethyl(2,4-dibromophenoxy)methyl, dimethyl(3,4-dibromophenoxy)methyl, dimethyl(p-fluorophenoxy)methyl, dimethyl(m-fluorophenoxy)methyl, dimethyl(o-fluorophenoxy)methyl, dimethyl(p-trifluoromethylphenoxy)methyl, dimethyl(m-trifluoromethylphenoxy)methyl, dimethyl(o-trifluoromethylphenoxy)methyl, dimethyl(p-nitrophenoxy)methyl, (p-cyanophenoxy)dimethylmethyl, dimethyl(p-phenylphenoxy)methyl, dimethyl(p-methylphenoxy)methyl, dimethyl(m-methylphenoxy)methyl, dimethyl(o-methylphenoxy)methyl, dimethyl(p-methoxyphenoxy)methyl, dimethyl(m-methoxyphenoxy)methyl, dimethyl(o-methoxyphenoxy)methyl, 2-phenoxyethyl, 2-(p-chlorophenoxy)ethyl, 2-(m-chlorophenoxy)ethyl, 2-(2,4-dichlorophenoxy)ethyl, 2-(3,4-dichlorophenoxy)ethyl, 2-(p-bromophenoxy)ethyl, 2-(m-bromophenoxy)ethyl, 2-(2,4-dibromophenoxy)ethyl, 2-(3,4-dibromophenoxy)ethyl, 2-(p-fluorophenoxy)ethyl, 2-(m-fluorophenoxy)ethyl, 2-(o-fluorophenoxy)ethyl, 2-(p-trifluoromethylphenoxy)ethyl, 2-(m-trifluoromethylphenoxy)ethyl, 2-(o-trifluoromethylphenoxy)ethyl, 2-(p-nitrophenoxy)ethyl, 2-(p-cyanophenoxy)ethyl, 2-(p-phenylphenoxy)ethyl, 2-(p-methylphenoxy)ethyl, 2-(m-methylphenoxy)ethyl, 2-(o-methylphenoxy)ethyl, 2-(p-methoxyphenoxy)ethyl, 2-(m-methoxyphenoxy)ethyl, 2-(o-methoxyphenoxy)ethyl, 3-phenoxypropyl, 1,1-dimethyl-3-phenoxypropyl, methylphenoxymethyl, 1-methyl-2-phenoxyethyl, 1-methyl-3-phenoxypropyl.

The examples of $R_2$ which is $-(CH_2CH_2O)_n-CH_3$ may include $-CH_2CH_2OCH_3$, $-CH_2CH_2OCH_2CH_2OCH_3$, $-(CH_2CH_2O)_3-CH_3$, $-(CH_2CH_2O)_4-CH_3$, $-(CH_2CH_2O)_5-CH_3$.

The examples of $R_2$ which is $-Z-R_7$ may include α-naphthyl, β-naphthyl, 2-pyridyl, 3-pyridyl, 4-pyridyl, α-furyl, β-furyl, α-thienyl, β-thienyl, α-naphthylmethyl, β-naphthylmethyl, 2-pyridylmethyl, 3-pyridylmethyl, 4-pyridylmethyl, α-furylmethyl, β-furylmethyl, α-thienylmethyl, β-thienylmethyl, 2-(α-naphthyl)ethyl, 2-(β-naphthyl)ethyl, 2-(2-pyridyl)ethyl, 2-(3-pyridyl)ethyl, 2-(4-pyridyl)ethyl, 2-(α-furyl)ethyl, 2-(β-furyl)ethyl, 2-(α-thienyl)ethyl, 2-(β-thienyl)ethyl, 3-(α-naphthyl)propyl, 3-(β-naphthyl)propyl, 3-(2-pyridyl)propyl, 3-(3-pyridyl)propyl, 3-(4-pyridyl)propyl, 3-(α-furyl)propyl, 3-(β-furyl)propyl, 3-(α-thienyl)propyl, 3-(β-thienyl)propyl.

The examples of $R_2$ which is $-C_rH_{2r}COOR_8$ may include methoxycarbonylmethyl, ethoxycarbonylmethyl, propoxycarbonylmethyl, 1-methoxycarbonylethyl, 1-ethoxycarbonylethyl, 1-propoxycarbonylethyl, 2-methoxycarbonylethyl, 2-ethoxycarbonylethyl, 2-propoxycarbonylethyl, 3-methoxycarbonylpropyl, 3-ethoxycarbonylpropyl.

The examples of $R_2$ represented by

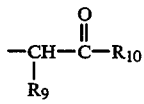

may include phenacyl, p-bromophenacyl, p-nitrophenacyl, p-phenylphenacyl, p-benzamidophenacyl, 2-naphthoylmethyl, α-benzoylphenacyl.

The compounds of the present invention which are represented by the formula are named after the nomenclature for prostaglandin and prostacyclin analogue which is defined by N. A. Nelson et al. [N. A. Nelson, J. Med. chem, 17, 911 (1974), and R. A. Johnson, D. R. Horton, N. A. Nelson, prostaglandins, 15, 737 (1978)]. Among the series of compounds, the fundamental compound (which is not included in the present invention) is represented by the following formula. By assigning the numerals as shown in the following formula, it is named 5,6,7-trinor-4,8-inter-m-phenylene $PGI_2$.

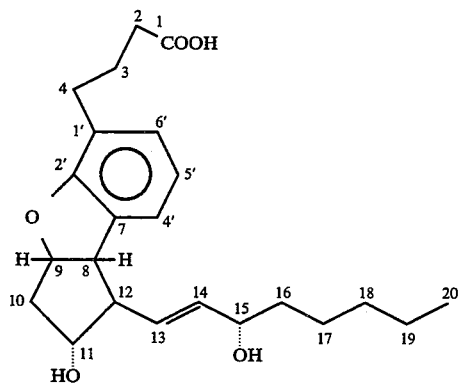

Although such a naming is not based on the literature, for the purpose of simplicity, this rule is employed only for naming $PGI_2$ derivatives of the present invention which have the characteristic cyclopenta[b]benzofuran structure. According to the nomenclature of the literature, this fundamental compound is named 9-deoxy-2,9α-epoxy-5,6,7-trinor-4,8-inter-m-phenylene $PGF_{1α}$. However, in the present invention, it is named 5,6,7-trinor-inter-m-phenylene $PGI_2$ based on the informal rule of nomenclature as described above. The compound of the present invention is named in accordance with the rule of the literature except for the point described above. Other than this point, the nomenclature is in accordance with the literature. The rule of nomenclature of the literature is also a simplified rule. If the fundamental compound is named in accordance with the formal rule of nomenclature of IUPAC, it is named taking the cyclopenta[b]benzofuran ring as a functional group.

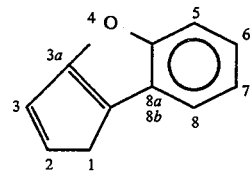

1H-cyclopenta[b]benzofuran

That is, the fundamental compound is named formally 4-[1β-(3-hydroxy-1-octenyl)-2α-hydroxy-3aβH,8bβH-2,3,3a,8b-tetrahydro-1H-cyclopenta[b]benzofuranyl]butanoic acid. However, in the present invention, it is named in accordance with the simplified rule as described above.

The naming of the compound of the present invention will now be described by way of examples and structural formulae thereof.

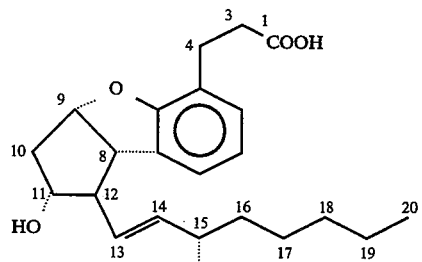

2,5,6,7-tetranor-4,8-inter-m-phenylene $PGI_2$

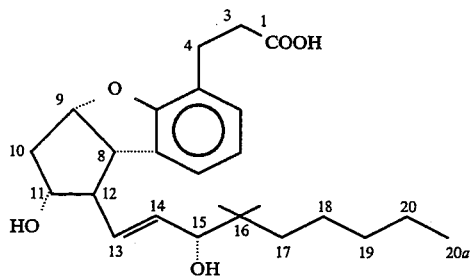

16,16-dimethyl-20a-homo-2,5,6,7-tetranor-4,8-inter-m-phenylene $PGI_2$

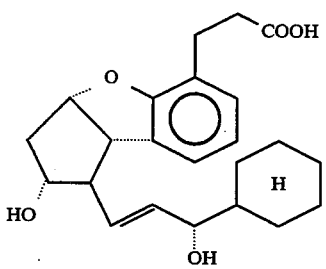

15-cyclohexyl-2,5,6,7,16,17,18,19,20-nonanor-4,8-inter-m-phenylene $PGI_2$

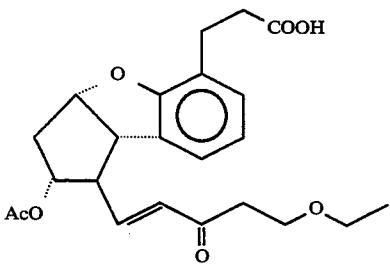

15-oxo-2,5,6,7-tetranor-18-oxa-4,8-inter-m-phenylene PGI$_2$, 11-acetate

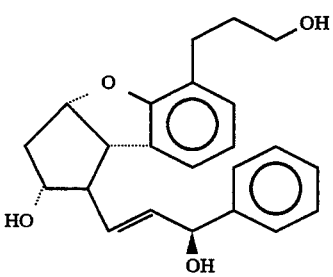

3-decarboxy-3-hydroxymethyl-15-phenyl-15-epi-2,5,6,7,16,17,18,19,20-nonanor-4,8-inter-m-phenylene PGI$_2$ In the present invention, the structural formula of a compound is represented to show only one optical isomer thereof. These structural formulae include the d-, l-, and dl-optical isomer and indication of the absolute configuration, R- and S- is omitted in the naming.

The examples of the compound of the present ivnetion will now be described based on the rule of nomenclature.

The examples of the compound with R$_4$ of normal or branched alkyl group may include 2,5,6,7,17,18,19,20-octanor-4,8-inter-m-phenylene PGI$_2$; 2,5,6,7,18,19,20-heptanor-4,8-inter-m-phenylene PGI$_2$; 2,5,6,7,19,20-hexanor-4,8-inter-m-phenylene PGI$_2$; 2,5,6,7,20-pentanor-4,8-inter-m-phenylene PGI$_2$; 2,5,6,7-tetranor-4,8-inter-m-phenylene PGI$_2$; 20a-homo-2,5,6,7-tetranor-4,8-inter-m-phenylene PGI$_2$; 20a,20b-dihomo-2,5,6,7-tetranor-4,8-inter-m-phenylene PGI$_2$; 20a,20b,20c-trihomo-2,5,6,7-tetranor-4,8-inter-m-phenylene PGI$_2$; 20a,20b,20c,20d-tetrahomo-2,5,6,7-tetranol-4,8-inter-m-phenylene PGI$_2$; 20a,20b,20c,20d,20e-pentahomo-2,5,6,7-tetranor-4,8-inter-m-phenylene PGI$_2$; 20a,20b,20c,20d,20e,20f-hexahomo-2,5,6,7-tetranor-4,8-inter-m-phenylene PGI$_2$; 20a,20b,20c,20d,20e,20f,20g-heptahomo-2,5,6,7-tetranor-4,8-inter-m-phenylene PGI$_2$; 16-methyl-2,5,6,7,18,19,20-heptanor,4,8-inter-m-phenylene PGI$_2$; 16-methyl-2,5,6,7,19,20-hexanor-4,8-inter-m-phenylene PGI$_2$; 16-methyl-2,5,6,7,20-pentanor-4,8-inter-m-phenylene PGI$_2$; 16-methyl-2,5,6,7-tetranor-4,8-inter-m-phenylene PGI$_2$; 16-methyl-20a-homo-2,5,6,7-tetranor-4,8-inter-m-phenylene PGI$_2$; 16-methyl-20a,20b-dihomo-2,5,6,7-tetranor-4,8-inter-m-phenylene PGI$_2$; 16-methyl-20a,20b,20c-trihomo-2,5,6,7-tetranor-4,8-inter-m-phenylene PGI$_2$; 16-methyl-20a,20b,20c,20d-tetrahomo-2,5,6,7-tetranor-4,8-inter-m-phenylene PGI$_2$; 16-methyl-20a,20b,20c,20d,20e-pentahomo-2,5,6,7-tetranor-4,8-inter-m-phenylene PGI$_2$; 16-methyl-20a,20b,20c,20d,20e,20f-hexahomo-2,5,6,7-tetranor-4,8-inter-m-phenylene PGI$_2$; 17-methyl-2,5,6,7,19,20-hexanor-4,8-inter-m-phenylene PGI$_2$; 17-methyl-2,5,6,7,20-pentanor-4,8-inter-m-phenylene PGI$_2$; 17-methyl-2,5,6,7-tetranor-4,8-inter-m-phenylene PGI$_2$; 17-methyl-20a-homo-2,5,6,7-tetranor-4,8-inter-m-phenylene PGI$_2$; 17-methyl-20a,20b-dihomo-2,5,6,7-tetranor-4,8-inter-m-phenylene PGI$_2$; 17-methyl-20a,20b,20c-trihomo-2,5,6,7-tetranor-4,8-inter-m-phenylene PGI$_2$; 17-methyl-20a,20b,20c,20d-tetrahomo-2,5,6,7-tetranor-4,8-inter-m-phenylene PGI$_2$; 17-methyl-20a,20b,20c,20d,20e-pentahomo-2,5,6,7-tetranor-4,8-inter-m-phenylene PGI$_2$; 17-methyl-20a,20b,20c,20d,20e,20f-hexahomo-2,5,6,7-tetranor-4,8-inter-m-phenylene PGI$_2$; 18-methyl-2,5,6,7,20-pentanor-4,8-inter-m-phenylene PGI$_2$; 18-methyl-2,5,6,7-tetranor-4,8-inter-m-phenylene PGI$_2$; 18-methyl-20a-homo-2,5,6,7-tetranor-4,8-inter-m-phenylene PGI$_2$; 18-methyl-20a,20b-dihomo-2,5,6,7-tetranor-4,8-inter-m-phenylene PGI$_2$; 18-methyl-20a,20b,20c-trihomo-2,5,6,7-tetranor-4,8-inter-m-phenylene PGI$_2$; 18-methyl-20a,20b,20c,20d-tetrahomo-2,5,6,7-tetranor-4,8-inter-m-phenylene PGI$_2$; 18-methyl-20a,20b,20c,20d,20e-pentahomo-2,5,6,7-tetranor-4,8-inter-m-phenylene PGI$_2$; 18-methyl-20a,20b,20c,20d,20e,20f-hexahomo-2,5,6,7-tetranor-4,8-inter-m-phenylene PGI$_2$; 19-methyl-2,5,6,7-tetranor-4,8-inter-m-phenylene PGI$_2$; 19-methyl-20a-homo-2,5,6,7-tetranor-4,8-inter-m-phenylene PGI$_2$; 19-methyl-20a,20b-dihomo-2,5,6,7-tetranor-4,8-inter-m-phenylene PGI$_2$; 19-methyl-20a,20b,20c-trihomo-2,5,6,7-tetranor-4,8-inter-m-phenylene PGI$_2$; 19-methyl-20a,20b,20c,20d-tetrahomo-2,5,6,7-tetranor-4,8-inter-m-phenylene PGI$_2$; 19-methyl-20a,20b,20c,20d,20e-pentahomo-2,5,6,7-tetranor-4,8-inter-m-phenylene PGI$_2$; 19-methyl-20a,20b,20c,20d,20e,20f-hexahomo-2,5,6,7-tetranor-4,8-inter-m-phenylene PGI$_2$; 20-methyl-20a-homo-2,5,6,7-tetranor-4,8-inter-m-phenylene PGL$_2$; 20-methyl-20a,20b-dihomo-2,5,6,7-tetranor-4,8-inter-m-phenylene PGI$_2$; 20-methyl-20a,20b,20c-trihomo-2,5,6,7-tetranor-4,8-inter-m-phenylene PGI$_2$; 20-methyl-20a,20b,20c,20d-tetrahomo-2,5,6,7-tetranor-4,8-inter-m-phenylene PGI$_2$; 20-methyl-20a,20b,20c,20d,20e-pentahomo-2,5,6,7-tetranor-4,8-inter-m-phenylene PGI$_2$; 20-methyl-20a,20b,20c,20d,20e,20f-hexahomo-2,5,6,7-tetranor-4,8-inter-m-phenylene PGI$_2$; 20a-methyl-20a,20b-dihomo-2,5,6,7-petranor-4,8-inter-m-phenylene PGI$_2$; 20a-methyl-20a,20b,20c-trihomo-2,5,6,7-tetranor-4,8-inter-m-phenylene PGI$_2$; 20a-methyl-20a,20b,20c,20d-tetrahomo-2,5,6,7-tetranor-4,8-inter-m-phenylene PGI$_2$; 20a-methyl-20a,20b,20c,20d,20e-pentahomo-2,5,6,7-tetranor-4,8-inter-m-phenylene PGI$_2$; 20a-methyl-20a,20b,20c,20d,20e,20f-hexahomo-2,5,6,7-tetranor-4,8-inter-m-phenylene PGI$_2$; 20b-methyl-20a,20b,20c-trihomo-2,5,6,7-tetranor-4,8-inter-m-phenylene PGI$_2$; 20b-methyl-20a,20b,20c,20d-tetrahomo-2,5,6,7-tetranor-4,8-inter-m-phenylene PGI$_2$; 20b-methyl-20a,20b,20c,20d,20e-pentahomo-2,5,6,7-tetranor-4,8-inter-m-phenylene PGI$_2$; 20b-methyl-20a,20b,20c,20d,20e,20f-hexahomo-2,5,6,7-tetranor-4,8-inter-m-phenylene PGI$_2$; 20c-methyl-20a,20b,20c,20d-tetrahomo-2,5,6,7-tetranor-4,8-inter-m-phenylene PGI$_2$; 20c-methyl-20a,20b,20c,20d,20e-pentahomo-2,5,6,7-tetranor-4,8-inter-m-phenylene PGI$_2$; 20c-methyl-20a,20b,20c,20d,20e,20f-hexahomo-2,5,6,7-tetranor-4,8-inter-m-phenylene PGI$_2$; 20d-methyl-20a,20b,20c,20d,20e-pentahomo-2,5,6,7,tetranor-4,8-inter-m-phenylene PGI$_2$; 20d-methyl-20a,20b,20c,20d,20e,20f-hexahomo-2,5,6,7-tetranor-4,8-inter-m-phenylene PGI$_2$; 20e-methyl-20a,20b,20c,20d,20e,20f-hexahomo-2,5,6,7-tetranor-4,8- inter-m-phenylene PGI$_2$; 16,16-dimethyl-2,5,6,7,18,19,20-heptanor-4,8-inter-m-phenylene PGI$_2$; 16,16-dimethyl-2,5,6,7,19,20-hexanor-4,8-inter-m-phenylene PGI$_2$; 16,16-dimethyl-2,5,6,7,20-pentanor-4,8-inter-m-phenylene PGI$_2$; 16,16-dimethyl-2,5,6,7-tetranor-4,8-inter-m-phenylene PGI$_2$; 16,16-dimethyl-20a-homo-2,5,6,7-tetranor-4,8-inter-m-phenylene PGI$_2$; 16,16-dimethyl-20a,20b-dihomo-2,5,6,7-tetranor-4,8-inter-m-phenylene PGI$_2$; 16,16-dimethyl-20a,20b,20c-trihomo-2,5,6,7-tetranor-4,8-inter-m-phenylene PGI$_2$; 16,16-dimethyl-20a,20b,20c,20d-tetrahomo-2,5,6,7-tetranor-4,8-inter-m-phenylene PGI$_2$; 16,16-dimethyl-20a,20b,20c,20d,20e-pentahomo-2,5,6,7-tetranor-4,8-inter-m-phenylene PGI$_2$; 17,17-dimethyl-2,5,6,7,19,20-hexanor-4,8-inter-m-phenylene PGI$_2$; 17,17-dimethyl-2,5,6,7,20-pentanor-4,8-inter-m-phenylene PGI$_2$; 17,17-dimethyl-2,5,6,7-tetranor-4,8-inter-m-phenylene PGI$_2$; 17,17-dimethyl-20a-homo-2,5,6,7-tetranor-4,8-inter-m-phenylene PGI$_2$; 17,17-dimethyl-20a,20b-dihomo-2,5,6,7-tetranor-4,8-inter-m-phenylene PGI$_2$; 17,17-dimethyl-20a,20b,20c-trihomo-2,5,6,7-tetranor-4,8-inter-m-phenylene PGI$_2$; 17,17-dimethyl-20a,20b,20c,20d-tetrahomo-2,5,6,7-tetranor-4,8-inter-m-phenylene PGI$_2$; 17,17-dimethyl-20a,20b,20c,20d,20e-pentahomo-2,5,6,7-tetranor-4,8-inter-m-phenylene PGI$_2$; 18,18-dimethyl-2,5,6,7,20-pentanor-4,8-inter-m-phenylene PGI$_2$; 18,18-dimethyl-2,5,6,7-tetranor-4,8-inter-m-phenylene PGI$_2$; 18,18-dimethyl-20a-homo-2,5,6,7-tetranor-4,8-inter-m-phenylene PGI$_2$; 18,18-dimethyl-20a,20b-dihomo-2,5,6,7-tetranor-4,8-inter-m-phenylene PGI$_2$; 18,18-dimethyl-20a,20b,20c-trihomo-2,5,6,7-tetranor-4,8-inter-m-phenylene PGI$_2$; 18,18-dimethyl-20a,20b,20c,20d-tetrahomo-2,5,6,7-tetranor-4,8-inter-m-phenylene PGI$_2$; 18,18-dimethyl-20a,20b,20c,20d,20e-pentahomo-2,5,6,7-tetranor-4,8-inter-m-phenylene PGI$_2$; 19,19-dimethyl-2,5,6,7-tetranor-4,8-inter-m-phenylene PGI$_2$; 19,19-dimethyl-20a-homo-2,5,6,7-tetranor-4,8-inter-m-phenylene PGI$_2$; 19,19-dimethyl-20a,20b-dihomo-2,5,6,7-tetranor-4,8-inter-m-phenylene PGI$_2$; 19,19-dimethyl-20a,20b,20c-trihomo-2,5,6,7-tetranor-4,8-inter-m-phenylene PGI$_2$; 19,19-dimethyl-20a,20b,20c,20d-tetrahomo-2,5,6,7-tetranor-4,8-inter-m-phenylene PGI$_2$; 19,19-dimethyl-20a,20b,20c,20d,20e-pentahomo-2,5,6,7-tetranor-4,8-inter-m-phenylene PGI$_2$; 20,20-dimethyl-20a-homo-2,5,6,7-tetranor-4,8-inter-m-phenylene PGI$_2$; 20,20-dimethyl-20a,20b-dihomo-2,5,6,7-tetranor-4,8-inter-m-phenylene PGI$_2$; 20,20-dimethyl-20a,20b,20c-trihomo-2,5,6,7-tetranor-4,8-inter-m-phenylene PGI$_2$; 20,20-dimethyl-20a,20b,20c,20d-tetrahomo-2,5,6,7-tetranor-4,8-inter-m-phenylene PGI$_2$; 20,20-dimethyl-20a,20b,20c,20d,20e-pentahomo-2,5,6,7-tetranor-4,8-inter-m-phenylene PGI$_2$; 20a,20a-dimethyl-20a,20b-dihomo-2,5,6,7-tetranor-4,8-inter-m-phenylene PGI$_2$; 20a,20a-dimethyl-20a,20b,20c-trihomo-2,5,6,7-tetranor-4,8-inter-m-phenylene PGI$_2$; 20a,20a-dimethyl-20a,20b,20c,20d-tetrahomo-2,5,6,7-tetranor-4,8-inter-m-phenylene PGI$_2$; 20a,20a-dimethyl-20a,20b,20c,20d,20e-pentahomo-2,5,6,7-tetranor-4,8-inter-m-phenylene PGI$_2$; 20b,20b-dimethyl-20a,20b,20c-trihomo-2,5,6,7-tetranor-4,8-inter-m-phenylene PGI$_2$; 20b,20b-dimethyl-20a,20b,20c,20d-tetrahomo-2,5,6,7-tetranor-4,8-inter-m-phenylene PGI$_2$; 20b,20b-dimethyl-20a,20b,20c,20d,20e-pentahomo-2,5,6,7-tetranor-4,8-inter-m-phenylene PGI$_2$; 20c,20c-dimethyl-20a,20b,20c,20d-tetrahomo-2,5,6,7-tetranor-4,8-inter-m-phenylene PGI$_2$; 20c,20c-dimethyl-20a,20b,20c,20d,20e-pentahomo-2,5,6,7-tetranor-4,8-inter-m-phenylene PGI$_2$; 20d,20d-dimethyl-20a,20b,20c,20d,20e-pentahomo-2,5,6,7-tetranor-4,8-inter-m-phenylene PGI$_2$; 16,16,17-trimethyl-2,5,6,7,19,20-hexanor-4,8-inter-m-phenylene PGI$_2$; 16,16,17-trimethyl-2,5,6,7,20-pentanor-4,8-inter-m-phenylene PGI$_2$; 16,16,17-trimethyl-2,5,6,7-tetranor-4,8-inter-m-phenylene PGI$_2$; 16,16,17-trimethyl-20a-homo-2,5,6,7-tetranor-4,8-inter-m-phenylene PGI$_2$; 16,16,17-trimethyl-20a,20b-dihomo-2,5,6,7-tetranor-4,8-inter-m-phenylene PGI$_2$; 16,16,17-trimethyl-20a,20b,20c-trihomo-2,5,6,7-tetranor-4,8-inter-m-phenylene PGI$_2$; 16,16,17-trimethyl-20a,20b,20c,20d-tetrahomo-2,5,6,7-tetranor-4,8-inter-m-phenylene PGI$_2$; and methyl ester, ethyl ester, butyl ester, isobutyl ester, phenyl ester, benzyl ester, phenethyl ester, cyclopentyl ester, cyclohexyl ester, cyclohexylmethyl ester, furylmethyl ester, 1-carbomethoxy ester, phenacyl ester and p-bromophenacyl ester thereof.

The examples of the compound with R$_4$ of a —Z—Ar may include 15-phenyl-2,5,6,7,16,17,18,19,20-nonanor-4,8-inter-m-phenylene PGI$_2$; 15-(2-chlorophenyl)-2,5,6,7,16,17,18,19,20-nonanor-4,8-inter-m-phenylene PGI$_2$; 15-(3-chlorophenyl)-2,5,6,7,16,17,18,19,20-nonanor-4,8-inter-m-phenylene PGI$_2$; 15-(4-chlorophenyl)-2,5,6,7,16,17,18,19,20-nonanor-4,8-inter-m-phenylene PGI$_2$; 15-(2-bromophenyl)-2,5,6,7,16,17,18,19,20-nonanor-4,8-inter-m-phenylene PGI$_2$; 15-(3-bromophenyl)-2,5,6,7,16,17,18,19,20-nonanor-4,8-inter-m-phenylene PGI$_2$; 15-(4-bromophenyl)-2,5,6,7,16,17,18,19,20-nonanor-4,8-inter-m-phenylene PGI$_2$; 15-(2-fluorophenyl)-2,5,6,7,16,17,18,19,20-nonanor-4,8-inter-m-phenylene PGI$_2$; 15-(3-fluorophenyl)-2,5,6,7,16,17,18,19,20-nonanor-4,8-inter-m-phenylene PGI$_2$; 15-(4-fluorophenyl)-2,5,6,7,16,17,18,19,20-nonanor-4,8-inter-m-phenylene PGI$_2$; 15-(2-methylphenyl)-2,5,6,7,16,17,18,19,20-nonanor-4,8-inter-m-phenylene PGI$_2$; 15-(3-methylphenyl)-2,5,6,7,16,17,18,19,20-nonanor-4,8-inter-m-phenylene PGI$_2$; 15-(4-methylphenyl)-2,5,6,7,16,17,18,19,20-nonanor-4,8-inter-m-phenylene PGI$_2$; 15-(2-methoxyphenyl)-2,5,6,7,16,17,18,19,20-nonanor-4,8-inter-m-phenylene PGI$_2$; 15-(4-methoxyphenyl)-2,5,6,7,16,17,18,19,20-nonanor-4,8-inter-m-phenylene PGI$_2$; 15-(4-nitrophenyl)-2,5,6,7,16,17,18,19,20-nonanor-4,8-inter-m-phenylene PGI$_2$; 15-(4-cyanophenyl)-2,5,6,7,16,17,18,19,20-nonanor-4,8-inter-m-phenylene PGI$_2$; 15-(3-trifluoromethylphenyl)-2,5,6,7,16,17,18,19,20-nonanor-4,8-inter-m-phenylene PGI$_2$; 15-(4-trifluoromethylphenyl)-2,5,6,7,16,17,18,19,20-nonanor-4,8-inter-m-phenylene PGI$_2$; 15-(2,4-dichlorophenyl)-2,5,6,7,16,17,18,19,20-nonanor-4,8-inter-m-phenylene PGI$_2$; 15-(3,4-dichlorophenyl)-2,5,6,7,16,17,18,19,20-nonanor-4,8-inter-m-phenylene PGI$_2$; 15-(3,4-dimethylphenyl)-2,5,6,7,16,17,18,19,20-nonanor-4,8-inter-m-phenylene PGI$_2$; 16-phenyl-2,5,6,7,17,18,19,20-octanor-4,8-inter-m-phenylene PGI$_2$; 16-(2-chlorophenyl)-2,5,6,7,17,18,19,20-octanor-4,8-inter-m-phenylene PGI$_2$; 16-(3-chlorophenyl)-2,5,6,7,17,18,19,20-octanor-4,8-inter-m-phenylene PGI$_2$; 16-(4-chlorophenyl)-2,5,6,7,17,18,19,20-octanor-4,8-inter-m-phenylene PGI$_2$; 16-(2-bromophenyl)-2,5,6,7,17,18,19,20-octanor-4,8-inter-m-phenylene PGI$_2$; 16-(3-bromophenyl)-2,5,6,7,17,18,19,20-octanor-4,8-inter-m-phenylene PGI$_2$; 16-(4-bromophenyl)-2,5,6,7,17,18,19,20-octanor-4,8-inter-m-phenylene PGI$_2$; 16-(2-fluorophenyl)-2,5,6,7,17,18,19,20-octanor-4,8-inter-m-phenylene PGI$_2$; 16-(3-fluorophenyl)-2,5,6,7,17,18,19,20-octanor- 4,8-inter-m-phenylene PGI$_2$; 16-(4-fluorophenyl)-2,5,6,7,17,18,19,20-octanor-4,8-inter-m-phenylene PGI$_2$; 16-(2-methylphenyl)-2,5,6,7,17,18,19,20-octanor-4,8-inter-m-phenylene PGI$_2$; 16-(3-methylphenyl)-2,5,6,7,17,18,19,20-octanor-4,8-inter-m-phenylene PGI$_2$; 16-(4-methylphenyl)-2,5,6,7,17,18,19,20-octanor-4,8-inter-m-phenylene PGI$_2$; 16-(2-methoxyphenyl)-2,5,6,7,17,18,19,20-octanor-4,8-inter-m-phenylene PGI$_2$; 16-(4-methoxyphenyl)-2,5,6,7,17,18,19,20-octanor-4,8-inter-m-phenylene PGI$_2$; 16-(4-nitrophenyl)-2,5,6,7,17,18,19,20-octanor-4,8-inter-m-phenylene PGI$_2$; 16-(4-cyanophenyl)-2,5,6,7,17,18,19,20-octanor-4,8-inter-m-phenylene PGI$_2$; 16-(3-trifluoromethylphenyl)-2,5,6,7,17,18,19,20-octanor-4,8-inter-m-phenylene PGI$_2$; 16-(4-trifluoromethylphenyl)-2,5,6,7,17,18,19,20-octanor-4,8-inter-m-phenylene PGI$_2$; 16-(2,4-dichlorophenyl)-2,5,6,7,17,18,19,20-octanor-4,8-inter-m-phenylene PGI$_2$; 16-(3,4-dichlorophenyl)-2,5,6,7,17,18,19,20-octanor-4,8-inter-m-phenylene PGI$_2$; 16-(3,4-dimethylphenyl)-2,5,6,7,17,18,19,20-octanor-4,8-inter-m-phenylene PGI$_2$; 16-phenyl-2,5,6,7,18,19,20-heptanor-4,8-inter-m-phenylene PGI$_2$; 16-(2-chlorophenyl)-2,5,6,7,18,19,20-heptanor-4,8-inter-m-phenylene PGI$_2$; 16-(3-chlorophenyl)-2,5,6,7,18,19,20-heptanor-4,8-inter-m-phenylene PGI$_2$; 16-(4-chlorophenyl)-2,5,6,7,18,19,20-heptanor-4,8-inter-m-phenylene PGI$_2$; 16-(2-bromophenyl)-2,5,6,7,18,19,20-heptanor-4,8-inter-m-phenylene PGI$_2$; 16-(3-bromophenyl)-2,5,6,7,18,19,20-heptanor-4,8-inter-m-phenylene PGI$_2$; 16-(4-bromophenyl)-2,5,6,7,18,19,20-heptanor-4,8-inter-m-phenylene PGI$_2$; 16-(2-fluorophenyl)-2,5,6,7,18,19,20-heptanor-4,8-inter-m-phenylene PGI$_2$; 16-(3-fluorophenyl)-2,5,6,7,18,19,20-heptanor-4,8-inter-m-phenylene PGI$_2$; 16-(4-fluorophenyl)-2,5,6,7,18,19,20-heptanor-4,8-inter-m-phenylene PGI$_2$; 16-(2-methylphenyl)-2,5,6,7,18,19,20-heptanor-4,8-inter-m-phenylene PGI$_2$; 16-(3-methylphenyl)-2,5,6,7,18,19,20-heptanor-4,8-inter-m-phenylene PGI$_2$; 16-(4-methylphenyl)-2,5,6,7,18,19,20-heptanor-4,8-inter-m-phenylene PGI$_2$; 16-(2-methoxyphenyl)-2,5,6,7,18,19,20-heptanor-4,8-inter-m-phenylene PGI$_2$; 16-(4-methoxyphenyl)-2,5,6,7,18,19,20-heptanor-4,8-inter-m-phenylene PGI$_2$; 16-(4-nitrophenyl)-2,5,6,7,18,19,20-heptanor-4,8-inter-m-phenylene PGI$_2$; 16-(4-cyanophenyl)-2,5,6,7,18,19,20-heptanor-4,8-inter-m-phenylene PGI$_2$; 16-(3-trifluoromethylphenyl)-2,5,6,7,18,19,20-heptanor-4,8-inter-m-phenylene PGI$_2$; 16-(4-trifluoromethylphenyl)-2,5,6,7,18,19,20-heptanor-4,8-inter-m-phenylene PGI$_2$; 16-(2,4-dichlorophenyl)-2,5,6,7,18,19,20-heptanor-4,8-inter-m-phenylene PGI$_2$; 16-(3,4-dichlorophenyl)-2,5,6,7,18,19,20-heptanor-4,8-inter-m-phenylene PGI$_2$; 16-(3,4-dimethylphenyl)-2,5,6,7,18,19,20-heptanor-4,8-inter-m-phenylene PGI$_2$; 16-methyl-16-phenyl-2,5,6,7,18,19,20-heptanor-4,8-inter-m-phenylene PGI$_2$; 16-(2-chlorophenyl)-16-methyl-2,5,6,7,18,19,20-heptanor-4,8-inter-m-phenylene PGI$_2$; 16-(3-chlorophenyl)-16-methyl-2,5,6,7,18,19,20-heptanor-4,8-inter-m-phenylene PGI$_2$; 16-(4-chlorophenyl)-16-methyl-2,5,6,7,18,19,20-heptanor-4,8-inter-m-phenylene PGI$_2$; 16-(2-bromophenyl)-16-methyl-2,5,6,7,18,19,20-heptanor-4,8-inter-m-phenylene PGI$_2$; 16-(3-bromophenyl)-16-methyl-2,5,6,7,18,19,20-heptanor-4,8-inter-m-phenylene PGI$_2$; 16-(4-bromophenyl)-16-methyl-2,5,6,7,18,19,20-heptanor-4,8-inter-m-phenylene PGI$_2$; 16-(2-fluorophenyl)-16-methyl-2,5,6,7,18,19,20-heptanor-4,8-inter-m-phenylene PGI$_2$; 16-(3-fluorophenyl)-16-methyl-2,5,6,7,18,19,20-heptanor-4,8-inter-m-phenylene PGI$_2$; 16-(4-fluorophenyl)-16-methyl-2,5,6,7,18,19,20-heptanor-4,8-inter-m-phenylene PGI$_2$; 16-(2-methylphenyl)-16-methyl-2,5,6,7,18,19,20-heptanor-4,8-inter-m-phenylene PGI$_2$; 16-(3-methylphenyl)-16-methyl-2,5,6,7,18,19,20-heptanor-4,8-inter-m-phenylene PGI$_2$; 16-(4-methylphenyl)-16-methyl-2,5,6,7,18,19,20-heptanor-4,8-inter-m-phenylene PGI$_2$; 16-(2-methoxyphenyl)-16-methyl-2,5,6,7,18,19,20-heptanor-4,8-inter-m-phenylene PGI$_2$; 16-(4-methoxyphenyl)-16-methyl-2,5,6,7,18,19,20-heptanor-4,8-inter-m-phenylene PGI$_2$; 16-(4-nitrophenyl)-16-methyl-2,5,6,7,18,19,20-heptanor-4,8-inter-m-phenylene PGI$_2$; 16-(4-cyanophenyl)-16-methyl-2,5,6,7,18,19,20-heptanor-4,8-inter-m-phenylene PGI$_2$; 16-(3-trifluoromethylphenyl)-16-methyl-2,5,6,7,18,19,20-heptanor-4,8-inter-m-phenylene PGI$_2$; 16-(4-trifluoromethylphenyl)-16-methyl-2,5,6,7,18,19,20-heptanor-4,8-inter-m-phenylene PGI$_2$; 16-(2,4-dichlorophenyl)-16-methyl-2,5,6,7,18,19,20-heptanor-4,8-inter-m-phenylene PGI$_2$; 16-(3,4-dichlorophenyl)-16-methyl-2,5,6,7,18,19,20-heptanor-4,8-inter-m-phenylene PGI$_2$; 16-(3,4-dimethylphenyl)-16-methyl-2,5,6,7,18,19,20-heptanor-4,8-inter-m-phenylene PGI$_2$; 17-phenyl-2,5,6,7,18,19,20-heptanor-4,8-inter-m-phenylene PGI$_2$; 17-(2-chlorophenyl)-2,5,6,7,18,19,20-heptanor-4,8-inter-m-phenylene PGI$_2$; 17-(3-chlorophenyl)-2,5,6,7,18,19,20-heptanor-4,8-inter-m-phenylene PGI$_2$; 17-(4-chlorophenyl)-2,5,6,7,18,19,20-heptanor-4,8-inter-m-phenylene PGI$_2$; 17-(2-bromophenyl)-2,5,6,7,18,19,20-heptanor-4,8-inter-m-phenylene PGI$_2$; 17-(3-bromophenyl)-2,5,6,7,18,19,20-heptanor-4,8-inter-m-phenylene PGI$_2$; 17-(4-bromophenyl)-2,5,6,7,18,19,20-heptanor-4,8-inter-m-phenylene PGI$_2$; 17-(2-fluorophenyl)-2,5,6,7,18,19,20-heptanor-4,8-inter-m-phenylene PGI$_2$; 17-(3-fluorophenyl)-2,5,6,7,18,19,20-heptanor-4,8-inter-m-phenylene PGI$_2$; 17-(4-fluorophenyl)-2,5,6,7,18,19,20-heptanor-4,8-inter-m-phenylene PGI$_2$; 17-(2-methylphenyl)-2,5,6,7,18,19,20-heptanor-4,8-inter-m-phenylene PGI$_2$; 17-(3-methylphenyl)-2,5,6,7,18,19,20-heptanor-4,8-inter-m-phenylene PGI$_2$; 17-(4-methylphenyl)-2,5,6,7,18,19,20-heptanor-4,8-inter-m-phenylene PGI$_2$; 17-(2-methoxyphenyl)-2,5,6,7,18,19,20-heptanor-4,8-inter-m-phenylene PGI$_2$; 17-(4-methoxyphenyl)-2,5,6,7,18,19,20-heptanor-4,8-inter-m-phenylene PGI$_2$; 17-(4-nitrophenyl)-2,5,6,7,18,19,20-heptanor-4,8-inter-m-phenylene PGI$_2$; 17-(4-cyanophenyl)-2,5,6,7,18,19,20-heptanor-4,8-inter-m-phenylene PGI$_2$; 17-(3-trifluoromethylphenyl)-2,5,6,7,18,19,20-heptanor-4,8-inter-m-phenylene PGI$_2$; 17-(4-trifluoromethylphenyl)-2,5,6,7,18,19,20-heptanor-4,8-inter-m-phenylene PGI$_2$; 17-(2,4-dichlorophenyl)-2,5,6,7,18,19,20-heptanor-4,8-inter-m-phenylene PGI$_2$; 17-(3,4-dichlorophenyl)-2,5,6,7,18,19,20-heptanor-4,8-inter-m-phenylene PGI$_2$; 17-(3,4-dimethylphenyl)-2,5,6,7,18,19,20-heptanor-4,8-inter-m-phenylene PGI$_2$; 16-methyl-17-phenyl-2,5,6,7,18,19,20-heptanor-4,8-inter-m-phenylene PGI$_2$; 17-(2-chlorophenyl)-16-methyl-2,5,6,7,18,19,20-heptanor-4,8-inter-m-phenylene PGI$_2$; 17-(3-chlorophenyl)-16-methyl-2,5,6,7,18,19,20-heptanor-4,8-inter-m-phenylene PGI$_2$; 17-(4-chlorophenyl)-16-methyl-2,5,6,7,18,19,20-heptanor-4,8-inter-m-phenylene PGI$_2$; 17-(2-bromophenyl)-16-methyl-2,5,6,7,18,19,20-heptanor-4,8-inter-m-phenylene PGI$_2$; 17-(3-bromophenyl)-16-methyl-2,5,6,7,18,19,20-heptanor-4,8-inter-m-phenylene PGI$_2$; 17-(4-bromophenyl)-16-methyl-2,5,6,7,18,19,20-heptanor-4,8-inter-m-phenylene PGI$_2$; 17-(2-fluorophenyl)-16-methyl-2,5,6,7,18,19,20-heptanor-4,8-inter-m-phenylene PGI$_2$; 17-(3-fluorophenyl)-16- methyl-2,5,6,7,18,19,20-heptanor-4,8-inter-m-phenylene PGI$_2$; 17-(4-fluorophenyl)-16-methyl-2,5,6,7,18,19,20-heptanor-4,8-inter-m-phenylene PGI$_2$; 17-(2-methylphenyl)-16-methyl-2,5,6,7,18,19,20-heptanor-4,8-inter-m-phenylene PGI$_2$; 17-(3-methylphenyl)-16-methyl-2,5,6,7,18,19,20-heptanor-4,8-inter-m-phenylene PGI$_2$; 17-(4-methylphenyl)-16-methyl-2,5,6,7,18,19,20-heptanor-4,8-inter-m-phenylene PGI$_2$; 17-(2-methoxyphenyl)-16-methyl-2,5,6,7,18,19,20-heptanor-4,8-inter-m-phenylene PGI$_2$; 17-(4-methoxyphenyl)-16-methyl-2,5,6,7,18,19,20-heptanor-4,8-inter-m-phenylene PGI$_2$; 17-(4-nitrophenyl)-2,5,6,7,18,19,20-heptanor-4,8-inter-m-phenylene PGI$_2$; 17-(4-cyanophenyl)-16-methyl-2,5,6,7,18,19,20-heptanor-4,8-inter-m-phenylene PGI$_2$; 17-(3-trifluoromethylphenyl)-16-methyl-2,5,6,7,18,19,20-heptanor-4,8-inter-m-phenylene PGI$_2$; 17-(4-trifluoromethylphenyl)-16-methyl-2,5,6,7,18,19,20-heptanor-4,8-inter-m-phenylene PGI$_2$; 17-(2,4-dichlorophenyl)-16-methyl-2,5,6,7,18,19,20-heptanor-4,8-inter-m-phenylene PGI$_2$; 17-(3,4-dichlorophenyl)-16-methyl-2,5,6,7,18,19,20-heptanor-4,8-inter-m-phenylene PGI$_2$; 17-(3,4-dimethylphenyl)-16-methyl-2,5,6,7,18,19,20-heptanor-4,8-inter-m-phenylene PGI$_2$; 16,16-dimethyl-17-phenyl-2,5,6,7,18,19,20-heptanor-4,8-inter-m-phenylene PGI$_2$; 7-(2-chlorophenyl)-16,16-dimethyl-2,5,6,7,18,19,20-heptanor-4,8-inter-m-phenylene PGI$_2$; 17-(3-chlorophenyl)-16,16-dimethyl-2,5,6,7,18,19,20-heptanor-4,8-inter-m-phenylene PGI$_2$; 17-(4-chlorophenyl)-16,16-dimethyl-2,5,6,7,18,19,20-heptanor-4,8-inter-m-phenylene PGI$_2$; 17-(2-bromophenyl)-16-16-dimethyl-2,5,6,7,18,19,20-heptanor-4,8-inter-m-phenylene PGI$_2$; 17-(3-bromophenyl)-16,16-dimethyl-2,5,6,7,18,19,20-heptanor-4,8-inter-m-phenylene PGI$_2$; 17-(4-bromophenyl)-16,16-dimethyl-2,5,6,7,18,19,20-heptanor-4,8-inter-m-phenylene PGI$_2$; 17-(2-fluorophenyl)-16,16-dimethyl-2,5,6,7,18,19,20-heptanor-4,8-inter-m-phenylene PGI$_2$; 17-(3-fluorophenyl)-16,16-dimethyl-2,5,6,7,18,19,20-heptanor-4,8-inter-m-phenylene PGI$_2$; 17-(4-fluorophenyl)-16,16-dimethyl-2,5,6,7,18,19,20-heptanor-4,8-inter-m-phenylene PGI$_2$; 17-(2-methylphenyl)-16,16-dimethyl-2,5,6,7,18,19,20-heptanor-4,8-inter-m-phenylene PGI$_2$; 17-(3-methylphenyl)-16,16-dimethyl-2,5,6,7,18,19,20-heptanor-4,8-inter-m-phenylene PGI$_2$; 17-(4-methylphenyl)-16,16-dimethyl-2,5,6,7,18,19,20-heptanor-4,8-inter-m-phenylene PGI$_2$; 17-(2-methoxyphenyl)-16,16-dimethyl-2,5,6,7,18,19,20-heptanor-4,8-inter-m-phenylene PGI$_2$; 17-(4-methoxyphenyl)-16,16-dimethyl-2,5,6,7,18,19,20-heptanor-4,8-inter-m-phenylene PGI$_2$; 17-(4-nitrophenyl)-16,16-dimethyl-2,5,6,7,18,19,20-heptanor-4,8-inter-m-phenylene PGI$_2$; 17-(4-cyanophenyl)-16,16-dimethyl-2,5,6,7,18,19,20-heptanor-4,8-inter-m-phenylene PGI$_2$; 17-(3-trifluoromethylphenyl)-16,16-dimethyl-2,5,6,7,18,19,20-heptanor-4,8-inter-m-phenylene PGI$_2$; 17-(4-trifluoromethylphenyl)-16,16-dimethyl-2,5,6,7,18,19,20-heptanor-4,8-inter-m-phenylene PGI$_2$; 17-(2,4-dichlorophenyl)-16,16-dimethyl-2,5,6,7,18,19,20-heptanor-4,8-inter-m-phenylene PGI$_2$; 17-(3,4-dichlorophenyl)-16,16-dimethyl-2,5,6,7,18,19,20-heptanor-4,8-inter-m-phenylene PGI$_2$; 17-(3,4-dimethylphenyl)-16,16-dimethyl-2,5,6,7,18,19,20-heptanor-4,8-inter-m-phenylene PGI$_2$; 18-phenyl-2,5,6,7,19,20-hexanor-4,8-inter-m-phenylene PGI$_2$; 18-phenyl-16,16-dimethyl-2,5,6,7,19,20-hexanor-4,8-inter-m-phenylene PGI$_2$; 19-phenyl-2,5,6,7,20-pentanor-4,8-inter-m-phenylene PGI$_2$; 19-phenyl-16,16-dimethyl-2,5,6,7,20-pentanor-4,8-inter-m-phenylene PGI$_2$; 20-phenyl-2,5,6,7-tetranor-4,8-inter-m-phenylene PGI$_2$; 20-phenyl-16,16-dimethyl-2,5,6,7-tetranor-4,8-inter-m-phenylene PGI$_2$; and methyl ester, ethyl ester, butyl ester, isobutyl ester, phenyl ester, benzyl ester, phenethyl ester, cyclopentyl ester, cyclohexyl ester, cyclohexylmethyl ester, furylmethyl ester, 1-carbomethoxy ester, phenacyl ester, p-bromophenacyl ester thereof.

The examples of the compound with R$_4$ represented by —Z—R$_5$ may include 15-cyclopropyl-2,5,6,7,16,17,18,19,20-nonanor-4,8-inter-m-phenylene PGI$_2$; 15-cyclobutyl-2,5,6,7,16,17,18,19,20-nonanor-4,8-inter-m-phenylene PGI$_2$; 15-cyclopentyl-2,5,6,7,16,17,18,19,20-nonanor-4,8-inter-m-phenylene PGI$_2$; 15-(2-methylcyclopentyl)-2,5,6,7,16,17,18,19,20-nonanor-4,8-inter-m-phenylene PGI$_2$; 15-(3-methylcyclopentyl)-2,5,6,7,16,17,18,19,20-nonanor-4,8-inter-m-phenylene PGI$_2$; 15-(2,5-dimethylcyclopentyl)-2,5,6,7,16,17,18,19,20-nonanor-4,8-inter-m-phenylene PGI$_2$; 15-(3,4-dimethylcyclopentyl)-2,5,6,7,16,17,18,19,20-nonanor-4,8-inter-m-phenylene PGI$_2$; 15-cyclohexyl-2,5,6,7,16,17,18,19,20-nonanor-4,8-inter-m-phenylene PGI$_2$; 15-(3-methylcyclohexyl)-2,5,6,7,16,17,18,19,20-nonanor-4,8-inter-m-phenylene PGI$_2$; 15-(3-ethylcyclohexyl)-2,5,6,7,16,17,18,19,20-nonanor-4,8-inter-m-phenylene PGI$_2$; 15-(3-propylcyclohexyl)-2,5,6,7,16,17,18,19,20-nonanor-4,8-inter-m-phenylene PGI$_2$; 15-(3-butylcyclohexyl)-2,5,6,7,16,17,18,19,20-nonanor-4,8-inter-m-phenylene PGI$_2$; 15-(3,3-dimethylcyclohexyl)-2,5,6,7,16,17,18,19,20-nonanor-4,8-inter-m-phenylene PGI$_2$; 15-(2,6-dimethylcyclohexyl)-2,5,6,7,16,17,18,19,20-nonanor-4,8-inter-m-phenylene PGI$_2$; 15-(2,4,6-trimethylcyclohexyl)-2,5,6,7,16,17,18,19,20-nonanor-4,8-inter-m-phenylene PGI$_2$; 15-cyclooctyl-2,5,6,7,16,17,18,19,20-nonanor-4,8-inter-m-phenylene PGI$_2$; 15-cyclododecyl-2,5,6,7,16,17,18,19,20-nonanor-4,8-inter-m-phenylene PGI$_2$; 16-cyclopropyl-2,5,6,7,17,18,19,20-octanor-4,8-inter-m-phenylene PGI$_2$; 16-cyclobutyl-2,5,6,7,17,18,19,20-octanor-4,8-inter-m-phenylene PGI$_2$; 16-cyclopentyl-2,5,6,7,17,18,19,20-octanor-4,8-inter-m-phenylene PGI$_2$; 16-(2-methylcyclopentyl)-2,5,6,7,17,18,19,20-octanor-4,8-inter-m-phenylene PGI$_2$; 16-(3-methylcyclopentyl)-2,5,6,7,17,18,19,20-octanor-4,8-inter-m-phenylene PGI$_2$; 16-(2,5-dimethylcyclopentyl)-2,5,6,7,17,18,19,20-octanor-4,8-inter-m-phenylene PGI$_2$; 16-(3,4-dimethylcyclopentyl)-2,5,6,7,17,18,19,20-octanor-4,8-inter-m-phenylene PGI$_2$; 16-cyclopentyl-16-methyl-2,5,6,7,18,19,20-heptanor-4,8-inter-m-phenylene PGI$_2$; 16-methyl-16-(2-methylcyclopentyl)-2,5,6,7,18,19,20-heptanor-4,8-inter-m-phenylene PGI$_2$; 16-methyl-16-(3-methylcyclopentyl)-2,5,6,7,18,19,20-heptanor-4,8-inter-m-phenylene PGI$_2$; 16-methyl-16-(2,5-dimethylcyclopentyl)-2,5,6,7,18,19,20-heptanor-4,8-inter-m-phenylene PGI$_2$; 16-methyl-16-(3,4-dimethylcyclopentyl)-2,5,6,7,18,19,20-heptanor-4,8-inter-m-phenylene PGI$_2$; 16-cyclohexyl-2,5,6,7,17,18,19,20-octanor-4,8-inter-m-phenylene PGI$_2$; 16-(3-methylcyclohexyl)-2,5,6,7,17,18,19,20-octanor-4,8-inter-m-phenylene PGI$_2$; 16-(3-ethylcyclohexyl)-2,5,6,7,17,18,19,20-octanor-4,8-inter-m-phenylene PGI$_2$; 16-(3-propylcyclohexyl)-2,5,6,7,17,18,19,20-octanor-4,8-inter-m-phenylene PGI$_2$; 16-(3-butylcyclohexyl)-2,5,6,7,17,18,19,20-octanor-4,8-inter-m-phenylene PGI$_2$; 16-(3,3-dimethylcyclohexyl)-2,5,6,7,17,18,19,20-octanor-4,8-inter-m-phenylene PGI$_2$; 16-(2,6-dimethylcyclohexyl)-2,5,6,7,17,18,19,20-octanor-4,8-inter-m-phenylene PGI₂; 16-(2,4,6-trimethylcyclohexyl)-2,5,6,7,17,18,19,20-octanor-4,8-inter-m-phenylene PGI₂; 16-cyclohexyl-16-methyl-2,5,6,7,18,19,20-heptanor-4,8-inter-m-phenylene PGI₂; 16-methyl-16-(3-methylcyclohexyl)-2,5,6,7,18,19,20-heptanor-4,8-inter-m-phenylene PGI₂; 16-methyl-16-(3-ethylcyclohexyl)-2,5,6,7,18,19,20-heptanor-4,8-inter-m-phenylene PGI₂; 16-methyl-16-(3-propylcyclohexyl)-2,5,6,7,18,19,20-heptanor-4,8-inter-m-phenylene PGI₂; 16-methyl-16-(3-butylcyclohexyl)-2,5,6,7,18,19,20-heptanor-4,8-inter-m-phenylene PGI₂; 16-methyl-16-(3,3-dimethylcyclohexyl)-2,5,6,7,18,19,20-heptanor-4,8-inter-m-phenylene PGI₂; 16-methyl-16-(2,6-dimethylcyclohexyl)-2,5,6,7,18,19,20-heptanor-4,8-inter-m-phenylene PGI₂; 16-methyl-16-(2,4,6-trimethylcyclohexyl)-2,5,6,7,18,19,20-heptanor-4,8-inter-m-phenylene PGI₂; 16-cycloheptyl-2,5,6,7,17,18,19,20-octanor-4,8-inter-m-phenylene PGI₂; 16-cyclooctyl-2,5,6,7,17,18,19,20-octanor-4,8-inter-m-phenylene PGI₂; 16-cyclododecyl-2,5,6,7,17,18,19,20-octanor-4,8-inter-m-phenylene PGI₂; 17-cyclopropyl-2,5,6,7,18,19,20-heptanor-4,8-inter-m-phenylene PGI₂; 17-cyclobutyl-2,5,6,7,18,19,20-heptanor-4,8-inter-m-phenylene PGI₂; 17-cyclopentyl-2,5,6,7,18,19,20-heptanor-4,8-inter-m-phenylene PGI₂; 17-(2-methylcyclopentyl)-2,5,6,7,18,19,20-heptanor-4,8-inter-m-phenylene PGI₂; 17-(3-methylcyclopentyl)-2,5,6,7,18,19,20-heptanor-4,8-inter-m-phenylene PGI₂; 17-(2,5-dimethylcyclopentyl)-2,5,6,7,18,19,20-heptanor-4,8-inter-m-phenylene PGI₂; 17-(3,4-dimethylcyclopentyl)-2,5,6,7,18,19,20-heptanor-4,8-inter-m-phenylene PGI₂; 17-cyclopentyl-16-methyl-2,5,6,7,18,19,20-heptanor-4,8-inter-m-phenylene PGI₂; 16-methyl-17-(2-methylcyclopentyl)-2,5,6,7,18,19,20-heptanor-4,8-inter-m-phenylene PGI₂; 16-methyl-17-(3-methylcyclopentyl)-2,5,6,7,18,19,20-heptanor-4,8-inter-m-phenylene PGI₂; 16-methyl-17-(2,5-dimethylcyclopentyl)-2,5,6,7,18,19,20-heptanor-4,8-inter-m-phenylene PGI₂; 16-methyl-17-(3,4-dimethylcyclopentyl)-2,5,6,7,18,19,20-heptanor-4,8-inter-m-phenylene PGI₂; 17-cyclopentyl-16,16-dimethyl-2,5,6,7,18,19,20-heptanor-4,8-inter-m-phenylene PGI₂; 16,16-dimethyl-17-(2-methylcyclopentyl)-2,5,6,7,18,19,20-heptanor-4,8-inter-m-phenylene PGI₂; 16,16-dimethyl-17-(3-methylcyclopentyl)-2,5,6,7,18,19,20-heptanor-4,8-inter-m-phenylene PGI₂; 16,16-dimethyl-17-(2,5-dimethylcyclopentyl)-2,5,6,7,18,19,20-heptanor-4,8-inter-m-phenylene PGI₂; 16,16-dimethyl-17-(3,4-dimethylcyclopentyl)-2,5,6,7,18,19,20-heptanor-4,8-inter-m-phenylene PGI₂; 17-cyclopentyl-17-methyl-2,5,6,7,19,20-hexanor-4,8-inter-m-phenylene PGI₂; 17-methyl-17-(2-methylcyclopentyl)-2,5,6,7,19,20-hexanor-4,8-inter-m-phenylene PGI₂; 17-methyl-17-(3-methylcyclopentyl)-2,5,6,7,19,20-hexanor-4,8-inter-m-phenylene PGI₂; 17-methyl-17-(2,5-dimethylcyclopentyl)-2,5,6,7,19,20-hexanor-4,8-inter-m-phenylene PGI₂; 17-methyl-17-(3,4-dimethylcyclopentyl)-2,5,6,7,19,20-hexanor-4,8-inter-m-phenylene PGI₂; 17-cyclohexyl-2,5,6,7,18,19,20-heptanor-4,8-inter-m-phenylene PGI₂; 17-(3-methylcyclohexyl)-2,5,6,7,18,19,20-heptanor-4,8-inter-m-phenylene PGI₂; 17-(3-ethylcyclohexyl)-2,5,6,7,18,19,20-heptanor-4,8-inter-m-phenylene PGI₂; 17-(3-propylcyclohexyl)-2,5,6,7,18,19,20-heptanor-4,8-inter-m-phenylene PGI₂; 17-(3-butylcyclohexyl)-2,5,6,7,18,19,20-heptanor-4,8-inter-m-phenylene PGI₂; 17-(3,3-dimethylcyclohexyl)-2,5,6,7,18,19,20-heptanor-4,8-inter-m-phenylene PGI₂; 17-(2,6-dimethylcyclohexyl)-2,5,6,7,18,19,20-heptanor-4,8-inter-m-phenylene PGI₂; 17-(2,4,6-trimethylcyclohexyl)-2,5,6,7,18,19,20-heptanor-4,8-inter-m-phenylene PGI₂; 17-cyclohexyl-16-methyl-2,5,6,7,18,19,20-heptanor-4,8-inter-m-phenylene PGI₂; 16-methyl-17-(3-methylcyclohexyl)-2,5,6,7,18,19,20-heptanor-4,8-inter-m-phenylene PGI₂; 17-(3ethylcyclohexyl)-16-methyl-2,5,6,7,18,19,20-heptanor-4,8-inter-m-phenylene PGI₂; 16-methyl-17-(3propylcyclohexyl)-2,5,6,7,18,19,20-heptanor-4,8-inter-m-phenylene PGI₂; 17-(3-butylcyclohexyl)-16-methyl-2,5,6,7,18,19,20-heptanor-4,8-inter-m-phenylene PGI₂; 16-methyl-17-(3,3-dimethylcyclohexyl)-2,5,6,7,18,19,20-heptanor-4,8-inter-m-phenylene PGI₂; 16-methyl-17-(2,6-dimethylcyclohexyl)-2,5,6,7,18,19,20-heptanor-4,8-inter-m-phenylene PGI₂; 16-methyl-17-(2,4,6trimethylcyclohexyl)-2,5,6,7,18,19,20-heptanor-4,8-inter-m-phenylene PGI₂; 17-cyclohexyl-16,16-dimethyl-2,5,6,7,18,19,20-heptanor-4,8-inter-m-phenylene PGI₂; 16,16-dimethyl-17-(3-methylcyclohexyl)-2,5,6,7,18,19,20-heptanor-4,8-inter-m-phenylene PGI₂; 17-(3-ethylcyclohexyl)-16,16-dimethyl-2,5,6,7,18,19,20-heptanor-4,8-inter-m-phenylene PGI₂; 16,16-dimethyl-17-(3-propylcyclohexyl)-2,5,6,7,18,19,20-heptanor-4,8-inter-m-phenylene PGI₂; 17-(3-butylcyclohexyl)-16,16-dimethyl-2,5,6,7,18,19,20-heptanor-4,8-inter-m-phenylene PGI₂; 16,16-dimethyl-17-(3,3-dimethylcyclohexyl)-2,5,6,7,18,19,20-heptanor-4,8-inter-m-phenylene PGI₂; 16,16-dimethyl-17-(2,6-dimethylcyclohexyl)-2,5,6,7,18,19,20-heptanor-4,8-inter-m-phenylene PGI₂; 16,16-dimethyl-17-(2,4,6-trimethylcyclohexyl)-2,5,6,7,18,19,20-heptanor-4,8-inter-m-phenylene PGI₂; 17-cyclohexyl-17-methyl-2,5,6,7,19,20-hexanor-4,8-inter-m-phenylene PGI₂; 17-methyl-17-(3-methylcyclohexyl)-2,5,6,7,19,20-hexanor-4,8-inter-m-phenylene PGI₂; 17-(3-ethylcyclohexyl)-17-methyl-2,5,6,7,19,20-hexanor-4,8-inter-m-phenylene PGI₂; 17-methyl-17-(3-propylcyclohexyl)-2,5,6,7,19,20-hexanor-4,8-inter-m-phenylene PGI₂; 17-(3-butylcyclohexyl)-17-methyl-2,5,6,7,19,20-hexanor-4,8-inter-m-phenylene PGI₂; 17-methyl-17-(3,3-dimethylcyclohexyl)-2,5,6,7,19,20-hexanor-4,8-inter-m-phenylene PGI₂; 17-methyl-17-(2,6-dimethylcyclohexyl)-2,5,6,7,19,20-hexanor-4,8-inter-m-phenylene PGI₂; 17-methyl-17-(2,4,6-trimethylcyclohexyl)-2,5,6,7,19,20-hexanor-4,8-inter-m-phenylene PGI₂; 17-cycloheptyl-2,5,6,7,18,19,20-heptanor-4,8-inter-m-phenylene PGI₂; 17-cyclooctyl-2,5,6,7,18,19,20-heptanor-4,8-inter-m-phenylene PGI₂; 17-cyclododecyl-2,5,6,7,18,19,20-heptanor-4,8-inter-m-phenylene PGI₂; 18-cyclopentyl-2,5,6,7,19,20-hexanor-4,8-inter-m-phenylene PGI₂; 18-(2-methylcyclopentyl)-2,5,6,7,19,20-hexanor-4,8-inter-m-phenylene PGI₂; 18-(3-methylcyclopentyl)-2,5,6,7,19,20-hexanor-4,8-inter-m-phenylene PGI₂; 18-(2,5-dimethylcyclopentyl)-2,5,6,7,19,20-hexanor-4,8-inter-m-phenylene PGI₂; 18-(3,4-dimethylcyclopentyl)-2,5,6,7,19,20-hexanor-4,8-inter-m-phenylene PGI₂; 18-cyclopentyl-16-methyl-2,5,6,7,19,20-hexanor-4,8-inter-m-phenylene PGI₂; 16-methyl-18-(2-methylcyclopentyl)-2,5,6,7,19,20-hexanor-4,8-inter-m-phenylene PGI₂; 16-methyl-18-(3-methylcyclopentyl)-2,5,6,7,19,20-hexanor-4,8-inter-m-phenylene PGI₂; 16-methyl-18-(2,5-dimethylcyclopentyl)-2,5,6,7,19,20-hexanor-4,8-inter-m-phenylene PGI₂; 16-methyl-18-(3,4-dimethylcyclopentyl)-2,5,6,7,19,20-hexanor-4,8-inter-m-phenylene PGI₂; 18-cyclopentyl-16,16-dimethyl-2,5,6,7,19,20-hexanor-4,8-inter-m-phenylene PGI₂; 16,16-dimethyl-18-(2-methylcyclopentyl)-2,5,6,7,19,20-hexanor-4,8-inter-m-phenylene PGI₂; 16,16-dimethyl-18-(3-methylcyclopentyl)-2,5,6,7,19,20-hexanor-4,8-inter-m-phenylene PGI₂; 16,16-dimethyl-18-(2,5-dimethylcyclopentyl)-

2,5,6,7,19,20-hexanor-4,8-inter-m-phenylene PGI₂; 16,16-dimethyl-18-(3,4-dimethylcyclopentyl)-2,5,6,7,19,20-hexanor-4,8-inter-m-phenylene PGI₂; 18-cyclopentyl-17,17-dimethyl-2,5,6,7,19,20-hexanor-4,8-inter-m-phenylene PGI₂; 17,17-dimethyl-18-(2-methylcyclopentyl)-2,5,6,7,19,20-hexanor-4,8-inter-m-phenylene PGI₂; 17,17-dimethyl-18-(3-methylcyclopentyl)-2,5,6,7,19,20-hexanor-4,8-inter-m-phenylene PGI₂; 17,17-dimethyl-18-(2,5-dimethylcyclopentyl)-2,5,6,7,19,20-hexanor-4,8-inter-m-phenylene PGI₂; 17,17-dimethyl-18-(3,4-dimethylcyclopentyl)-2,5,6,7,19,20-hexanor-4,8-inter-m-phenylene PGI₂; 18-cyclohexyl-2,5,6,7,19,20-hexanor-4,8-inter-m-phenylene PGI₂; 18-(3-methylcyclohexyl)-2,5,6,7,19,20-hexanor-4,8-inter-m-phenylene PGI₂; 18-(3-ethylcyclohexyl)-2,5,6,7,19,20-hexanor-4,8-inter-m-phenylene PGI₂; 18-(3-propylcyclohexyl)-2,5,6,7,19,20-hexanor-4,8-inter-m-phenylene PGI₂; 18-(3-butylcyclohexyl)-2,5,6,7,19,20-hexanor-4,8-inter-m-phenylene PGI₂; 18-(3,3-dimethylcyclohexyl)-2,5,6,7,19,20-hexanor-4,8-inter-m-phenylene PGI₂; 18-(2,6-dimethylcyclohexyl)-2,5,6,7,19,20-hexanor-4,8-inter-m-phenylene PGI₂; 18-(2,4,6-trimethylcyclohexyl)-2,5,6,7,19,20-hexanor-4,8-inter-m-phenylene PGI₂; 18-cyclohexyl-16-methyl-2,5,6,7,19,20-hexanor-4,8-inter-m-phenylene PGI₂; 16-methyl-18-(3-methylcyclohexyl)-2,5,6,7,19,20-hexanor-4,8-inter-m-phenylene PGI₂; 18-(3-ethylcyclohexyl)-16-methyl-2,5,6,7,19,20-hexanor-4,8-inter-m-phenylene PGI₂; 16-methyl-18-(3-propylcyclohexyl)-2,5,6,7,19,20-hexanor-4,8-inter-m-phenylene PGI₂; 18-(3-butylcyclohexyl)-16-methyl-2,5,6,7,19,20-hexanor-4,8-inter-m-phenylene PGI₂; 16-methyl-18-(3,3-dimethylcyclohexyl)-2,5,6,7,19,20-hexanor-4,8-inter-m-phenylene PGI₂; 16-methyl-18-(2,6-dimethylcyclohexyl)-2,5,6,7,19,20-hexanor-4,8-inter-m-phenylene PGI₂; 16-methyl-18-(2,4,6-trimethylcyclohexyl)-2,5,6,7,19,20-hexanor-4,8-inter-m-phenylene PGI₂; 18-cyclohexyl-16,16-dimethyl-2,5,6,7,19,20-hexanor-4,8-inter-m-phenylene PGI₂; 16,16-dimethyl-18-(3-methylcyclohexyl)-2,5,6,7,19,20-hexanor-4,8-inter-m-phenylene PGI₂; 18-(3-ethylcyclohexyl)-16,16-dimethyl-2,5,6,7,19,20-hexanor-4,8-inter-m-phenylene PGI₂; 16,16-dimethyl-18-(3-propylcyclohexyl)-2,5,6,7,19,20-hexanor-4,8-inter-m-phenylene PGI₂; 18-(3-butylcyclohexyl)-16,16-dimethyl-2,5,6,7,19,20-hexanor-4,8-inter-m-phenylene PGI₂; 16,16-dimethyl-18-(3,3-dimethylcyclohexyl)-2,5,6,7,19,20-hexanor-4,8-inter-m-phenylene PGI₂; 16,16-dimethyl-18-(2,6-dimethylcyclohexyl)-2,5,6,7,19,20-hexanor-4,8-inter-m-phenylene PGI₂; 16,16-dimethyl-18-(2,4,6-trimethylcyclohexyl)-2,5,6,7,19,20-hexanor-4,8-inter-m-phenylene PGI₂; 18-cyclohexyl-17,17-dimethyl-2,5,6,7,19,20-hexanor-4,8-inter-m-phenylene PGI₂; 17,17-dimethyl-18-(3-methylcyclohexyl)-2,5,6,7,19,20-hexanor-4,8-inter-m-phenylene PGI₂; 18-(3-ethylcyclohexyl)-17,17-dimethyl-2,5,6,7,19,20-hexanor-4,8-inter-m-phenylene PGI₂; 17,17-dimethyl-18-(3-propylcyclohexyl)-2,5,6,7,19,20-hexanor-4,8-inter-m-phenylene PGI₂; 18-(3-butylcyclohexyl)-17,17-dimethyl-2,5,6,7,19,20-hexanor-4,8-inter-m-phenylene PGI₂; 17,17-dimethyl-18-(3,3-dimethylcyclohexyl)-2,5,6,7,19,20-hexanor-4,8-inter-m-phenylene PGI₂; 17,17-dimethyl-18-(2,6-dimethylcyclohexyl)-2,5,6,7,19,20-hexanor-4,8-inter-m-phenylene PGI₂; 17,17-dimethyl-18-(2,4,6-trimethylcyclohexyl)-2,5,6,7,19,20-hexanor-4,8-inter-m-phenylene PGI₂; 19-cyclopentyl-2,5,6,7,20-pentanor-4,8-inter-m-phenylene PGI₂; 19-(2-methylcyclopentyl)-2,5,6,7,20-pentanor-4,8-inter-m-phenylene PGI₂; 19-(3-methylcyclopentyl)-2,5,6,7,20-pentanor-4,8-inter-m-phenylene PGI₂; 19-(2,5-dimethylcyclopentyl)-2,5,6,7,20-pentanor-4,8-inter-m-phenylene PGI₂; 19-(3,4-dimethylcyclopentyl)-2,5,6,7,20-pentanor-4,8-inter-m-phenylene PGI₂; 19-cyclopentyl-16-methyl-2,5,6,7,20-pentanor-4,8-inter-m-phenylene PGI₂; 16-methyl-19-(2-methylcyclopentyl)-2,5,6,7,20-pentanor-4,8-inter-m-phenylene PGI₂; 16-methyl-19-(3-methylcyclopentyl)-2,5,6,7,20-pentanor-4,8-inter-m-phenylene PGI₂; 16-methyl-19-(2,5-dimethylcyclopentyl)-2,5,6,7,20-pentanor-4,8-inter-m-phenylene PGI₂; 16-methyl-19-(3,4-dimethylcyclopentyl)-2,5,6,7,20-pentanor-4,8-inter-m-phenylene PGI₂; 19-cyclopentyl-16,16-dimethyl-2,5,6,7,20-pentanor-4,8-inter-m-phenylene PGI₂; 16,16-dimethyl-19-(2-methylcyclopentyl)-2,5,6,7,20-pentanor-4,8-inter-m-phenylene PGI₂; 16,16-dimethyl-19-(3-methylcyclopentyl)-2,5,6,7,20-pentanor-4,8-inter-m-phenylene PGI₂; 16,16-dimethyl-19-(2,5-dimethylcyclopentyl)-2,5,6,7,20-pentanor-4,8-inter-m-phenylene PGI₂; 16,16-dimethyl-19-(3,4-dimethylcyclopentyl)-2,5,6,7,20-pentanor-4,8-inter-m-phenylene PGI₂; 19-cyclopentyl-17,17-dimethyl-2,5,6,7,20-pentanor-4,8-inter-m-phenylene PGI₂; 17,17-dimethyl-19-(2-methylcyclopentyl)-2,5,6,7,20-pentaol-4,8-inter-m-phenylene PGI₂; 17,17-dimethyl-19-(3-methylcyclopentyl)-2,5,6,7,20-pentanor-4,8-inter-m-phenylene PGI₂; 17,17-dimethyl-19-(2,5-dimethylcyclopentyl)-2,5,6,7,20-pentanor-4,8-inter-m-phenylene PGI₂; 17,17-dimethyl-19-(3,4-dimethylcyclopentyl)-2,5,6,7,20-pentanor-4,8-inter-m-phenylene PGI₂; 19-cyclohexyl-2,5,6,7,20-pentanor-4,8-inter-m-phenylene PGI₂; 19-(3-methylcyclohexyl)-2,5,6,7,20-pentanor-4,8-inter-m-phenylene PGI₂; 19-(3ethylcyclohexyl)-2,5,6,7,20-pentanor-4,8-inter-m-phenylene PGI₂; 19-(3-propylcyclohexyl)-2,5,6,7,20-pentanor-4,8-inter-m-phenylene PGI₂; 19-(3butylcyclohexyl)-2,5,6,7,20-pentanor-4,8-inter-m-phenylene PGI₂; 19-(3,3-dimethylcyclohexyl)-2,5,6,7,20-pentanor-4,8-inter-m-phenylene PGI₂; 19-(2,6-dimethylcyclohexyl)-2,5,6,7,20-pentanor-4,8-inter-m-phenylene PGI₂; 19-(2,4,6-trimethylcyclohexyl)-2,5,6,7,20-pentanor-4,8-inter-m-phenylene PGI₂; 19-cyclohexyl-16-methyl-2,5,6,7,20-pentanor-4,8-inter-m-phenylene PGI₂; 16-methyl-19-(3-methylcyclohexyl)-2,5,6,7,20-pentanor-4,8-inter-m-phenylene PGI₂; 19-(3ethylcyclohexyl)-16-methyl-2,5,6,7,20-pentanor-4,8-inter-m-phenylene PGI₂; 16-methyl-19-(3-propylcyclohexyl)-2,5,6,7,20-pentanor-4,8-inter-m-phenylene PGI₂; 19-(3butylcyclohexyl)-16-methyl-2,5,6,7,20-pentanor-4,8-inter-m-phenylene PGI₂; 16-methyl-19-(3,3-dimethylcyclohexyl)-2,5,6,7,20-pentanor-4,8-inter-m-phenylene PGI₂; 16-methyl-19-(2,6-dimethylcyclohexyl)-2,5,6,7,20-pentanor-4,8-inter-m-phenylene PGI₂; 16-methyl-19-(2,4,6-trimethylcyclohexyl)-2,5,6,7,20-pentanor-4,8-inter-m-phenylene PGI₂; 19-cyclohexyl-16,16-dimethyl-2,5,6,7,20-pentanor-4,8-inter-m-phenylene PGI₂; 16,16-dimethyl-19-(3-methylcyclohexyl)-2,5,6,7,20-pentanor-4,8-inter-m-phenylene PGI₂; 19-(3-ethylcyclohexyl)-16,16-dimethyl-2,5,6,7,20-pentanor-4,8-inter-m-phenylene PGI₂; 16,16-dimethyl-19-(3-propylcyclohexyl)-2,5,6,7,20-pentanor-4,8-inter-m-phenylene PGI₂; 19-(3-butylcyclohexyl)-16,16-dimethyl-2,5,6,7,20-pentanor-4,8-inter-m-phenylene PGI₂; 16,16-dimethyl-19-(3,3-dimethylcyclohexyl)-2,5,6,7,20-pentanor-4,8-inter-m-phenylene PGI₂; 16,16-dimethyl-19-(2,6-dimethylcyclohexyl)-2,5,6,7,20-pentanor-4,8-inter-m-phenylene PGI₂; 16,16-dimethyl-19-(2,4,6-trimethylcyclohexyl)-2,5,6,7,20-pentanor-4,8-inter-m-phenylene PGI₂; 19-cyclohexyl-17,17-dimethyl-2,5,6,7,20-pentanor-4,8-inter-m-phenylene PGI₂;

17,17-dimethyl-19-(3-methylcyclohexyl)-2,5,6,7,20-pentanor-4,8-inter-m-phenylene PGI$_2$; 19-(3-ethylcyclohexyl)-17,17-dimethyl-2,5,6,7,20-pentanor-4,8-inter-m-phenylene PGI$_2$; 17,17-dimethyl-19-(3-propylcyclohexyl)-2,5,6,7,20-pentanor-4,8-inter-m-phenylene PGI$_2$; 19-(3-butylcyclohexyl)-17,17-dimethyl-2,5,6,7,20-pentanor-4,8-inter-m-phenylene PGI$_2$; 17,17-dimethyl-19-(3,3-dimethylcyclohexyl)-2,5,6,7,20-pentanor-4,8-inter-m-phenylene PGI$_2$; 17,17-dimethyl-19-(2,6-dimethylcyclohexyl)-2,5,6,7,20-pentanor-4,8-inter-m-phenylene PGI$_2$; 17,17-dimethyl-19-(2,4,6-trimethylcyclohexyl)-2,5,6,7,20-pentanor-4,8-inter-m-phenylene PGI$_2$; and methyl ester, ethyl ester, butyl ester, isobutyl ester, phenyl ester, benzyl ester, phenethyl ester, cyclopentyl ester, cyclohexyl ester, cyclohexylmethyl ester, furylmethyl ester, 1-carbomethoxy ester, phenacyl ester and p-bromophenacyl ester thereof.

The examples of the compound with R$_4$ represented by —C$_r$H$_{2r}$—O—R$_6$ may include 2,5,6,7,19,20-hexanor-17-oxa-4,8-inter-m-phenylene PGI$_2$; 2,5,6,7,20-pentanor-17-oxa-4,8-inter-m-phenylene PGI$_2$; 2,5,6,7-tetranor-17-oxa-4,8-inter-m-phenylene PGI$_2$; 20a-homo-2,5,6,7-tetranor-17-oxa-4,8-inter-m-phenylene PGI$_2$; 20a,20b-dihomo-2,5,6,7-tetranor-17-oxa-4,8-inter-m-phenylene PGI$_2$; 20a,20b,20c-trihomo-2,5,6,7-tetranor-17-oxa-4,8-inter-m-phenylene PGI$_2$; 16,16-dimethyl-2,5,6,7,19,20-hexanor-17-oxa-4,8-inter-m-phenylene PGI$_2$; 16,16-dimethyl-2,5,6,7,20-pentanor-17-oxa-4,8-inter-m-phenylene PGI$_2$; 16,16-dimethyl-2,5,6,7-tetranor-17-oxa-4,8-inter-m-phenylene PGI$_2$; 16,16-dimethyl-20a-homo-2,5,6,7-tetranor-17-oxa-4,8-inter-m-phenylene PGI$_2$; 16,16-dimethyl-20a,20b-dihomo-2,5,6,7-tetranor-17-oxa-4,8-inter-m-phenylene PGI$_2$; 16,16-dimethyl-20a,20b,20c-trihomo-2,5,6,7-tetranor-17-oxa-4,8-inter-m-phenylene PGI$_2$; 18-methyl-2,5,6,7,20-pentanor-17-oxa-4,8-inter-m-phenylene PGI$_2$; 18-methyl-2,5,6,7-tetranor-17-oxa-4,8-inter-m-phenylene PGI$_2$; 18,18-dimethyl-2,5,6,7,20-pentanor-17-oxa-4,8-inter-m-phenylene PGI$_2$; 16,16,18-trimethyl-2,5,6,7,20-pentanor-17-oxa-4,8-inter-m-phenylene PGI$_2$; 16,16,18-trimethyl-2,5,6,7-tetranor-17-oxa-4,8-inter-m-phenylene PGI$_2$; 16,16,18,18-tetramethyl-2,5,6,7,20-pentanor-17-oxa-4,8-inter-m-phenylene PGI$_2$; 2,5,6,7,20-pentanor-18-oxa-4,8-inter-m-phenylene PGI$_2$; 2,5,6,7-tetranor-18-oxa-4,8-inter-m-phenylene PGI$_2$; 20a-homo-2,5,6,7-tetranor-18-oxa-4,8-inter-m-phenylene PGI$_2$; 20a,20b-dihomo-2,5,6,7-tetranor-18-oxa-4,8-inter-m-phenylene PGI$_2$; 20a,20b,20c-trihomo-2,5,6,7-tetranor-18-oxa-4,8-inter-m-phenylene PGI$_2$; 20a,20b,20c,20d-tetrahomo-2,5,6,7-tetranor-18-oxa-4,8-inter-m-phenylene PGI$_2$; 16,16-dimethyl-2,5,6,7,20-pentanor-18-oxa-4,8-inter-m-phenylene PGI$_2$; 16,16-dimethyl-2,5,6,7-tetranor-18-oxa-4,8-inter-m-phenylene PGI$_2$; 16,16-dimethyl-20a-homo-2,5,6,7-tetranor-18-oxa-4,8-inter-m-phenylene PGI$_2$; 16,16-dimethyl-20a,20b-dihomo-2,5,6,7-tetranor-18-oxa-4,8-inter-m-phenylene PGI$_2$; 16,16-dimethyl-20a,20b,20c-trihomo-2,5,6,7-tetranor-18-oxa-4,8-inter-m-phenylene PGI$_2$; 16,16-dimethyl-20a,20b,20c,20d-tetrahomo-2,5,6,7-tetranor-18-oxa-4,8-inter-m-phenylene PGI$_2$; 2,5,6,7-tetranor-19-oxa-4,8-inter-m-phenylene PGI$_2$; 20a-homo-2,5,6,7-tetranor-19-oxa-4,8-inter-m-phenylene PGI$_2$; 20a,20b-dihomo-2,5,6,7-tetranor-19-oxa-4,8-inter-m-phenylene PGI$_2$; 16,16-dimethyl-2,5,6,7-tetranor-19-oxa-4,8-inter-m-phenylene PGI$_2$; 16,16-dimethyl-20a-homo-2,5,6,7-tetranor-19-oxa-4,8-inter-m-phenylene PGI$_2$; 16-methyl-2,5,6,7-tetranor-17-oxa-4,8-inter-m-phenylene PGI$_2$; 16-methyl-20a-homo-2,5,6,7-tetranor-17-oxa-4,8-inter-m-phenylene PGI$_2$; 16,16-dimethyl-20a,20b-dihomo-2,5,6,7-tetranor-19-oxa-4,8-inter-m-phenylene PGI$_2$; 20a-homo-2,5,6,7-tetranor-20-oxa-4,8-inter-m-phenylene PGI$_2$; 20a,20b-dihomo-2,5,6,7-tetranor-20-oxa-4,8-inter-m-phenylene PGI$_2$; 16,16-dimethyl-20a-homo-2,5,6,7-tetranor-20-oxa-4,8-inter-m-phenylene PGI$_2$; 16,16-dimethyl-20a,20b-dihomo-2,5,6,7-tetranor-20-oxa-4,8-inter-m-phenylene PGI$_2$; 16-cyclopentyloxy-2,5,6,7,17,18,19,20-octanor-4,8-inter-m-phenylene PGI$_2$; 16-(2-methylcyclopentyloxy)-2,5,6,7,17,18,19,20-octanor-4,8-inter-m-phenylene PGI$_2$; 16-(3-methylcyclopentyloxy)-2,5,6,7,17,18,19,20-octanor-4,8-inter-m-phenylene PGI$_2$; 16-(2,5-dimethylcyclopentyloxy)-2,5,6,7,17,18,19,20-octanor-4,8-inter-m-phenylene PGI$_2$; 16-(3,4-dimethylcyclopentyloxy)-2,5,6,7,17,18,19,20-octanor-4,8-inter-m-phenylene PGI$_2$; 16-cyclohexyloxy-2,5,6,7,17,18,19,20-octanor-4,8-inter-m-phenylene PGI$_2$; 16-(4-methylcyclohexyloxy)-2,5,6,7,17,18,19,20-octanor-4,8-inter-m-phenylene PGI$_2$; 16-(4-ethylcyclohexyloxy)-2,5,6,7,17,18,19,20-octanor-4,8-inter-m-phenylene PGI$_2$; 16-(4-propylcyclohexyloxy)-2,5,6,7,17,18,19,20-octanor-4,8-inter-m-phenylene PGI$_2$; 16-(4-butylcyclohexyloxy)-2,5,6,7,17,18,19,20-octanor-4,8-inter-m-phenylene PGI$_2$; 16-(4,4-dimethylcyclohexyloxy)-2,5,6,7,17,18,19,20-octanor-4,8-inter-m-phenylene PGI$_2$; 16-(2,6-dimethylcyclohexyloxy)-2,5,6,7,17,18,19,20-octanor-4,8-inter-m-phenylene PGI$_2$; 16-(2,4,6-trimethylcyclohexyloxy)-2,5,6,7,17,18,19,20-octanor-4,8-inter-m-phenylene PGI$_2$; 16-cyclopentyloxy-2,5,6,7,18,19,20-heptanor-4,8-inter-m-phenylene PGI$_2$; 16-(2-methylcyclopentyloxy)-2,5,6,7,18,19,20-heptanor-4,8-inter-m-phenylene PGI$_2$; 16-(3-methylcyclopentyloxy)-5,6,7,18,19,20-heptanor-4,8-inter-m-phenylene PGI$_2$; 16-(2,5-dimethylcyclopentyloxy)-2,5,6,7,18,19,20-heptanor-4,8-inter-m-phenylene PGI$_2$; 16-(3,4-dimethylcyclopentyloxy)-2,5,6,7,18,19,20-heptanor-4,8-inter-m-phenylene PGI$_2$; 16-cyclohexyloxy-2,5,6,7,18,19,20-heptanor-4,8-inter-m-phenylene PGI$_2$; 16-(4-methylcyclohexyloxy)-2,5,6,7,18,19,20-heptanor-4,8-inter-m-phenylene PGI$_2$; 16-(4-ethylcyclohexyloxy)-2,5,6,7,18,19,20-heptanor-4,8-inter-m-phenylene PGI$_2$; 16-(4-propylcyclohexyloxy)-2,5,6,7,18,19,20-heptanor-4,8-inter-m-phenylene PGI$_2$; 16-(4-butylcyclohexyloxy)-2,5,6,7,18,19,20-heptanor-4,8-inter-m-phenylene PGI$_2$; 16-(4,4-dimethylcyclohexyloxy)-2,5,6,7,18,19,20-heptanor-4,8-inter-m-phenylene PGI$_2$; 16-(2,6-dimethylcyclohexyloxy)-2,5,6,7,18,19,20-heptanor-4,8-inter-m-phenylene PGI$_2$; 16-(2,4,6-trimethylcyclohexyloxy)-2,5,6,7,18,19,20-heptanor-4,8-inter-m-phenylene PGI$_2$; 16-cyclopentyloxy-16-methyl-2,5,6,7,18,19,20-heptanor-4,8-inter-m-phenylene PGI$_2$; 16-methyl-16-(2-methylcyclopentyloxy)-2,5,6,7,18,19,20-heptanor-4,8-inter-m-phenylene PGI$_2$; 16-methyl-16-(3-methylcyclopentyloxy)-2,5,6,7,18,19,20-heptanor-4,8-inter-m-phenylene PGI$_2$; 16-(2,5-dimethylcyclopentyloxy)-16-methyl-2,5,6,7,18,19,20-heptanor-4,8-inter-m-phenylene PGI$_2$; 16-(3,4-dimethylcyclopentyloxy)-16-methyl-2,5,6,7,18,19,20-heptanor-4,8-inter-m-phenylene PGI$_2$; 16-cyclohexyloxy-16-methyl-2,5,6,7,18,19,20-heptanor-4,8-inter-m-phenylene PGI$_2$; 16-methyl-16-(4-methylcyclohexyloxy)-2,5,6,7,18,19,20-heptanor-4,8-inter-m-phenylene PGI$_2$; 16-(4-ethylcyclohexyloxy)-16-methyl-2,5,6,7,18,19,20-heptanor-4,8-inter-m-phenylene PGI$_2$; 16-methyl-16-(4-propylcyclohexyloxy)-2,5,6,7,18,19,20-heptanor-4,8-inter-m-phenylene PGI$_2$; 16-(4-butylcyclohexyloxy)-16-methyl-2,5,6,7,18,19,20-heptanor-4,8- inter-m-phenylene PGI₂; 16-(4,4-dimethylcyclohexyloxy)-16-methyl-2,5,6,7,18,19,20-heptanor-4,8-inter-m-phenylene PGI₂; 16-(2,6-dimethylcyclohexyloxy)-16-methyl-2,5,6,7,18,19,20-heptanor-4,8-inter-m-phenylene PGI₂; 16-methyl-16-(2,4,6-trimethylcyclohexyloxy)-2,5,6,7,18,19,20-heptanor-4,8-inter-m-phenylene PGI₂; 17-cyclopentyloxy-2,5,6,7,18,19,20-heptanor-4,8-inter-m-phenylene PGI₂; 17-(2-methylcyclopentyloxy)-2,5,6,7,18,19,20-heptanor-4,8-inter-m-phenylene PGI₂; 17-(3-methylcyclopentyloxy)-2,5,6,7,18,19,20-heptanor-4,8-inter-m-phenylene PGI₂; 17-(2,5-dimethylcyclopentyloxy)-2,5,6,7,18,19,20-heptanor-4,8-inter-m-phenylene PGI₂; 17-(3,4-dimethylcyclopentyloxy)-2,5,6,7,18,19,20-heptanor-4,8-inter-m-phenylene PGI₂; 17-cyclohexyloxy-2,5,6,7,18,19,20-heptanor-4,8-inter-m-phenylene PGI₂; 17-(4-methylcyclohexyloxy)-2,5,6,7,18,19,20-heptanor-4,8-inter-m-phenylene PGI₂; 17-(4-ethylcyclohexyloxy)-2,5,6,7,18,19,20-heptanor-4,8-inter-m-phenylene PGI₂; 17-(4-propylcyclohexyloxy)-2,5,6,7,18,19,20-heptanor-4,8-inter-m-phenylene PGI₂; 17-(4-butylcyclohexyloxy)-2,5,6,7,18,19,20-heptanor-4,8-inter-m-phenylene PGI₂; 17-(4,4-dimethylcyclohexyloxy)-2,5,6,7,18,19,20-heptanor-4,8-inter-m-phenylene PGI₂; 17-(2,6-dimethylcyclohexyloxy)-2,5,6,7,18,19,20-heptanor-4,8-inter-m-phenylene PGI₂; 17-(2,4,6-trimethylcyclohexyloxy)-2,5,6,7,18,19,20-heptanor-4,8-inter-m-phenylene PGI₂; 17-cyclopentyloxy-16-methyl-2,5,6,7,18,19,20-heptanor-4,8-inter-m-phenylene PGI₂; 16-methyl-17-(2-methylcyclopentyloxy)-2,5,6,7,18,19,20-heptanor-4,8-inter-m-phenylene PGI₂; 16-methyl-17-(3-methylcyclopentyloxy)-2,5,6,7,18,19,20-heptanor-4,8-inter-m-phenylene PGI₂; 17-(2,5-dimethylcyclopentyloxy)-16-methyl-2,5,6,7,18,19,20-heptanor-4,8-inter-m-phenylene PGI₂; 17-(3,4-dimethylcyclopentyloxy)-16-methyl-2,5,6,7,18,19,20-heptanor-4,8-inter-m-phenylene PGI₂; 17-cyclohexyloxy-16-methyl-2,5,6,7,18,19,20-heptanor-4,8-inter-m-phenylene PGI₂; 16-methyl-17-(4-methylcyclohexyloxy)-2,5,6,7,18,19,20-heptanor-4,8-inter-m-phenylene PGI₂; 17-(4-ethylcyclohexyloxy)-16-methyl-2,5,6,7,18,19,20-heptanor-4,8-inter-m-phenylene PGI₂; 16-methyl-17-(4-propylcyclohexyloxy)-2,5,6,7,18,19,20-heptanor-4,8-inter-m-phenylene PGI₂; 17-(4-butylcyclohexyloxy)-16-methyl-2,5,6,7,18,19,20-heptanor-4,8-inter-m-phenylene PGI₂; 17-(4,4-dimethylcyclohexyloxy)-16-methyl-2,5,6,7,18,19,20-heptanor-4,8-inter-m-phenylene PGI₂; 17-(2,6-dimethylcyclohexyloxy)-16-methyl-2,5,6,7,18,19,20-heptanor-4,8-inter-m-phenylene PGI₂; 16-methyl-17-(2,4,6-trimethylcyclohexyloxy)-2,5,6,7,18,19,20-heptanor-4,8-inter-m-phenylene PGI₂; 17-cyclopentyloxy-16,16-dimethyl-2,5,6,7,18,19,20-heptanor-4,8-inter-m-phenylene PGI₂; 16,16-dimethyl-17-(2-methylcyclopentyloxy)-2,5,6,7,18,19,20-heptanor-4,8-inter-m-phenylene PGI₂; 16,16-dimethyl-17-(3-methylcyclopentyloxy)-2,5,6,7,18,19,20-heptanor-4,8-inter-m-phenylene PGI₂; 16,16-dimethyl-17-(2,5-dimethylcyclopentyloxy)-2,5,6,7,18,19,20-heptanor-4,8-inter-m-phenylene PGI₂; 16,16-dimethyl-17-(3,4-dimethylcyclopentyloxy)-2,5,6,7,18,19,20-heptanor-4,8-inter-m-phenylene PGI₂; 17-cyclohexyloxy-16,16-dimethyl-2,5,6,7,18,19,20-heptanor-4,8-inter-m-phenylene PGI₂; 16,16-dimethyl-17-(4-methylcyclohexyloxy)-2,5,6,7,18,19,20-heptanor-4,8-inter-m-phenylene PGI₂; 17-(4-ethylcyclohexyloxy)-16,16-dimethyl-2,5,6,7,18,19,20-heptanor-4,8-inter-m-phenylene PGI₂; 16,16-dimethyl-17-(4-propylcyclohexyloxy)-2,5,6,7,18,19,20-heptanor-4,8-inter-m-phenylene PGI₂; 17-(4-butylcyclohexyloxy)-16,16-dimethyl-2,5,6,7,18,19,20-heptanor-4,8-inter-m-phenylene PGI₂; 17-(4,4-dimethylcyclohexyloxy)-16,16-dimethyl-2,5,6,7,18,19,20-heptanor-4,8-inter-m-phenylene PGI₂; 17-(2,6-dimethylcyclohexyloxy)-16,16-dimethyl-2,5,6,7,18,19,20-heptanor-4,8-inter-m-phenylene PGI₂; 16,16-dimethyl-17-(2,4,6-trimethylcyclohexyloxy)-2,5,6,7,18,19,20-heptanor-4,8-inter-m-phenylene PGI₂; 16-phenoxy-2,5,6,7,17,18,19,20-octanor-4,8-inter-m-phenylene PGI₂; 16-(2-chlorophenoxy)-2,5,6,7,17,18,19,20-octanor-4,8-inter-m-phenylene PGI₂; 16-(3-chlorophenoxy)-2,5,6,7,17,18,19,20-octanor-4,8-inter-m-phenylene PGI₂; 16-(4-chlorophenoxy)-2,5,6,7,17,18,19,20-octanor-4,8-inter-m-phenylene PGI₂; 16-(2-bromophenoxy)-2,5,6,7,17,18,19,20-octanor-4,8-inter-m-phenylene PGI₂; 16-(3-bromophenoxy)-2,5,6,7,17,18,19,20-octanor-4,8-inter-m-phenylene PGI₂; 16-(4-bromophenoxy)-2,5,6,7,17,18,19,20-octanor-4,8-inter-m-phenylene PGI₂; 16-(2-fluorophenoxy)-2,5,6,7,17,18,19,20-octanor-4,8-inter-m-phenylene PGI₂; 16-(3-fluorophenoxy)-2,5,6,7,17,18,19,20-octanor-4,8-inter-m-phenylene PGI₂; 16-(4-fluorophenoxy)-2,5,6,7,17,18,19,20-octanor-4,8-inter-m-phenylene PGI₂; 16-(2-methylphenoxy)-2,5,6,7,17,18,19,20-octanor-4,8-inter-m-phenylene PGI₂; 16-(3-methylphenoxy)-2,5,6,7,17,18,19,20-octanor-4,8-inter-m-phenylene PGI₂; 16-(4-methylphenoxy)-2,5,6,7,17,18,19,20-octanor-4,8-inter-m-phenylene PGI₂; 16-(4-methoxyphenoxy)-2,5,6,7,17,18,19,20-octanor-4,8-inter-m-phenylene PGI₂; 16-(3-trifluoromethylphenoxy)-2,5,6,7,17,18,19,20-octanor-4,8-inter-m-phenylene PGI₂; 16-(4-trifluoromethylphenoxy)-2,5,6,7,17,18,19,20-octanor-4,8-inter-m-phenylene PGI₂; 16-phenoxy-2,5,6,7,18,19,20-heptanor-4,8-inter-m-phenylene PGI₂; 16-(2-chlorophenoxy)-2,5,6,7,18,19,20-heptanor-4,8-inter-m-phenylene PGI₂; 16-(3-chlorophenoxy)-2,5,6,7,18,19,20-heptanor-4,8-inter-m-phenylene PGI₂; 16-(4-chlorophenoxy)-2,5,6,7,18,19,20-heptanor-4,8-inter-m-phenylene PGI₂; 16-(2-bromophenoxy)-2,5,6,7,18,19,20-heptanor-4,8-inter-m-phenylene PGI₂; 16-(3-bromophenoxy)-2,5,6,7,18,19,20-heptanor-4,8-inter-m-phenylene PGI₂; 16-(4-bromophenoxy)-2,5,6,7,18,19,20-heptanor-4,8-inter-m-phenylene PGI₂; 16-(2-fluorophenoxy)-2,5,6,7,18,19,20-heptanor-4,8-inter-m-phenylene PGI₂; 16-(3-fluorophenoxy)-2,5,6,7,18,19,20-heptanor-4,8-inter-m-phenylene PGI₂; 16-(4-fluorophenoxy)-2,5,6,7,18,19,20-heptanor-4,8-inter-m-phenylene PGI₂; 16-(2-methylphenoxy)-2,5,6,7,18,19,20-heptanor-4,8-inter-m-phenylene PGI₂; 16-(3-methylphenoxy)-2,5,6,7,18,19,20-heptanor-4,8-inter-m-phenylene PGI₂; 16-(4-methylphenoxy)-2,5,6,7,18,19,20-heptanor-4,8-inter-m-phenylene PGI₂; 16-(4-methoxyphenoxy)-2,5,6,7,18,19,20-heptanor-4,8-inter-m-phenylene PGI₂; 16-(3-trifluoromethylphenoxy)-2,5,6,7,18,19,20-heptanor-4,8-inter-m-phenylene PGI₂; 16-(4-trifluoromethylphenoxy)-2,5,6,7,18,19,20-heptanor-4,8-inter-m-phenylene PGI₂; 16-methyl-16-phenoxy-2,5,6,7,18,19,20-heptanor-4,8-inter-m-phenylene PGI₂; 16-(2-chlorophenoxy)-16-methyl-2,5,6,7,18,19,20-heptanor-4,8-inter-m-phenylene PGI₂; 16-(3-chlorophenoxy)-16-methyl-2,5,6,7,18,19,20-heptanor-4,8-inter-m-phenylene PGI₂; 16-(4-chlorophenoxy)-16-methyl-2,5,6,7,18,19,20-heptanor-4,8-inter-m-phenylene PGI₂; 16-(2-bromophenoxy)-16-methyl-2,5,6,7,18,19,20-heptanor-4,8-inter-m-phenylene PGI₂; 16-(3-bromophenoxy)-16-methyl-2,5,6,7,18,19,20-heptanor-4,8-inter-m-phenylene PGI₂; 16-(4-bromophenoxy)-16-methyl-2,5,6,7,18,19,20-heptanor-4,8-inter-m-phenylene PGI₂; 16-(2-fluorophenoxy)-16-methyl-2,5,6,7,18,19,20-heptanor-4,8-inter-m-phenylene PGI$_2$; 16-(3-fluorophenoxy)-16-methyl-2,5,6,7,18,19,20-heptanor-4,8-inter-m-phenylene PGI$_2$; 16-(4-fluorophenoxy)-16-methyl-2,5,6,7,18,19,20-heptanor-4,8-inter-m-phenylene PGI$_2$; 16-methyl-16-(2-methylphenoxy)-2,5,6,7,18,19,20-heptanor-4,8-inter-m-phenylene PGI$_2$; 16-methyl-16-(3-methylphenoxy)-2,5,6,7,18,19,20-heptanor-4,8-inter-m-phenylene PGI$_2$; 16-methyl-16-(4-methylphenoxy)-2,5,6,7,18,19,20-heptanor-4,8-inter-m-phenylene PGI$_2$; 16-methyl-16-(4-methoxyphenoxy)-2,5,6,7,18,19,20-heptanor-4,8-inter-m-phenylene PGI$_2$; 16-methyl-16-(3-trifluoromethylphenoxy)-2,5,6,7,18,19,20-heptanor-4,8-inter-m-phenylene PGI$_2$; 16-methyl-16-(4-trifluoromethylphenoxy)-2,5,6,7,18,19,20-heptanor-4,8-inter-m-phenylene PGI$_2$; 17-phenoxy-2,5,6,7,18,19,20-heptanor-4,8-inter-m-phenylene PGI$_2$; 17-(2-chlorophenoxy)-2,5,6,7,18,19,20-heptanor-4,8-inter-m-phenylene PGI$_2$; 17-(3-chlorophenoxy)-2,5,6,7,18,19,20-heptanor-4,8-inter-m-phenylene PGI$_2$; 17-(4-chlorophenoxy)-2,5,6,7,18,19,20-heptanor-4,8-inter-m-phenylene PGI$_2$; 17-(2-bromophenoxy)-2,5,6,7,18,19,20-heptanor-4,8-inter-m-phenylene PGI$_2$; 17-(3-bromophenoxy)-2,5,6,7,18,19,20-heptanor-4,8-inter-m-phenylene PGI$_2$; 17-(4-bromophenoxy)-2,5,6,7,18,19,20-heptanor-4,8-inter-m-phenylene PGI$_2$; 17-(2-fluorophenoxy)-2,5,6,7,18,19,20-heptanor-4,8-inter-m-phenylene PGI$_2$; 17-(3-fluorophenoxy)-2,5,6,7,18,19,20-heptanor-4,8-inter-m-phenylene PGI$_2$; 17-(4-fluorophenoxy)-2,5,6,7,18,19,20-heptanor-4,8-inter-m-phenylene PGI$_2$; 17-(2-methylphenoxy)-2,5,6,7,18,19,20-heptanor-4,8-inter-m-phenylene PGI$_2$; 17-(3-methylphenoxy)-2,5,6,7,18,19,20-heptanor-4,8-inter-m-phenylene PGI$_2$; 17-(4-methylphenoxy)-2,5,6,7,18,19,20-heptanor-4,8-inter-m-phenylene PGI$_2$; 17-(4-methoxyphenoxy)-2,5,6,7,18,19,20-heptanor-4,8-inter-m-phenylene PGI$_2$; 17-(3-trifluoromethylphenoxy)-2,5,6,7,18,19,20-heptanor-4,8-inter-m-phenylene PGI$_2$; 17-(4-trifluoromethylphenoxy)-2,5,6,7,18,19,20-heptanor-4,8-inter-m-phenylene PGI$_2$; 16-methyl-17-phenoxy-2,5,6,7,18,19,20-heptanor-4,8-inter-m-phenylene PGI$_2$; 17-(2-chlorophenoxy)-16-methyl-2,5,6,7,18,19,20-heptanor-4,8-inter-m-phenylene PGI$_2$; 17-(3-chlorophenoxy)-16-methyl-2,5,6,7,18,19,20-heptanor-4,8-inter-m-phenylene PGI$_2$; 17-(4-chlorophenoxy)-16-methyl-2,5,6,7,18,19,20-heptanor-4,8-inter-m-phenylene PGI$_2$; 17-(2-bromophenoxy)-16-methyl-2,5,6,7,18,19,20-heptanor-4,8-inter-m-phenylene PGI$_2$; 17-(3-bromophenoxy)-16-methyl-2,5,6,7,18,19,20-heptanor-4,8-inter-m-phenylene PGI$_2$; 17-(4-bromophenoxy)-16-methyl-2,5,6,7,18,19,20-heptanor-4,8-inter-m-phenylene PGI$_2$; 17-(2-fluorophenoxy)-16-methyl-2,5,6,7,18,19,20-heptanor-4,8-inter-m-phenylene PGI$_2$; 17-(3-fluorophenoxy)-16-methyl-2,5,6,7,18,19,20-heptanor-4,8-inter-m-phenylene PGI$_2$; 17-(4-fluorophenoxy)-16-methyl-2,5,6,7,18,19,20-heptanor-4,8-inter-m-phenylene PGI$_2$; 16-methyl-17-(2-methylphenoxy)-2,5,6,7,18,19,20-heptanor-4,8-inter-m-phenylene PGI$_2$; 16-methyl-17-(3-methylphenoxy)-2,5,6,7,18,19,20-heptanor-4,8-inter-m-phenylene PGI$_2$; 16-methyl-17-(4-methylphenoxy)-2,5,6,7,18,19,20-heptanor-4,8-inter-m-phenylene PGI$_2$; 16-methyl-17-(4-methoxyphenoxy)-2,5,6,7,18,19,20-heptanor-4,8-inter-m-phenylene PGI$_2$; 16-methyl-17-(3-trifluoromethylphenoxy)-2,5,6,7,18,19,20-heptanor-4,8-inter-m-phenylene PGI$_2$; 16-methyl-17-(4-trifluoromethylphenoxy)-2,5,6,7,18,19,20-heptanor-4,8-inter-m-phenylene PGI$_2$; 16,16-dimethyl-17-phenoxy-2,5,6,7,18,19,20-heptanor-4,8-inter-m-phenylene PGI$_2$; 17-(2-chlorophenoxy)-16,16-dimethyl-2,5,6,7,18,19,20-heptanor-4,8-inter-m-phenylene PGI$_2$; 17-(3-chlorophenoxy)-16,16-dimethyl-2,5,6,7,18,19,20-heptanor-4,8-inter-m-phenylene PGI$_2$; 17-(4-chlorophenoxy)-16,16-dimethyl-2,5,6,7,18,19,20-heptanor-4,8-inter-m-phenylene PGI$_2$; 17-(2-bromophenoxy)-16,16-dimethyl-2,5,6,7,18,19,20-heptanor-4,8-inter-m-phenylene PGI$_2$; 17-(3-bromophenoxy)-16,16-dimethyl-2,5,6,7,18,19,20-heptanor-4,8-inter-m-phenylene PGI$_2$; 17-(4-bromophenoxy)-16,16-dimethyl-2,5,6,7,18,19,20-heptanor-4,8-inter-m-phenylene PGI$_2$; 16,16-dimethyl-17-(2-fluorophenoxy)-2,5,6,7,18,19,20-heptanor-4,8-inter-m-phenylene PGI$_2$; 16,16-dimethyl-17-(3-fluorophenoxy)-2,5,6,7,18,19,20-heptanor-4,8-inter-m-phenylene PGI$_2$; 16,16-dimethyl-17-(4-fluorophenoxy)-2,5,6,7,18,19,20-heptanor-4,8-inter-m-phenylene PGI$_2$; 16,16-dimethyl-17-(2-methylphenoxy)-2,5,6,7,18,19,20-heptanor-4,8-inter-m-phenylene PGI$_2$; 16,16-dimethyl-17-(3-methylphenoxy)-2,5,6,7,18,19,20-heptanor-4,8-inter-m-phenylene PGI$_2$; 16,16-dimethyl-17-(4-methylphenoxy)-2,5,6,7,18,19,20-heptanor-4,8-inter-m-phenylene PGI$_2$; 16,16-dimethyl-17-(4-methoxyphenoxy)-2,5,6,7,18,19,20-heptanor-4,8-inter-m-phenylene PGI$_2$; 16,16-dimethyl-17-(3-trifluoromethylphenoxy)-2,5,6,7,18,19,20-heptanor-4,8-inter-m-phenylene PGI$_2$; 16,16-dimethyl-17-(4-trifluoromethylphenoxy)-2,5,6,7,18,19,20-heptanor-4,8-inter-m-phenylene PGI$_2$; and methyl ester, ethyl ester, butyl ester, isobutyl ester, phenyl ester, benzyl ester, phenethyl ester, cyclopentyl ester, cyclohexyl ester, cyclohexylmethyl ester, furylmethyl ester, 1-carbomethoxy ester, phenacyl ester and p-bromophenacycl ester thereof.

The examples of the compound with X of —CH$_2$—CH$_2$— may include 2,5,6,7-tetranor-13,14-dihydro-4,8-inter-m-phenylene PGI$_2$; 20a-homo-2,5,6,7-tetranor-13,14-dihydro-4,8-inter-m-phenylene PGI$_2$; 16-methyl-2,5,6,7,18,19,20-heptanor-13,14-dihydro-4,8-inter-m-phenylene PGI$_2$; 16,16-dimethyl-2,5,6,7,18,19,20-heptanor-13,14-dihydro-4,8-inter-m-phenylene PGI$_2$; 16,16-dimethyl-2,5,6,7,19,20-hexanor-13,14-dihydro-4,8-inter-m-phenylene PGI$_2$; 16,16-dimethyl-2,5,6,7,20-pentanor-13,14-dihydro-4,8-inter-m-phenylene PGI$_2$; 16,16-dimethyl-2,5,6,7-tetranor-13,14-dihydro-4,8-inter-m-phenylene PGI$_2$; 16,16-dimethyl-20a-homo-2,5,6,7-tetranor-13,14-dihydro-4,8-inter-m-phenylene PGI$_2$; 16,16-dimethyl-20a,20b-dihomo-2,5,6,7-tetranor-13,14-dihydro-4,8-inter-m-phenylene PGI$_2$; 16,16-dimethyl-20a,20b,20c-trihomo-2,5,6,7-tetranor-13,14-dihydro-4,8-inter-m-phenylene PGI$_2$; 16,16,17-trimethyl-2,5,6,7,19,20-hexanor-13,14-dihydro-4,8-inter-m-phenylene PGI$_2$; 17,17-dimethyl-2,5,6,7-tetranor-13,14-dihydro-4,8-inter-m-phenylene PGI$_2$; 18,18-dimethyl-2,5,6,7-tetranor-13,14-dihydro-4,8-inter-m-phenylene PGI$_2$; 15-methyl-2,5,6,7-tetranor-13,14-dihydro-4,8-inter-m-phenylene PGI$_2$; 16-methyl-2,5,6,7-tetranor-13,14-dihydro-4,8-inter-m-phenylene PGI$_2$; 17-methyl-2,5,6,7-tetranor-13,14-dihydro-4,8-inter-m-phenylene PGI$_2$; 17-methyl-20a-homo-2,5,6,7-tetranor-13,14-dihydro-4,8-inter-m-phenylene PGI$_2$; 16,16-dimethyl-2,5,6,7,20-pentanor-18-oxa-13,14-dihydro-4,8-inter-m-phenylene PGI$_2$; 16,16-dimethyl-2,5,6,7-tetranor-18-oxa-13,14-dihydro-4,8-inter-m-phenylene PGI$_2$; 16,16-dimethyl-20a-homo-2,5,6,7-tetranor-18-oxa-13,14-dihydro-4,8-inter-m-phenylene PGI$_2$; 16-phenoxyl-2,5,6,7,17,18,19,20-octanor-13,14-dihydro-4,8-inter-m-phenylene PGI$_2$; 16,16-dimethyl-16-phenoxy-2,5,6,7,17,18,19,20-octanor-13,14-dihydro-4,8-inter-m-phenylene PGI$_2$; 15-phenyl-2,5,6,7,16,17,18,19,20- nonanor-13,14-dihydro-4,8-inter-m-phenylene PGI$_2$; 16-phenyl-2,5,6,7,17,18,19,20-octanor-13,14-dihydro-4,8-inter-m-phenylene PGI$_2$; 17-phenyl-2,5,6,7,18,19,20-heptanor-13,14-dihydro-4,8-inter-m-phenylene PGI$_2$; 15-(2-methylphenyl)-2,5,6,7,16,17,18,19,20-nonanor-13,14-dihydro-4,8-inter-m-phenylene PGI$_2$; 15-(4-methylphenyl)-2,5,6,7,16,17,18,19,20-nonanor-13,14-dihydro-4,8-inter-m-phenylene PGI$_2$; 15-(3-fluorophenyl)-2,5,6,7,16,17,18,19,20-nonanor-13,14-dihydro-4,8-inter-m-phenylene PGI$_2$; 15-(4-trifluoromethylphenyl)-2,5,6,7,16,17,18,19,20-nonanor-13,14-dihydro-4,8-inter-m-phenylene PGI$_2$; 15-(2-chlorophenyl)-2,5,6,7,16,17,18,19,20-nonanor-13,14-dihydro-4,8-inter-m-phenylene PGI$_2$; 15-(3-chlorophenyl)-2,5,6,7,16,17,18,19,20-nonanor-13,14-dihydro-4,8-inter-m-phenylene PGI$_2$; 15-(4-chlorophenyl)-2,5,6,7,16,17,18,19,20-nonanor-13,14-dihydro-4,8-inter-m-phenylene PGI$_2$; 16-methyl-16-phenyl-2,5,6,7,18,19,20-heptanor-13,14-dihydro-4,8-inter-m-phenylene PGI$_2$; 16,16-dimethyl-17-phenyl-2,5,6,7,18,19,20-heptanor-13,14-dihydro-4,8-inter-m-phenylene PGI$_2$; 15-cyclopentyl-2,5,6,7,16,17,18,19,20-nonanor-13,14-dihydro-4,8-inter-m-phenylene PGI$_2$; 15-cyclohexyl-2,5,6,7,16,17,18,19,20-nonanor-13,14-dihydro-4,8-inter-m-phenylene PGI$_2$; 16-cyclopentyl-2,5,6,7,17,18,19,20-octanor-13,14-dihydro-4,8-inter-m-phenylene PGI$_2$; 16-cyclohexyl-2,5,6,7,17,18,19,20-octanor-13,14-dihydro-4,8-inter-m-phenylene PGI$_2$; 17-cyclohexyl-2,5,6,7,18,19,20-heptanor-13,14-dihydro-4,8-inter-m-phenylene PGI$_2$; 16-cyclohexyl-16-methyl-2,5,6,7,18,19,20-heptanor-13,14-dihydro-4,8-inter-m-phenylene PGI$_2$; 17-cyclohexyl-16,16-dimethyl-2,5,6,7,18,19,20-heptanor-13,14-dihydro-4,8-inter-m-phenylene PGI$_2$.

The examples of the compound with R$_1$ of —CH$_2$—CH$_2$—CH$_2$—OH may include 3-decarboxy-3-hydroxymethyl-2,5,6,7-tetranor-4,8-inter-m-phenylene PGI$_2$; 3-decarboxy-3-hydroxymethyl-20a-homo-2,5,6,7-tetranor-4,8-inter-m-phenylene PGI$_2$; 3-decarboxy-3-hydroxymethyl-16-methyl-2,5,6,7,18,19,20-heptanor-4,8-inter-m-phenylene PGI$_2$; 3-decarboxy-3-hydroxymethyl-16,16-dimethyl-2,5,6,7,18,19,20-heptanor-4,8-inter-m-phenylene PGI$_2$; 3-decarboxy-3-hydroxymethyl-16,16-dimethyl-2,5,6,7,19,20-hexanor-4,8-inter-m-phenylene PGI$_2$; 3-decarboxy-3-hydroxymethyl-16,16-dimethyl-2,5,6,7,20-pentanor-4,8-inter-m-phenylene PGI$_2$; 3-decarboxy-3-hydroxymethyl-16,16-dimethyl-2,5,6,7-tetranor-4,8-inter-m-phenylene PGI$_2$; 3-decarboxy-3-hydroxymethyl-16,16-dimethyl-20a-homo-2,5,6,7-tetranor-4,8-inter-m-phenylene PGI$_2$; 3-decarboxy-3-hydroxymethyl-16,16-dimethyl-20a,20b-dihomo-2,5,6,7-tetranor-4,8-inter-m-phenylene PGI$_2$; 3-decarboxy-3-hydroxymethyl-16,16-dimethyl-20a,20b,20c-trihomo-2,5,6,7-tetranor-4,8-inter-m-phenylene PGI$_2$; 3-decarboxy-3-hydroxymethyl-16,16,17-trimethyl-2,5,6,7,19,20-hexanor-4,8-inter-m-phenylene PGI$_2$; 3-decarboxy-3-hydroxymethyl-17,17-dimethyl-2,5,6,7-tetranor-4,8-inter-m-phenylene PGI$_2$; 3-decarboxy-3-hydroxymethyl-18,18-dimethyl-2,5,6,7-tetranor-4,8-inter-m-phenylene PGI$_2$; 3-decarboxy-3-hydroxymethyl-16-methyl-2,5,6,7-tetranor-4,8-inter-m-phenylene PGI$_2$; 3-decarboxy-3-hydroxymethyl-17-methyl-2,5,6,7-tetranor-4,8-inter-m-phenylene PGI$_2$; 3-decarboxy-3-hydroxymethyl-17-methyl-20a-homo-2,5,6,7-tetranor-4,8-inter-m-phenylene PGI$_2$; 3-decarboxy-3-hydroxymethyl-16,16-dimethyl-2,5,6,7,20-pentanor-18-oxa-4,8-inter-m-phenylene PGI$_2$; 3-decarboxy-3-hydroxymethyl-16,16-dimethyl-2,5,6,7-tetranor-18-oxa-4,8-inter-m-phenylene PGI$_2$; 3-decarboxy-3-hydroxymethyl-16,16-dimethyl-20a-homo-2,5,6,7-tetranor-18-oxa-4,8-inter-m-phenylene PGI$_2$; 3-decarboxy-3-hydroxymethyl-16-phenoxy-2,5,6,7,17,18,19,20-octanor-4,8-inter-m-phenylene PGI$_2$; 3-decarboxy-3-hydroxymethyl-16,16-dimethyl-16-phenoxy-2,5,6,7,17,18,19,20-octanor-4,8-inter-m-phenylene PGI$_2$; 3-decarboxy-3-hydroxymethyl-15-phenyl-2,5,6,7,16,17,18,19,20-nonanor-4,8-inter-m-phenylene PGI$_2$; 3-decarboxy-3-hydroxymethyl-16-phenyl-2,5,6,7,17,18,19,20-octanor-4,8-inter-m-phenylene PGI$_2$; 3-decarboxy-3-hydroxymethyl-17-phenyl-2,5,6,7,18,19,20-heptanor-4,8-inter-m-phenylene PGI$_2$; 3-decarboxy-3-hydroxymethyl-15-(2-methylphenyl)-2,5,6,7,16,17,18,19,20-nonanor-4,8-inter-m-phenylene PGI$_2$; 3-decarboxy-3-hydroxymethyl-15-(4-methylphenyl)-2,5,6,7,16,17,18,19,20-nonanor-4,8-inter-m-phenylene PGI$_2$; 3-decarboxy-3-hydroxymethyl-15-(3-fluorophenyl)-2,5,6,7,16,17,18,19,20-nonanor-4,8-inter-m-phenylene PGI$_2$; 3-decarboxy-3-hydroxymethyl-15-(4-trifluoromethylphenyl)-2,5,6,7,16,17,18,19,20-nonanor-4,8-inter-m-phenylene PGI$_2$; 3-decarboxy-3-hydroxymethyl-15-(2-chlorophenyl)-2,5,6,7,16,17,18,19,20-nonanor-4,8-inter-m-phenylene PGI$_2$; 3-decarboxy-3-hydroxymethyl-15-(3-chlorophenyl)-2,5,6,7,16,17,18,19,20-nonanor-4,8-inter-m-phenylene PGI$_2$; 3-decarboxy-3-hydroxymethyl-15-(4-chlorophenyl)-2,5,6,7,16,17,18,19,20-nonanor-4,8-inter-m-phenylene PGI$_2$; 3-decarboxy-3-hydroxymethyl-16-methyl-16-phenyl-2,5,6,7,18,19,20-heptanor-4,8-inter-m-phenylene PGI$_2$; 3-decarboxy-3-hydroxymethyl-16,16-dimethyl-17-phenyl-2,5,6,7,18,19,20-heptanor-4,8-inter-m-phenylene PGI$_2$; 3-decarboxy-3-hydroxymethyl-15-cyclopentyl-2,5,6,7,16,17,18,19,20-nonanor-4,8-inter-m-phenylene PGI$_2$; 3-decarboxy-3-hydroxymethyl-15-cyclohexyl-2,5,6,7,16,17,18,19,20-nonanor-4,8-inter-m-phenylene PGI$_2$; 3-decarboxy-3-hydroxymethyl-16-cyclopentyl-2,5,6,7,17,18,19,20-octanor-4,8-inter-m-phenylene PGI$_2$; 3-decarboxy-3-hydroxymethyl-16-cyclohexyl-2,5,6,7,17,18,19,20-octanor-4,8-inter-m-phenylene PGI$_2$; 3-decarboxy-3-hydroxymethyl-17-cyclohexyl-2,5,6,7,18,19,20-heptanor-4,8-inter-m-phenylene PGI$_2$; 3-decarboxy-3-hydroxymethyl-16-cyclohexyl-16-methyl-2,5,6,7,18,19,20-heptanor-4,8-inter-m-phenylene PGI$_2$; 3-decarboxy-3-hydroxymethyl-17-cyclohexyl-16,16-dimethyl-2,5,6,7,18,19,20-heptanor-4,8-inter-m-phenylene PGI$_2$; 3-decarboxy-3-hydroxymethyl-2,5,6,7-tetranor-13,14-dihydro-4,8-inter-m-phenylene PGI$_2$; 3-decarboxy-3-hydroxymethyl-20a-homo-2,5,6,7-tetranor-13,14-dihydro-4,8-inter-m-phenylene PGI$_2$; 3-decarboxy-3-hydroxymethyl-16-methyl-2,5,6,7,18,19,20-heptanor-13,14-dihydro-4,8-inter-m-phenylene PGI$_2$; 3-decarboxy-3-hydroxymethyl-16,16-dimethyl-2,5,6,7,18,19,20-heptanor-13,14-dihydro-4,8-inter-m-phenylene PGI$_2$; 3-decarboxy-3-hydroxymethyl-16,16-dimethyl-2,5,6,7,19,20-hexanor-13,14-dihydro-4,8-inter-m-phenylene PGI$_2$; 3-decarboxy-3-hydroxymethyl-16,16-dimethyl-2,5,6,7,20-pentanor-13,14-dihydro-4,8-inter-m-phenylene PGI$_2$; 3-decarboxy-3-hydroxymethyl-16,16-dimethyl-2,5,6,7-tetranor-13,14-dihydro-4,8-inter-m-phenylene PGI$_2$; 3-decarboxy-3-hydroxymethyl-16,16-dimethyl-20a-homo-2,5,6,7-tetranor-13,14-dihydro-4,8-inter-m-phenylene PGI$_2$; 3-decarboxy-3-hydroxymethyl-16,16-dimethyl-20a,20b-dihomo-2,5,6,7-tetranor-13,14-dihydro-4,8-inter-m-phenylene PGI$_2$; 3-decarboxy-3-hydroxymethyl-16,16-dimethyl-20a,20b,20c-trihomo-2,5,6,7-tetranor-13,14-dihydro-4,8-inter-m-phenylene PGI$_2$; 3-decarboxy-3-hydroxymethyl-16,16,17-trimethyl-2,5,6,7,19,20-hexanor-13,14-dihydro-4,8-inter-m-phenylene PGI$_2$; 3-decarboxy-3-hydroxymethyl-17,17-dimethyl-2,5,6,7-tetranor-13,14-dihydro-4,8-inter-m-phenylene PGI$_2$; 3-decarboxy-3-hydroxymethyl-18,18-dimethyl-2,5,6,7-tetranor-13,14-dihydro-4,8-inter-m-phenylene PGI$_2$; 3-decarboxy-3-hydroxymethyl-15-methyl-2,5,6,7-tetranor-13,14-dihydro-4,8-inter-m-phenylene PGI$_2$; 3-decarboxy-3-hydroxymethyl-16-methyl-2,5,6,7-tetranor-13,14-dihydro-4,8-inter-m-phenylene PGI$_2$; 3-decarboxy-3-hydroxymethyl-17-methyl-2,5,6,7-tetranor-13,14-dihydro-4,8-inter-m-phenylene PGI$_2$; 3-decarboxy-3-hydroxymethyl-17-methyl-20a-homo-2,5,6,7-tetranor-13,14-dihydro-4,8-inter-m-phenylene PGI$_2$; 3-decarboxy-3-hydroxymethyl-16,16-dimethyl-2,5,6,7,20-pentanor-13,14-dihydro-4,8-inter-m-phenylene PGI$_2$; 3-decarboxy-3-hydroxymethyl-16,16-dimethyl-2,5,6,7-tetranor-18-oxa-13,14-dihydro-4,8-inter-m-phenylene PGI$_2$; 3-decarboxy-3-hydroxymethyl-16,16-dimethyl-20a-homo-2,5,6,7-tetranor-18-oxa-13,14-dihydro-4,8-inter-m-phenylene PGI$_2$; 3-decarboxy-3-hydroxymethyl-16-phenoxy-2,5,6,7,17,18,19,20-octanor-13,14-dihydro-4,8-inter-m-phenylene PGI$_2$; 3-decarboxy-3-hydroxymethyl-16,16-dimethyl-16-phenoxy-2,5,6,7,17,18,19,20-octanor-13,14-dihydro-4,8-inter-m-phenylene PGI$_2$; 3-decarboxy-3-hydroxymethyl-15-phenyl-2,5,6,7,16,17,18,19,20-nonanor-13,14-dihydro-4,8-inter-m-phenylene PGI$_2$; 3-decarboxy-3-hydroxymethyl-16-phenyl-2,5,6,7,17,18,19,20-octanor-13,14-dihydro-4,8-inter-m-phenylene PGI$_2$; 3-decarboxy-3-hydroxymethyl-17-phenyl-2,5,6,7,18,19,20-heptanor-13,14-dihydro-4,8-inter-m-phenylene PGI$_2$; 3-decarboxy-3-hydroxymethyl-15-(2-methylphenyl)-2,5,6,7,16,17,18,19,20-nonanor-13,14-dihydro-4,8-inter-m-phenylene PGI$_2$; 3-decarboxy-3-hydroxymethyl-15-(4-methylphenyl)-2,5,6,7,16,17,18,19,20-nonanor-13,14-dihydro-4,8-inter-m-phenylene PGI$_2$; 3-decarboxy-3-hydroxymethyl-15-(3-fluorophenyl)-2,5,6,7,16,17,18,19,20-nonanor-13,14-dihydro-4,8-inter-m-phenylene PGI$_2$; 3-decarboxy-3-hydroxymethyl-15-(4-trifluoromethylphenyl)-2,5,6,7,16,17,18,19,20-nonanor-13,14-dihydro-4,8-inter-m-phenylene PGI$_2$; 3-decarboxy-3-hydroxymethyl-15-(2-chlorophenyl)-2,5,6,7,16,17,18,19,20-nonanor-13,14-dihydro-4,8-inter-m-phenylene PGI$_2$; 3-decarboxy-3-hydroxymethyl-15-(3-chlorophenyl)-2,5,6,7,16,17,18,19,20-nonanor-13,14-dihydro-4,8-inter-m-phenylene PGI$_2$; 3-decarboxy-3-hydroxymethyl-15-(4-chlorophenyl)-2,5,6,7,16,17,18,19,20-nonanor-13,14-dihydro-4,8-inter-m-phenylene PGI$_2$; 3-decarboxy-3-hydroxymethyl-16-methyl-16-phenyl-2,5,6,7,18,19,20-heptanor-13,14-dihydro-4,8-inter-m-phenylene PGI$_2$; 3-decarboxy-3-hydroxymethyl-16,16-dimethyl-17-phenyl-2,5,6,7,18,19,20-heptanor-13,14-dihydro-4,8-inter-m-phenylene PGI$_2$; 3-decarboxy-3-hydroxymethyl-15-cyclopentyl-2,5,6,7,16,17,18,19,20-nonanor-13,14-dihydro-4,8-inter-m-phenylene PGI$_2$; 3-decarboxy-3-hydroxymethyl-15-cyclohexyl-2,5,6,7,16,17,18,19,20-nonanor-13,14-dihydro-4,8-inter-m-phenylene PGI$_2$; 3-decarboxy-3-hydroxymethyl-16-cyclopentyl-2,5,6,7,17,18,19,20-octanor-13,14-dihydro-4,8-inter-m-phenylene PGI$_2$; 3-decarboxy-3-hydroxymethyl-16-cyclohexyl-2,5,6,7,17,18,19,20-octanor-13,14-dihydro-4,8-inter-m-phenylene PGI$_2$; 3-decarboxy-3-hydroxymethyl-17-cyclohexyl-2,5,6,7,18,19,20-heptanor-13,14-dihydro-4,8-inter-m-phenylene PGI$_2$; 3-decarboxy-3-hydroxymethyl-16-cyclohexyl-16-methyl-2,5,6,7,18,19,20-heptanor-13,14-dihydro-4,8-inter-m-phenylene PGI$_2$; 3-decarboxy-3-hydroxymethyl-17-cyclohexyl-2,5,6,7,18,19,20-heptanor-13,14-dihydro-4,8-inter-m-phenylene PGI$_2$.

Among these compounds, the preferred compounds may include 2,5,6,7-tetranor-4,8-inter-m-phenylene PGI$_2$; 20a-homo-2,5,6,7-tetranor-4,8-inter-m-phenylene PGI$_2$; 16-methyl-2,5,6,7-tetranor-4,8-inter-m-phenylene PGI$_2$; 16-methyl-20a-homo-2,5,6,7-tetranor-4,8-inter-m-phenylene PGI$_2$; 17-methyl-2,5,6,7-tetranor-4,8-inter-m-phenylene PGI$_2$; 17-methyl-20a-homo-2,5,6,7-tetranor-4,8-inter-m-phenylene PGI$_2$; 16,16-dimethyl-2,5,6,7-tetranor-4,8-inter-m-phenylene PGI$_2$; 16,16-dimethyl-20a-homo-2,5,6,7-tetranor-4,8-inter-m-phenylene PGI$_2$; 15-phenyl-2,5,6,7,16,17,18,19,20-nonanor-4,8-inter-m-phenylene PGI$_2$; 15-(4-chlorophenyl)-2,5,6,7,16,17,18,19,20-nonanor-4,8-inter-m-phenylene PGI$_2$; 15-(4-bromophenyl)-2,5,6,7,16,17,18,19,20-nonanor-4,8-inter-m-phenylene PGI$_2$; 15-(4-fluorophenyl)-2,5,6,7,16,17,18,19,20-nonanor-4,8-inter-m-phenylene PGI$_2$; 15-(4-nitrophenyl)-2,5,6,7,16,17,18,19,20-nonanor-4,8-inter-m-phenylene PGI$_2$; 15-(4-methylphenyl)-2,5,6,7,16,17,18,19,20-nonanor-4,8-inter-m-phenylene PGI$_2$; 15-(2-fluorophenyl)-2,5,6,7,16,17,18,19,20-nonanor-4,8-inter-m-phenylene PGI$_2$; 15-(2,6-difluorophenyl)-2,5,6,7,16,17,18,19,20-nonanor-4,8-inter-m-phenylene PGI$_2$; 15-(3,4-difluorophenyl)-2,5,6,7,16,17,18,19,20-nonanor-4,8-inter-m-phenylene PGI$_2$; 15-(3-fluorophenyl)-2,5,6,7,16,17,18,19,20-nonanor-4,8-inter-m-phenylene PGI$_2$; 15-(4-methylsulfonylaminophenyl)-2,5,6,7,16,17,18,19,20-nonanor-4,8-inter-m-phenylene PGI$_2$; 17-phenyl-2,5,6,7,18,19,20-heptanor-4,8-inter-m-phenylene PGI$_2$; 16-methyl-17-phenyl-2,5,6,7,18,19,20-heptanor-4,8-inter-m-phenylene PGI$_2$; 16,16-dimethyl-17-phenyl-2,5,6,7,18,19,20-heptanor-4,8-inter-m-phenylene PGI$_2$; 15-cyclopentyl-2,5,6,7,16,17,18,19,20-nonanor-4,8-inter-m-phenylene PGI$_2$; 15-cyclohexyl-2,5,6,7,16,17,18,19,20-nonanor-4,8-inter-m-phenylene PGI$_2$; 15-cycloheptyl-2,5,6,7,16,17,18,19,20-nonanor-4,8-inter-m-phenylene PGI$_2$; 16,16-dimethyl-17-cyclopentyl-2,5,6,7,18,19,20-heptanor-4,8-inter-m-phenylene PGI$_2$; 16,16-dimethyl-17-cyclohexyl-2,5,6,7,18,19,20-heptanor-4,8-inter-m-phenylene PGI$_2$; 16-methyl-17-cyclopentyl-2,5,6,7,18,19,20-heptanor-4,8-inter-m-phenylene PGI$_2$; 16-methyl-17-cyclohexyl-2,5,6,7,18,19,20-heptanor-4,8-inter-m-phenylene PGI$_2$; 2,5,6,7-tetranor-17-oxa-4,8-inter-m-phenylene PGI$_2$; 20a-homo-2,5,6,7-tetranor-17-oxa-4,8-inter-m-phenylene PGI$_2$; 16-methyl-2,5,6,7-tetranor-17-oxa-4,8-inter-m-phenylene PGI$_2$; 16-methyl-20a-homo-2,5,6,7-tetranor-17-oxa-4,8-inter-m-phenylene PGI$_2$; 16,16-dimethyl-2,5,6,7-tetranor-17-oxa-4,8-inter-m-phenylene PGI$_2$; 16-phenoxy-2,5,6,7,17,18,19,20-octanor-4,8-inter-m-phenylene PGI$_2$; 16-methyl-16-phenoxy-2,5,6,7,17,18,19,20-octanor-4,8-inter-m-phenylene PGI$_2$; 16-methyl-16-phenoxy-2,5,6,7,18,19,20-heptanor-4,8-inter-m-phenylene PGI$_2$; 2,5,6,7-tetranor-18-oxa-4,8-inter-m-phenylene PGI$_2$; 16-methyl-2,5,6,7-tetranor-18-oxa-4,8-inter-m-phenylene PGI$_2$; 16,16-dimethyl-2,5,6,7-tetranor-18-oxa-4,8-inter-m-phenylene PGI$_2$; 16-cyclopentyloxy-2,5,6,7,17,18,19,20-octanor-4,8-inter-m-phenylene PGI$_2$; 16-cyclopentyloxy-2,5,6,7,18,19,20-heptanor-4,8-inter-m-phenylene PGI$_2$; 16-cyclopentyloxy-16-methyl-2,5,6,7,18,19,20-heptanor-4,8-inter-m-phenylene PGI$_2$; 16-cyclohexyloxy-2,5,6,7,17,18,19,20-octanor-4,8-inter-m-phenylene PGI$_2$; 16-cyclohexyloxy-2,5,6,7,18,19,20-heptanor-4,8-inter-m-phenylene PGI$_2$; 16-methyl-16-cyclohexyl-2,5,6,7,18,19,20-heptanor-4,8-inter-m-phenylene PGI$_2$; methyl ester thereof; and 3-decarboxy-3-hydroxymethyl-16-methyl-16-phenoxy-2,5,6,7,18,19,20-heptanor-4,8-inter-m-phenylene PGI$_2$.

In the present invention, the examples of the most preferred compound with R$_1$ represented by CH$_2$CH$_2$COOR$_2$ and with X of —CH=CH— may include (1) the compound with R$_4$ of a normal alkyl group having 1 to 12 carbon atoms or a branched alkyl group having 3 to 12 carbon atoms: 16-methyl-2,5,6,7-tetranor-4,8-inter-m-phenylene PGI$_2$; 16-methyl-2,5,6,7-tetranor-4,8-inter-m-phenylene PGI$_2$ methyl ester; 17-methyl-2,5,6,7-tetranor-4,8-inter-m-phenylene PGI$_2$; and 17-methyl-2,5,6,7-tetranor-4,8-inter-m-phenylene PGI$_2$ methyl ester;

(2) the compound with R$_4$ represented by —Z—Ar—: 15-phenyl-2,5,6,7,16,17,18,19,20-nonanor-4,8-inter-m-phenylene PGI$_2$; 16-methyl-17-phenyl-2,5,6,7,18,19,20-heptanor-4,8-inter-m-phenylene PGI$_2$; and 16,16-dimethyl-17-phenyl-2,5,6,7,18,19,20-heptanor-4,8-inter-m-phenylene PGI$_2$;

(3) the compound with R$_4$ which is —C$_t$H$_{2t}$—O—R$_6$: 16-methyl-16-phenoxy-2,5,6,7,17,18,19,20-octanor-4,8-inter-m-phenylene PGI$_2$; 16-methyl-16-phenoxy-2,5,6,7,18,19,20-heptanor-4,8-inter-m-phenylene PGI$_2$; 16-methyl-16-phenoxy-2,5,6,7,18,19,20-heptanor-4,8-inter-m-phenylene PGI$_2$ methyl ester.

Further, the examples of the preferred compound with R$_1$ of CH$_2$CH$_2$CH$_2$OH may include 3-decarboxy-3-hydroxymethyl-16-methyl-16-phenoxy-2,5,6,7,18,19,20-heptanor-4,8-inter-m-phenylene PGI$_2$.

Among the compounds of the present invnetion, the compound having R$_1$ represented by —CH$_2$CH$_2$COOR$_2$, R$_2$ of hydrogen atom, methyl or ethyl, R$_3$ represented by hydrogen atom, and X represented by —CH=CH— may be prepared by the following method as shown in step A.

Step A

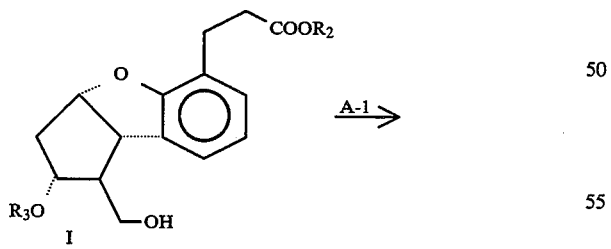

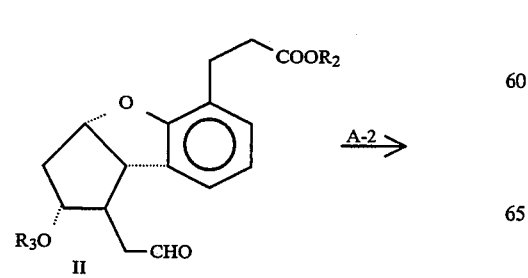

Step A -continued

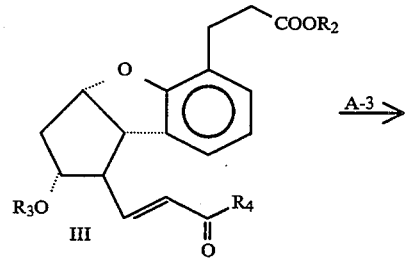

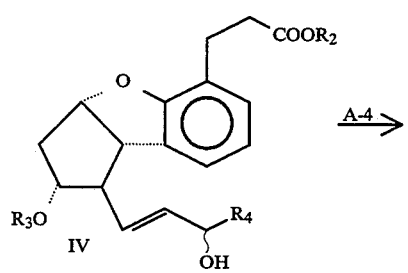

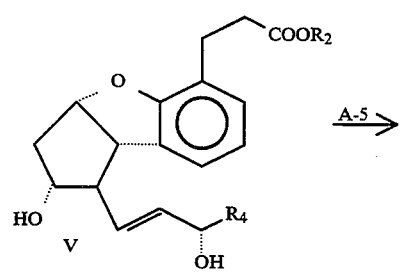

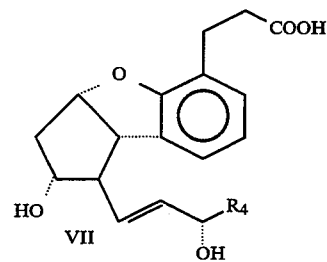

+

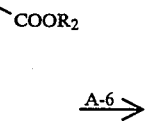

-continued

Step A

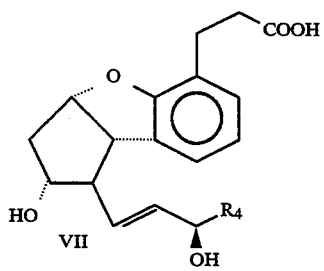

The step A-1 is so-called the process of oxidation of alcohol to aldehyde and may be employed various oxidizing agent for the oxidation. Generally, the oxidizers such as a complex of chromic acid anhydride and pyridine (collins' reagent), dimethylsulfoxide-dicyclohexylcarbodiimido, dimethylsulfide-Cl and N-bromosuccinimide-Cl may preferably be employed for oxidation of the compound represented by the general formula I (wherein $R_2$ represents ester residue).

The step A-2 may be conducted by condensing aldehyde II and dimethyl phosphonate represented by the following general formula:

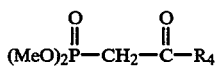

(wherein $R_4$ has the same meaning as in the formula). Generally, in order to carry out this reaction, dimethyl phosphonate may be reacted with a metal hydride (sodium hydride, pottassium hydride etc.) in ethereal solvent such as tetrahydrofuran and dimethoxyethane to obtain a salt thereof. Then aldehyde II is added thereto. The reaction may be carried out at a temperature ranging from $-30°$ C. to $100°$ C., and usually may be carried out at room temperature. Dimethy phosphonate employed in this reaction may be systhesized in accordance with the following reaction (see E. J. Corey et al. J. Am. Chem. Soc., 88, 5654 (1966)).

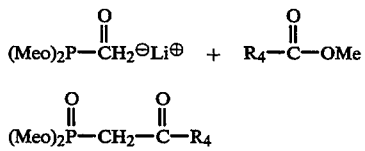

In step A-3, $\alpha,\beta$-unsaturated ketone III group may be converted into allyl alcohol IV. Gnerally reducing agent may be employed for this purpose. However, it needs to select the reducing agent which may reduce only ketone moiety while not reducing ester moiety in Compound III. In general, metal hydride, aluminium trialkoxy compound and dialkyl aluminium compound may preferably be employed for this purpose. The preferred examples of the reducing agent may include zinc borohydride ($Zn(BH_4)_2$), a reagent of sodium borohydride and cerium trichloride, diisobutyl-(2,6-dimethylphenoxy) aluminium and triisopropoxy aluminium. However, the examples the reducing agent by no means limited thereto.

Generally, when this reaction is carried out using sodium borohydride/cerium trichloride reagent, the preferred result may be obtained. In this case, methanol may be most preferably employed as a solvent. In cases where zinc borohydride and organic aluminium reducing agent is used, estereal solvent such as ether, tetrahydrofuran and dimethoxyethane may preferably be employed. The reaction may be carried out at a temperature ranging from $-110°$ C. to $80°$ C., preferably $-78°$ C. to room temperature.

The compound obtained by conducting step A-3 is generally the mixture (IV) of 15-$\alpha$ and 15-$\beta$ thereof. However, the mixture may be used as a starting material of step A-4 without separation.

Step A-4 is a process of ester interchange of $R_3$ group. Step A-4 may be carried out easily. That is, the Compound IV is dissolved in methanol and then an appropriate base is added to this solution and the thus obtained mixture is left to stand at a temperature of $-30°$ C. to $100°$ C. As a base, anhydrous sodium carbonate, anhydrous potassium carbonate, sodium methoxide and potassium methoxide may be preferably employed. In this case, it is needed the base and methanol are anhydrous in order to obtain a high yield of the Compound V. The compound obtained in step A-4 is the mixture of 15-$\alpha$ (V) and 15-$\beta$ (VI) thereof. The mixture of 15-$\alpha$ and 15-$\beta$ thereof may be separated by column chromatography (normal phase silica gel, eluant: ethyl acetate/cyclohexane).

Step A-5 and step A-6 are processes of hydrolysis of methyl ester Compounds V and VI, respectively. Generally in order to carry out these reactions, the Compound V or VI may be reacted with the base in aqueous alcohol such as aqueous methanol and aqueous ethanol, or aqueous ethereal solvent such as aqueous dioxane and aqueous tetrahydrofuran. As the base, inorganic base such as sodium hydroxide, potassium hydroxide, sodium carbonate and potassium carbonate may preferably be employed. These reactions may be carried out at a temperature ranging from $-20°$ C. to $150°$ C. However, reaction speed which is enough to carry out may be obtained at room temperature.

Compound I in Step A having $R_2$ of methyl group may be prepared by conducting the steps as shown in Step B. $R_3$ has the same meaning as in said formula. The examples thereof are described in detail in Reference Example 1 to 4.

An example of manufacturing process of the starting material IX in Step B is described in Japanese Patent Disclosure (Kokai) No. 144277/82 by the present inventors.

Step B

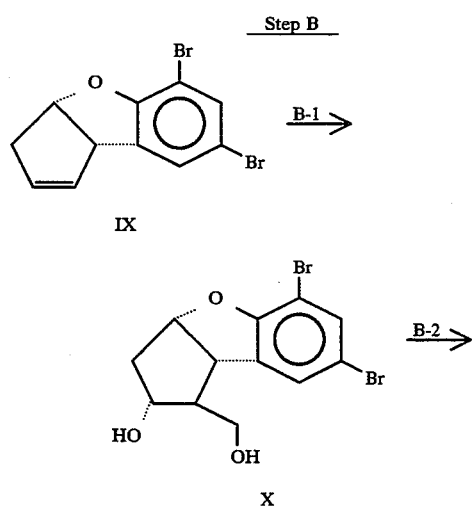

-continued
Step B

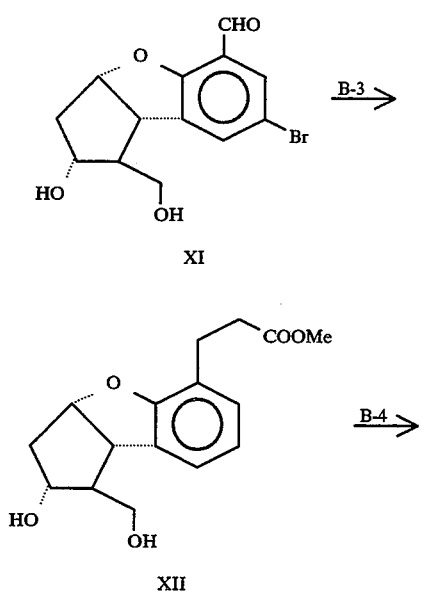

Compound I in Step A represented by the formula in which $R_2$ is ethyl group may be prepared by conducting the steps as shown in Step C. $R_3$ has the same meaning as in said formula. The examples thereof are described in detail in Reference Examples 5 to 8.

An example of manufacturing process of the starting material XIV in Step C is described in Japanese Patent Disclosure (Kokai) No. 124778/83 by the present inventors.

Step C

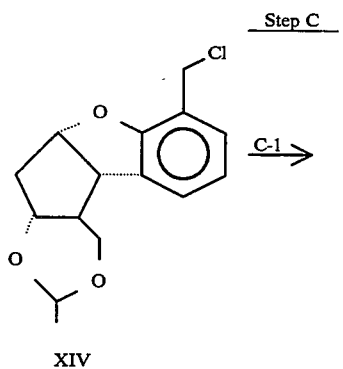

-continued
Step C

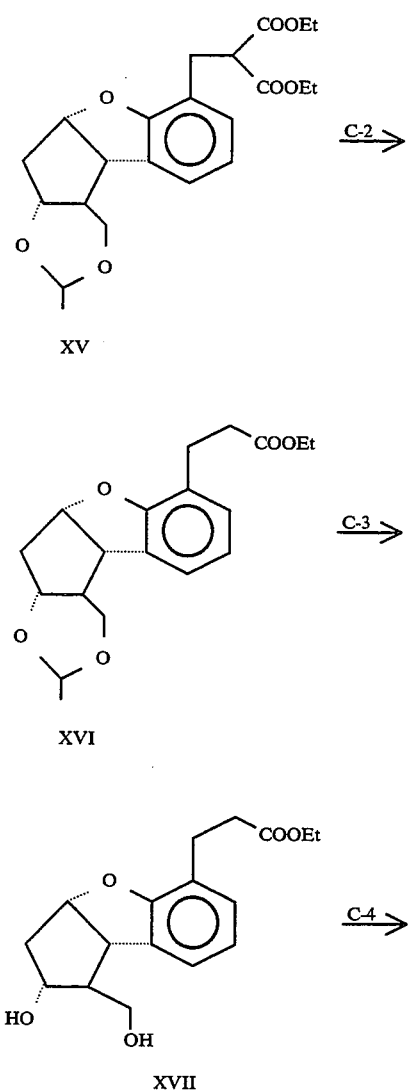

Among the compounds of the present invention, the compound which has $R_1$ represented by $-CH_2CH_2COOR_2$, ($R_2$ is hydrogen atom or methyl), $R_3$ represented by hydrogen atom, and X represented by $-CH_2-CH_2-$ may be prepared by conducting the steps in Step D.

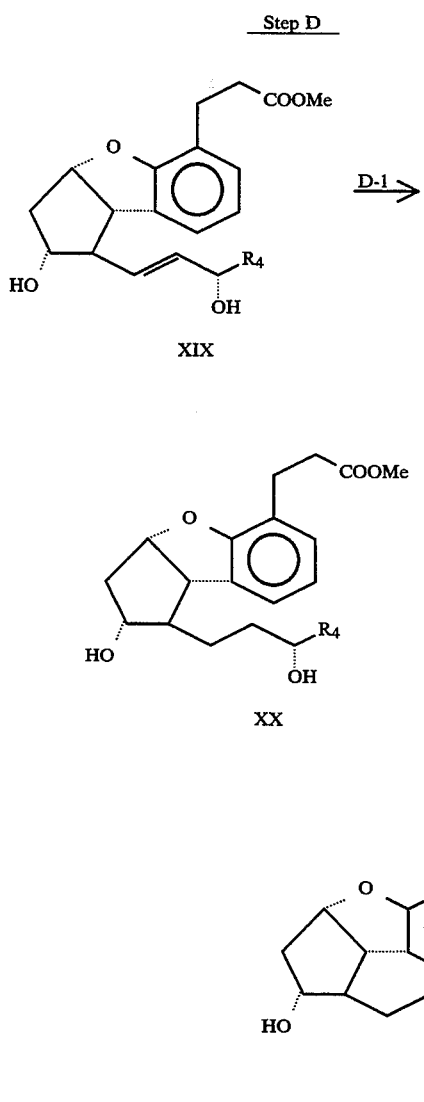

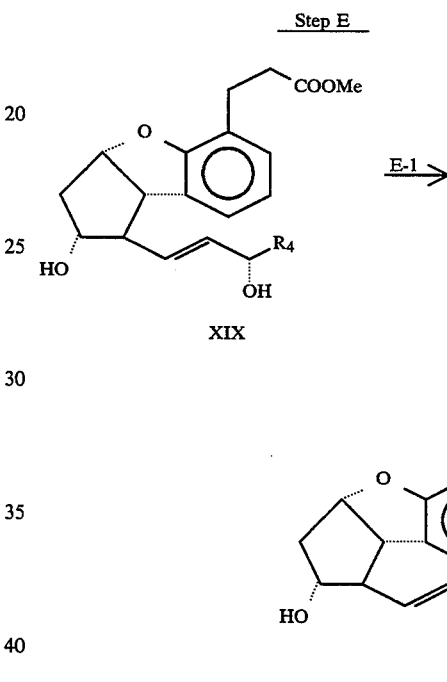

Step D-1 is a reducing process of the double bond of Compounds XIX by hydrogenation. Generally, a so called olefin catalyst such as metal palladium, palladium on active carbone, palladium/barium sulfate and Raney nickel may preferably be employed in the hydrogenation. The preferred examples of solvent may include alcohols such as methanol and ethanol, ethereal solvents such as ether, tetrahydrofuran, dimethoxyethane and dioxane, or polar solvents such as ethyl acetate. This reaction may be carried out at a temperature ranging from −20° C. to 100° C., preferably 0° C. to 40° C.

Step D-2 may be conducted by the same procedure as in Step A-5 and Step A-6.

Among the compounds of the present invention, the compound having $R_1$ of —$CH_2CH_2CH_2OH$ and $R_3$ of hydrogen atom may be prepared by reducing the Compounds XIX. Generally this compound may be prepared using a compound with $R_2$ of methyl by connducting the step as shown in Step E.

Step E-1 by which ester group is reduced may be conducted by the action of diisobutyl aluminium hydride in a nonpolar solvent such as benzene and tolene, or by the action of lithium aluminium hydride in an ethereal solvent such as tetrahydrofuran, ethylether and dimethoxyethane. The reaction may be carried out at a temperature ranging from −78° C. to 100° C. However, sufficient reaction speed may be obtained even at room temperature.

Among the compounds of the present invention, optically active substance of the Compounds VII and VIII represented by the general formula may be prepared by conducting steps in Step A using optically active substance of the Compound I represented by the general formula. The optically active Compound I may be prepared in accordance with steps in Step F.

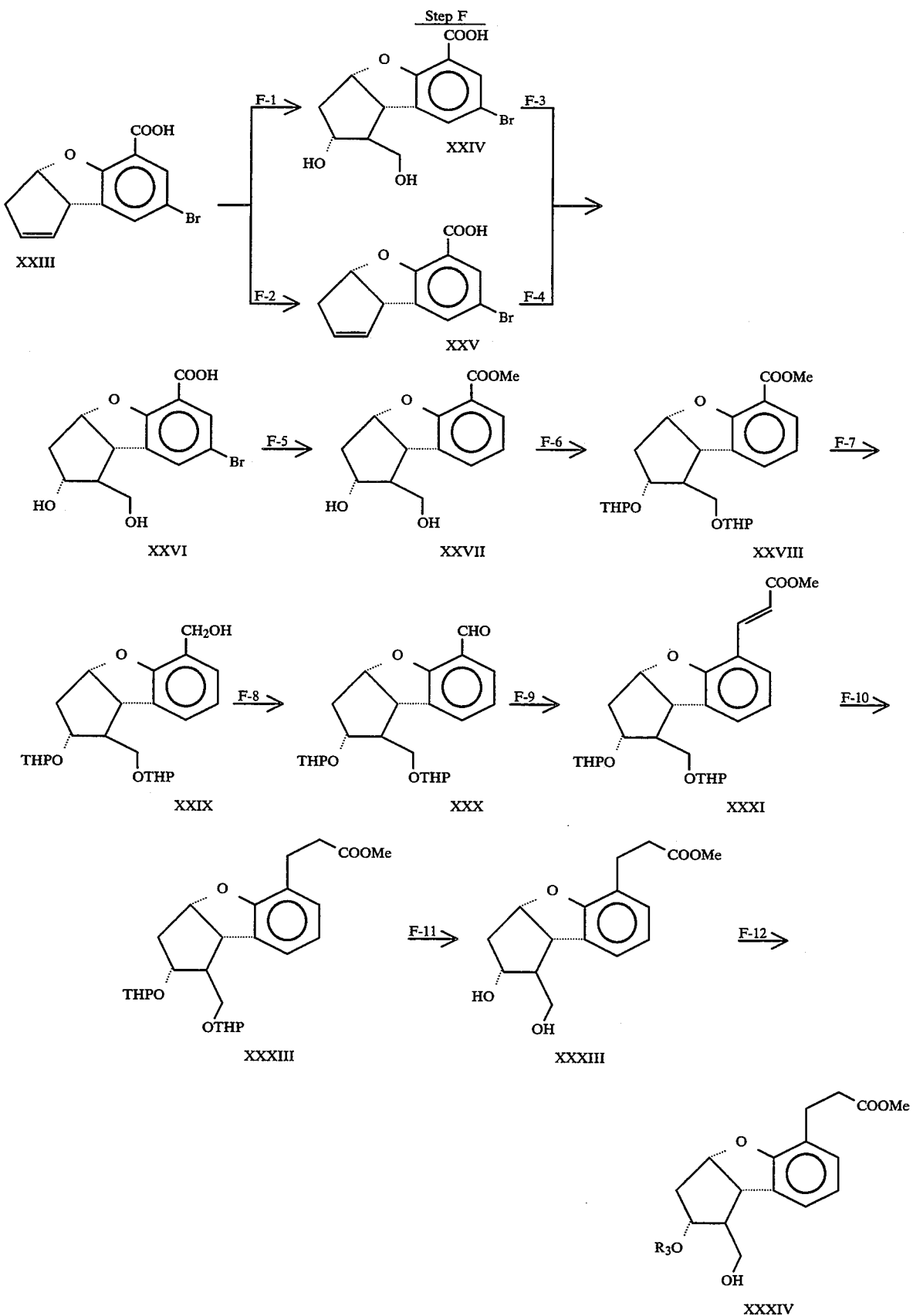
An example of manufacturing process of the starting material XXIII in Step F is described in Japanese Patent Step F-1 and step F-4 are processes of changing Compound XXIII into Compound XXIV, and changing Compound XXV into Compound XXVI, respectively by Prins reaction. An example thereof is described in Japanese Patent Disclosure (Kokai) No. 124778/83 by the present inventors.

Steps F-2 and F-3 are processes of converting rasemic body into optically active substance by so called optical resolution. Step F-2 is described in Japanese Patent Disclosure (Kokai) No. 161371/84 and step F-3 will be explained in detail in Reference Example 10.

Step F-5 is a process of conducting dehalogenation and esterification at the same time. Generally, this step may be conducted by hydrogenation. In more detail, this reaction may be carried out under hydrogen pressure of 1 to 10 atms utilizing a catalyst such as palladium on carbon, palladium-barium sulfate and Raney nickel. Preferred reaction speed of esterification may be obtained by heating to reflux under argon atomosphere using not less than 300 equivalents of methanol after dehalogenation.

Step F-6 is a process of converting the hydroxyl group of Compound XXVII into tetrahydropyranyl ether, and may be conducted by reacting dihydropyrane in a halocarbon solvent such as dichloromethane and chloroform, or ethereal solvent such as tetrahydrofuran and dimethoxyethane in the presence of an acid catalyst. The preferred examples of the acid catalyst may include hydrochloric acid, acetic acid, p-tolenesulfonic acid and phosphoric acid. However, the acid catalyst is by no means limited thereto. The reaction may be carried out at a temperature ranging from 0° C. to 50° C. However, generally preferred reaction speed may be obtained at room temperature.

In Step F-7, the same procedure as in Step E-1 may be conducted.

Step F-8 is a process of oxidizing benzylalcohol to benzaldehyde, and may be carried out by reacting the benxylalcohol with excess manganese oxide in a nonpolar solvent such as n-hexane and benzene, halocarbon solvent such as dichloromethane and chloroform, or an ethereal solvent such as tetrahydrofuran and ethylether.

Step F-9 is a process of converting the benzaldehyde to $\alpha,\beta$-unsaturated ester by Witting reaction by which two carbons are elongated. Generally, this reaction may be carried out by reacting Compound XXX with carbomethoxymethylenetriphenylphosphorane in a nonpolar solvent such as benzene and tolene. This reaction may be carried out at a temperature ranging from 0° C. to 100° C. However, the preferred reaction speed may be obtained at room temperature.

In Step F-10, the same procedure as in Step F-5 may be conducted.

Step F-11 is a process of removing tetrahydopyranyl group using acid catalyst. This step may be conducted by adding an appropriate amount of an acid catalyst such as hydrochloric acid, acetic acid, p-toluenesulfonic acid and phosphoric acid, although the acid catalyst is not limited thereto. The examples of solvent may include aqueous solvents such as acetonitrile-water, tetrahydrofran-acetic acid-water, acetic acid and water, as well as methanol or ethanol.

Step F-12 may be accomplished by conducting the the same procedure as in step B-4.

Among the compounds of the present invention, the compound having $R_1$ represented by $-CH_2CH_2COOR_2-$ in which $R_2$ does not represent hydrogen atom or a cation; that is, in which $R_2$ represents an ester residue, may be prepared by esterification of the corresponding carboxylic acid having hydrogen as $R_2$. A variety of methods of esterification are known. The method by action of diazoalkane, the method in which a silver or tertiary amine salt of a carboxylic acid is reacted with an active halides, and mixed acid anhydride method may be most preferably employed for preparing the compound of the present invnetion. In the method using diazoalkane, the desired product may be obtained easily by allowing the carboxylic acid to contact the diazoalkane in a solvent. The examples of diazoalkane may include diazomethane, diazoethane, diazopropane and diazodecane, although not limited thereto. In a second method, a silver or tertiary amine salt of carboxylic acid is reacted in an aprotic polar solvent such as dimethylformamide and acetonitrile. The examples of active halide may include benzyl chloride, benzyl bromide, p-bromobenzyl bromide, p-methoxybenzyl bromide, p-phenylbenzyl bromide, phenacyl bromide, p-bromophenacyl bromide, p-nitrophenacyl btomide and $\alpha$-benzoylphenacyl bromide, although not limited thereto.

The third method, that is, the mixed acid anhydride method may most widely be employed, so that most of compounds of the present invention may be prepared by this method. In this method, a salt of carboxylic acid is first reacted with ethylchlorocarbonate, pivaloyl chloride and p-toluenesulfonic acid chloride to obtain a mixed acid anhydride. Then excess alcohol $R_2OH$ ($R_2$ has the same meaning as in said formula except that it does not represent hydrogen atom or cation) is added thereto and the resultant is heated. The examples of the alcohol may include, although not limited thereto, methanol, ethanol, propanol, butanol, octanol, decanol, isopropanol, 2-ethyl-hexanol, benzyl alcohol, p-bromobenzyl alcohol, phenethyl alcohol, cyclopentyl alcohol, cyclopentylmethyl alcohol, cyclohexanol, cyclohexylmethyl alcohol, 2-methoxyethanol, 2-(2-methoxyethoxy)ethanol, hydroxyacetic acid methyl ester, lactic acid ethyl ester, $\gamma$-hydroxybutylic acid methyl ester, 2-butyne-1-ol, 2-pentyne-1-ol, 1,3-di-(o)-methyl glycerin, 1,3-diacetyl glycerin, phenol, p-bromophenol, p-fluorophenol, m-chlorophenol, m-fluorophenol, 3,4-dichlorophenol, m-fluorophenol, 3,4-dichlorophenol, p-(trifluoromethyl)phenol, p-methylphenol, 3,4-dimethylphenol, p-methoxyphenol, 4-phenoxyphenol, and p-benzoylaminophenol.

The compound of the present invetion exhibits excellent pharmacological effect such as platelet aggregation inhibitory effect, platelet adhesion inhibitory effect, vasodilation effect, gastric acid sceretion inhibitory effect, gastoric cytoprotection effect, bronchodilating effect, luteolytic effect and uterine constricting effect.

Since the compound of the present invention has strong platelet aggregation inhibitory effect, platelet adhesion inhibitory effect, vasodilation effect, lipid depressing effect, cholesterol depressing effect and neutral fat depressing effect, these compounds are effective on the treatment and the prevention of hypertension, myocardial infarction, angina pectoris, ischemic cerebral desease such as cerebral infarction, TIA, peripheral circulatary disturbance (Burger's disease, Raynaud's disease, Behcet's syndrome, purpurea obliterance (thrombocytopenic purpura), arterio-venous fistula, liver disease and renal disease), atherosclerosis, arteriosclerosis, diabetic platelet dysfunction retinal vascular obstruction, hyperlipidemia, vibration disease, etc.

That is, pharmaceutical composition containing the PGI$_2$ derivative of the present invention as an effective ingredient may be employed as antihypertensive agent, agent for ischemic cerebral disease, agent for myocardial infarction, agent for angina pectoris, agent for TIA, agent for peripheral circulation disturbance, antiatherosclerotic agent, antithrombotic agent, antiulcer agent, antihyperlipidemic agent, liver protecting agent, agent for retinal vascular obstruction, antiinflammatory and analgesic agent, agent for vibration disease, antiasthmatic agent, labour inducer, estrus cycle synchronizing agent, agent for nephritis, antimetastasis agent.

For this purpose, the compound of the present invention may be administered via intravenous injection, intraarterial injection, intramuscular injection, endermic administration, subcutaneous injection or oral administration. In case of oral administration or rectal application, the compound may be given once to four times a day at a dose of 0.01 µg/kg/day to 10 mg/kg/day. In case of intravenous infusion or intraarterial infection, the preferred results may be obtained by administerring at a dose of 0.1 ng/kg/min to 1 µg/kg/min. In case of usual intravenous injection, intramuscluar injection or subcutaneous injection, the compound may be given once to four times a day at a dose of 0.01 µg/kg/dat to 10 mg/kg/day. In these cases, the dose may be selected within the range depending on age, sex and conditions of the patient, and the number of times of administration. In case of endermic administration, the dose may be depend on the dosage forms of the drugs. However, the absorbed dose of weight (kg) per day is adjusted within 0.001 µg/kg to 10 mg/kg.

The compound of the present invention may be employed for the purpose of preservation of platelet. For this purpose, the compound of the present invention may be added to a platelet concentrate to a level of 0.01 ng/ml to 1 µg/ml.

The compound of the present invention is effective for prevention of platelet aggregation or adhesion which happens when artificial heart and lung, artificial kidney, artifical liver, artifical valve or artifical vessel is used. For this purpose, the compound of the present invention may be formulated for oral administration or for injection. In case of oral administration, the compound of the present invention may give effect when a dose of 0.01 µg/kg to 10 mg/kg is employed. It is also effective to infuse the compound of the present invention to an inlet of a blood circuit of an artificial organ. In this case, the compound of the present invention may be infused at a rate of 0.01 ng/kg/min to 1 mg/kg/min.

The compound of the present invention is useful for protecting and curing by duodenal ulcer, gastoric ulcer, chromic gastritis and digestive organ disorders induced by the administration of non-steroidal anti-inflammatory drugs. In cases where the compound of the present invention is given by oral administration or intravenous injection for this purpose, the dose may be selected within the range of 0.01 µg/kg/day to 1 mg/kg/day. The compound of the present invention may be administered generally once to four times a day.

The compound of the present invention is useful to ameliorate the breath when sufferring from a disease such as asthma, bronchitis and pneumonia. For this purpose, the compound of the present invention may be given by oral administration or inhalant administration at a dose of 0.001 µg/kg to 1 mg/kg.

The compound of the present invention is useful for the induction of labour and the relaxation and softening of uterine cervix. For this purpose, it is preferred to give the compound by oral administration, intravaginal administration or intravenous infusion.

In case of oral administration or intravaginal administration, the compound of the present invention may be given at a dose of 0.01 µg/kg to 5 mg/kg. In case of intravenous infusion, the drug may be administrated at a rate of 0.01 ng/kg/min to 1 µg/kg/min.

The compound of the invention is useful for the synchronization of estrus cycle in mammal (e.g., cow, horse, pig, sheep). For this purpose, generally it may be given at a dose of 0.01 µg/kg to 10 mg/kg by oral administration, intravaginal administration or intramuscular injection.

The compound of the present invention is useful for the treatment of congestion of nasal mucosa. For this purpose, it may be given in the form of aerosol containing 0.1 µg/ml to 10 mg/ml of the compounds, or in the form of ointmant, linimant or lotion containing 0.01 µg/ml to 1 mg/ml of the compounds.

The compound of the present invention is useful for improving symptom of hepatitis and nephritis. For this purpose, it may be given at a dose of 0.01 µg/kg to 1 mg/kg by oral administration or intravenous injection.

The compound of the present invention is useful for the prophylaxis of cancer metastasis. For this purpose, it may be given once to four times a day at a dose of 0.01 µg/kg/day to 1 mg/kg/day by oral administration or intravenous injection. The compound of the present invention may also be given by intravenous infusion. In this case, it may be given at a rate of 0.01 ng/kg/min to 100 µg/kg/min.

The compound of the present invention is useful for anti-inflammatory and analgesics. For this purpose, it may be given at a dose of 0.01 µg/kg/day to 1 mg/kg/day by oral administration or intravenous injection.

The compound of the present invention may be given by oral administration in the solid form containing starch, lactose, sucrose, glucose, microcrystal cellulose, clay-like vehicles, coloring agents, lubricants, binders, disintegrators or coating materials. Further, the compound of the present invention may be administrated parenterally in the form of a sterilized solution and the solution may contain other solutes such as sodium chloride or glucose in the amount sufficient to make the solution isotonic. Since the compound of the present invention has the stable chemical structure, there is no difficulties in formulation. As a result, it may be applied in a variety of forms such as preparation for oral administration (tablet, powder, granule), injections, suppository, ointment and lotion.

EXAMPLES

The present invention will now be explained by way of examples thereof.

Reference Example 1

5,7-dibromo-2α-hydroxy-1β-hydroxymethyl-3aβH,8bβH-2,3,3a,8b-tetrahydro-1H-cyclopenta[b]benzofuran (1)

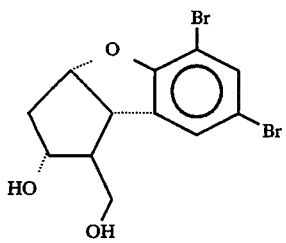

(1)

In 400 ml of acetic acid, 33 g of 5,7-dibromo-3aβH,8bβH-3a,8b-dihydro-3H-cyclopenta[b]benzofuran and 66 g of s-trioxane were dissolved. To this stirred solution at 80° C. 30 ml of concentrated sulfuric acid was added and the resulting mixture was stirred for 15 hours. After cooling, acetic acid was removed. The residue was dissolved in 100 ml of ethyl acetate and washed with 500 ml of water and then washed with saturated aqueous sodium hydrogen carbonate solution (500 ml×5). Further, aqueous phase was extracted with 500 ml of ethyl acetate. The ethyl acetate layers were combined and dried and concentrated to obtain 46 g of an oily product. The thus obtained oily product was dissolved in 400 ml of methanol and 150 ml of aqueous 3N sodium hydroxide solution was added thereto and the resulting mixture was stirred for 30 minutes at room temperature. After concentrating, the resulting mixture was added to 50 ml of 6N hydrochloric acid and the resulting mixture was extracted with ethyl acetate (300 ml×5). The extracted solutions were combined and were washed with 200 ml and 100 ml of water, and 100 ml of brine, and was dried and concentrated to obtain 30 g of an oily product. The thus obtained oily product was recrystallized from n-hexane-ethyl acetate to obtain 16 g of colorless crystals. The structure of this product was confirmed by the following data.

m.p. 126°–128° C. IR (KBr method): 3300, 2970, 2925, 2870, 1600, 1575, 750, 730 cm$^{-1}$ NMR (90 MNz, CDCl$_3$, δ): 2.05(2H,m), 2.54(1H,m), 3.68(3H,m), 4.04(3H,m), 5.24(1H,ddd,J=9.5, 7.2, 5.0 Hz), 7.22(1H,d,J=2.0 Hz), 7.39(1H,d,J=2.0 Hz) MASS (EI method, m/e): 366, 364, 362 (M+)

Reference Example 2

7-bromo-2α-acetoxy-1β-hydroxymethyl-3aβH,8bβH-2,3,3a,8b-tetrahydro-5-1H-cyclopenta[b]benzofurancarbaldehyde (2)

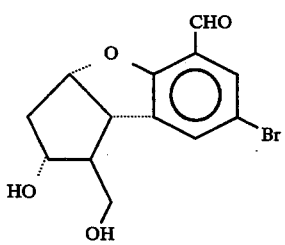

(2)

In 900 ml of anhydrous THF, 100 g (275 mmol) of 5,7-dibromo-2α-hydroxy-1β-hydroxymethyl-3aβH,8bβH-2,3,3a,8b-tetrahydro-1H-cyclopenta[b]benxofuran was dissolved. To this solution, 327 ml of cyclohexyl magnesium chloride in anhydrous THF was added under argon atmosphere at 0° C. and the resulting mixture was allowed to room temperature followed by being stirred for 10 minutes. To the thus obtained reaction mixture, 273 ml (505 mmol) of above Grignard reagent was added and the resulting mixture was stirred for 2 hours at 40° C. The mixture was allowed to cool to room temperature and 150 ml of anhydrous DMF was added dropwise thereto and the resulting mixture was stirred for 30 minutes. After the thus obtained reaction mixture was cooled down to 0° C., 800 ml of ether and 600 ml of 3N hydrochloric acid were added thereto followed by being extracted 5 times with ethyl acetate. The organic layers were combined, washed with saturated aqueous sodium hydrogen carbonate solution and brine, and dried over anhydrous mangesium sulfate.

After concentrating the resulting mixture, the residue was recrystallized from ethyl acetate to obtain 52.3 g (167 mmol) of 7-bromo-2α-acetoxy-1β-hydroxymethyl-3aβH,8bβH-2,3,3a,8b-tetrahydro-5-1H-cyclopenta[b]benzofuran carbaldehyde. The mother liquor was reconcentrated and recrystallized with ethyl acetate to obtain 16.5 g (52.7 mmol) of the above aldehyde (total yield 80%).

The structure of this compound was confirmed by the following data. m.p. 143°–144° C. IR (KBr method): 3440, 3050, 2960, 2890, 2740, 1680, 1595, 1580, 1440, 1385, 1325, 1220, 1200, 1100, 1070, 1045, 1010, 950, 900, 870, 830, 780, 740, 695, 600, 560, 515 cm$^{-1}$ NMR (90 MHz, DMSO-d$_6$, δ): 1.7–2.5(3H,m), 3.2–4.0(4H,m), 4.5–4.9(2H,m), 5.37(1H,ddd,J=4.6, 7.2, 9.0 Hz), 7.5–7.7(2H,m), 10.02(1H,S) MASS (EI method, m/e): 312, 314 (M+)

| Element Analysis | C | H | Br |
|---|---|---|---|
| Calcd. (C$_{13}$H$_{13}$O$_4$Br) | 49.86 | 4.19 | 25.52 |
| Found | 49.75 | 4.30 | 25.48 |

Reference Example 3

2α-hydroxy-1β-hydroxymethyl-3aβH,8bβH-2,3,3a,8b-tetrahydro-5-1H-cyclopenta[b]benzofuran propionic acid methyl ester (3)

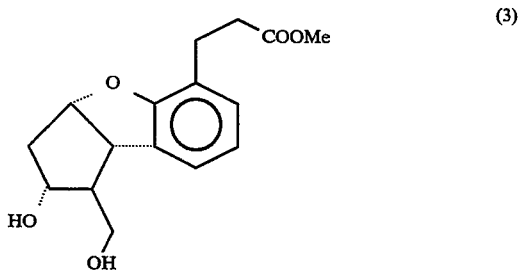

(3)

In anhydrous THF (400 ml), 31.2 ml (233 mmol) of diisopropylamine was dissolved. To this solution, 134 ml (1.66N, 223 mmol) of n-butyl-lithium in hexane was added at −10° C. and the resulting mixture was stirred for 30 minutes. The thus obtained reaction mixture was cooled to −78° C. and 21.9 ml (223 mmol) of anhydrous ethyl acetate was added thereto. After stirring for 30 minutes, 10 g (31.9 mol) of 7-bromo-2α-hydroxy-1β-hydroxymethyl-3aβH,8bβH-2,3,3a,8b-tetrahydro-5-1H-cyclopenta[b]benzofuran carbaldehyde in anhydrous HMPA (100 ml) was added dropwise for about 5 minutes to thereto while the reaction temperature did not rise more than −60° C. The resulting mixture was stirred for 10 minutes. To thus obtained mixture, 300 ml of ether and 180 ml of 3N hydrochloric acid were added and the resultant was extracted 3 times with ethyl acetate. The organic layers were combined and washed with saturated aqueous sodium hydrogensulfite solution and with water to remove nonreacted aldehyde, followed by being washed with saturated aqueous sodium hydrogen carbonate solution, water and brine. After drying, the organic layers were concentrated to obtain about 20 g of an oily product. The thus obtained oily product was dissolved in 100 ml of methanol and 4 g of 10% palladium carbon was added thereto and the resulting mixture was stirred for 20 hours under hydrogen atmosphere. The thus obtained reaction mixture was filtered and then aqueous sodium hydrogen carbonate solution was added to the filtrate and the resultant was concentrated. Water was added to the residue and the resultant was extracted with ethyl acetate. The organic layers were washed with water and brine, dried over anhydrous magnesium sulfate and concentrated. The residue was dissolved in anhydrous methanol (100 ml). To this solution, 1.6 ml of 4.89N sodium methoxide was added and the resulting mixture was stirred for 3 hours at room temperature. To the thus obtained reaction mixture, 0.58 ml of acetic acid was added and the resultant was concentrated. The residue was dissolved in ethyl acetate. This solution was washed with saturated aqueous sodium hydrogen carbonate solution, water and brine, dried and concentrated. The residue was purified by column chromatography (eluant; ethyl acetate:cyclohexane=1:1) to obtain 5.91 g of 2α-hydroxy-1β-hydroxymethyl-3aβH,8bβH-2,3,3a,8b-tetrahydrofuran propionic acid methyl ester (yield 74%).

The structure of this product was confirmed by the following data. m.p. 88.5°–90.0° C. (Recrystallization Solvent:ethyl acetate:cyclohexane) IR (KBr method): 3400, 2960, 2910, 2860, 1700, 1590, 1470, 1440, 1360, 1330, 1290, 1280, 1250, 1220, 1185, 1105, 1055, 1010, 980, 950, 915, 895, 850, 835, 805, 770, 745, 590, 450, 340 cm$^{-1}$ NMR (400 MHz, CDCl$_3$, δ): 1.97(1H,ddd,J=5.4, 8.3, 13.7 Hz), 2.05(1H,dq,J=5.4, 7.8 Hz), 2.51(1H,dt,J=6.8, 13.7 Hz), 2.5–2.7(2H,m), 2.8–3.0(2H,m), 3.15(1H,br.s), 3.2(1H,m), 3.38(1H,dd,J=7.8, 8.6 Hz), 3.64(3H,S), 3.65–3.7(1H,m), 3.8–3.9(1H,m), 4.0–4.1(1H,m), 5.08(1H,ddd,J=5.4, 6.8, 8.6 Hz), 6.76(1H,dd,J=6.8, 7.3 Hz), 6.94(1H,d,J=6.8 Hz), 7.02(1H,d,J=7.3 Hz) MASS (EI method, m/e): 292 (M+)

| Element Analysis | C | H |
|---|---|---|
| Calcd. (C$_{16}$H$_{20}$O$_5$) | 65.74 | 6.90 |
| Found | 65.71 | 6.90 |

Reference Example 4

2α-acetoxy-1β-hydroxymethyl-3aβH,8bβH-2,3,3a,8b-tetrahydro-5-1H-cyclopenta[b]benzofuran propionic acid methyl ester (4)

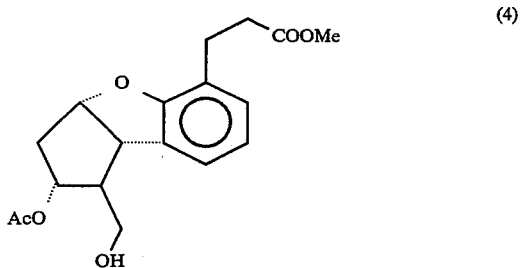

In anhydrous THF (600 ml), 46 g (158 mmol) of 2α-hydroxy-1β-hydroxymethyl-3aβH,8bβH-2,3,3a,8b-tetrahydro-5-1H-cyclopenta[b]benzofuran propionic acid methyl ester was dissolved. To this solution, 88 ml (632 mmol) of anhydrous triethylamine and 88 g (316 mmol) of trityl chloride were added and the resulting mixture was heated to reflux for 6 hours. To the thus obtained reaction mixture, 165 ml (2.05 mol) of anhydrous pyridine and 193 ml (2.05 mol) of acetic anhydride were added and the resulting mixture was stirred for 48 hours at room temperature. The thus obtained reaction mixture was cooled to 0° C. and 500 ml of 5.5N hydrochloric acid in methanol was added thereto and the resulting mixture was stirred for 8 hours at room temperature. Further, the resulting mixture was cooled to 0° C. and 280 g of sodium hydrogen carbonate was added to attain pH 6 followed by being concentrated. To the residue, 800 ml of ethyl acetate was added and the resultant was filtered. The filtrate was washed with 6N hydrochloric acid, water and brine, dried over anhydrous magnesium sulfate and concentrated. The thus obtained residue was purified by column chromatography (silica gel, eluant; ethyl acetate:cyclohexane=1:3) to obtain 43.2 g of 2α-acetoxy-1β-hydroxymethyl-3aβH,8bβH-2,3,3a,8b-tetrahydro-5-1H-cyclopenta[b]benzofuran propionic acid methyl ester (yield 82%).

The structure of this product was confirmed by the following data. m.p. 56°–57° C. (Recrystallization Solvent:ether:hexane) IR (KBr method) 3530, 3480, 3050, 2950, 2875, 1720, 1600, 1455, 1375, 1330, 1245, 1200, 1170, 1080, 1060, 1010, 980, 940, 850, 790, 760, 740, 650, 610, 530, 390, 325 cm$^{-1}$ NMR (400 MHz, CDCl$_3$, δ) 1.83(3H,S), 2.1–2.3(3H,m), 2.55(1H,dt,J=6.3, 14.2 Hz), 2.6–2.8(2H,m), 2.8–3.0(2H,m), 3.6–3.8(3H,m), 3.67(3H,S), 5.07(1H,q,J=6.3 Hz), 5.20(1H,ddd,J=3.4, 6.3, 8.3 Hz), 6.77(1H,t,J=7.3 Hz), 6.96(1H,d,J=7.3 Hz), 7.05(1H,d,J=7.3 Hz) MASS (EI method, m/e): 334 (M+)

| Element Analysis | C | H |
|---|---|---|
| Calcd. (C$_{18}$H$_{22}$O$_6$) | 64.65 | 6.63 |
| Found | 64.62 | 6.62 |

Reference Example 5

2-ethoxycarbonyl-3-[3-methyl-4aβH-,5aβH,10bβH,10cβH-1,4a, 5,5a, 10b, 10c-hexahydro-2,4-dioxyno[5,4-a]-7cyclopenta[b]benzofuran propionic acid ethyl ester (5)

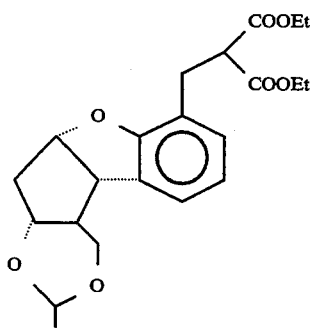

(5)

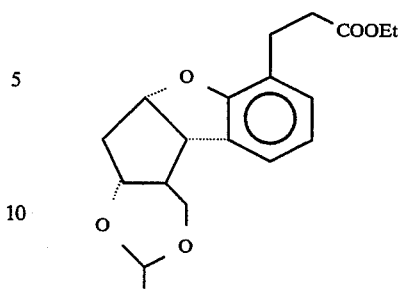

(6)

Under argon atmosphere, 1.098 g of sodium hydride (60% dispersion in mineral oil) was washed three times with 15 ml of n-pentane, dried under reduced pressure and 70 ml of anhydrous THF was added thereto. To the resultant, 5.12 ml of diethyl malonate was added under cooling in iced water. Then 3.8514 g of 7-chloromethyl-3-methyl-4aβH, 5aβH, 10bβH, 10cβH-1,4a,5-,5a,10b,10c-hexahydro-2,4-dioxyno[5,4-a]-cyclopenta[b]benzofuran was dissolved in 30 ml of anhydrous THF. This solution was added to the previously obtained mixture and the resulting mixture was heated to reflux for 3 hours and 40 minutes.

To the thus obtained reaction mixture, 100 ml of saturated aqueous ammonium chloride solution was added and the resulting mixture was extracted each once with 70 ml, 60 ml and 50 ml of ethyl acetate. The organic layers were combined, washed with 180 ml of water and 150 ml of brine, dried over anhydrous magnesium sulfate and concentrated to obtain 9.5580 g of an oily product. The thus obtained oily product was purified by column chromatography (silica gel Art. 7734, eluant; ethyl acetate:cyclohexane=1:5) to obtain 5.541 g of the captioned product (yield 99%).

The structure of this product was confirmed by the following data. m.p. 49°–50° C. (Recrystallization Solvent:ethy acetate:cyclohexane=1:10) IR (KBr method): 2975, 2930, 2898, 2851, 2810, 1738, 1725, 1598, 1455, 1415, 1380, 1362, 1339, 1308, 1241, 1208, 1199, 1178, 1152, 1110, 1080, 1057, 1034, 1002, 963, 941, 882, 863, 837, 782, 746, 708, 697, 668, 637, 602 cm$^{-1}$ NMR (90 MHz, CDCl$_3$, δ): 1.20(6H,t,J=7.04 Hz), 1.36(3H,d,J=5.06 Hz), 1.55–2.18(2H,m), 2.55–3.98(5H,m), 4.15(4H,q,J=7.04 Hz), 3.98–4.28(2H,m), 4.39(1H,dd,J=4.48, 10.38 Hz), 4.72(1H,q,J=5.06 Hz), 4.97–5.27(1H,m), 6.63–7.10(3H,m) MASS (EI method, m/e): 404 (M+)

Reference Example 6

3-methyl-4a H, 5a H, 10b H, 10c H-1,4a,5,5a,10b,10c-hexahydro-2,4-dioxyno[5,4-a]-7-cyclopenta[b]benzofuran propionic acid ethyl ester (6)

In 50 ml of DMSO, 4.85 g of 2-ethoxycarbonyl-3-[3-methyl-4aβH, 5aβH, 10bβH, 10cαH-1,4a,5,5a,10b,10c-hexahydro-2,4-dioxyno[5,4-a]-7-cyclopenta[b]benzofuranyl]propionic acid ethyl ester was dissolved. To this solution, 0.81 ml of water and 878 mg of sodium chloride were added, and the resulting mixture was heated for 5.5 hours at a temperature of 180° to 183° C. under argon atmosphere. To the thus obtained reaction mixture, 100 ml of water was added and the resulting mixture was extracted each once with 70 ml, 60 ml and 50 ml of ethyl acetate. The organic layers were combined, washed with 100 ml of brine, dried over anhydrous magnesium sulfate and concentrated to obtain 4.108 g of an oily product. The thus obtained oily product was purified by column chromatography (silica gel Art. 7734, eluant; ethyl acetate:cyclohexane=1:2) to obtain 3.2924 g of the captioned products (yield 82.7%).

The structure of this product was confirmed by the following data. m.p. 70-71° C. (Recrystallization Solvent:ethyl acetate:cyclohexane=1:15) IR (KBr method): 2980, 2930, 2850, 1725, 1593, 1444, 1410, 1380, 1350, 1331, 1302, 1259, 1231, 1210, 1180, 1159, 1116, 1084, 1068, 1035, 1010, 959, 881, 860, 809, 782, 741, 600 cm$^{-1}$ NMR (90 MHz, CDCl$_3$, δ): 1.23(3H,t,J=7.15 Hz), 1.36(3H,d,J=5.06 Hz), 1.72–2.15(2H,m), 2.50–3.50(7H,m), 3.71(1H,t,J=10.7 Hz), 4.12(2H,q,J=7.15 Hz), 4.40(1H,dd,J=4.40, 10.60 Hz), 4.72(1H,q,J=5.06 Hz), 5.00–5.24(1H,m), 6.67–7.08(3H,m) MASS (EI method, m/e): 332 (M+)

Reference Example 7

2α-hydroxy-1β-hydroxymethyl-3aβH, 8bβH-2,3,3a,8b-tetrahydro-5-1H-cyclopenta[b]benzofuran propionic acid ethyl ester (7)

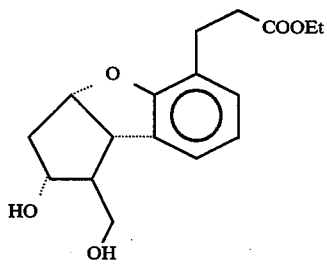

(7)

In 15 ml of methanol, 1.1172 g of 3-methyl-4aβH, 5aβH, 10bβH, 10cαH-1,4a,5,5a,10b,10c-hexahydro-2,4-dioxyno[5,4-a]-7-cyclopenta[b]benzofuran propionic acid ethyl ester was dissolved. After cooling the solution in iced water, 3.5 ml of 1N hydrochloric acid was added thereto and the resulting mixutre was stirred for 4 hours at room temperature. To the thus obtained reaction mixture, 4.0 g of sodium hydrogen carbonate was added and the resultant was concentrated. Then 70 ml of water was added to the concentrate and the resultant was extracted each once with 50 ml, 40 ml and 30 ml of ethyl acetate. The organic layers were combined, washed each once with 100 ml of water and with 100 ml of brine and dried over anhydrous magnesium sulfate to obtain 1.2211 g of an oily product. The thus obtained oily product was purified by Lobar column (Type B commercially available from Merck & Co., Inc., eluant; ethyl acetate) to obtain 1.02810 g of the captioned product (yield 99%).

The structure of this product was confirmed by the following data. m.p. 69°–70° C. (Recrystallization Solvent:ethyl acetate:cyclohexane=2:1) IR (KBr method): 3348, 2980, 2925, 2865, 1725, 1590, 1443, 1418, 1370, 1345, 1299, 1244, 1122, 1110, 1080, 1061, 1045, 1012, 999, 981, 958, 910, 896, 863, 840, 810, 765, 743, 663 cm$^{-1}$ NMR (90 MHz, CDCl$_3$, δ): 1.22(3H,t,J=7.15 Hz), 2.05(2H,s), 1.81–2.29(3H,m), 2.42–3.00(4H,m), 3.30–3.50(1H,m), 3.65–4.26(3H,m), 4.11(2H,q,J=7.15 Hz), 5.02–5.26(1H,m), 6.68–7.08(3H,m) MASS (EI method, m/e): 306 (M+)

Reference Example 8

2α-acetoxy-1β-hydroxymethyl-3aβH,8bβH-2,3,3a,8b-tetrahydro-5-1H-cyclopenta[b]benzofuran propionic acid ethyl ester (8)

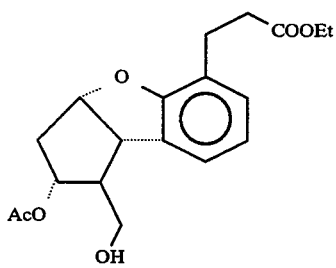

In 20 ml of anhydrous THF, 1.0002 g of 2α-hydroxy-1β-hydroxymethyl-3aβH,8bβH-2,3,3a,8b-tetrahydro-5-1H-cyclopenta[b]benzofuran propionic acid ethyl ester was dissolved. To this solution, 1.14 ml of triethylamine and 1.24 g of trithyl chloride were added and under argon atmosphere, the resulting mixture was refluxed for 5 hours and 45 minutes. The thus obtained reaction mixture was allowed to cool to at room temperature and 0.8 ml of pyridine and 0.72 ml of anhydrous acetate were added thereto and the resulting mixture was stirred overnight. Further, 9 ml of pyridine and 7 ml of anhydrous acetate were added thereto and the resulting mixture was stirred for 2.5 hours. The thus obtained mixture was concentrated and 50 ml of 1N hydrochloric acid was added thereto followed by being extracted 3 times with 50 ml of ethyl acetate. The organic layers were combined, washed each once with 100 ml of saturated aqueous sodium hydrogen carbonate solution, 100 ml of water and 100 ml of brine, dried over anhydrous magnesium sulfate and concentrated. To the residue, 9 ml of methanol and 6 ml of THF were added and then 6 ml of 5.2N hydrochloric acid/methanol was added and the resulting mixture was stirred for 24 minutes at room temperature. To the thus obtained reaction mixture, 4.5 g of sodium hydrogen carbonate was added. After concentration of the mixture, 70 ml of water was added to the residue and the resultant was extracted with ethyl acetate (50 ml×1, 30 ml×2). The organic layers were combined, washed each once with 100 ml of water and 100 ml of brine, dried over anhydrous magnesium sulfate and concentrated to obtain 2.3615 g of an oily product. The thus obtained oily product was purified by column chromatography (silica gel; Art. 7734) to obtain 794.1 mg of the desired product (yield 69.7%). In this case, methyl ester thereof was obtained with a yield of 33% by weight. Recovery of the starting material was 298.4 mg (yield 29.8%).

The structure of this product was confirmed by the following data. IR (liquid film method): 3450, 2930, 1725, 1592, 1447, 1366, 1242, 1186, 1061, 1015, 951, 935, 844, 742 cm$^{-1}$ NMR (90 MHz, CDCl$_3$, δ): 1.24(3H,t,J=7.03 Hz), 1.83(3H,s), 1.97(1H,s), 2.02–3.02(7H,m), 3.55–3.79(3H,m), 4.13(2H,q,J=7.03 Hz), 3.95–5.33(2H,m), 6.63–7.13(3H,m) (ethyl ester:-methyl ester=2:1) MASS (EI method, m/e): 348 (M+)

Reference Example 9 d-2α-tetrahydropyranyloxy-1β-tetrahydropyranyloxymethyl-3aβH,8bβH-2,3,3a,8b-tetrahydro-5-1H-cyclopenta[b]benzofuran carboxylic acid methyl ester (9)

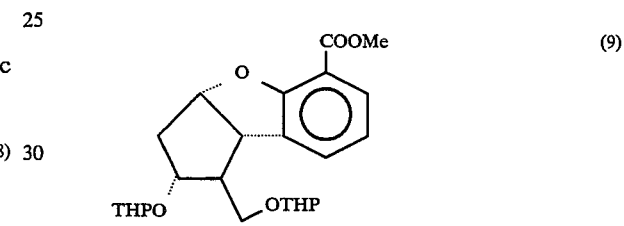

To 102 ml (1.78 mol) of acetic acid, 25.0 g (89.0 mmol) of d-7-bromo-3aβH,8bβH-3a,8b-dihydro-5-3H-cyclopenta[b]benzofuran carboxylic acid and 16.0 g (178 mmol) of trioxane were added. To this suspension, 9.40 ml (169 mmol) of concentrated sulfuric acid was added slowly and the resulting mixute was stirred for 5 hours at 70° C. The thus obtained reaction mixture was concentrated and 300 ml of methanol, 50 ml of water and 90. ml of 10N aqueous sodium hyrdoxide solution were added to the residue followed by being refluxed for 2 hours. Further, the thus obtained reaction mixture was stirred for 10 hours at room temperature and filtered. The precipitate was washed with methanol (70 ml×3) and the filtrate were combined. To the filtrate, 100 ml of 1N hydrochloric acid was added and the resultant was concentrated. To the residue, 400 ml of ethyl acetate was added and the resultant was washed with 100 ml of water. The water layer was reextracted with ethyl acetate (150 ml×6). The organic layers were combined, washed with 300 ml of brine, dried over anhydrous magnesium sulfate and concentrated to obtain 35.4 g of a concentrate. Then this concentrate was dissolved in 300 ml of methanol and 5.00 g of 10% palladium on active carbon was added thereto and the resulting mixture was stirred under hydrogen atmosphere for 3 hours at room temperautre. To the thus obtained reaction mixture, 500 ml of methanol was added under nitrogen atmosphere and the resulting mixture was refluxed for an hour. Further, the thus obtained solution was stirred for 12 hours at room temperature and 7.50 g (89.3 mmol) of sodium hydrogen carbonate was added thereto. The resulting mixture was stirred for 30 minutes at room temperature and was filtered. The filtrate was concentrated and the residue was dissolved in 250 ml of THF. To this solution, 846 mg (4.45 mmol) of p-toluene sulfonic acid and 29.9 g (356 mmol) of 3,4-dihydro-2H-pyrane were added and the resulting mixture was stirred for 3 hours at room temperature. To the thus obtained reaction mixture, 352 mg (4.45 mmol) of pyridine was added and the resultant was concentrated. To the residue, 400 ml of ethyl acetate was added and the resultant was washed with 150 ml of water and 150 ml of brine, dried over anhydrous magnesium sulfate and concentrated to obtain 38.7 g of an oily product. The thus obtained oily product was purified by column chromarograpgy (silica gel, eluant; ethyl acetate:cyclohexane=1:2) to obtain 23.7 g (54.8 mmol) of d-2α-tetrahydropyranyloxy-1β-tetrahydropyranyloxymethyl-3aβH,8bβH-2,3,3a,8b-tetrahydro-5-1H-cyclopenta[b]benzofuran carboxylic acid methyl ester with a yield of 61.1% by weight.

The structure of this product was confirmed by the following data. $[\alpha]_D^{25}=+85.3°$ (C=0.788, EtOH) IR (liquid film method): 3000, 2930, 2850, 1710, 1610, 1440, 1340, 1280, 1260, 1200, 1170, 1120, 1050, 1010, 960, 890, 850, 800, 740 cm$^{-2}$ NMR (270 MHz, CDCl$_3$, δ) 1.1–2.0(12H,m), 2.05–2.6(3H,m), 3.3–4.3(11H,m), 4.5–4.7(2H,m), 5.3–5.45(1H,m), 6.8–6.9(1H,m), 7.3–7.5(1H,m), 7.65–7.8(1H,m) MASS (El method, m/e): 432 (M+) High resolution mass spectrum: Calcd. (C$_{24}$H$_{32}$O$_7$, M+) 432.2148 Found (M+) 432.2166

Reference Example 10 d-7-bromo-2α-hydroxy-1β-hydroxymethyl-3aβH,8bβH-2,3,3a,8b-tetrahydro-5-1H-cyclopenta[b]benzofuran carboxylic acid (10)

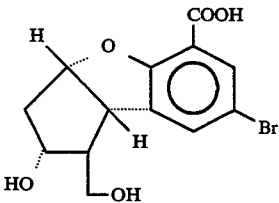

(10)

In 70 ml of ethanol, 32.5 g (99 mmol) of dl-7-bromo-2α-hydroxy-1β-hydroxymethyl-3aβH,8bβH-2,3,3a,8b-tetrahydro-5-1H-cyclopenta[b]benzofuran carboxylic acid and 21.7 g (99 mmol) of d-cis-N-benzyl-2-hydroxymethycyclohexylamine were dissolved under heating and then the solution was allowed to cool to room temperature. Then a seed of a d-amine salt of a d-carboxylic acid was inoculated thereto and the resultant was left to stand for 3 days. The thus obtained crystals were recrystallized from 70 ml of ethanol and then recrystallized from 10 ml of 50% aqueous methanol solution to obtain 5.30 g of salt of d-7-bromo-2αhydroxy-1β-hydroxymethyl-3aβH,8bβH-2,3,3a,8b-tetrahydro-5-1H-cyclopenta[b]benzofuran carboxylic acid-d-cis-N-benzyl-2-hydroxymethylcyclohexylamine (yield 9.8%).

The thus obtained crystals were suspended in 40 ml of distilled water and 6 ml of 6N sulfuric acid was added thereto. The resulting mixture was stirred for 30 minutes to precipitate d-carboxylic acid. After removing the solvent by filtration, the crystals were washed with 10 ml of acetone and dried to obtain 3.00 g of d-7-bromo-2α-hydroxy-1β-hydroxymethyl-3aβH,8bβH-2,3,3a,8b-tetrahydro-5-1H-cyclopenta[b]benzofuran carboxylic acid with a yield of 9.3% by weight. After converting the carboxylic acid to methyl ester by diazomethane, the optical purity thereof was measured by liquid chromatography.

Opical purity: not less than 99% column: YMC-pack A-K03, 4.6×250 mm mobile phase: n-hexane/ethanol/methylene chloride=85/10/5 flow rate: 1 ml/min oven temp: room temp $[\alpha]_D^{20}=+15.2°$ (C=0.92, MeOH) m.p. 115.5°–116.5° C. IR (KBr method): 3640, 3500, 3400–2500, 3110, 2980, 2850, 1695, 1650, 1605, 1450, 1390, 1370, 1350, 1335, 1305, 1300, 1260, 1240, 1220, 1170, 1120, 1075, 1020, 995, 950, 915, 885, 870, 840, 795, 790, 690, 655, 620, 560, 525 cm$^{-1}$ NMR (400 MHz, CDCl$_3$-DMSO-D$_6$, δ) 2.02–2.10(2H,m), 2.50–2.57(1H,m), 2.80–3.20(3H,bs), 3.60(1H,t,J=7.8 Hz), 3.66(1H,dd,J=5.4, 10.5 Hz), 3.78(1H,dd,J=5.4, 10.4 Hz), 4.01(1H,q,J=6.5 Hz), 5.31(1H,ddd,J=5.4, 7.8, 9.3 Hz), 7.52 (1H,m), 7.81(1H,d,J=2.4 Hz) MASS (EI method, m/e): 328, 330 (M+) High resolution mass spectrum Calcd. (C$_{13}$H$_{13}$O$_5$Br, M+) 327.9909 Found (M+) 327.9928

Reference Example 11 d-2α-hydroxy-1β-hydroxymethyl-3aβH,8bβH-2,3,3a,8b-tetrahydro-5-1H-cyclopenta[b]benzofuran carboxylic acid methyl ester (11)

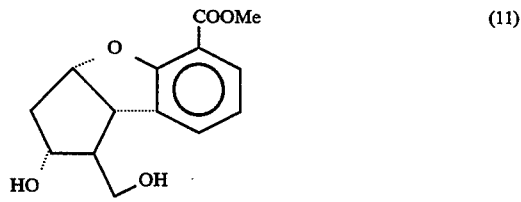

(11)

In 1.5 l of methanol, 29.18 g (88.4 mmol) of d-7-bromo-2α-hydroxy-1β-hydroxymethyl-3aβH,8bβH-2,3,3a,8b-tetrahydro-5-1H-cyclopenta[b]benzofuran carboxylic acid was dissolved. To this solution, 3 g of 10% palladium on active carbon was added and the resulting mixture was stirred for 2 hours under hydrogen atmosphere. Then hydrogen was substituted with argon and the thus obtained reaction mixture was refluxed for 3 hours followed by being filtered. The filtrate was concentrated and 200 ml of water was added to the residue. The resultant was extracted with chloroform (300 ml×3), washed with 100 ml of brine, dried over anhydrous magnesium sulfate and concentrated to obtain 22.3 g of crude crystals. The thus obtained crystals were recrystallized from ethyl acetate to obtain 20.87 g (79.1 mmol) of d-2α-hydroxy-1β-hydroxymethyl-3aβH,8bβH-2,3,3a,8b-tetrahydro-5-1H-cyclopenta[b]benzofuran carboxylic acid methyl ester (89.4%) as prism crystals.

The structure of this product was confirmed by the following data. $[\alpha]_D^{20}=+109.6°$ (C=1.028 MeOH) m.p. 154°–155° C. IR (KBr method): 3280, 3170, 3030, 2990, 2950, 2900, 1720, 1605, 1445, 1430, 1370, 1355, 1315, 1275, 1250, 1220, 1190, 1170, 1140, 1105, 1075, 1065, 1055, 1040, 1115, 995, 965, 930, 905, 880, 855, 840, 765, 710, 625 cm$^{-2}$ NMR (400 MHz, CDCl$_3$-DMSO-d$_6$, δ) 2.01–2.08(2H,m), 2.56–2.63(1H,m), 3.54(1H,t,J=8.3 Hz), 3.78(2H,t,J=5.4 Hz), 3.88(3H,s), 4.05(1H,d,J=4.9 Hz), 4.01–4.08(1H,m), 4.14(1H,t,J=5.3 Hz), 5.26(2H,ddd,J=5.3, 8.3, 9.3 Hz), 6,86(1H,t,J=7.3 Hz), 7.41(1H,m), 7.70(1H,dd,J=1.0, 7.3 Hz) MASS (EI method, m/e): 264 (M+) High resolution mass spectrum Calcd. (C$_{14}$H$_{16}$O$_5$, M+) 264.0962 Found (M+) 264.0980

Reference Example 12 d-2α-hydroxy-1β-hydroxymethyl-3aβH,8bβH-2,3,3a,8b-tetrahydro-5-1H-cyclopenta[b]benzofuran propionic acid methyl ester (12)

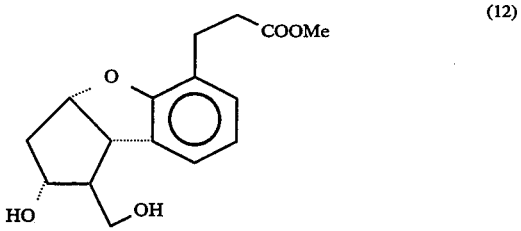

In 250 ml of anhydrous THF, 47.20 g (187.30 mmol) of d-2α-hydroxy-1β-hydroxymethyl-3aβH,8bβH-2,3,3a,8b-tetrahydro-5-1H-cyclopenta[b]benzofuran carboxylic acid methyl ester was dissolved and 47.60 ml (515.80 mmol) of dihydropyrane was added thereto. To the resulting mixture, 150 ml of p-toluene sulfonic acid in THF (obtained by dissolving 3.636 g of p-toluene surfuric acid in 180 ml of THF and dring the resultant over Molecular sieves 4A1/16) was added under cooling in iced water and the resulting mixture was stirred for 3 hours at room temperature. To the thus obtained reaction mixture, 20 g of sodium hydrogen carbonate was added. After stirring for 10 minutes at room temperature, the resulting mixture was filtered under suction through Celite and the filtrate was concentrated. To the residue, 200 ml of water was added and the resultant was extracted with ethyl acetate (200 ml×2). The organic layers were combined, washed with 300 ml of brine, dried over anhydrous sodium sulfate (80 g) and concentrated to obtain 114.58 g of an oily product.

Then 5.331 g (140.47 mmol) of lithium aluminium hydride was added to 250 ml of anhydrous THF and the resulting mixture was stirred under argone atmosphere. To the mixture, 114.58 g of the previously obtained oily product in 150 ml of anhydrous THF was added dropwise under cooling in iced water and the resulting mixture was stirred for 15 minutes. To the thus obtained reaction mixture, 100 ml of ethyl acetate was added under cooling in iced water and then 15 ml of saturated aqueous sodium sulfate solution was added thereto. The thus obtained mixture was filtered under suction through Celite and the filtrate was concentrated to obtain 91.2 g of an oily product.

Further, 91.2 g of the thus obtained oily product was dissolved in 350 ml of dichloromethane. To this solution, 350 g of active manganese oxide was added under cooling in iced water and the resulting mixture was stirred overnight at room temperature. The thus obtained reaction mixture was filtered under suction through Celite and the filtrate was concentrated to obtain 81.21 g of an oily product. Further, the thus obtained oily product was dissolved in 1000 ml of benzene and 93.8 g (280.95 mmol) of carbomethoxymethylenetriphenylphosphoran was added thereto. The resulting mixture was stirred for 2 days at room temperature. The thus obtained mixture was concentrated and the triphenylphosphine oxide was removed from the residue by column chromatography (silica gel, eluant; ethyl acetate:cyclohexane=1:4) to obtain 82.58 g of an oily product.

Then 82.58 g of the thus obtained oily product was dissolved in 400 ml of methanol and 10 g of palladium/- carbon was added thereto under argon atmosphere. After argon was substituted with hydrogen, the resulting mixture was stirred overnight at room temperature. The thus obtained reaction mixture was filtered under suction through Celite and the filtrate was concentrated to obtain 79.14 g of an oily product. Finally, 79.14 g of the thus obtained oily product was dissolved in 400 ml of methanol and 2.4 g of p-toluene sulfonic acid was added thereto under cooling in iced water, and the resulting mixture was stirred overnight at room temperature. To the thus obtained reaction mixture, 20 g of sodium hydrogen carbonate was added. After stirring for 20 minutes at room temperature, the resultant was filtered under suction through Celite and the filtrate was concentrated. To the residue, 100 ml of water was added and the resultant was extracted with ethyl acetate (100 ml×2). The organic layers were combined, washed with 100 ml of brine, dried over anhydrous sodium sulfate (30 g) and concentrated. The residue was recrystallized from ethyl acetate/cyclohexane (6:1) to obtain 32.51 g (111.34 mmol) of d-2α-hydroxy-1β-hydroxymethyl-3aβH,8bβH-2,3,3a,8b-tetrahydro-1H-5-cyclopenta[b]benzofuran propionic acid methyl ester as colorless needle-shaped crystals with a yield of 59.4% by weight.

The structure of this product was confirmed by the following data. m.p. 110°–110.5° C. $[\alpha]_D^{20} = +30.52°$ (C=0.868, MeOH) IR (KBr method): 3400, 2950, 2905, 2855, 1700, 1591, 1456, 1442, 1359, 1321, 1293, 1279, 1243, 1213, 1181, 1155, 1102, 1059, 1010, 968, 950, 919, 899, 843, 833, 802, 766, 742, 620, 580, 542, 521, 500, 443 cm$^{-1}$ NMR (400 MHz, CDCl$_3$, δ): 1.8–1.9(1H,brs), 2.01–2.08(1H,m), 2.12–2.20(1H,m), 2.2–2.3(1H,brs), 2.55–2.72(3H,m), 2.84–2.97(2H,m), 3.39–3.45(1H,m), 3.66(3H,s), 3.76–3.83(1H,m), 3.94–4.00(1H,m), 4.10–4.18(1H,m), 5.10–5.19(1H,m), 6.79(1H,t,J=7.32 Hz), 6.97(1H,d,J=7.32 Hz), 7.04(1H,d,J=7.32 Hz) MASS (EI method, m/e): 292 (M+)

Reference Example 13

15-oxo-2,5,6,7-tetranor-4,8-inter-m-phenylene PGI$_2$ ethyl ester, 11-acetate (13)

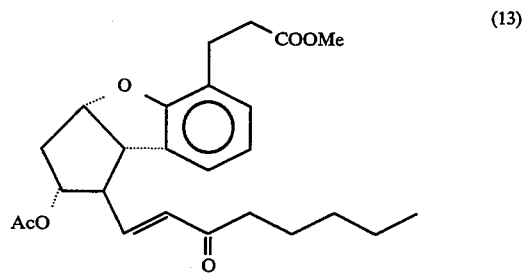

In 10 ml of anhydrous THF, 760.1 mg of 2α-acetoxy-1β-hydroxymethyl-3aβH,8bβH-2,3,3a,8b-tetrahydro-5-1H-cyclopenta[b]benzofuran propionic acid ethyl ester was dissolved. To this solution, 0.18 ml of anhydrous pyridine, 3 ml of anhydrous DMSO and 0.13 ml of trifluoro acetic acid were added. Then 902 mg of dicyclohexylcarbodiimide (D.D.C) was added thereto and the resulting mixture was stirred for an hour and 40 minutes under argon atmosphere at room temperature. The thus obtained reaction mixture was cooled in iced water and 1.14 g of calcium carbonate was added thereto and the resulting mixture was stirred for 20 minutes.

Then 262 mg of sodium hydride (60% dispersion in mineral oil) was suspended in 60 ml of anhydrous THF. To this suspension, 1.7 g of dimethyl 2-oxoheptylphosphonate in 10 ml of anhydrous THF was added under cooling in iced water and the resulting mixture was stirred for 30 minutes under argon atmosphere at room temperature. To the thus obtained reaction mixture, the supernatant of the previously obtained reaction mixture of aldehyde ester was added using a syringe under cooling in iced water. The residue was washed with 10 ml and 5 ml of anhydrous THF and the supernatant obtained in the washing was added to the mixture and the resulting mixture was stirred for 30 minutes at room temperature. To the thus obtained mixture, 5 ml of water and 5 ml of 1N hydrochloric acid were added to attain pH 7. After concentrating the mixture, 50 ml of water was added thereto and the resultant was extracted 3 times with 50 ml of ethyl acetate. The organic layers were combined, washed with 100 ml of water and 100 ml of brine, dried over anhydrous magnesium sulfate and concentrated. The thus obtained residue was purified by column chromatography (silica gel; Art 7734, eluant; ethyl acetate:cyclohexane=1:3) to obtain 887.2 mg of the desired product (yield 91.7%). The structure of this product was confirmed by the following data.

IR (liquid film method): 2950, 2920, 2855, 1730, 1668, 1622, 1594, 1444, 1368, 1299, 1239, 1182, 1060, 980, 949, 850, 786, 740, 700 cm$^{-1}$ NMR (400 MHz, CDCl$_3$, $\delta$): 0.70–0.97(3H,m), 1.05–1.81(6H,m), 1.17(3H,t,J=7.03 Hz), 1.70(3H,S), 1.90–2.22(1H,m), 2.38–4.01(8H,m), 3.51–3.74(1H,m), 4.06(2H,q,J=7.03 Hz), 4.81–5.32(2H,m), 6.13(1H,d,J=16.7 Hz), 6.51–7.01(4H,m) MASS (EI method, m/e): 442 (M+)

Reference Example 14

15-oxo-20a-homo-2,5,6,7-tetranor-4,8-inter-m-phenylene PGI$_2$ methyl ester, 11-acetate (14)

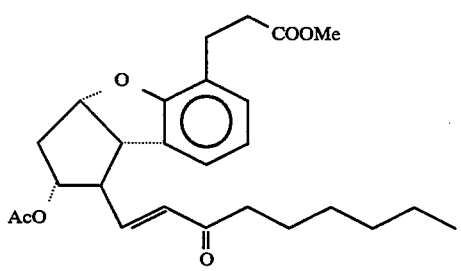

(14)

In 20 ml of anhydrous THF, 1.51 g of 2α-acetoxy-1β-hydroxymethyl-3a$\beta$H,8b$\beta$H-2,3,3a,8b-tetrahydro-5-1H-cyclopenta[b]benzofuran propionic acid methyl ester was dissolved. To this solution, 5 ml of anhydrous DMSO was added and then 0.42 ml of anhydrous pyridine and 0.26 ml of trifluoro acetic acid were added thereto. Then 1.86 g of D.C.C. (dicyclohexylcarbodiimide) was added to the resulting mixture and the thus obtained mixture was stirred for 2.5 hours under argon atmosphere at room temperature. And then, to the thus obtained reaction mixture, 2.39 g of calcium carbonate was added and the resulting mixture was stirred. Then 0.23 g of sodium hydride (60% dispersion in mineral oil) was suspended in 10 ml of anhydrous THF. To this suspension, 1.60 g of dimethyl 2-oxooctanylphosphonate in 6 ml of anhydrous THF was added dropwise and the resulting mixture was stirred for 20 minutes under argon atmosphere at room temperature. To the thus obtained reaction mixture, the supernatant of the previously obtained reaction mixture of aldehyde ester was added using a syringe under cooling in iced water. The residue was washed 3 times with 5 ml of anhydrous THF and the supernatant obtained in the washing was added the reaction mixture. After the resulting mixture was stirred for 30 minutes at room temperature, 100 ml of saturated aqueous ammonium chloride solution was added to attain pH 7 and the resultant was extracted 3 times with 70 ml of ethyl acetate. The organic layers were combined, washed with water and brine, dried over anhydrous sodium sulfate and concentrated. The thus obtained mixture was passed through a short column of silica gel to remove solids, and then was purified by column chromatography (Lobar column commercially available from Merck & Co., Inc., eluant; ethyl acetate:cyclohexane =1:3) to obtain 1.08 g of 15-oxo-20a-homo-2,5,6,7-tetranol-4,8-inter-m-phenylene PGI$_2$ methyl ester, 11-acetate (yield 54%).

The structure of this product was confirmed by the following data. m.p. 48.5°–49.3° C. (Recrystallization Solvent:ethyl acetate:n-hexane=5:4) IR (KBr method): 3450, 2960, 2930, 2860, 1735, 1695, 1640, 1460, 1380, 1335, 1245, 1200, 1070, 1015, 990, 960, 900, 7510, 610 cm$^{-1}$ NMR (90 MHz, CDCl$_3$, $\delta$): 0.89(3H,bs), 1.16–1.72(8H,m), 1.77(3H,S), 1.95–2.33(1H,m), 2.45–3.10(8H,m), 3.67(3H,S), 3.69(1H,t,J=ca,7.2 Hz), 5.00(1H,dd,J=10.8 Hz, 5.39 Hz), 5.08–5.40(1H,m), 6.18(1H,dd,J=15.8 Hz, 0.88 Hz), 6.60–7.08(4H,m) MASS (EI method, m/e): 442 (M+)

Reference Example 15

16,16-dimethyl-15-oxo-2,5,6,7-tetranor-4,8-inter-m-phenylene PGI$_2$, methyl ester, 11-acetate (15)

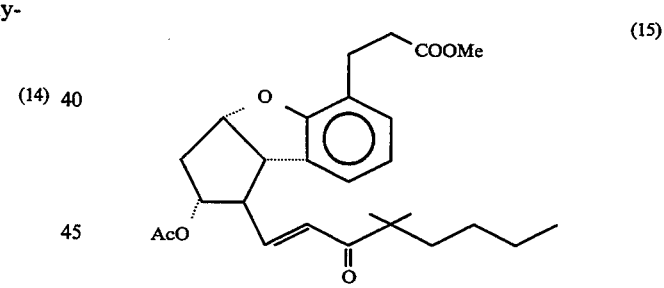

(15)

In 20 ml of anhydrous THF, 1.0011 g of 2α-acetoxy-1β-hydroxyl-3a$\beta$H,8b$\beta$H-2,3,3a,8b-tetrahydro-5-1H-cyclopenta[b]benzofuran propionic acid methyl ester was dissolved. To this solution, 0.24 ml of anhydrous pyridine, 6 ml of anhydrous DMSO, 0.18 ml of trifluoro acetic acid and 1.25 g of dicyclohexylcarbodiimide (D.C.C) were added and the resulting mixture was stirred for 2 hours at room temperature. The thus obtained reaction mixture was cooled in iced water and 1.48 g of calcium carbonate was added thereto and the resulting mixture was stirred for 20 minutes followed by being left to stand.

Then 216 mg of sodium hydride (60% dispersion in mineral oil) was suspended in 30 ml of anhydrous THF. To this suspension, 1.5 g of dimethyl 3,3-dimethyl-2-oxoheptylphosphonate in 5 ml of anhydrous THF was added and the resulting mixture was stirred for 30 minutes under argon atmosphere at room temperature. To the thus obtained reaction mixture, the supernatant of the previously obtained reaction mixture of aldehyde ester was added using a syringe under cooling in iced water. The residue was washed with 10 ml and 5 ml of anhydrous THF and the supernatant obtained in the washing was added to the reaction mixture and the resulting mixture was stirred for 30 minutes at room temperature. To the thus obtained mixture, 60 ml of saturated aqueous ammonium chloride solution was added and the resultant was extracted 3 times with 40 ml of ethyl acetate. The organic layers were combined, washed each once with 80 ml of water and 80 ml of brine, dried over anhydrous magnesium sulfate and concentrated. The thus obtained residue was purified by column chromatography (silica gel; Art 7734, eluant; ethyl acetate:cyclohexane =1:2) to remove cyclohexyl urea generated as a by-product and excess Wordsworth's reagent, and to obtain 1.7469 g of an oily product. The thus obtained oily product was purified by Lobar column (commercially available from Merck & Co., Inc., eluant; ethyl acetate:cychlohexane=1:3) to obtain 1.1883 g of the desired product (yield 86.8%).

The structure of this product was confirmed by the following data. IR (liquid film method): 2930, 2860, 1735, 1682, 1620, 1598, 1444, 1362, 1239, 1192, 1062, 1044, 1080, 945, 850, 784, 746 cm$^{-1}$ NMR (400 MHz, CDCl$_3$, δ): 0.73–1.01(3H,m), 1.13(6H,s), 1.78(3H,s), 1.01–2.29(7H,m), 2.45–3.08(6H,m), 3.67(3H,s), 3.52–3.78(1H,m), 4.98(1H,q,J=6.21 Hz), 5.10–5.41(1H,m), 6.47–7.11(5H,m) MASS (EI method, m/e): 456 (M+)

Reference Example 16

16-methyl-15-oxo-2,5,6,7-tetranor-4,8-inter-m-phenylene PGI$_2$ methyl ester, 11-acetate (16)

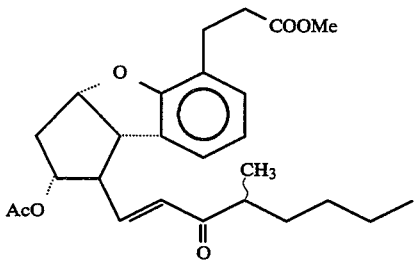

(16)

In 6 ml of anhydrous THF, 945 mg (2.83 mmol) of 2α-acetoxy-1β-hydroxymethyl-3aβH,8bβH-2,3,3a,8b-tetrahydro-5-1H-cyclopenta[b]benzofuran propionic acid methyl ester was dissolved. Under cooling in iced water, 0.073 ml of anhydrous pyridine, 0.068 ml of anhydrous trifluoro acetic acid, 2.11 ml of anhydrous dimethylsulfoxide and 0.92 g of dicyclohexylcarbodiimide were added to this solution under argon atmosphere and the resulting mixture was stirred for 3 hours at room temperature. Then 170 mg (4.24 mmol) of sodium hydride (60% dispersion in mineral oil) was suspended in 8 ml of anhydrous THF. To this suspension, 1.0 g (4.24 mmol) of dimethyl 3-methyl-2-oxoheptylphosphonate in 15 ml of anhydrous THF was added dropwise at room temperature and the resulting mixture was stirred for 30 minutes under argon atmosphere at room temperature. To the thus obtained reaction mixture, the previously obtained reaction mixture of aldehyde ester was added under cooling in iced water and the mixture was stirred for 30 minutes at room temperature. Acetic acid was added thereto to neutralize and the resultant was filtered. The filtrate was concentrated and 20 ml of water was added to the residue. The resulting mixture was extracted 2 times with 60 ml of ethyl acetate. The organic layers were combined, washed each once with 20 ml of water and 20 ml of brine, dried over anhydrous sodium sulfate and concentrated. The thus obtained residue was subjected to column chromatography (silica gel; Art 7734, eluant; ethyl acetate:cyclohexane=1:5) to remove by-products and excess Wordsworth's reagent, and then to Lobar column (eluant; ethyl acetate:cyclohexane=1:4) to obtain 995 mg of 16-methyl-15-oxo-2,5,6,7-tetranor-4,8-inter-m-phenylene PGI$_2$ methyl ester, 11-acetate (yield 79.6%).

The structure of this product was confirmed by the following data. IR (liquid film method): 2920, 2850, 1730, 1685, 1660, 1620, 1590, 1540, 1445, 1360, 1310, 1290, 1230, 1195, 1060, 1020, 970, 940, 885, 840, 740 cm$^{-1}$ NMR (90 MHz, CDCl$_3$, δ): 0.90(3H,t,J=7.0 Hz), 1.11(3H,d,J=7.0 Hz), 1.2–1.5(6H,m), 1.77, 1.78(3H,s), 2.1–2.2(1H,m), 2.6–2.8(4H,m), 2.85–3.0(3H,m), 3.67(3H,s), 3.65–3.75(1H,m), 5.00(1H,q,J=6.0 Hz), 5.2–5.3(1H,m), 6.27(1H,d,J=15.4 Hz), 6.77(1H,t,J=7.3 Hz), 6.79(1H,dd,J=15.4, 8.4 Hz), 6.96(1H,d,J=7.3 Hz), 6.98(1H,d,J=7.3 Hz) MASS (EI method, m/e): 442 (M+)

Reference Example 17

17-(s)-methyl-15-oxo-2,5,6,7-tetranor-4,8-inter-m-phenylene PGI$_2$ methyl ester, 11-acetate (17)

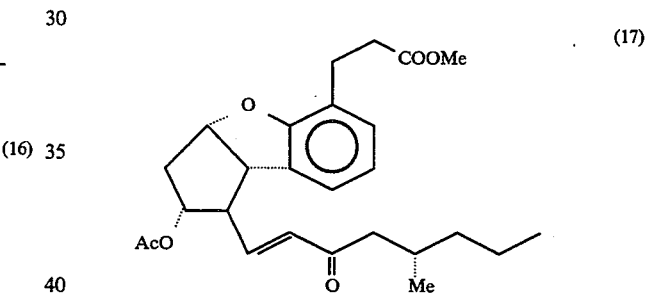

(17)

In 6 ml of anhydrous THF, 1 g (2.99 mmol) of 2α-acetoxy-1β-hydroxymethyl-3aβH,8bβH-2,3,3a,8b-tetrahydro-5-1H-cyclopenta[b]benzofuran propionic acid methyl ester was dissolved. To this solution, 0.073 ml of anhydrous pyridine, 0.068 ml of anhydrous trifluoro acetic acid, 11 ml of anhydrous DMSO and 0.92 g (4.46 mmol) of D.C.C were added under stirring and under cooling in iced water and the resulting mixture was stirred for 3 hours at room temperature. Then 0.18 g of sodium hydride (60% dispersion in mineral oil) was suspended in 8 ml of anhydrous THF. To this suspension, 0.9 g of dimethyl 4-(s)-methyl-2-oxoheptylphosphonate in 5 ml of anhydrous THF was added under cooling in iced water and under stirring, and the resulting mixture was stirred for 30 minutes at room temperature. To the thus obtained reaction mixture, the previously obtained reaction mixture of aldehyde ester was added under cooling in iced water and the resulting mixture was stirred for 10 minutes uncer cooling in iced water. To the thus obtained mixture, acetic acid was added to attain pH 7. The thus obtained precipitate was removed by filtration and the filtrate was concentrated. The thus obtained residue was purified by column chromatography (silica gel (40 g), eluant; ethyl acetate:cyclohexane=1:6) to obtain 1.2 g of the desired product (yield 94%).

The structure of this product was confirmed by the following data. IR (liquid film method): 2950, 2920, 2850, 1735, 1690, 1670, 1620, 1440, 1365, 1230, 1180, 1050, 980, 740 cm$^{-1}$ NMR (90 MHz, CDCl$_3$, δ): 0.80–1.00(6H,m), 1.00–1.50(6H,m,), 1.85(3H,s), 1.90–3.10(8H,m), 3.65(3H,s), 3.70(1H,m), 5.00(1H,q,J=5.9 Hz), 5.25(1H,m), 6.20(1H,dd,J=15.6 Hz, 0.7 Hz), 6.60–7.05(4H,m) MASS (EI method, m/e): 442 (M+)

Reference Example 18

15-cyclopentyl-15-oxo-2,5,6,7,16,17,18,19,20-nonanor-4,8-inter-m-phenylene PGI$_2$ methyl ester, 11-acetate (18)

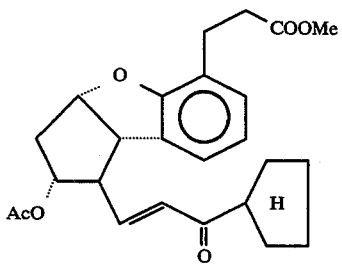

(18)

In 15 ml of anhydrous THF, 1.23 g of 2α-acetoxy-1β-hydroxymethyl-3aβH,8bβH-2,3,3a,8b-tetrahydro-5-1H-cyclopenta[b]benzofuran propionic acid methyl ester was dissolved. To this solution, 5 ml of anhydrous DMSO was added and 1.52 g of D.C.C. (dicyclohexylcarbodiimide) was dissolved therein and 0.35 ml of anhydrous pyridine and 0.22 ml of trifluoro acetic acid were added thereto. The resulting mixture was stirred for 2.2 hours under argon atmosphere at room temperature. To the thus obtained reaction mixture, 1.85 g of calcium carbonate was added and the resulting mixture was stirred. Then 0.19 g of sodium hydride (60% dispersion in mineral oil) was suspended in 10 ml of anhydrous THF. To this suspension, 1.22 g of dimethyl 2-cyclopentyl-2-oxoethylphosphonate in 4 ml of anhydrous THF was added dropwise and the resulting mixture was stirred for 15 minutes under argon atmosphere at room temperature. To the thus obtained reaction mixture, the supernatant of the previously obtained reaction mixture of aldehyde ester was added using a syringe. The residue was washed 2 times with 2 ml of anhydrous THF and the supernatant obtained in the washing was added to the mixture. After the reaction mixture was stirred for 2.5 hours, to the thus obtained mixture, 100 ml of saturated ammonium chloride solution was added to attain pH 7 and the resultant was extracted 3 times with 70 ml of ethyl acetate. The organic layers were combined, washed with water and brine, dried over anhydrous sodium sulfate and concentrated. Then the thus obtained mixture was passed through a short column of silica gel to remove the solids. Further, the resultant was purified by column chromatography (Lobar column commercially available from Merck & Co., Inc., eluant; ethyl acetate:cyclohexane=1:3) to obtain 1.15 g of 15-cyclopentyl-15-oxo-2,5,6,7,16,17,18,19,20-nonanor-4,8-inter-m-phenylene PGI$_2$ methyl ester, 11-acetate (yield 73%).

The structure of this product was confirmed by the following data. IR (liquid film method): 3400, 3050, 2990, 2950, 2870, 2300, 1730, 1690, 1660, 1630, 1600, 1480, 1450, 1430, 1420, 1365, 1260, 1240, 1200, 1150, 1060, 980, 950, 900, 850, 740, 700 cm$^{-1}$ NMR (90 MHz, CDCl$_3$,): 1.55–2.32(9H,m), 1.77(3H,s), 2.40–3.24(7H,m), 3.67(3H,s), 3.69(1H,t,J=ca,7.2 Hz), 5.01(1H,dd,J=11.8 Hz, 5.9 Hz), 5.09–5.40(1H,m), 6.23(1H,dd,J=15.7 Hz, 1.0 Hz), 6.64–7.06(4H,m) MASS (EI method, m/e): 426 (M+)

Reference Example 19

15-cyclohexyl-15-oxo-2,5,6,7,16,17,18,19,20-nonanor-4,8-inter-m-phenylene PGI$_2$ methyl ester, 11acetate (19)

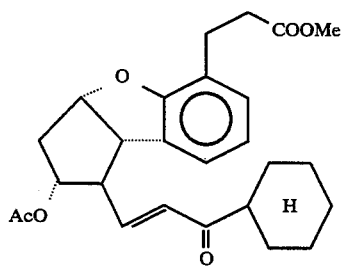

(19)

In 15 ml of anhydrous THF, 1.20 g of 2α-acetoxy-1β-hydroxymethyl-3aβH,8bβH-2,3,3a,8b-tetrahydro-5-1H-cyclopenta[b]benzofuran propionic acid methyl ester was dissolved. To this solution, 5 ml of anhydrous DMSO and 1.28 g of D.C.C. (dicyclohexylcarbodiimide) were added and then 0.29 ml of anhydrous pyridine and 0.18 ml of trifluoro acetic acid were added thereto. The resulting mixture was stirred for 2.5 hours under argon atmosphere at room temperature. To the thus obtained reaction mixture, 1.56 g of calcium carbonate was added and the resultant was stirred. Then 0.15 g of sodium hydride (60% dispersion in mineral oil) was suspended in 10 ml of anhydrous THF. To this suspension, 1.09 g of dimethyl 2-cyclohexyl-2-oxoethylphosphonate in 2 ml of anhydrous THF was added dropwise and the resulting mixture was stirred for 25 minutes under argon atmosphere at room temperature. To the thus obtained reaction mixture, the supernatant of the previously obtained reaction mixture of aldehyde ester was added using a syringe. The residue was washed 3 times with 3 ml of anhydrous THF and the supernatant obtained in the washing was added to the mixture. After the reaction mixture was stirred for 2 hours, to the thus obtained mixture, 100 ml of saturated ammonium chloride solution was added thereto to attain pH 7 and the resultant was extracted 3 times with 70 ml of ethyl acetate. The organic layers were combined, washed with water and brine, dried over anhydrous sodium sulfate and concentrated. Then the thus obtained mixture was passed through a short column of silica gel to remove solids. Further, the resultant was purified by column chromatography (Lobar column commercially available from Merck & Co., Inc., eluant; ethyl acetate:cyclohexane=1:2) to obtain 1.06 g of 15-cyclohexyl-15-oxo-2,5,6,7,16,17,18,19,20-nonanor-4,8-inter-m-phenylene PGI$_2$ methyl ester, 11-acetate (yield 77%).

The structure of this product was confirmed by the following data. IR (liquid film method): 3020, 2995, 2860, 2500, 1730, 1690, 1660, 1625, 1600, 1550, 1480, 1450, 1370, 1320, 1240, 1220, 1060, 1030, 1015, 980, 955, 930, 890, 850, 760, 670 cm$^{-1}$ NMR (90 MHz, CDCl$_3$, δ): 1.12–1.60(8H,m), 1.60–2.32(3H,m), 1.76(3H,s), 2.45–3.09(7H,m), 3.67(3H,s), 3.70(1H,t,J=ca,7.6 Hz), 4.85–5.40(2H,m), 6.26(1H,dd,J=15.8, 0.9 Hz), 6.62–7.06(4H,m) MASS (EI method, m/e): 440 (M+)

Reference Example 20

16-cyclopentyl-15-oxo-2,5,6,7,17,18,19,20-octanor-4,8-inter-m-phenylene PGI₂ methyl ester, 11-acetate (20)

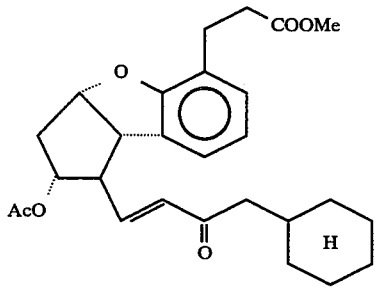

In 6 ml of anhydrous THF, 1.0 g (2.99 mmol) of 2α-acetoxy-1β-hydroxymethyl-3aβH,8bβH-2,3,3a,8b-tetrahydro-5-1H-cyclopenta[b]benzofuran propionic acid methyl ester was dissolved. Under cooling in iced water, 0.073 ml of anhydrous pyridine, 0.068 ml of trifluoro acetic acid, 2.11 ml of anhydrous dimethylsulfoxide and 0.92 g of dicyclohexylcarbodiimide were added to this solution under argon atmosphere. The resulting mixture was stirred for 3 hours at room temperature. Then 0.18 g (4.49 mmol) of sodium hydride (60% dispersion in mineral oil) was suspended in 9 ml of anhydrous THF. To this suspension, 1.12 g (4.49 mmol) of dimethyl 3-cyclohexyl-2-oxopropylphosphonate in 5 ml of anhydrous THF was added dropwise and the resulting mixture was stirred for 30 minutes under argon atmosphere at room temperature. To the thus obtained reaction mixture, the previously obtained reaction mixture of aldehyde ester was added under cooling in iced water. The resulting mixture was stirred for 30 minutes at room temperature. To the thus obtained mixture, acetic acid was added to neutralize the mixture and the resultant was filtered. The filtrate was concentrated and 20 ml of water was added to the residue. The resultant was extracted 2 times with 60 ml of ethyl acetate. The organic layers were combined, washed each once with 20 ml of water and 20 ml of brine, dried over anhydrous magnesium sulfate and concentrated. The thus obtained residue was subjected to column chromatography (silica gel, eluant; ethyl acetate:cyclohexane=1:5) to separate by-products and excess Wordsworth's reagent. Further, the resultant was purified by column chromatography (Lobar column, eluant; ethyl acetate:cyclohexane=1:4) to obtain 1.21 g of 16-cyclohexyl-15-oxo-2,5,6,7,17,18,19,20-octanor-4,8-inter-m-phenylene PGI₂ methyl ester, 11-acetate (yield 89%).

The structure of this product was confirmed by the following data. IR (liquid film method): 2920, 2840, 1730, 1685, 1660, 1620, 1590, 1540, 1440, 1565, 1310, 1230, 1180, 1060, 970, 910, 845, 725 cm⁻¹ NMR (90 MHz, CDCl₃, δ): 0.9–1.4(6H,m), 1.6–1.75(4H,m), 1.77(3H,s), 1.8–1.9(1H,m), 2.15(1H,ddd,J=3.4, 5.7, 14.6 Hz), 2.44(2H,d,J=6.8 Hz), 2.55–2.7(3H,m), 2.8–3.0(3H,m), 3.67(3H,s), 3.6–3.7(1H,m), 5.01(1H,q,J=5.7 Hz), 5.26(1H,ddd,J=3.4, 7.3, 8.8 Hz), 6.19(1H,dd,J=1.0, 15.6 Hz), 6.75(1H,dd,J=8.0, 15.6 Hz), 6.77(1H,t,J=7.5 Hz), 6.96(1H,d,J=7.5 Hz), 6.98(1H,d,J=7.5 Hz) MASS (EI method, m/e): 454 (M+)

Reference Example 21

17-cyclohexyl-16,16-dimethyl-15-oxo-2,5,6,7,18,19,20-heptanor-4,8-inter-m-phenylene PGI₂ methyl ester, 11-acetate (21)

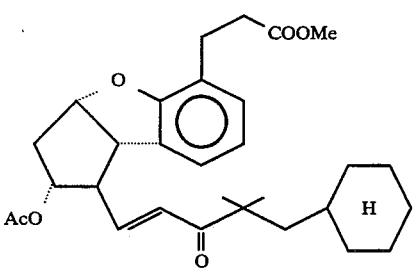

In 10 ml of anhydrous THF, 1.01 g (3.02 mmol) of 2α-acetoxy-1β-hydroxymethyl-3aβH,8bβH-2,3,3a,8b-tetrahydro-5-1H-cyclopenta[b]benzofuran acetic acid methyl ester was dissolved. To this solution, 0.24 ml (3.02 mmol) of anhydrous pyridine, 4 ml of anhydrous DMSO, 0.12 ml (1.51 mmol) of trifluoro acetic acid and 1.2478 g (6.04 mmol) of D.C.C. were added under argon atmosphere. The resulting mixture was stirred for 2 hours at room temperature. To the thus obtained reaction mixture, 982.4 mg (9.82 mmol) of calcium carbonate was added and the resultant was stirred for 15 minutes followed by being left to stand.

Then 181.2 mg (4.53 mmol) of sodium hydride (60% dispersion in mineral oil) was suspended in 20 ml of anhydrous THF. Under cooling in iced water, 1.3137 g (4.53 mmol) of dimethyl 4-cyclohexyl-3,3-dimethyl-2-oxobutylphosphonate in 5 ml of anhydrous THF was added dropwise and the resulting mixture was stirred for 30 minutes under argon atmosphere at room temperature. To the thus obtained reaction mixture, the supernatant of the previously obtained reaction mixture of aldehyde ester was added using a syringe under cooling in iced water. The residue was washed with anhydrous THF (10 ml, 5 ml×2) and the supernatant obtained in the washing was added the mixture. After reaction mixture was stirred for 5 minutes at room temperature, 40 ml of saturated aqueous ammonium chloride solution was added thereto and the resultant was extracted 3 times with 30 ml of ethyl acetate. The organic layers were combined, washed each once with 70 ml of water and 70 ml of brine, dried over anhydrous sodium sulfate (25 g) and concentrated. Then the thus obtained residue was purified by column chromatography (silica gel, eluant; ethyl acetate:cyclohexane=1:4) to obtain 1.3562 g (2.73 mmol) of 17-cyclohexyl-16,16-dimethyl-15-oxo-2,5,6,7,18,19,20-heptanor-4,8-inter-m-phenylene PGI₂ methyl ester, 11-acetate as a colorless oily product (yield 91%).

The structure of this product was confirmed by the following data. IR (liquid film method): 2910, 2850, 1728, 1680, 1620, 1590, 1442, 1382, 1321, 1293, 1230, 1186, 1106, 1052, 976, 943, 888, 841, 740 cm⁻¹ NMR (400 MHz, CDCl₃, δ): 0.80–0.92(2H,m), 0.98–1.38(4H,m), 1.13(3H,s), 1.14(3H,s), 1.48–1.67(7H,m), 1.79(3H,s), 2.08–2.17(1H,m), 2.60–2.72(3H,m), 2.87–2.98(3H,m), 3.63–3.70(1H,m), 3.68(3H,s), 4.96–5.02(1H,m), 5.22–5.28(1H,m), 6.60(1H,d,J=15.13 Hz), 6.76(1H,t,J=7.32 Hz), 6.82(1H,dd,J=8.79, 15.13 Hz), 6.95(1H,d,J=7.32 Hz), 6.99(1H,d,J=7.32 Hz) MASS (EI method, m/e): 496 (M+)

Reference Example 22

15-oxo-15-phenyl-2,5,6,7,16,17,18,19,20-nonanor-4,8-inter-m-phenylene PGI$_2$ methyl ester, 11-acetate (22)

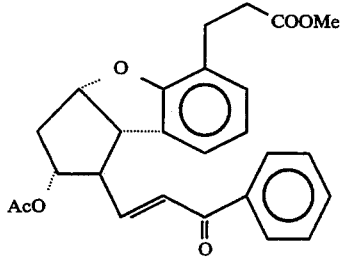

(22)

In 20 ml of anhydrous THF, 1.75 g of 2α-acetoxy-1β-hydroxymethyl-3aβH,8bβH-2,3,3a,8b-tetrahydo-5-1H-cyclopenta[b]benzofuran propionic acid methyl ester was dissolved. To this solution, 0.42 ml of anhydrous pyridne, 8 ml of anhydrous DMSO, 0.31 ml of trifluoro acetic acid and 2.18 g of dicyclohexylcarbodiimide (D.C.C) were added, and the resulting mixture was stirred for an hour at room temperature. The thus obtained reaction mixture was cooled in iced water and 2.59 g of calcium carbonate was added thereto followed by being stirred for 20 minutes. Then 419.2 mg of sodium hydride (60% dispersion in mineral oil) was suspended in 90 ml of anhydrous THF. To this suspension, 2.99 g of dimethyl 2-oxo-2-phenylethylphosphonate in 10 ml of anhydrous THF was added under cooling in iced water and the resulting mixture was stirred for 30 minutes under argon atmosphere at room temperature. To the thus obtained reaction mixture, the supernatant of the previously obtained reaction mixture of aldehyde ester was added using a syringe under cooling in iced water. The residue was washed each once with 10 ml and 5 ml of anhydrous THF and the supernatant obtained in the washing was added the mixture followed by being stirred for 30 minutes at room temperature. To the thus obtained mixture, 100 ml of saturated aqueous ammonium chloride solution was added and the resultant was extracted 3 times with 80 ml of ethyl acetate. The organic layers were washed each once with 150 ml of water and 150 ml of brine, dried over anhydrous magnesium sulfate and concentrated. Then the thus obtained residue was subjected to column chromatography (silica gel; Art. 7734, eluant; ethyl acetate:cyclohexane=1:1) to separate by-product of dicyclohexyl urea and excess reagent and to obtain 3.037 g of an oily product. The thus obtained oily product was purified by Lobar coloron (Type B commercially available from Merck & Co., Inc., eluant; ethyl acetate:cyclohexane=2:5) to obtain 2.0206 g of the desired product (yield 89%).

The structure of this product was confirmed by the following data. IR (liquid film method): 2930, 2850, 1735, 1668, 1618, 1595, 1575, 1446, 1365, 1238, 1065, 1045, 1010, 975, 943, 848, 775, 742, 700 cm$^{-1}$ NMR (90 MHz, CDCl$_3$, δ): 1.79(3H,s), 2.17–2.33(3H,m), 2.50–3.20(6H,brm), 3.68(3H,s), 3.67–3.89(1H,m), 4.97–5.42(2H,m), 6.66–7.12(5H,m), 7.34–7.70(3H,m), 7.82–8.06(2H,m) MASS (EI method, m/e): 434 (M+)

Reference Example 23

15-oxo-16-phenyl-2,5,6,7,17,18,19,20-octanor-4,8-inter-m-phenylene PGI$_2$ methyl ester, 11-acetate (23)

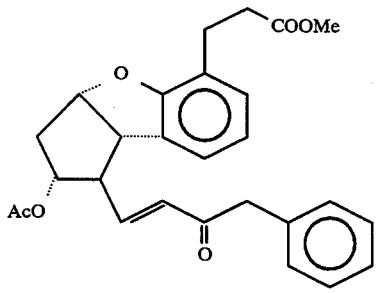

(23)

In 25 ml of anhydrous THF, 1.5 g (4.48 mmol) of 2α-acetoxy-1β-hydroxymethyl-3aβH,8bβH-2,3,3a,8b-tetrahydro-5-1H-cyclopenta[b]benzofuran propionic acid methyl ester was dissolved. To this solution, 3.2 ml of anhydrous DMSO, 0.11 ml (1.39 mmol) of anhydrous pyridine, 0.097 ml (1.25 mmol) of trifluoro acetic acid and 1.39 g (6.72 mmol) of D.C.C. (dicyclohexylcarbodiimide) were added under argon atmosphere and the resulting mixture was stirred for an hour at room temperature. Then 249 mg (6.50 mmol) of sodium hydride (60% dispersion in mineral oil) was suspended in 30 ml of anhydrous THF. To this suspension, 1.63 g (6.72 mmol) of dimethyl 3-phenyl-2-oxo-propylphosphonate in 5 ml of anhydrous THF was added and the resulting mixture was stirred for 30 minutes at room temperature. To the thus obtained reaction mixture, the previously obtained reaction mixture of aldehyde ester was added at a temperature of 0° C. and the resultant was stirred for 15 minutes at room temperature. To the thus obtained mixture, acetic acid was added to attain pH 7, and the resultant was concentrated. Ethyl acetate was added to the residue and the resultant was filtered. The filtrate was washed with water and brine and dried. Then the thus obtained residue was passed through a short. column of silica gel to remove solids. Further, the resultant was purified by column chromatography (Lobar column commercially available from Merck & Co., Inc., eluant; ethyl acetate:cyclohexane=1:3.5) to obtain 1.39 g of 15-oxo-16-phenyl-2,5,6,7,17,18,19,20-octanor-4,8-inter-m-phenylene PGI$_2$ methyl ester, 11-acetate (yield 69%).

The structure of this product was confirmed by the following data. IR (liquid film method): 2950, 1740, 1690, 1630, 1600, 1495, 1460, 1370, 1240, 1070, 980, 950, 850, 745, 705 cm$^{-1}$ NMR (90 MHz, CDCl$_3$, δ): 1.75(3H,s), 1.9–2.3(1H,m), 2.4–3.0(6H,m), 3.4–3.6(1H,m), 3.66(3H,s), 3.84(2H,s), 4.95(1H,q,J=6.5 Hz), 5.20(1H,ddd,J=3.9, 7.7, 8.2 Hz), 6.21(1H,dd,J=0.9, 15.6 Hz), 6.6–7.0 (4H,m), 7.1–7.5(5H,m) MASS (EI method, m/e): 448 (M+)

Reference Example 24

15-oxo-17-phenyl-2,5,6,7,18,19,20-heptanor-4,8-inter-m-phenylene PGI$_2$ methyl ester, 11-acetate (24)

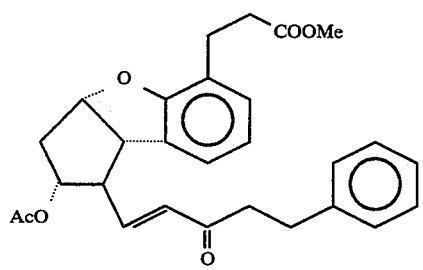 (24)

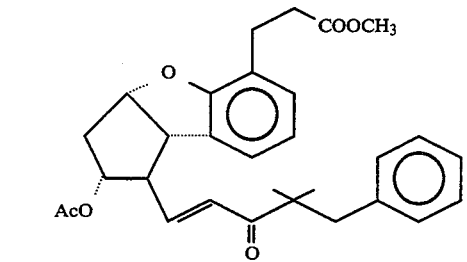 (25)

In 6 ml of anhydrous THF, 1.0 g of 2α-acetoxy-1β-hydroxymethyl-3aβH,8bβH-2,3,3a,8b-tetrahydo-5-1H-cyclopenta[b]benzofuran propionic acid methyl ester was dissolved. To this stirred solution, 0.073 ml of anhydrous pyridine, 0.068 ml of anhydrous trifluoro acetic acid, 2.11 ml of anhydrous DMSO and 0.92 g of dicyclohexylcarbodiimide were added under cooling in iced water and under argon atmosphere. The resulting mixture was stirred for 3 hours at room temperature. Then 0.18 g (4.49 mmol) of sodium hydride (60% dispersion in mineral oil) was suspended in 9 ml of anhydrous THF. To this suspension, 1.15 g (4.49 mmol) of dimethyl 2-oxo-4-phenyl-butylphosphonate in 5 ml of anhydrous THF was added dropwise at room temperature and the resulting mixture was stirred for 30 minutes under argon atmosphere at room temperature. To the thus obtained reaction mixture, the previously obtained reaction mixture of aldehyde ester was added and the resulting mixture was stirred for 30 minutes at room temperature. The thus obtained mixture was neutralized with acetic acid and the mixture was filtered. The filtrate was concentrated and 20 ml of water was added to the residue and the resultant was extracted with ethyl acetate (60 ml×2). The organic layers were combined, washed each once with 20 ml of water and 20 ml of brine, dried over anhydrous magnesium sulfate and concentrated. Then the thus obtained residue was subjected to column chromatography (silica gel, eluant; ethyl acetate:cyclohexane=1:5) to remove by-products and excess Wordsworth's reagent, and then to column chromatography (Lobar column commercially available from Merck & Co., Inc., eluant; ethyl acetate:cyclohexane=1:4) to obtain 1.15 g of 15-oxo-17-phenyl-2,5,6,7,18,19,20-heptanor-4,8-inter-m-phenylene PGI$_2$ methyl ester, 11-acetate (yield 87%).

The structure of this product was confirmed by the following data. NMR (400 MHz, CDCl$_3$, δ): 1.77(3H,s), 2.13(1H,ddd,J=3.9, 6.2, 14.2 Hz), 2.55–2.7(3H,m), 2.85–3.0(7H,m), 3.6–3.7(1H,m), 3.67(3H,s), 4.97(1H,q,J=6.2 Hz), 5.23(1H,ddd,J=3.9, 6.8, 8.3 Hz), 6.73(1H,dd,J=7.8, 16.0 Hz), 6.76(1H,t,J=7.3 Hz), 6.93(1H,d,J=7.3 Hz), 6.99(1H,d,J=7.3 Hz), 7.2–7.4(5H,m) MASS (EI method, m/e): 462 (M$^+$)

Reference Example 25

16,16-dimethyl-15-oxo-17-phenyl-2,5,6,7,18,19,20-heptanor-4,8-inter-m-phenylene PGI$_2$ methyl ester, 11-acetate (25)

In 15 ml of anhydrous THF, 1 g (2.993 mmol) of 2α-acetoxy-1β-hydroxymethyl-3aβH,8bβH-2,3,3a,8b-tetrahydro-5-1H-cyclopenta[b]benzofuran propionic acid methyl ester was dissolved under argon atmosphere. To this stirred solution, 5 ml of anhydrous dimethylsulfoxide, 0.936 g (4.489 mmol) of N,N'-dicylohexylcabodiimide, 0.24 ml (3.0 mmol) of pyridine and 0.12 ml (1.50 mmol) of trifluoro acetic acid were added at room temperature. After stirring for 6 hours at room temperature, calcium carbonate was added to the mixture and the resulting mixture was stirred for 15 minutes. The thus obtained mixture was left to stand and the supernatant thereof was taked out. The precipitate was washed with tetrahydrofuran (7 ml×3) and these washes and the supernatants were combined. The 180 mg (4.49 mmol) of sodium hydride (60% dispersion in mineral oil) was suspended in 10 ml of anhydrous tetrahydrofuran. To this suspension, 1.26 g (4.49 mmol) of dimethyl 3-oxo-4,4-dimethyl-5-phenyl-butylphosphonate in 5 ml of anhydrous THF was added under cooling in iced water and the resulting mixture was stirred for 2 hours. To the thus obtained reaction mixture, the previously obtained supernatant was added under cooling in iced water and the resulting mixture was stirred for 5 minutes at the same temperature followed by being stirred overnight at room temperature. To the thus obtained mixture, 40 ml of saturated aqueous ammonium chloride solution was added and the mixture was stirred. The resultant was extracted with ethyl acetate (30 ml×3). The organic layers were combined, washed each once with 70 ml of water and with brine and dried over anhydrous sodium sulfate. Then ethyl acetate was evaporated under reduced pressure to obtain orange crystals. The thus obtained crystals were subjected to column chromatography (silica gel, eluant; cyclohexane:ethyl acetate=1:2) to obtain a yellow oily product. The thus obtained oily product was purified by column chromatography (Lobar column Type B commercially available from Merck & Co., Inc., eluant; cyclohexane:ethyl acetate=4:1) to obtain 1.17 g (2.383 mmol) of 16,16-dimethyl-15-oxo-17-phenyl-2,5,6,7,18,19,20-heptanor-4,8-inter-m-phenylene PGI$_2$ methyl ester, 11-acetate with a 80% yield.

The structure of this product was confirmed by the following data. IR (liquid film method): 3100, 3080, 3050, 2980, 2890, 1750, 1690, 1635, 1605, 1503, 1460, 1380, 1335, 1305, 1250, 1205, 1190, 1170, 1050, 1010, 990, 960, 930, 905, 820, 795, 755, 710 cm$^{-1}$ NMR (400 MHz, CDCl$_3$, δ): 1.15(3H,s), 1.16(3H,s), 1.77(3H,s), 2.10–2.16(1H,m), 2.61–2.68 (3H,m), 2.81–2.98(5H,m), 3.63–3.68(4H,m), 4.96–5.01(1H,m), 5.22–5.27(1H,m), 6.58–6.62(1H,m), 6.74–6.87(2H,m), 6.92–7.00(2H,m), 7.08–7.09(2H,m), 7.19–7.26(3H,m) MASS (EI method, m/e): 490 (M$^+$)

Reference Example 26 d-17-phenyl-15-oxo-2,5,6,7,18,19,20-heptanor-4,8-inter-m-phenylene PGI₂ methyl ester, 11-acetate (26)

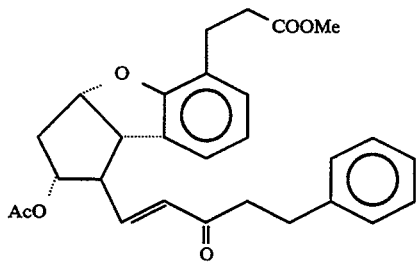

(26)

In 6 ml of anhydrous THF, 750 mg (2.25 mmol) of d-2α-acetoxy-1β-hydroxymethyl-3aβH,8bβH-2,3,3a,8b-tetrahydro-5-1H-cyclopenta[b]benzofuran propionic acid methyl ester was dissolved under argon atmosphere. To this stirred solution, 0.056 ml (0.694 mmol) of pyridine, 0.052 ml (0.675 mmol) of trifluoro acetic acid, 2.0 ml (28.2 mmol) of DMSO and 700 mg (3.39 mmol) of D.C.C were added. The resulting mixture was stirred for 3 hours at room temperature. Then 180 mg (4.5 mmol) of sodium hydride (60% dispersion in mineral oil) was suspended in 6 ml of anhydrous THF under argon atmosphere. To this suspension, 1.15 g (4.5 mmol) of dimethyl 2-oxo-4-phenyl-butylphosphonate in 5 ml of anhydrous THF was added dropwise under cooling in iced water and the resulting mixture was stirred for 30 minutes. To the thus obtained reaction mixture, the previously obtained reaction mixture of aldehyde ester was added under cooling in iced water and the resulting mixture was stirred for 30 minutes. The thus obtained mixture was neutralized with acetic acid and the mixture was filtered. The inorganic material was washed with ethyl acetate (10 ml×3) and the thus obtained filtrate was concentrated. To the thus obtained residue, 30 ml of water was added and the resultant was extracted once with 100 ml of ethyl acetate. The ethyl acetate layer was washed each once with 20 ml of water and 20 ml of brine, dried over anhydrous sodium sulfate and concentrated. Then the thus obtained residue was subjected to column chromatography (silica gel (50 g), eluant; ethyl acetate:cyclohexane=1:5), and then to column chromatography (Lobar column commercially available from Merck & Co., Inc.) to obtain 801.5 mg (1.73 mmol) of d-17-phenyl-15-oxo-2,5,6,7,18,19,20-heptanor-4,8-inter-m-phenylene PGI₂ methyl ester, 11-acetate (yield 76.9%).

The structure of this product was confirmed by the following data. $[\alpha]_D^{25} = +112.75°$ (C=0.98, MeOH) IR (liquid film method): 3020, 2940, 1720, 1670, 1625, 1590, 1440, 1360, 1290, 1230, 1190, 1055, 970, 940, 850, 745, 695 cm⁻¹ NMR (400 MHz, CDCl₃, δ): 1.77(3H,s), 2.0–2.2 (1H,m), 2.5–2.8(3H,m), 2.8–3.0(7H,m), 3.6–3.7(1H,m), 3.67(3H,s), 4.97(1H,q,J=6.0 Hz), 5.2–5.4(1H,m), 6.18(1H,dd,J=15.9, 0.98 Hz), 6.73(1H,dd,J=15.9, 8.3 Hz), 6.76(1H,t,J=7.6 Hz), 6.92(1H,d,J=7.6 Hz), 6.98(1H,d,J=7.6 Hz), 7.1–7.25(3H,m), 7.25–7.4(2H,m) MASS (EI method, m/e): 462 (M⁺)

Reference Example 27 d-15-chlorophenyl-15-oxo-2,5,6,7,16,17,18,19,20-nonanor-4,8-inter-m-phenylene PGI₂ methyl ester, 11-acetate (27)

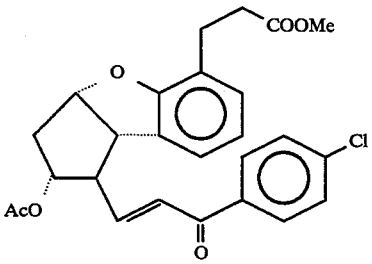

(27)

In 6 ml of anhydrous THF, 751 mg (2.25 mmol) of d-2α-acetoxy-1β-hydroxymethyl-3aβH,8bβH-2,3,3a,8b-tetrahydro-5-1H-cyclopenta[b]benzofuran propionic acid methyl ester was dissolved under argon atmosphere. To this stirred solution, 0.056 ml (0.69 mmol) of pyridine, 0.052 ml (0.68 mmol) of trifluoro acetic acid, 2.0 ml (28.2 mmol) of DMSO and 700 mg (3.4 mmol) of D.C.C. were added. The resulting mixture was stirred for 2.5 hours at room temperature. Then 1.62 mg (4.05 mmol) of sodium hydride (60% dispersion in mineral oil) was suspended in 6 ml of anhydrous THF under argon atmosphere. To this suspension, dimethyl 2-oxo-2-p-chlorophenyl-ethylphosphonate in 5 ml of anhydrous THF was added dropwise under cooling in iced water and the resulting mixture was stirred for 30 minutes under cooling in iced water. To the thus obtained reaction mixture, the previously obtained reaction mixture of aldehyde ester was added under cooling in iced water and the resulting mixture was stirred for 30 minutes. The thus obtained mixture was neutralized with acetic acid and the resultant was filtered. The inorganic material was washed with ethyl acetate (10 ml 5) and the filtrates were combined and concentrated. To the thus obtained residue, 30 ml of water was added and the resultant was extracted with ethyl acetate (50 ml×2). The ethyl acetate layers were washed each once with 30 ml of water and 30 ml of brine, dried over anhydrous sodium sulfate and concentrated. Then the thus obtained residue was subjected to column chromatography (silica gel, eluant; ethyl acetate:cyclohexane=1:5) to remove solids, and then to column chromatography (Lobar column commercially available from Merck & Co., Inc., eluant; ethyl acetate:cyclohexane=1:5) to obtain 871 mg (1.86 mmol) of d-15-p-chlorophenyl-15-oxo-2,5,6,7,16,17,18,19,20-nonanor-4,8-inter-m-phenylene PGI₂ methyl ester, 11-acetate (yield 82.7%).

The structure of this product was confirmed by the following data. $[\alpha]_D^{25} = +131.34°$ (C=1.292, MeOH) IR (liquid film method): 2940, 1720, 1665, 1610, 1470, 1360, 1320, 1230, 1085, 1060, 1010, 940, 910, 850, 825, 740, 665 cm⁻¹ NMR (400 MHz, CDCl₃, δ): 1.79(3H,s), 2.1–2.3(1H,m), 2.6–2.8(3H,m), 2.8–3.0(2H,m), 3.0–3.1(1H,m), 3.68(3H,s), 3.7–3.8(1H,m), 5.0–5.1(1H,m), 5.2–5.4(1H,m), 6.78(1H,t,J=7.6 Hz), 6.9–7.1(4H,m), 7.4–7.6(2H,m), 7.8–8.0(2H,m), MASS (EI method, m/e): 468 (M⁺)

Reference Example 28 d-16-(R)-methyl-15-oxo-17-phenyl-2,5,6,7.18,19,20-heptanor-4,8-inter-m-phenylene PGI$_2$ methyl ester, 11-acetate (28)

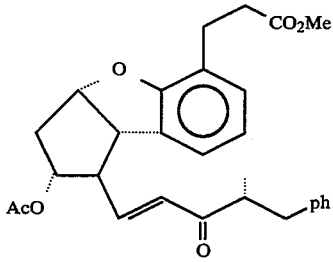

In 10 ml of anhydrous THF, 1.0118 g (3.03 mmol) of d-2α-acetoxy-1β-hydroxymethyl-3aβH,8bβH-2,3,3a,8b-tetrahydro-5-1H-cyclopenta[b]benzofuran propionic acid methyl ester was dissolved under argon atmosphere. To this stirred solution, 4.2 ml (59.8 mmol) of anhydrous DMSO, 0.28 ml (3.51 mmol) of anhydrous pyridine, 0.47 ml (6.10 mmol) of anhydrous trifluoro acetic acid and 1.01 g (4.90 mmol) of D.C.C. were added at 0° C. The resulting mixture was stirred for 4 hours at room temperature. Then 0.27 g (6.75 mmol) of sodium hydride (60% dispersion in mineral oil) was suspended in 10 ml of anhydrous THF. To this suspension, 1.78 g (6.59 mmol) of dimethyl 3-(R)-methyl-2-oxo-4-phenylbutylphosphonate in 9 ml of anhydrous THF was added under argon atmosphere at 0° C. and the resulting mixture was stirred for 2 hours at room temperature. To the thus obtained reaction mixture, the previously obtained reaction mixture of aldehyde ester was added using a syringe. Further, the residue was washed with anhydrous THF (5 ml×3) and the washes were added to the mixture. The resulting mixture was stirred overnight at room temperature. To the thus obtained mixture, 20 ml of saturated aqueous ammonium chloride solution was added and the resultant was extracted with ethyl acetate (50 ml×4). Then ethyl acetate layers were washed each once with 50 ml of water and 50 ml of brine, dried over anhydrous sodium sulfate and concentrated. Then the thus obtained residue was subjected to column chromatography (silica gel, eluant; ethyl acetate:cyclohexane=1:4) to remove by-products. Further, the thus obtained oily product was purified by column chromatography (silica gel, eluant; ethyl acetate:cyclohexane=1:4) to obtain pure d-16-(R)-methyl-15-oxa-17-phenyl-2,5,6,7,18,19,20-heptanor-4,8-inter-m-phenylene PGI$_2$ methyl ester, 11-acetate with 73.2% yield.

The structure of this product was confirmed by the following data. $[\alpha]_D^{20} = +52.48°$ (C=1.13, MeOH) IR (liquid film method): 3025, 2930, 1731, 1691, 1664, 1624, 1598, 1544, 1449, 1369, 1321, 1298, 1235, 1195, 1173, 1063, 983, 950, 917, 850, 787, 747, 702 cm$^{-1}$ NMR (100 MHz, CDCl$_3$, δ): 1.13(3H,d,J=6.59 Hz), 1.74(3H,s), 1.93–2.30(1H,m), 2.30–3.30(9H,m), 3.45–3.80(1H,m), 3.67(3H,s), 4.80–5.06(1H,m), 5.06–5.35(1H,m), 6.16(1H,dd,J=4.73, 0.88 Hz), 6.52–7.42(9H,m) MASS (EI method, m/e): 476 (M+)

Reference Example 29 d-16-(S)-methyl-15-oxo-17-phenyl-2,5,6,7.18,19,20-heptanor-4,8-inter-m-phenylene PGI$_2$ methyl ester, 11-acetate (29)

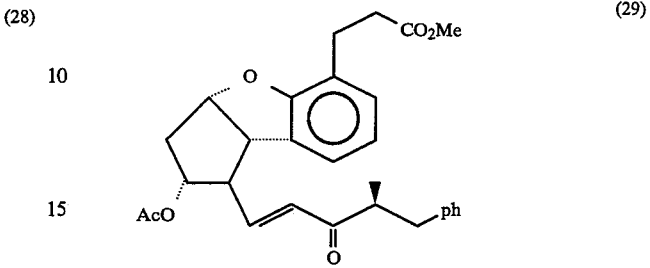

In 10 ml of anhydrous THF, 7048 mg (2.11 mmol) of d-2α-acetoxy-1β-hydroxymethyl-3aβH,8bβH-2,3,3a,8b-tetrahydro-5-1H-cyclopenta[b]benzofuran propionic acid methyl ester was dissolved under argon atmosphere. To this stirred solution, 3.0 ml (41.8 mmol) of anhydrous DMSO, 0.19 ml (2.30 mmol) of anhydrous pyridine, 0.08 ml (1.05 mmol) of anhydrous trifluoro acetic acid and 0.65 g (3.14 mmol) of D.C.C. were added at 0° C. The resulting mixture was stirred for 3 hours at room temperature. Then 0.15 g (3.76 mmol) of sodium hydride (60% dispersion in mineral oil) was suspended in 5 ml of anhydrous THF. To this suspension, 1.00 g (3.71 mmol) of dimethyl 3-(S)-methyl-2-oxo-4-phenylbuthylphosphonate in 6 ml of anhydrous THF was added under argon atmosphere at 0° C. and the resulting mixture was stirred for 1 hour at room temperature. To the thus obtained reaction mixture, the previously obtained reaction mixture of aldehyde ester was added using a syringe. Further, the residue was washed with anhydrous THF (5 ml×3) and the washes were added to the mixture. The resulting mixture was stirred for 30 minutes at room temperature. To the thus obtained mixture, 15 ml of saturated aqueous ammonium chloride solution was added and the resultant was extracted with ethyl acetate (50 ml×4). Then ethyl acetate layers were washed each once with 50 ml of water and 50 ml of brine, dried over anhydrous sodium sulfate and concentrated. Then the thus obtained residue was subjected to column chromatography (silica gel, eluant; ethyl acetate:cyclohexane=1:2) to remove by-products. Further, the thus obtained oily product was purified by column chromatography (silica gel, eluant; ethyl acetate:cyclohexane=1:4) to obtain pure d-16-(S)-methyl-15-oxo-17-phenyl-2,5,6,7,18,19,20-heptanor-4,8-inter-m-phenylene PGI$_2$ methyl ester, 11-acetate with 97.5% yield.

The structure of this product was confirmed by the following data. $[\alpha]_D^{20} = +142.56°$ (C=1.02, MeOH) IR (liquid film method): 2930, 1733, 1686, 1661, 1621, 1446, 1364, 1236, 1193, 1063, 976, 943, 843, 743, 701, 663 cm$^{-1}$ NMR (100 MHz, CDCl$_3$, δ): 1.14(3H,d,J=6.59 Hz), 1.75(3H,s), 1.94–2.25(1H,m), 2.37–3.32(9H,m), 3.40–3.78(1H,m), 3.67(3H,s), 4.80–5.07(1H,s), 5.08–5.35(1H,m), 6.14(1H,d,J=15.83 Hz), 6.52–7.40(9H,m) MASS (EI method, m/e): 476 (M+)

Reference Example 30

15-oxo-2,5,6,7-tetranor-17-oxa-4,8-inter-m-phenylene PGI$_2$ methyl ester, 11-acetate (30)

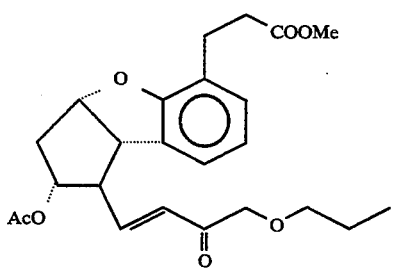 (30)

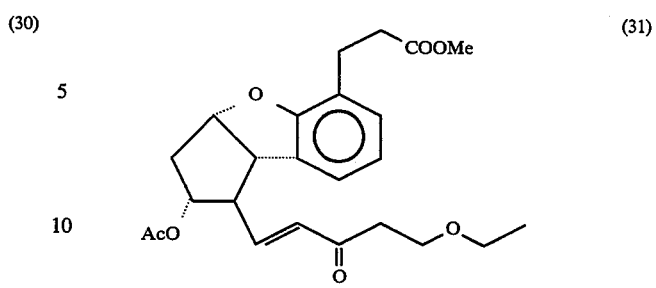 (31)

In 15 ml of anhydrous THF, 1.27 g of 2α-acetoxy-1β-hydroxymethyl-3aβH,8bβH-2,3,3a,8b-tetrahydro-5-1H-cyclopenta[b]benzofuran propionic acid methyl ester was dissolved. To this stirred solution, 5 ml of anhydrous DMSO was added and then 1.57 g of D.C.C. (dicyclohexylcarbodiimide), 0.36 ml of anhydrous pyridine and 0.22 ml of trifluoro acetic acid were added. The resulting mixture was stirred for 2.5 hours under argon atmosphere at room temperature. To the thus obtained reaction mixture, 1.91 g of calcium carbonate was added and the resulting mixture was stirred. Then 0.18 g of sodium hydride (60% dispersion in mineral oil) was suspended in anhydrous THF. To this suspension, 1.28 g of dimethyl 1-oxo-2-propoxypropanylphosphonate in 2 ml of anhydrous THF was added dropwise and the resulting mixture was stirred for 15 minutes under argon atmosphere at room temperature. To the thus obtained reaction mixture, the supernatant of the previously obtained reaction mixture of aldehyde ester was added using a syringe. Further, the residue was washed with THF (3 ml×3) and the washes were added to the mixture. After sirring the resulting mixture overnight, to the thus obtained mixture, 100 ml of saturated aqueous ammonium chloride solution was added to attain pH 7 and the resultant was extracted with ethyl acetate (70 ml×3). The organic layers were combined, washed with water and brine, dried over anhydrous sodium sulfate and concentrated. Then the thus obtained mixture was passed through a short column of silica gel to remove solids. Further, the resultant was purified by column chromatography-(Lobar column commercially from Merck & Co., Inc., eluant; ethyl acetate:cyclohexane=1:3) to obtain 699 mg of 15-oxo-2,5,6,7-tetranor-17-oxa-4,8-inter-m-phenylene PGI$_2$ methyl ester, 11-acetate (yield 42%).

The structure of this product was confirmed by the following data. IR (liquid film method): 3160, 2960, 2880, 1735, 1695, 1670, 1620, 1600, 1480, 1455, 1440, 1420, 1370, 1320, 1300, 1270, 1240, 1200, 1160, 1120, 1060, 1045, 1010, 980, 955, 915, 860, 740, 700 cm$^{-1}$ NMR (90 MHz, CDCl$_3$, δ): 0.85–1.05(3H,m), 1.10–1.72(4H,m), 1.77(3H,s), 1.98–2.32(1H,m), 2.45–3.12(5H,m), 3.47(2H,t,J=6.6 Hz), 3.67(3H,s), 4.18(2H,s), 4.87–5.13(1H,m), 5.13–5.40(1H,m), 6.44(1H,d,J=15.8 Hz), 6.65–7.10(4H,m) MASS (EI method, m/e): 430 (M+)

Reference Example 31

15-oxo-2,5,6,7-tetranor-18-oxa-4,8-inter-m-phenylene PGI$_2$ methyl ester, 11-acetate (31)

In 16 ml of anhydrous THF, 1.0 g (2.99 mmol) of 2α-acetoxy-1β-hydroxymethyl-3aβH,8bβH-2,3,3a,8b-tetrahydro-5-1H-cyclopenta[b]benzofuran propionic acid methyl ester was dissolved. To the stirred solution, 0.073 ml of anhydrous pyridine, 0.068 ml of anhydrous trifluoro acetic acid, 2.11 ml of anhydrous dimethylsulfoxide and 0.92 g of D.C.C. were added under cooling in iced water and under argon atmosphere. The resulting mixture was stirred for 3 hours at room temperature. Then 0.18 g (4.5 mmol) of sodium hydride (60% dispersion in mineral oil) was suspended in 8 ml of anhydrous THF. To this suspension, 1.01 g (4.49 mmol) of dimethyl 2-oxo-4-ethoxy-buthylphosphonate in 5 ml of anhydrous THF was added dropwise at room temperature and the resulting mixture was stirred for 30 minutes under argon atmosphere at room temperature. To the thus obtained reaction mixture, the previously obtained reaction mixture of aldehyde ester was added under cooling in iced water and the resulting mixture was stirred for 30 minutes at room temperature. The thus obtained mixture was neutralized with acetic acid and the resultant was filtered. The filtrate was concentrated and 20 ml of water was added to the residue followed by being extracted with ethyl acetate (60 ml×2). The organic layers were combined, washed each once with 20 ml of water and 20 ml of brine, dried over anhydrous magnesium sulfate and concentrated. The thus obtained residue was subjected to column chromatography (silica gel, eluant; ethyl acetate:cyclohexane=1:5) to remove by-products and excess Wordsworth's reagent, and then to column chromatography (Rorber column, eluant; ethyl acetate:cyclohexane=1:4) to obtain 1.14 g of 15-oxo-2,5,6,7-tetranor-18-oxa-4,8-inter-m-phenylene PGI$_2$ methyl ester, 11-acetate (yield 88.6%).

The structure of this product was confirmed by the following data. IR (liquid film method): 2970, 2950, 2875, 1730, 1690, 1670, 1630, 1600, 1550, 1450, 1370, 1230, 1190, 1100, 1060, 980, 940, 850, 750 cm$^{-1}$ NMR (400 MHz, CDCl$_3$, δ): 1.20(3H,t,J=7.0 Hz), 1.78(3H,s), 2.15(1H,ddd,J=3.6, 6.1, 14.4 Hz), 2.6–2.7(3H,m), 2.8–3.0(5H,m), 3.51(2H,q,J=7.0 Hz), 3.68(3H,s), 3.65–3.8(3H,m), 5.00(1H,q,J=6.1 Hz), 5.26(1H,ddd,J=3.6, 7.1, 8.5 Hz), 6.23(1H,dd,J=1.0, 16.1 Hz), 6.77(1H,t,J=7.5 Hz), 6.8(1H,dd,J=7.8, 16.1 Hz), 6.9–7.0(2H,m) MASS (EI method, m/e): 430 (M+)

Reference Example 32

16,16-dimethyl-15-oxo-2,5,6,7-tetranor-18-oxa-4,8-inter-m-phenylene PGI$_2$ methyl ester, 11-acetate (32)

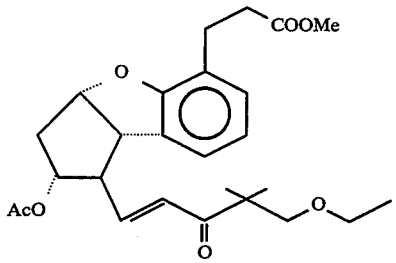 (32)

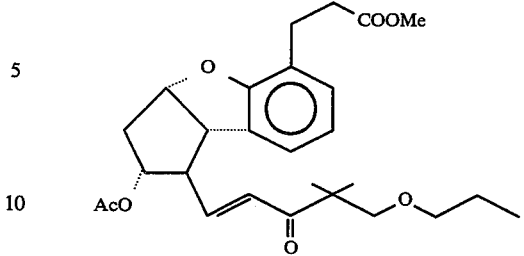 (33)

In 6 ml of anhydrous THF, 1.0 g (2.99 mmol) of 2α-acetoxy-1β-hydroxymethyl-3aβH,8bβH-2,3,3a,8b-tetrahydro-5-1H-cyclopenta[b]benzofuran propionic acid methyl ester was dissolved under argon atmosphere. To this stirred solution, 0.073 ml (0.9 mmol) of pyridine, 0.068 ml (0.88 mmol) of trifluoro acetic acid, 2.11 ml (29.7 mmol) of DMSO and 0.82 g (3.97 mmol) of D.C.C. were added. The resulting mixture was stirred for 2.5 hours at room temperature. Then 192 mg (4.8 mmol) of sodium hydride (60% dispersion in mineral oil) was suspended in 6 ml of anhydrous THF under argon atmosphere. To this suspension, 1.21 g (4.8 mmol) of dimethyl 3,3-dimethyl-2-oxo-5-oxa-heptylphosphonate in 3 ml of anhydrous THF was added dropwise under cooling in iced water and the resulting mixture was stirred for 30 minutes. To the thus obtained reaction mixture, the previously obtained reaction mixture of aldehyde ester was added under cooling in iced water and the resulting mixture was stirred for 30 minutes at 0° C. The thus obtained mixture was neutralized with acetic acid. After filtrering the resultant, the filtrate was concentrated. To the thus obtained residue, 10 ml of water was added and the resultant was extracted with ethyl acetate (50 ml×2). Ethyl acetate layers were washed each once with 20 ml of water and 10 ml of brine, dried over anhydrous sodium sulfate and concentrated. Then the thus obtained residue was subjected to column chromatography (silica gel, eluant; ethyl acetate:cyclohexane=1:5), and then to column chromatography (Lobar column commercially available from Merck & Co., Inc., eluant; ethyl acetate:cyclohexane=1:6) to obtain 1.05 g (2.29 mmol) of 16,16-dimethyl-15-oxo-2,5,6,7-tetranor-4,8-inter-m-phenylene PGI$_2$ methyl ester, 11-acetate as a colorless oily product (yield 76.6%).

The structure of this product was confirmed by the following data. IR (liquid film method): 2970, 2920, 2860, 1730, 1680, 1620, 1590, 1445, 1360, 1320, 1290, 1230, 1190, 1110, 1065, 975, 940, 890, 850, 740 cm$^{-1}$ NMR (400 MHz, CDCl$_3$, δ): 1.16(3H,t,J=6.8 Hz), 1.17(6H,s), 1.76(3H,s), 2.1–2.2(1H,m), 2.5–2.8(3H,m), 2.8–3.0(3H,m), 3.4–3.5(4H,m), 3.68(3H,s), 3.6–3.7(1H,m), 4.98(1H,q,J=5.86 Hz), 5.2–5.3(1H,m), 6.62(1H,dd,J=15.1, 0.97 Hz), 6.7–6.9(2H,m), 6.9–7.0(1H,m) MASS (EI method, m/e): 458 (M+)

Reference Example 33

16,16-dimethyl-15-oxo-20a-homo-2,5,6,7-tetranor-18-oxa-4,8-inter-m-phenylene PGI$_2$ methyl ester, 11-acetate (33)

In 15 ml of anhydrous THF, 1.0613 g (3.18 mmol) of 2α-acetoxy-1β-hydroxymethyl-3aβH,8bβH-2,3,3a,8b-tetrahydro-5-1H-cyclopenta[b]benzofuran acetic acid methyl ester was dissolved under argon atmosphere. To this stirred solution, 0.26 ml (3.18 mmol) of anhydrous pyridine, 5 ml of anhydrous DMSO and 0.12 ml (1.59 mmol) of trifluoro acetic acid and 994.1 mg (4.77 mmol) of D.C.C. were added. The resulting mixture was stirred for 2 hours and 40 minutes at room temperature. To the thus obtained mixture, 1.034 g (10.34 mmol) of calcium carbonate was added and the resultant was stirred for 15 minutes followed by being left to stand.

Then 190.8 mg (4.77 mmol) of sodium hydride (60% dispersion in mineral oil) was suspended in 20 ml of anhydrous THF. To this suspension, 1.35 g (4.77 mmol) of dimethyl 3,3-dimethyl-2-oxo-4-oxa-octylphosphonate in 5 ml of anhydrous THF was added under cooling in iced water and the resulting mixture was stirred for 30 minutes under argon atmosphere at room temperature. To the thus obtained reaction mixture, the supernatant of the previously obtained reaction mixture of aldehyde ester was added using a syringe. Further, the residue was washed with anhydrous THF (10 ml, 5 ml×2) and the supernatant obtained in the washing was added to the mixture. The reaction mixture was stirred for 10 minutes at room temperature. To the thus obtained mixture, 50 ml of saturated aqueous ammonium chloride solution was added and the resultant was extracted with ethyl acetate (30 ml 3). Then organic layers were combined, washed each once with 70 ml of water and 70 ml of brine, dried over anhydrous sodium sulfate (30 g) and concentrated. Then the thus obtained residue was purified by column chromatography (silica gel, eluant; ethyl acetate:cyclohexane=1:3) to obtain 1.4194 g (3.01 mmol) of 16,16-dimethyl-15-oxo-20a-homo-2,5,6,7-tetranor-18-oxa-4,8-inter-m-phenylene PGI$_2$ methyl ester, 11-acetate as a colorless oily product with a 95% yield.

The structure of this product was confirmed by the following data. IR (liquid film method): 2951, 2855, 1730, 1682, 1621, 1591, 1443, 1361, 1321, 1296, 1230, 1189, 1104, 1060, 1004, 980, 950, 889, 848, 743 cm$^{-1}$ NMR (400 MHz, CDCl$_3$, δ): 0.88(3H,t,J=7.3 Hz), 1.16(6H,s), 1.51–1.57(2H,m), 1.75(3H,s), 2.10–2.17(1H,m), 2.57–2.71(3H,m), 2.87–2.93(2H,m), 2.93–2.99(1H,m), 3.36(2H,t,J=6.3 Hz), 3.44(2H,brs), 3.67(3H,s), 3.65–3.69(1H,m), 4.95–5.01(1H,m), 5.22–5.28(1H,m), 6.62(1H,d,J=15.1 Hz), 6.76(1H,t,J=7.3 Hz), 6.81(1H,dd,J=8.3, 15.1 Hz), 6.96–7.01(2H,m) MASS (EI method, m/e): 472 (M+)

Reference Example 34

16-cyclopentyloxy-15-oxo-2,5,6,7,17,18,19,20-octanor-4,8-inter-m-phenylene PGI$_2$ methyl ester, 11-acetate (34)

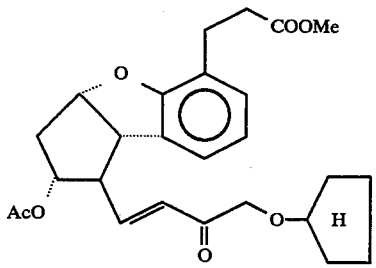 (34)

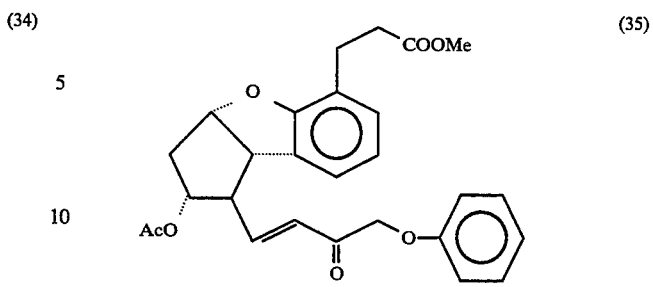 (35)

In 25 ml of anhydrous THF, 1.5 g (4.48 mmol) of 2α-acetoxy-1β-hydroxymethyl-3aβH,8bβH-2,3,3a,8b-tetrahydro-5-1H-cyclopenta[b]benzofuran propionic acid methyl ester was dissolved. To this stirred solution, 3.2 ml of anhydrous DMSO, 0.11 ml (1.39 mmol) of anhydrous pyridine, 0.097 ml (1.25 mmol) of trifluoro acetic acid and 1.39 g (6.72 mmol) of D.C.C. (dicyclohexylcarbodiimide) were added under argon atmosphere. The resulting mixture was stirred for 3 hours at room temperature. Then 249 mg (6.50 mmol) of sodium hydride (60% dispersion in mineral oil) was suspended in 10 ml of anhydrous THF. To this suspension, 1.68 g (6.72 mmol) of dimethyl 3-(cyclopentyloxy)-2-oxopropylphosphonate in 10 ml of anhydrous THF was added and the resulting mixture was stirred for 30 minutes at room temperature. To the thus obtained reaction mixture, the previously obtained reaction mixture of aldehyde ester was added at 0° C. and the resulting mixture was stirred for 30 minutes at room temperature. To the thus obtained reaction mixture, acetic acid was added to attain pH 6 and the resultant was concentrated. Ethyl acetate was added to the residue and the resultant was filtered. The filtrate was washed with water and brine. After drying and concentrating the resultant, the thus obtained mixture was passed through a short column of silica gel to remove solids. Further, the resultant was purified by column chromatography (Lobar column commercially available from Merck & Co., Inc., eluant; ethyl acetate:cyclohexane=1:4) to obtain 1.67 g of 16-cyclopentyloxy-15-oxo-2,5,6,7,17,18,19,20-octanor-4,8-inter-m-phenylene PGI$_2$ methyl ester, 11-acetate (yield 82%).

The structure of this product was confirmed by the following data. IR (liquid film method): 2950, 1730, 1690, 1620, 1600, 1450, 1370, 1240, 1110, 1065, 980, 850, 750 cm$^{-1}$ NMR (90 MHz, CDCl$_3$, δ): 1.4–1.9(8H,m), 1.77(3H,s), 2.0–2.3(1H,m), 2.4–3.1(6H,m), 3.6–3.8(1H,m), 3.67(3H,s), 3.8–4.1(1H,m), 4.14(2H,s), 5.00(1H,q,J=5.9 Hz), 5.1–5.4(1H,m), 6.47(1H,dd,J=0.7, 15.8 Hz), 6.7–7.1 (4H,m) MASS (EI method, m/e): 456 (M+)

Reference Example 35

16-phenoxy-15-oxo-2,5,6,7,17,18,19,20-octanor-4,8-inter-m-phenylene PGI$_2$ methyl ester, 11-acetate (35)

In 25 ml of anhydrous THF, 1.5 g (4.48 mmol) of 2α-acetoxy-1β-hydroxymethyl-3aβH,8bβH-2,3,3a,8b-tetrahydro-5-1H-cyclopenta[b]benzofuran propionic acid methyl ester was dissolved. To this stirred solution, 3.2 ml of anhydrous DMSO, 0.11 ml (1.39 mmol) of anhydrous pyridine, 0.097 ml (1.25 mmol) of trifluoro acetic acid and 1.39 g (6.72 mmol) of D.C.C. (dicyclohexylcarbodiimide) were added under argon atmosphere. The resulting mixture was stirred for 2 hours at room temperature. Then 249 mg (6.50 mmol) of sodium hydride (60% dispersion in mineral oil) was suspended in 10 ml of anhydrous THF. To this suspension, 1.74 g (6.72 mmol) of dimethyl 3-phenoxy-2-oxo-propylphosphonate in 10 ml of anhydrous THF was added and the resulting mixture was stirred for 30 minutes at room temperature. To the thus obtained reaction mixture, the previously obtained reaction mixture of aldehyde ester was added at 0° C. Then the resulting mixture was allowed to room temperature and the mixture was stirred for 30 minutes. To the thus obtained reaction mixture, acetic acid was added to attain pH 7 and the resultant was concentrated. Ethyl acetate was added to the residue and the resultant was filtered. The filtrate was washed with water and brine. After drying and concentrating the mixture, the thus obtained mixture was passed through a short column of silica gel to remove solids. Further, the resultant was purified by column chromatography (Lobar column commercially available from Merck Co., Inc., eluant; ethyl acetate:cyclohexane=1:3) to obtain 1.35 g of 16-phenoxy-15-oxo-2,5,6,7,17,18,19,20-octanor-4,8-inter-m-phenylene PGI$_2$ methyl ester, 11-acetate (yield 65%).

The structure of this product was confirmed by the following data. IR (liquid film method): 2950, 1730, 1620, 1600, 1490, 1450, 1365, 1300, 1260, 1060, 850, 750, 690 cm$^{-1}$ NMR (90 MHz, CDCl$_3$, δ): 1.76(3H,s), 2.09(1H,ddd,J=3.8, 6.5, 14.3 Hz), 2.5–3.1(6H,m), 3.5–3.8(1H,m), 3.67(3H,s), 4.71(2H,s), 4.98(1H,q,J=6.5 Hz), 5.1–5.4(1H,m), 6.54(1H,dd,J=0.7, 15.6 Hz), 6.7–7.5(9H,m) MASS (EI method, m/e): 464 (M+)

Reference Example 36

16-methyl-16-phenoxy-15-oxo-2,5,6,7,18,19,20-heptanor-4,8-inter-m-phenylene PGI$_2$ methyl ester, 11acetate (36)

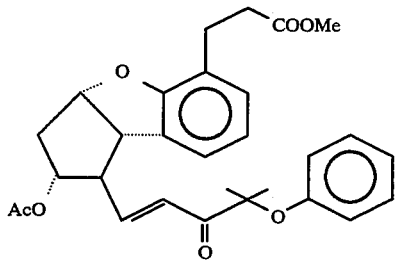

(36)

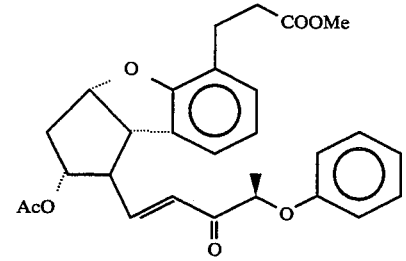

(37)

In 9 ml of anhydrous THF, 1.5 g (4.49 mmol) of 2α-acetoxy-1β-hydroxymethyl-3aβH,8bβH-2,3,3a,8b-tetrahydro-5-1H-cyclopenta[b]benzofuran propionic acid methyl ester was dissolved under argon atmosphere. To this stirred solution, 0.11 ml (1.36 mmol) of pyridine, 0.102 ml (1.32 mmol) of trifluoro acetic acid, 3.17 ml (44.6 mmol) of DMSO and 1.23 g (5.96 mmol) of D.C.C. were added. The resulting mixture was stirred for 2.5 hours at room temperature. Then 270 mg (6.74 mmol) of sodium hydride (60% dispersion in mineral oil) was suspended in 10 ml of anhydrous THF under argon atmosphere. To this suspension, 1.92 g (6.74 mmol) of dimethyl 3,3-dimethyl-3-phenoxy, 2-oxo-propylphosphonate in 5 ml of anhydrous THF was added dropwise under cooling in iced water and the resulting mixture was stirred for 30 minutes. To the thus obtained reaction mixture, the previously obtained reaction mixture of aldehyde ester was added under cooling in iced water and the resulting mixture was stirred for 30 minutes at 0° C. The thus obtained reaction mixture was neutralized with acetic acid. After filtering the mixture, the filtrate was concentrated. To the thus obtained residue, 20 ml of water was added and the resultant was extracted with ethyl acetate (50 ml×2). Ethyl acetate layers were washed each once with 20 ml of water and 10 ml of brine, dried over anhydrous sodium sulfate and concentrated. The thus residue was subjected to column chromatography (silica gel (60 g), eluant; ethyl acetate:cyclohexane=1:5), and then to column chromatography (Lobar column commercially available from Merck & Co., Inc., eluant; ethyl acetate:cyclohexane=1:6) to obtain 1.88 g (3.82 mmol) of 16-methyl-16-phenoxy-15-oxo-2,5,6,7,17,18,19,20-heptanor-4,8-inter-m-phenylene PGI$_2$ methyl ester, 11-acetate as a colorless oily product (yield 85.1%).

The structure of this product was confirmed by the following data. IR (liquid film method): 2970, 2920, 1725, 1690, 1620, 1590, 1480, 1440, 1370, 1230, 1150, 1060, 950, 880, 750, 690 cm$^{-1}$ NMR (100 MHz, CDCl$_3$, δ): 1.4–1.7(6H,m), 1.71(3H,s), 1.8–2.2(1H,m), 2.2–3.1(6H,m), 3.65(3H,s), 3.4–3.8(1H,m), 5.7–6.3(2H,m), 7.5–8.4(10H,m) MASS (EI method, m/e): 492 (M+)

Reference Example 37 d-16-(R)-methyl-16-phenoxy-15-oxo-2,5,6,7,17,18,19,20-octanor-4,8-inter-m-phenylene PGI$_2$ methyl ester, 11-acetate (37)

In 7 ml of anhydrous THF, 874 mg (2.62 mmol) of d-2α-acetoxy-1β-hydroxymethyl-3aβH,8bβH-2,3,3a,8b-tetrahydro-5-1H-cyclopenta[b]benzofuran propionic acid methyl ester was dissolved under argon atmosphere. To this stirred solution, 0.065 ml (0.81 mmol) of pyridine and 0.06 ml (0.79 mmol) of trifluoro acetic acid, 2.33 ml (32.8 mmol) of DMSO and 0.82 g (3.97 mmol) of D.C.C. were added. The resulting mixture was stirred for 3 hours at room temperature. Then 188 mg (4.7 mmol) of sodium hydride (60% dispersion in mineral oil) was suspended in 6 ml of anhydrous THF under argon atmosphere. To this suspension, 1.28 g (4.7 mmol) of dimethyl 3-(R)-methyl-3-phenoxy-2-oxo-propylphosphonate in 5 ml of anhydrous THF was added dropwise under cooling in iced water and the resulting mixture was stirred for 30 minutes. To the thus obtained reaction mixture, the previously obtained reaction mixture of aldehyde ester was added under cooling in iced water and the resulting mixture was stirred for an hour at room temperature. The thus obtained reaction mixture was neutralized with acetic acid. After filterring the mixture, the filtrate was concentrated. To the thus obtained residue, 30 ml of water was added and the resultant was extracted with ethyl acetate (100 ml×1). Ethyl acetate layers were washed each once with 30 ml of water and 30 ml of brine, dried over anhydrous sodium sulfate and concentrated. The thus obtained residue was subjected to column chromatography (silica gel (40 g), eluant; ethyl acetate:cyclohexane=1:7), and then to column chromatography (Lobar column commercially available from Merck & Co., Inc., eluant; ethyl acetate:cyclohexane=1:3) to obtain 806 mg (1.69 mmol) of d-16-(R)-methyl-16-phenoxy-15-oxo-2,5,6,7,17,18,19,20-octanor-4,8-inter-m-phenylene PGI$_2$ methyl ester, 11-acetato as a colorless oily product (yield 64.5%).

The structure of this product was confirmed by the following data. $[\alpha]_D^{20} = +219.4°$ (C=0.84, MeOH) IR (liquid film method): 3020, 2970, 2925, 1720, 1690, 1615, 1590, 1480, 1440, 1360, 1315, 1230, 1165, 1120, 1060, 980, 880, 860, 840, 790, 745, 690 cm$^{-1}$ NMR (400 MHz, CDCl$_3$, δ): 1.55(3H,d,J=6.7 Hz), 1.76(3H,s), 1.9–2.1(1H,m), 2.4–2.7(3H,m), 2.8–3.0(3H,m), 3.5–3.6(1H,m), 3.66(3H,s), 4.75(1H,q,J=7.0 Hz), 4.93(1H,q,J=6.7 Hz), 5.1–5.2(1H,m), 6.5–6.7(3H,m), 6.8–6.9(2H,m), 6.9–7.1(3H,m), 7.2–7.4(2H,m) MASS (EI method, m/e): 478 (M+)

Reference Example 38 d-16-(S)-methyl-16-phenoxy-15-oxo-2,5,6,7,17,18,19,20-octanor-4,8-inter-m-phenylene PGI$_2$ methyl ester, 11-acetate (38)

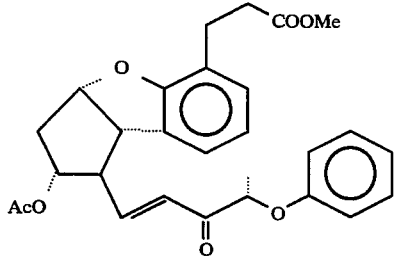

(38)

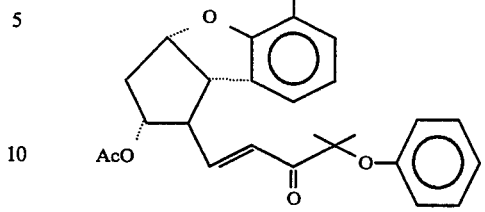

(39)

In 8 ml of anhydrous THF, 1.0 g (2.99 mmol) of d-2α-acetoxy-1β-hydroxymethyl-3aβH,8bβH-2,3,3a,8b-tetrahydro-5-1H-cyclopenta[b]benzofuran propionic acid methyl ester was dissolved under argon atmosphere. To this stirred solution, 0.073 ml (0.9 mmol) of pyridine and 0.067 ml (0.87 mmol) of trifluoro acetic acid, 2.12 ml (29.9 mmol) of DMSO and 0.8 g (3.9 mmol) of D.C.C. were added. The resulting mixture was stirred for 3 hours at room temperature. Then 192 mg (5.0 mmol) of sodium hydride (60% dispersion in mineral oil) was suspended in 7 ml of anhydrous THF under argon atmosphere. To this suspension, 1.36 g (5 mmol) of dimethyl 3-(S)-methyl-3-phenoxy-2-oxo-propylphosphonate in 5 ml of anhydrous THF was added dropwise under cooling in iced water and the resulting mixture was stirred for 30 minutes. To the thus obtained reaction mixture, the previously obtained reaction mixture of aldehyde ester was added under cooling in iced water and the resulting mixture was stirred for an hour at room temperature. The thus obtained reaction mixture was neutralized with acetic acid. The resultant was filtered and inorganic materials were washed with ethyl acetate (10 ml×5). These washes and the filtrate were combined and concentrated. To the thus obtained residue, 30 ml of water was added and the resultant was extracted with ethyl acetate (70 ml×1). Ethyl acetate layer was washed with water (30 ml×1) and brine (30 ml×1), dried over anhydrous sodium sulfate and concentrated. The thus obtained residue was subjected to column chromatography (silica gel, eluant; ethyl acetate:cyclohexane=1:5) to remove solids, and then to column chromatography (Lobar column commercially available from Merck & Co., Inc., eluant; ethyl acetate:cyclohexane=1:5) to obtain 885 mg (1.85 mmol) of d-16-(S)-methyl-16-phenoxy-15-oxo-2,5,6,7,17,18,19,20-octanor-4,8-inter-m-phenylene PGI$_2$ methyl ester, 11-acetate as a oily product (yield 61.8%).

The structure of this product was confirmed by the following data. $[\alpha]_D^{20} = +83.84$ (C=0.78, MeOH) IR (liquid film method): 2930, 1730, 1620, 1595, 1485, 1450, 1365, 1230, 1190, 1170, 1060, 980, 845, 800, 750, 690 cm$^{-1}$ NMR (400 MHz, CDCl$_3$, δ): 1.57(3H,d,J=6.8 Hz), 1.68(3H,s), 2.0–2.2(1H,m), 2.5–2.7(3H,m), 2.7–3.0(3H,m), 3.61(1H,t,J=7.6 Hz), 3.67(3H,s), 4.76(1H,q,J=6.8 Hz) 4.92(1H,q,J=6.5 Hz), 5.1–5.3(1H,m), 6.7–6.8(2H,m), 6.84(2H,d,J=7.8 Hz), 6.9–7.1(3H,m), 7.2–7.4(2H,m) MASS (EI method, m/e): 478 (M$^+$)

Reference Example 39 d-16-methyl-16-phenoxy-15-oxo-2,5,6,7,18,19,20-heptanor-4,8-inter-m-phenylene PGI$_2$ methyl ester, 11-acetate (39)

In 80 ml of anhydrous THF, 14.01 g (41.95 mmol) of d-2α-acetoxy-1β-hydroxymethyl-3aβH,8bβH-2,3,3a,8b-tetrahydro-5-1H-cyclopenta[b]benzofuran propionic acid methyl ester was dissolved under argon atmosphere. To this solution, 3.39 ml (41.95 mmol) of anhydrous pyridine, 40 ml of anhydrous DMSO, 1.62 ml (20.98 mmol) of trifluoro acetic acid and 12.98 g (62.92 mmol) of D.C.C. were added under argon atmosphere. The resulting mixture was stirred for 2.5 hours at room temperature. To the thus obtained reaction mixture, 13.65 g (136.34 mmol) of calcium carbonate was added and the resulting mixture was stirred for 30 minutes followed by being left to stand.

Then 2.52 g (62.92 mmol) of sodium hydride (60% dispersion in mineral oil) was suspended in 150 ml of anhydrous THF. To this suspension, 18.0 g (62.92 mmol) of dimethyl 3-methyl-3-phenoxy-2-oxo-butyl-phosphonate in 20 ml of anhydrous THF was added dropwise under cooling in iced water and under argon atmosphere, and the resulting mixture was stirred for 30 minutes at room temperature. To the thus obtained reaction mixture, the supernatant of the previously obtained reaction mixture of aldehyde ester was added using a syringe under cooling in iced water. The residue was washed with anhydrous THF (50 ml×4) and the supernatant obtained in the washing was added the mixture. After the thus obtained reaction mixture was stirred for 40 minutes at room temperature, 4.5 ml of acetic acid was added thereto and the mixture was concentrated. To the thus obtained residue, 200 ml of water was added and the resultant was extracted with ethyl acetate (200 ml×2, 100 ml×1). The organic layers were combined, washed with 400 ml of brine, dried over anhydrous sodium sulfate (40 g) and concentrated. The thus obtained residue was purified by column chromatography (silica gel, eluant; ethyl acetate:cyclohexane=1:5) to obtain 17.90 g (36.38 mmol) of d-16-methyl-16-phenoxy-15-oxo-2,5,6,7,18,19,20-heptanor-4,8-inter-m-phenylene PGI$_2$ methyl ester, 11-acetate as a colorless oily product (yield 86.7%).

The structure of this product was confirmed by the following data. $[\alpha]_D^{20} = +99.38°$ (C=0.974, MeOH) IR (liquid film method): 2980, 2940, 1730, 1693, 1622, 1592, 1484, 1444, 1370, 1321, 1294, 1235, 1193, 1150, 1060, 983, 950, 885, 860, 748, 694 cm$^{-1}$ NMR (400 MHz, CDCl$_3$, δ): 1.52(3H,s), 1.55(3H,s), 1.71(3H,s), 1.95–2.03(1H,m), 2.50–2.67(3H,m), 2.82–2.92(3H,m), 3.53–3.58(1H,m), 3.66(3H,s), 4.90–4.97(1H,m), 5.10–5.15(1H,m), 6.60–6.64(2H,m), 6.72–6.80(3H,m), 6.91–7.05(3H,m), 7.20–7.28(2H,m) MASS (EI method, m/e): 492 (M$^+$)

EXAMPLE 1

2,5,6,7-tetranor-4,8-inter-m-phenylene PGI$_2$ methyl ester (40) and 15-epimer thereof (41)

(40)

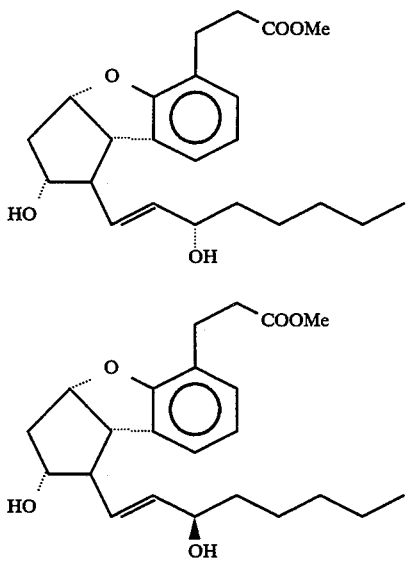

(41)

In 10 ml of methanol, 887 mg of 15-oxo-2,5,6,7-tetranor-4,8-inter-m-phenylene PGI$_2$ methyl ester, 11-acetate was dissolved and then 1.12 g of cerium chloride heptahydrate was dissolved. To this stirred solution, 91.2 mg of sodium borohydride was added under cooling in iced water, and the resulting mixture was stirred for 10 minutes. To the mixture, 10 ml of saturated aqueous sodium hydrogen carbonate solution was added. After concentrating the resulting mixture, 50 ml of water was added to the residue and the resultant was extracted each once with 50 ml, 40 ml and 30 ml of ethyl acetate. The organic layers were combined, washed each once with 100 ml of water and with 100 ml of brine, dried over anhydrous magnesium sulfate and concentrated to obtain 1.0729 g of an oily product. Then the thus obtained oily product was dissolved in 15 ml of anhydrous methanol. To this solution, 0.02 ml of 4.89N sodium methoxide was added and the resulting mixture was stirred under argon atmosphere at room temperature for 1.5 hours. The pH of the thus obtained reaction mixture was adjusted to 4 by adding 0.4 ml of acetic acid and the mixture was concetrated. To the residue, 20 ml of water was added and the resultant was extracted with ethyl acetate (20 ml×3). The organic layers were combined, washed with 40 ml each of saturated aqueous sodium hydrogen carbone solution, water and brine, dried over anhydrous magnesium sulfate, and concentrated to obtain 857 mg of an oily product. The thus obtained oily product was purified by Lobar column (Type B commercially available from Merck & Co., Inc., eluant; ethyl acetate:cyclohexane=6:1) to firstly obtain 409.1 mg (yield of 46.1%) of 15-epi-2,5,6,7-tetranor-4,8-inter-m-phenylene PGI$_2$ methyl ester having low polarity. Then 322.7 mg (yield of 36.4%) of 2,5,6,7-tetranor-4,8-inter-m-phenylene PGI$_2$ methyl ester was obtained from high polar fractions. The structures of these compounds were confirmed by the following data.

2,5,6,7-tetranor-4,8-inter-m-phenylene PGI$_2$ methyl ester m.p. 62°-64° (Recrystallization Solvent:ethyl acetate:n-hexane=1:5) IR (KBr method): 3350, 2925, 2855, 1735, 1593, 1444, 1342, 1250, 1190, 1078, 1028, 963, 884, 860, 830, 741 cm$^{-1}$ NMR (400 MHz, CDCl$_3$, δ): 0.88–0.93(3H,m), 1.28–1.65(10H,m), 1.95–2.02(1H,m), 2.40–2.46(1H,m), 2.60–2.70(3H,m), 2.83–2.92(2H,m), 3.44(1H,t,J=8.61 Hz), 3.66(3H,s), 3.89–3.95(1H,m), 4.09–4.15(1H,m), 5.08–5.15(1H,m), 5.56–5.67(2H,m), 6.76(1H,t,J=7.33 Hz), 6.95–6.98(2H,m) MASS (EI method, m/e): 388 (M+) High resolution mass spectrum Calcd. (C$_{23}$H$_{32}$O$_5$, M+): 388.2250 Found (M+): 388.2264

15-epi-2,5,6,7-tetranor-4,8-inter-m-phenylene PGI$_2$ methyl ester m.p. 58°-60° C. (Recrystallization Solvent:ethyl acetate:cyclohexane=1:3) IR (KBr method): 3325, 2920, 2955, 1732, 1595, 1445, 1419, 1360, 1259, 1205, 1179, 1159, 1090, 1064, 1044, 990, 965, 942, 890, 858, 849, 777, 760, 739, 655 cm$^{-1}$ NMR (400 MHz, CDCl$_3$, δ): 0.85–0.95(3H,m), 1.21–1.49(6H,m), 1.49–1.64(3H,m), 1.69–1.74(1H,m), 1.98–2.05(1H,m), 2.48–2.53(1H,m), 2.57–2.72(3H,m), 2.84–2.93(2H,m), 3.51(1H,t,J=8.06 Hz), 3.66(3H,s), 3.92–4.00(1H,m), 4.11–4.19(1H,m), 5.12–5.19(1H,m), 5.63–5.73(2H,m), 6.77(1H,t,J=7.33 Hz), 6.99(1H,d,J=7.33 Hz), 7.01(1H,d,J=7.33 Hz) MASS (EI method, m/e): 388 (M+) High resolution mass spectrum Calcd. (C$_{23}$H$_{32}$O$_5$, M+): 388.2250 Found (M+): 388.2223

EXAMPLE 2

2,5,6,7-tetranor-4,8-inter-m-phenylene PGI$_2$ (42)

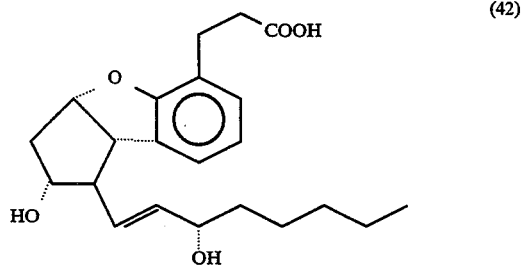

(42)

In 10 ml of methanol, 250 mg of 2,5,6,7-tetranor-4,8-inter-m-phenylene PGI$_2$ methyl ester was dissolved and then 3 ml of 1N sodium hydroxide was added thereto. The resulting mixture was stirred for 3 hours under argon atmosphere at room temperature. To thus obtained reaction mixture, 3.5 ml of 1N hydrochloric acid was added to attain pH2 and then 30 ml of water was added thereto followed by being extracted 3 times with 30 ml of ethyl acetate. The organic layers were combined, washed with water (50 ml×2) and with brine (50 ml×1), dried over anhydrous magnesium sulfate and concentrated to obtain 233.1 mg of the captioned compound as a pure product (yield 100%).

The structure of this product was confirmed by the following data. m.p. 107°-108° C. (Recrystallization Solvent:ethyl acetate:cyclohexane=6:1) IR (KBr method): 3458, 3350(3625–2100), 2910, 2840, 1690, 1595, 1450, 1410, 1330, 1310, 1280, 1244, 1183, 1144, 1080, 1064, 1028, 960, 943, 910, 860, 780, 740, 720, 642, 615 cm$^{-1}$ NMR (400 MHz, CDCl$_3$, δ): 0.86–0.94(3H,m), 1.24–1.67(10H,m), 1.92–2.01(1H,m), 2.36–2.42(1H,m), 2.59–2.74(3H,m), 2.81–2.95(2H,m), 3.41(1H,t,J=8.42 Hz), 3.85–3.93(1H,m), 4.07–4.14(1H,m), 5.06–5.13(1H,m), 5.51–5.64(2H,m), 6.75(1H,t,J=7.33 Hz), 6.94(1H,d,J=7.33 Hz), 6.98(1H,d,J=7.33 Hz) MASS (EI method, m/e): 374 (M+) High resolution mass spectrum Calcd. (C$_{22}$H$_{30}$O$_5$, M+): 374.2093 Found (M+): 374.2082

EXAMPLE 3

20a-homo-2,5,6,7-tetranor-4,8-inter-m-phenylene PGI$_2$ methyl ester (43) and 15-epimer thereof (44)

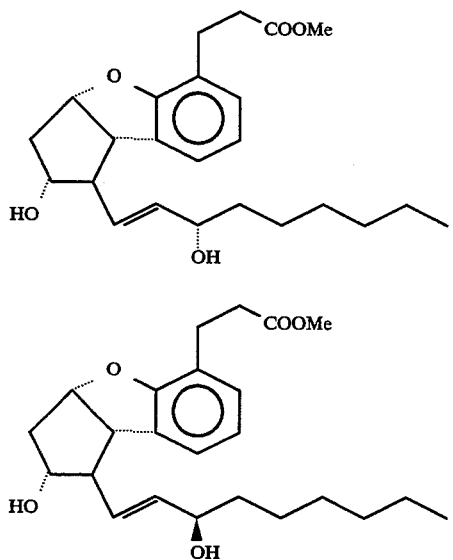

In 10 ml of methanol, 1.00 g of 15-oxo-20a-homo-2,5,6,7-tetranor-4,8-inter-m-phenylene PGI$_2$ methyl ester, 11-acetate was dissolved and then 1.27 g of cerium chloride heptahydrate was added thereto. To this stirred mixture, 85.7 mg of sodium borohydride was added under cooling in iced water and the resulting mixture was stirred for 20 minutes. To the mixture, 10 ml of saturated aqueous sodium hydrogen carbonate solution was added and the resulting mixture was concentrated. To the residue, 50 ml of water was added and the resultant was extracted with ethyl acetate (50 ml×3). The organic layers were combined, washed with water and with brine, dried over anhydrous magnesium sulfate and concentrated to obtain 997 mg of an oily product. Then the thus obtained oily product was dissolved in 10 ml of anhydrous methanol. To this solution, 92 ul of 4.89N sodium methoxide was added and the resulting mixture was stirred under argon atmosphere at room temperature for 1.5 hours. The pH of the thus obtained reaction mixture was adjusted to 7 by adding acetic acid and the mixture was concetrated. To the residue, 50 ml of water was added and the resultant was extracted with ethyl acetate (50 ml×3). The organic layers were combined, washed with saturated aqueous sodium hydrogen carbone solution, water and brine, dried over anhydrous sodium sulfate, and concentrated to obtain 948 mg of an oily product. The thus obtained oily product was purified by column chromarography (Lobar column Type B commercially available from Merck & Co., Inc., eluant; ethyl acetate:cyclohexane=6:1) to firstly obtain 440 mg (yield 49%) of 15-epi-20a-homo-2,5,6,7-tetranor-4,8-inter-m-phenylene PGI$_2$ methyl ester having low polarity. Then 339 mg (yield 38%) of 20a-homo-2,5,6,7-tetranor-4,8-inter-m-phenylene PGI$_2$ methyl ester was obtained from high polar fractions.

The structures of these compounds were confirmed by the following data.

20a-homo-2,5,6,7-tetranor-4,8-inter-m-phenylene PGI$_2$ methyl ester m.p. 58.0°–59.5° C. (Recrystallization Solvent:ethyl acetate:n-hexane=1:7) IR (KBr method): 3340, 3060, 3020, 2960, 2930, 2870, 1738, 1677, 1597, 1445, 1362, 1320, 1300, 1278, 1265, 1245, 1200, 1160, 1140, 1130, 1090, 1078, 1060, 1045, 1038, 1030, 985, 948, 925, 885, 860, 840, 780, 760, 745, 730, 620, 535, 500 cm$^{-1}$ NMR (400 MHz, CDCl$_3$, δ): 0.90(3H,bS), 1.24–1.45(8H,m), 1.46–1.66(2H,m), 1.94–2.03(1H,m), 2.44(1H,dd,J=15.6 Hz, 7.8 Hz), 2.58–2.70(3H,m), 2.85–2.94(2H,m), 3.44(1H,t,J=8.5 Hz), 3.66(3H,S), 3.93(1H,dd,J=7.8 Hz, 2.4 Hz), 4.12(1H,dd,J=7.8 Hz, 2.0 Hz), 5.09–5.20(1H,m), 5.55–5.70(2H,m), 6.76(1H,t,J=7.5 Hz), 6.92–7.02(2H,m) MASS (EI method, m/e): 402 (M+) High resolution mass spectrum Calcd. (C$_{24}$H$_{34}$O$_5$, M+): 402.2406 Found (M+): 402.2423

15-epi-20a-homo-2,5,6,7-tetranor-4,8-inter-m-phenylene PGI$_2$ methyl ester m.p. 66.0°–67.0° C. (Recrystallization Solvent:ethyl acetate:cyclohexane=1:5) IR (KBr method): 3330, 2950, 2920, 2850, 1730, 1600, 1445, 1420, 1360, 1350, 1330, 1260, 1240, 1220, 1205, 1180, 1160, 1095, 1065, 1045, 1035, 995, 965, 945, 930, 910, 895, 860, 840, 780, 760, 740, 660, 560, 520, 495 cm$^{-1}$ NMR (400 MHz, CDCl$_3$, δ): 0.89(3H,bS), 1.22–1.50(8H,m), 1.50–1.62(2H,m), 1.98–2.05(1H,m), 2.48–2.58(1H,m), 2.56–2.73(3H,m), 2.84–2.96(2H,m), 3.50(1H,t,J=8.3 Hz), 3.66(3H,S), 3.96(1H,dd,J=13.9 Hz, 7.6 Hz), 4.12–4.20(1H,m), 5.12–5.19(1H,m), 5.64–5.76(2H,m), 6.76(1H,t,J=7.3 Hz), 6.95–7.05(2H,m) MASS (EI method, m/e): 402 (M+) High resolution mass spectrum Calcd. (C$_{24}$H$_{34}$O$_5$, M+): 402.2406 Found (M+): 402.2436

EXAMPLE 4

20a-homo-2,5,6,7-tetranor-4,8-inter-m-phenylene PGI$_2$ (45)

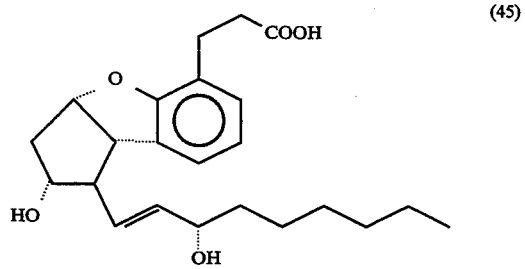

In 5 ml of methanol, 197 mg of 20a-homo-2,5,6,7-tetranor-4,8-inter-m-phenylene PGI$_2$ methyl ester was dissolved and then 2.4 ml of 1N sodium hydroxide was added thereto and the resulting mixture was stirred overnight at room temperature. To thus obtained reaction mixture, 1N hydrochloric acid was added to attain pH4 and then 30 ml of water was added thereto followed by being extracted with ethyl acetate (30 ml×3). The organic layers were combined, washed with water and brine, dried over anhydrous sodium sulfate and concentrated to obtain 188 mg of 20a-homo-2,5,6,7-tetranor-4,8-inter-m-phenylene PGI$_2$ as a pure product (yield 99%).

The structure of this product was confirmed by the following data. m.p. 151.0°–153.0° C. (Recrystallization Solvent:ethyl acetate) IR (KBr method): 3480, 3380, 2930, 2860, 1690, 1610, 1460, 1420, 1340, 1320, 1300, 1290, 1270, 1250, 1190, 1150, 1085, 1070, 1050, 1040, 1000, 960, 945, 860, 780, 725, 650, 630 cm$^{-1}$ NMR (400

MHz, CDCl₃, δ): 0.84–0.96(3H,bS), 1.20–1.43(8H,m), 1.43–1.55(1H,m), 1.55–1.66(1H,m), 1.91–2.02(1H,m), 2.37(1H,dd,J=16.4 Hz, 8.1 Hz), 2.57–2.74(3H,m), 2.78–3.00(2H,m), 3.39(1H,t,J=8.6 Hz), 3.87(1H,dd,J=8.3 Hz, 2.4 Hz), 4.08(1H,dd,J=13.2 Hz, 6.8 Hz), 5.05–5.13(1H,m), 5.49–5.65(2H,m), 6.75(1H,t,J=7.5 Hz), 6.93(1H,d,J=7.3 Hz), 6.97(1H,d,J=7.3 Hz) MASS (EI method, m/e): 388 (M+) High resolution mass spectrum Calcd. (C₂₃H₃₂O₅, M+): 388.2249 Found (M+): 338.2246

EXAMPLE 5

16,16-dimethyl-2,5,6,7-tetranor-4,8-inter-m-phenylene PGI₂ methyl ester (46) and 15-epimer thereof (47)

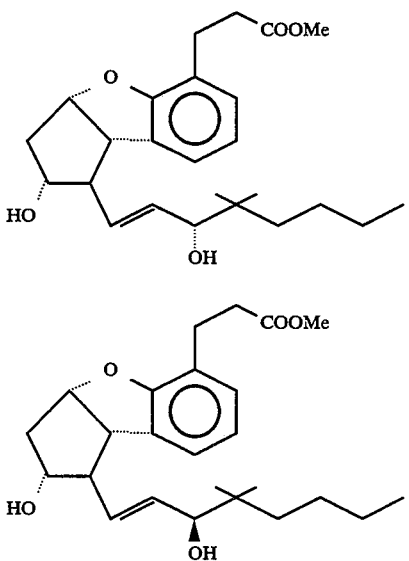

In 20 ml of methanol, 1.1576 g of 16,16-dimethyl-15-oxo-2,5,6,7-tetranor-4,8-inter-m-phenylene PGI₂ methyl ester, 11-acetate was dissolved and then 1.47 g of cerium chloride heptahydrate was dissolve therein. To this stirred mixture, 133 mg of sodium borohydride was added under cooling in iced water and the mixture was stirred for 20 minutes. After concentrating the thus obtained reaction mixture, 50 ml of water was added thereto. The resultant was extracted with ethyl acetate (50 ml×3). The organic layers were combined, washed once with 100 ml each of water and brine, dried over anhydrous magnesium sulfate and concentrated. To the thus obtained residue, 15 ml of anhydrous methanol and 0.021 ml of 4.89N sodium methoxide were added and the resulting mixture was stirred for 3 hours at room temperature. To the thus obtained reaction mixture, 0.1 ml of acetic acid was added and the resultant was concentrated. To the thus obtained residue, 25 ml of water was added and the resultant was extracted with ethyl acetate (20 ml×3). The organic layers were combined, washed once with 50 ml each of water and brine, dried over anhydrous magnesium sulfate and concentrated to obtain 1.2653 g of an oily product. The thus obtained oily product was purified by column chromarography (Lobar column Type B commercially available from Merck & Co., Inc., eluant; ethyl acetate:cyclohexane=6:1) to firstly obtain 452.6 mg (yield 42.8%) of 16,16-dimethyl-15-epi-2,5,6,7-tetranor-4,8-inter-m-phenylene PGI₂ methyl ester having low polarity. Then 468.5 mg (yield 44.3%) of 16,16-dimethyl-2,5,6,7-tetranor-4,8-inter-m-phenylene PGI₂ methyl ester was obtained from high polar fractions.

The structures of these compounds were confirmed by the following data.

16,16-dimethyl-2,5,6,7-tetranor-4,8-inter-m-phynylene PGI₂ methyl ester m.p. 67°–68° C. (Recrystallization Solvent:ethyl acetate:n-hexane=1:12) IR (KBr method): 3360, 2950, 2867, 1735, 1597, 1450, 1370, 1330, 1300, 1270, 1222, 1190, 1175, 1150, 1100, 1072, 1032, 1013, 990, 970, 881, 859, 830, 743, 618 cm⁻¹ NMR (400 MHz, CDCl₃, δ): 0.89–0.94(3H,m), 0.87(3H,s), 0.90(3H,s), 1.17–1.38(6H,m), 1.76–1.82(1H,m), 1.96–2.03(1H,m), 2.25–2.32(1H,m), 2.44–2.49(1H,m), 2.61–2.69(3H,m), 2.85–2.93(2H,m), 3.46(1H,t,J=8.61 Hz), 3.66(3H,s), 3.84–3.89(1H,m), 3.90–3.98(1H,m), 5.09–5.18(1H,m), 5.61–5.73(2H,m), 6.76(1H,t,J=7.33 Hz), 6.96–6.99(2H,m) MASS (EI method, m/e): 416 (M+) High resolution mass spectrum Calcd. (C₂₅H₃₆O₅, M+): 416.2563 Found (M+): 416.2579

16,16-dimethyl-15-epi-2,5,6,7-tetranor-4.8-inter-m-phynylene PGI₂ methyl ester m.p. 105° C. (Recrystallization Solvent:ethyl acetate:n-hexane=1:3) IR (KBr method): 3415, 2940, 2852, 1735, 1624, 1598, 1448, 1440, 1361, 1342, 1303, 1270, 1244, 1230, 1184, 1150, 1061, 1020, 983, 955, 882, 863, 806, 760, 740, 620 cm⁻¹ NMR (400 MHz, CDCl₃, δ): 0.88–0.96(3H,m), 0.88(3H,S), 0.91(3H,S), 1.18–1.38(6H,m), 1.48–1.53(1H,m), 1.66–1.74(1H,m), 1.99–2.05(1H,m), 2.51–2.56(1H,m), 2.59–2.67(3H,m), 2.87–2.91(2H,m), 3.52(1H,t,J=8.24 Hz), 3.66(3H,S), 3.88–3.90(1H,m), 3.93–4.00(1H,m), 5.14–5.19(1H,m), 5.65–5.77(2H,m), 6.77(1H,t,J=7.33 Hz), 6.98(1H,d,J=7.33 Hz), 7.01(1H,d,J=7.33 Hz) MASS (EI method, m/e): 416 (M+) High resolution mass spectrum Calcd. (C₂₅H₃₆O₅, M+): 416.2563 Found (M+): 416.2553

EXAMPLE 6

16,16-dimethyl-2,5,6,7-tetranor-4,8-inter-m-phenylene PGI₂ (48)

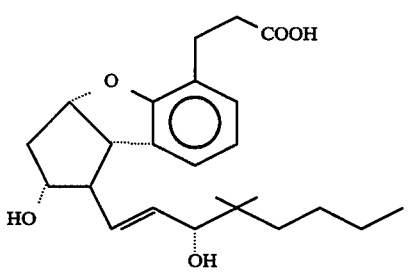

In 10 ml of methanol, 301.2 mg of 16,16-dimethyl-2,5,6,7-tetranor-4,8-inter-m-phenylene PGI₂ methyl ester was dissolved and then 3.8 ml of 1N sodium hydroxide was added thereto and the resulting mixture was stirred for 2.5 hours at room temperature. The thus obtained reaction mixture was concentrated. To the residue, 10 ml of water was added and then 3.8 ml of 1N hydrochloric acid was added thereto. The resultant was extracted with ethyl acetate (10 ml×3). The organic layers were combined, washed once with 20 ml of each water and with brine, dried over anhydrous magnesium sulfate and concentrated to obtain 207.2 mg of the captioned compound as a pure product (yield 93.3%).

The structure of this product was confirmed by the following data. m.p. 148°–148.5° C. (Recrystallization Solvent:acetone:n-hexane=5:2) IR (KBr method): 3410 (36.75–2200), 2960, 2930, 2860, 1700, 1595, 1455, 1420, 1375, 1298, 1267, 1248, 1204, 1105, 1065, 1015, 990, 960, 918, 848, 823, 804, 785, 765, 743 cm$^{-1}$ NMR (400 MHz, CDCl$_3$-10% DMSO-d$_6$, δ): 0.90–0.94(3H,m), 0.86(3H,s), 0.90(3H,s), 1.17–1.40(6H,m), 1.88–1.97(1H,m), 2.30–2.37(1H,m), 2.56–2.72(4H,m), 2.83–2.92(2H,m), 3.39(1H,t,J=9.16 Hz), 3.78–4.04(3H,m), 5.06–5.12(1H,m), 5.56–5.69(2H,m), 6.76(1H,t,J=7.33 Hz), 6.93(1H,d,J=7.33 Hz), 6.99(1H,d,J=7.33 Hz) MASS (EI method, m/e): 402 (M+) High resolution mass spectrum Calcd. (C$_{24}$H$_{34}$O$_5$, M+): 402.2406 Found (M+): 402.2401

EXAMPLE 7

16-methyl-2,5,6,7-tetranor-4,8-inter-m-phenylene PGI$_2$ methyl ester (49) and 15-epimer thereof (50)

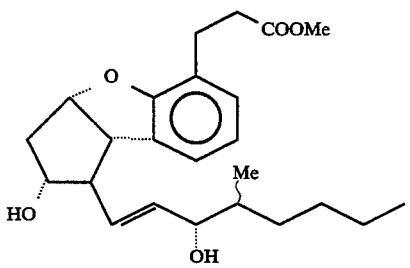
(49)

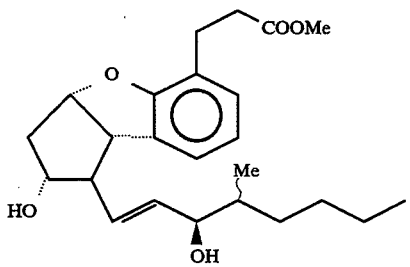
(50)

In 50 ml of methanol, 965 mg (2.18 mmol) of 16-methyl-15-oxo-2,5,6,7-tetranor-4,8-inter-m-phenylene PGI$_2$ methyl ester, 11-acetate was dissolved and then 815 mg (2.8 mmol) of cerium chloride heptahydrate was added. To this stirred mixture, 124 mg (3.28 mmol) of sodium borohydride was added under cooling in iced water and the resulting mixture was concentrated. To the thus obtained reaction mixture, 30 ml of water was added and then 100 ml of ethyl acetate was added thereto. The mixture was filtered and the precipitate was washed with ethyl acetate (30 ml×3). The organic layers were combined, washed once with 30 ml each of water and brine, dried over anhydrous sodium sulfate and concentrated to obtain 960 mg of an oily product. Then 960 mg of the thus obtained oily product was dissolved in 25 ml of anhydrous methanol. To this solution, 0.414 ml (2.16 mmol) of 5.22N sodium methoxide was added and the resulting mixture was stirred for 3 hours at room temperature. To the thus obtained reaction mixture, 0.05 ml of acetic acid was added and the resultant was concentrated. To the thus obtained residue, 20 ml of water was added and the resultant was extracted with ethyl acetate (50 ml x×2). The organic layers were combined, washed once with 20 ml each of water and brine, dried over anhydrous sodium sulfate and concentrated. The thus obtained residue was purified by column chromatography (Lobar column Type B commercially available from Merck & Co., Inc., eluant; ethyl acetate:cyclohexane=2:1) to firstly obtain 376 mg (yield 43.3%) of 16-methyl-15-epi-2,5,6,7-tetranor-4,8-inter-m-phenylene PGI$_2$ methyl ester having low polarity. Then 330 mg (yield 38%) of 16-methyl-2,5,6,7-tetranor-4,8-inter-m-phenylene PGI$_2$ methyl ester was obtained from high polar fractions.

The structures of these compounds were confirmed by the following data.

16-methyl-15-epi-2,5,6,7-tetranor-4,8-inter-m-phynylene PGI$_2$ methyl ester m.p. 84.8°–86.0° C. (Recrystallization Solvent:ethyl acetate:n-hexane=2:1) IR (KBr method): 3350, 2975, 2930, 1735, 1600, 1450, 1370, 1345, 1330, 1295, 1250, 1190, 1150, 1095, 1085, 1010, 960, 860, 750 cm$^{-1}$ NMR (400 MHz, CDCl$_3$, δ): 0.85–1.0(6H,m), 1.05–1.8(9H,m), 2.02(1H,ddd,J=5.0, 8.4, 3.6 Hz), 2.52(1H,q,J=8.1 Hz), 2.6–2.7(3H,m), 2.85–2.95(2H,m), 3.51(1H,t,J=8.1 Hz), 3.66(3H,S), 3.9–4.1(2H,m), 5.16(1H,ddd,J=5.0, 7.0, 8.1 Hz), 5.6–5.75(2H,m), 6.77(1H,t,J=7.3 Hz), 6.98(1H,d,J=7.3 Hz), 7.01(1H,d,J=7.3 Hz) MASS (EI method, m/e): 402 (M+) Element Analysis Calcd. (C$_{24}$H$_{34}$O$_5$) C71.61 H8.51 Found 71.68 8.65

16-methyl-2,5,6,7-tetranor-4,8-inter-m-phynylene PGI$_2$ methyl ester m.p. 87.9°–89.5° C. (Recrystallization Solvent:ethyl acetate:n-hexane=2:1) IR (KBr method): 3370, 2960, 2920, 1730, 1590, 1440, 1360, 1290, 1185, 1060, 1030, 995, 960, 880, 850, 740 cm$^{-1}$ NMR (400 MHz, CDCl$_3$, δ): 0.85–1.0(6H,m), 1.05–1.7(7H,m), 1.75–1.9(1H,m), 1.99(1H,ddd,J=5.0, 8.6, 13.6 Hz), 2.2–2.25(1H,m), 2.47(1H,q,J=8.4 Hz), 2.6–2.7(2H,m), 2.85–2.95(2H,m), 3.46(1H,t,J=8.4 Hz), 3.66(3H,s), 3.9–4.05(2H,m), 5.13(1H,ddd,J=5.0, 7.3, 8.4 Hz) MASS (EI method, m/e): 402 (M+) Element Analysis Calcd. (C$_{24}$H$_{34}$O$_5$) C71.61 H8.51 Found 71.53 8.63

EXAMPLE 8

16-methyl-2,5,6,7-tetranor-4,8-inter-m-phenylene PGI$_2$ (51)

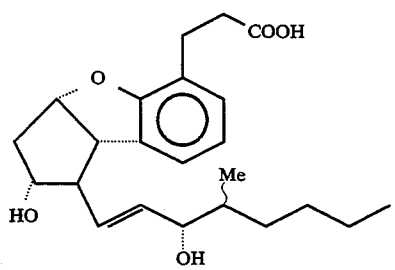
(51)

In 25 ml of methanol, 242 mg (0.602 mmol) of 16-methyl-2,5,6,7-tetranor-4,8-inter-m-phenylene PGI$_2$ methyl ester was dissolved and then 5.5 ml (5.42 mmol) of 0.986N sodium hydroxide was added thereto under cooling in iced water. The resulting mixture was stirred for 5 hours at room temperature. To thus obtained reaction mixture, 5.5 ml (5.5 mmol) of 1N hydrochloric acid was added and the resulting mixture was concentrated. To the thus obtained residue, 20 ml of water was added and the resultant was extracted with ethyl acetate (50 ml×2). The organic layers were combined, washed once with 10 ml each of water and brine, dried over anhydrous sodium sulfate and concentrated. The thus obtained residue was recrystallized from 15 ml of ethyl acetate and from 0.5 ml of n-hexane to obtain 180 mg of the captioned product (yield 77%).

The structure of this product was confirmed by the following data. m.p. 122.1°–123.0° C. (Recrystallization Solvent:ethyl acetate:n-hexane=3:1) IR (KBr method): 3460, 2960, 2930, 2860, 1700, 1595, 1455, 1420, 1370, 1300, 1265, 1200, 1070, 1020, 985, 970, 920, 855, 745 cm$^{-1}$ NMR (400 MHz, CDCl$_3$, δ): 0.85–1.0(6H,m), 1.05–1.7(7H,m), 1.97(1H,ddd,J=5.1, 8.8, 13.9 Hz), 2.41(1H,q,J=8.4 Hz), 2.55–2.75(3H,m), 2.8–3.0(2H,m), 3.42(1H,t,J=8.4 Hz), 3.85–4.0(2H,m), 3.0–5.0(2H,m), 5.11(1H,ddd,J=5.1, 7.3, 8.4 Hz), 5.55–5.7(2H,m), 6.75(1H,t,J=7.3 Hz), 6.95(1H,d,J=7.3 Hz), 6.98(1H,d,J=7.3 Hz) MASS (EI method, m/e): 388 (M+) Element Analysis Calcd. (C$_{23}$H$_{32}$O$_5$) C71.10 H8.30 Found 71.02 8.43

EXAMPLE 9

16-methyl-15-epi-2,5,6,7-tetranor-4,8-inter-m-phenylene PGI$_2$ (52)

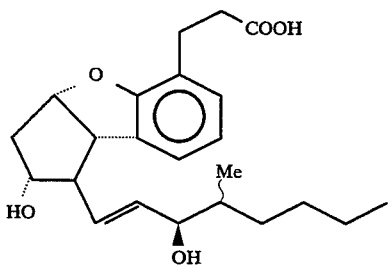

In 2.0 ml of methanol, 290 mg (0.72 mmol) of 16-methyl-15-epi-2,5,6,7-tetranor-4,8-inter-m-phenylene PGI$_2$ methyl ester was dissolved and then 5.9 ml (5.8 mmol) of 0.986N sodium hydroxide was added thereto under cooling in iced water, and the resulting mixture was stirred for 5 hours at room temperature. To thus obtained reaction mixture, 5.8 ml (5.8 mmol) of 1N hydrochloric acid was added and the resulting mixture was concentrated. To the thus obtained residue, 20 ml of water was added and the resultant was extracted with ethyl acetate (50 ml×2). The organic layers were combined, washed once with 10 ml each of water and brine, dried over anhydrous sodium sulfate and concentrated. The thus obtained residue was recrystallized from 1.5 ml of ethyl acetate and from 0.5 ml of n-hexane to obtain 228 mg of the captioned compound (yield 81.6%).

The structure of this product was confirmed by the following data. m.p. 97.4°–98.1° C. (Recrystallization Solvent:ethyl acetate:n-hexane=3:1) IR (KBr method): 3400, 2960, 2930, 1715, 1695, 1600, 1450, 1400, 1375, 1350, 1315, 1290, 1260, 1230, 1200, 1190, 1155, 1090, 1080, 1040, 1000, 970, 860, 835, 785, 770, 740 cm$^{-1}$ NMR (400 MHz, CDCl$_3$, δ): 0.85–1.0(6H,m), 1.05–1.7(7H,m), 2.00(1H,ddd,J=5.0, 8.1, 13.7 Hz), 2.50(1H,q,J=8.1 Hz), 2.60(1H,dt,J=6.7, 13.7 Hz), 2.6–2.75(2H,m), 2.85–2.95(2H,m), 3.48(1H,t,J=8.1 Hz), 3.95(1H,m), 4.0–4.1(1H,m), 3.5–5.0(2H,m), 5.14(1H,ddd,J=5.0, 6.7, 8.1 Hz), 5.6–5.75(2H,m), 6.76(1H,t,J=7.3 Hz), 6.95–7.05(2H,m) MASS (EI method, m/e): 388 (M+) Element Analysis Calcd. (C$_{23}$H$_{32}$O$_5$) C71.10 H8.30 Found 71.02 8.43

EXAMPLE 10

17-(S)-methyl-2,5,6,7-tetranor-4,8-inter-m-phenylene PGI$_2$ methyl ester (53)

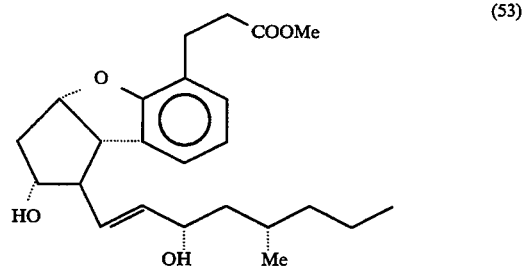

In 44 ml of methanol, 17-(S)-methyl-15-oxo-2,5,6,7-tetranor-4,8-inter-m-phenylene PGI$_2$ methyl ester, 11-acetate was dissolved and then 1.3 g of cerium chloride heptahydrate was added thereto. To the stirred mixture, 125 mg of sodium borohydride was added under cooling in iced water and the resulting mixture was stirred for 10 minutes. Saturated aqueous sodium hydrogen carbonate solution was added to the thus obtained reaction mixture and the resulting mixture was concentrated. To the residue, 20 ml of ethyl acetate was added and the resultant was filtered. The filtrate was separated and water layer was extracted each once with 20 ml, 10 ml and 5 ml of ethyl acetate. The organic layers were combined, washed each once with 10 ml of water and 5 ml of brine, dried over and concentrated to obtain 1.3 g of an oily product. The thus obtained oily product was subjected to azeotropic distillation with benzene 3 times. The residue was dissolved in 48 ml of anhydrous methanol. To this solution, 0.144 ml of 5.22N sodium methoxide was added and the resulting mixture was stirred for 3.5 hours under argon atmosphere at room temperature. The pH of the thus obtained reaction mixture was adjusted to 7 by adding acetic acid and the mixture was concetrated. To the residue, 50 ml of ethyl acetate was added and the resultant was washed once with 5 ml each of water and brine, dried over and concentrated to obtain 1.2 g of diol. The thus obtained diol was purified by column chromarography (Lobar column Type B commercially available from Merck & Co., Inc., eluant; ethyl acetate:cyclohexane=3:1) to obtain 240 mg of the captioned product.

The structure of this compound was confirmed by the following data. [α]$_D^{23}$= +67.73° (C=3.36, CHCl$_3$) IR (liquid film method): 3350, 2950, 2920, 2860, 1740, 1595, 1440, 1360, 1295, 1250, 1190, 1160, 965, 925, 885, 860, 835, 745 cm$^{-1}$ NMR (400 MHz, CDCl$_3$, δ): 0.90(6H,m), 1.15(1H,m), 1.20–1.60(6H,m), 1.90(1H,m), 2.35(1H,q,J=8.3 Hz), 2.65(2H,m), 2.88(1H,t,J=7.0 Hz), 3.40(1H,t,J=8.8 Hz), 3.65(3H,s), 3.88(1H,dd,J=14.1 Hz, 6.8 Hz), 4.20(1H,dd,J=15.6 Hz, 1.0 Hz), 5.08(1H,m), 5.52(1H,dd,J=15.1 Hz, 7.3 Hz), 5.60(1H,dd,J=15.1 Hz, 8.3 Hz), 6.73(1H,t,J=7.3 Hz), 6.92(1H,d,J=7.3 Hz), 6.97(1H,d,J=7.3 Hz) MASS (EI method, m/e): 402 (M+)

EXAMPLE 11

17-(S)-methyl-2,5,6,7-tetranor-4,8-inter-m-phenylene PGI$_2$ (54)

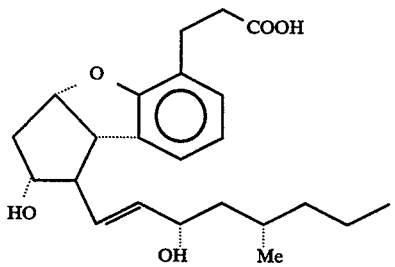

(54)

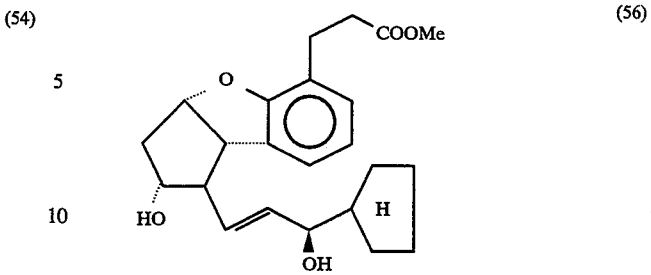

In 17 ml of methanol, 160 mg of 17-(S)-methyl-2,5,6,7-tetranor-4,8-inter-m-phenylene PGI$_2$ methyl ester was dissolved and then 4.45 ml of 1N sodium hydroxide was added thereto and the resulting mixture was stirred for 18 hours under argon atmosphere at room temperature. The thus obtained reaction mixture was concentrated and the residue was cooled down in iced water. To the residue, 4.45 ml of 1N hydrochloric acid was added to attain pH4 and then the resultant was extracted 3 times with ethyl acetate. The organic layers were combined, washed once with 5 ml each of water and brine, dried over and concentrated to obtain 120 mg of the captioned compound. This compound was recrystallized from ethylacetate-n-hexane to 90 mg of pure compound.

The structure of this product was confirmed by the following data. $[\alpha]_D^{23} = +72.88°$ (C=2.32, CHCl$_3$) m.p. 61°-63° C. IR (KBr method): 3650-2200, 1705, 1595, 1450, 1420, 1345, 1305, 1270, 1205, 1150, 1080, 1025, 975, 950, 925, 862, 745 cm$^{-1}$ NMR (400 MHz, CDCl$_3$, δ): 1.90(6H,m), 1.15(1H,m), 1.20-1.55(6H,m), 1.90(1H,m), 2.30(1H,q,J=8.3 Hz), 2.62(3H,m), 2.85(2H,m), 3.35(1H,t,J=8.8 Hz), 3.83(1H,dd,J=15.2 Hz, 6.4 Hz), 4.17(1H,dd,J=14.2 Hz, 6.9 Hz), 5.04(1H,m), 5.45(1H,dd,J=15.1, 7.3 Hz), 5.55(1H,dd,J=15.1 Hz, 8.8 Hz), 6.71(1H,t,J=7.3 Hz), 6.86(1H,d,J=7.3 Hz), 6.90(1H,d,J=7.3 Hz) MASS (EI method, m/e): 388 (M+) High resolution mass spectrum Calcd. (C$_{23}$M$_{32}$O$_5$, M+): 388.2250 Found (M+): 388.2240

EXAMPLE 12

15-cyclopentyl-2,5,6,7,16,17,18,19,20-nonanor-4,8-inter-m-phenylene PGI$_2$ methyl ester (55) and 15-epimer thereof (56)

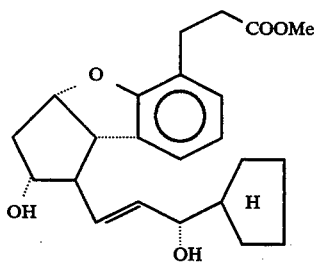

In 10 ml of methanol, 1.10 g of 15-cyclopentyl-15-oxo-2,5,6,7,16,17,18,18,20-nonanor-4,8-inter-m-phenylene PGI$_2$ methyl ester, 11-acetate was dissolved and then 1.45 g of cerium chloride heptahydrate was added. To the stirred mixture, 98.0 mg of sodium borohydride was added under cooling in iced water, and the resulting mixture was stirred for 15 minutes. To the thus obtained reaction mixture, 10 ml of saturated aqueous sodium hydrogen carbonate solution was added and the resulting mixture was concentrated. To the residue, 50 ml of water was added and the resultant was extracted with ethyl acetate (50 ml×3). The organic layers were combined, washed with water and with brine saline, dried over anhydrous sodium sulfate and concentrated to obtain 1.09 g of an oily product. The thus obtained oily product was dissolved in 10 ml of anhydrous methanol. To this solution, 104 ul of 4.89N sodium methoxide was added and the resulting mixture was stirred for 2.5 hours under argon atmosphere at room temperature. The pH of the thus obtained reaction mixture was adjusted to 4 by adding acetic acid. After concentrating the mixture, 50 ml of water was added therto and the resultant was extracted with ethyl acetate (30 ml×3). The organic layers were combined, washed with saturated aqueous sodium hydrogen carbonate solution, water and brine, dried over anhydrous sodium sulfate and concentrated to obtain 980 mg of on oily product. The thus obtained oily product was purified by column chromatography (Lobar column commercially available from Merck & Co., Inc., eluant; ethyl acetate:cyclohexane=6:1) to firstly obtain 171 mg (yield of 17%) of 15-cyclopentyl-15-epi-2,5,6,7,16,17,18,19,20-nonanor-4,8-inter-m-phenylene PGI$_2$ methyl ester having low polarity. Then 429 mg (yield of 44%) of 15-cyclopentyl-2,5,6,7,16,17,18,19,20-nonanor-4,8-inter-m-phenylene PGI$_2$ methyl ester having high polarity was obtained.

The structures of these products were confirmed by the following data.

15-cyclopentyl-2,5,6,7,16,17,18,19,20-nonanor-4,8-inter-m-phenylene PGI$_2$ methyl ester m.p. 114.0°-116.0° C. (Recrystallization Solvent:ethyl acetate:n-hexane=1:2) IR (KBr method): 3390, 3300, 2950, 2860, 1740, 1590, 1480, 1450, 1440, 1420, 1370, 1350, 1330, 1300, 1260, 1250, 1240, 1200, 1190, 1180, 1160, 1120, 1100, 1070, 1020, 980, 960, 910, 880, 860, 840, 820, 780, 750, 620, 600, 580, 520, 500 cm$^{-1}$ NMR (400 MHz, CDCl$_3$, δ): 1.21-1.32(1H,bs), 1.33-1.45(1H,bs), 1.52-1.75(5H,m), 1.77-1.88(1H,bs), 1.92-2.05(2H,m), 2.42(1H,dd,J=15.9 Hz, 8.1 Hz), 2.59-2.72(3H,m), 2.85-2.94(2H,m), 3.43(1H,t,J=8.5 Hz), 3.66(3H,s), 3.86-3.95(2H,m), 5.07-5.15(1H,m), 5.56-5.68(2H,m), 6.76(1H,t,J=7.3 Hz), 6.93-7.02(2H,m) MASS (EI method, m/e): 386 (M+) High resolution mass spectrum Calcd. (C$_{23}$H$_{30}$O$_5$, M+): 386.2097 Found (M+): 386.2070

15-cyclopentyl-15-epi-2,5,6,7,16,17,18,19,20-nonanor-4,8-inter-m-phenylene PGI₂ methyl ester m.p. 105.5°–116.0° C. (Recrystallization Solvent:ethyl acetate) IR (KBr method): 3500, 3280, 3180, 2950, 2900, 2870, 1720, 1705, 1670, 1600, 1500, 1480, 1450, 1400, 1410, 1350, 1310, 1300, 1270, 1250, 1210, 1200, 1150, 1110, 1090, 1060, 1030, 1005, 990, 970, 940, 900, 880, 860, 830, 780, 740, 700, 670, 620, 600, 550, 520, 500, 470 cm$^{-1}$ NMR (400 MHz, CDCl₃, δ): 1.23–1.33(1H,bs), 1.35–1.46(1H,bs), 1.51–1.72(5H,m), 1.77–1.88(1H,bs), 1.95–2.08(2H,m), 2.47–2.55(1H,m), 2.85–2.94(2H,m), 3.50(1H,t,J=8.3 Hz), 3.66(3H,s), 3.92–3.99(2H,m), 5.12–5.19(1H,m), 5.65–5.76(2H,m), 6.77(1H,t,J=7.6 Hz), 6.96–7.06(2H,m) MASS (EI method, m/e): 386 (M$^+$) High resolution mass spectrum Calcd. (C₂₃H₃₀O₅, M$^+$): 386.2097 Found (M$^+$): 386.2098

EXAMPLE 13

15-cyclopentyl-2,5,6,7,16,17,18,19,20-nonanor-4,8-inter-m-phenylene PGI₂ (57)

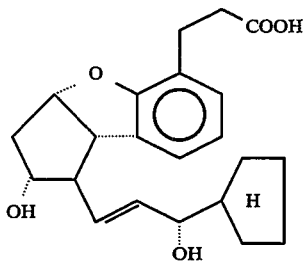

(57)

In 5 ml of methanol, 122 mg of 15-cyclopentyl-2,5,6,7,16,17,18,19,20-nonanor-4,8-inter-m-phenylene PGI₂ methyl ester was dissolved. To this solution, 1.5 ml of 1N sodium hydroxide was added and the resulting mixture was stirred overnight at room temperature. The pH of the thus obtained reaction mixture was adjusted to 4 by adding 1N hydrochloric acid. To the mixture, 30 ml of water was added and the resultant was extracted with ethyl acetate (30 ml×3). The organic layers were combined, washed with water and brine, dried over anhydrous sodium sulfate and concetrated to obtain 114 mg (yield 97%) of 15-cyclopentyl-2,5,6,7,16,17,18,19,20-nonanor-4,8-inter-m-phenylene PGI₂ as a pure product.

The structure of this product was confirmed by the following data. m.p. 151.0°–152.5° C. (Recrystallization Solvent:acetone:n-hexane=5:7) IR (KBr method): 3400, 3300, 3050, 2950, 2860, 1720, 1705, 1690, 1600, 1480, 1450, 1410, 1370, 1350, 1330, 1300, 1290, 1260, 1250, 1240, 1210, 1190, 1160, 1120, 1100, 1080, 1020, 1000, 980, 960, 910, 895, 860, 840, 820, 780, 770, 740, 700, 620, 600, 560, 520, 505 cm$^{-1}$ NMR (400 MHz, CDCl₃, δ): 0.85–0.94(1H,m), 1.22–1.35(2H,m), 1.35–1.47(1H,m), 1.51–1.73(5H,m), 1.77–1.87(1H,bs), 1.93–2.06(2H,m), 2.45(1H,dd,J=14.9 Hz, 7.1 Hz), 2.57–2.76(3H,m), 2.84–2.99(2H,m), 3.45(1H,t,J=8.3 Hz), 3.88–3.97(2H,m), 5.08–5.16(1H,m), 5.58–5.70(2H,m), 6.76(1H,t,J=7.3 Hz), 6.94–7.02(2H,m) MASS (EI method, m/e): 372 (M$^+$) High resolution mass spectrum Calcd. (C₂₂H₂₈O₅, M$^+$): 372.1937 Found (M$^+$): 372.1944

EXAMPLE 14

15-cyclohexyl-2,5,6,7,16,17,18,19,20-nonanr-4,8-inter-m-phenylene PGI₂ methyl ester (58) and 15-epimer thereof (59)

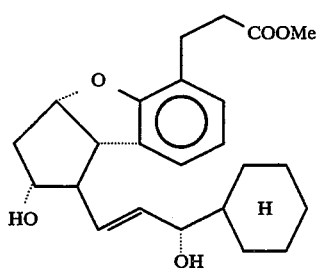

(58)

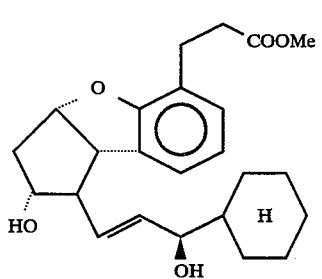

(59)

In 10 ml of methanol, 1.04 g of 15-cyclohexyl-15-oxo-2,5,6,7,16,17,18,18,20-nonanor-4,8-inter-m-phenylene PGI₂ methyl ester, 11-acetate was dissolved and then 1.32 g of cerium chloride heptahydrate was added. To the stirred mixture, 90 mg of sodium borohydride was added under cooling in iced water and the resulting mixture was stirred for 15 minutes. To the thus obtained reaction mixture, 10 ml of saturated aqueous sodium hydrogen carbonate solution was added and the resulting mixture was concentrated. To the residue, 50 ml of water was added and the resultant was extracted with ethyl acetate (50 ml×3). The organic layers were combined, washed with water and brine, dried over anhydrous sodium sulfate and concentrated to obtain 1.01 g of an oily product. The thus obtained oily product was dissolved in 10 ml of anhydrous methanol. To this solution, 88 μl of 5.22N sodium methoxide was added and the resulting mixture was stirred for 2.5 hours under argon atmosphere at room temperature. The pH of the thus obtained reaction mixture was adjusted to 4 by adding acetic acid. After concentrating the mixture, 50 ml of water was added thereto and the resultant was extracted with ethyl acetate (30 ml×3). The organic layers were combined, washed with saturated aqueous sodium hydrogen carbonate solution, water and brine, dried over anhydrous sodium sulfate and concentrated to obtain 912 mg of on oily product. The thus obtained oily product was purified by column chromatography (Lobar column commercially available from Merck & Co., Inc., eluant; ethyl acetate:cyclohexane=6:1) to firstly obtain 390 mg (yield 43%) of 15-cyclohexyl-15-epi-2,5,6,7,16,17,18,19,20-nonanor-4,8-inter-m-phenylene PGI₂ methyl ester having low polarity. Then 439 mg (yield 48%) of 15-cyclohexyl-2,5,6,7,16,17,18,19,20-nonanor-4,8-inter-m-phenylene PGI₂ methyl ester having high polarity was obtained.

The structures of these products were confirmed by the following data.

15-cyclohexyl-2,5,6,7.16,17,18,19,20-nonanor-4,8-inter-m-phenylene PGI₂ methyl ester m.p. 114.5°–115.5° C. (Recrystallization Solvent: ethyl acetate:n-hexane=5:4) IR (KBr method): 3390, 2910, 2850, 1725, 1590, 1480, 1440, 1365, 1340, 1320, 1300, 1280, 1260, 1250, 1230, 1200, 1180, 1150, 1140, 1110, 1095, 1065, 1040, 1020, 990, 975, 950, 890, 860, 830, 820, 800, 795, 750, 740, 700, 620, 600, 560, 510, 490 cm⁻¹ NMR (400 MHz, CDCl₃, δ): 0.94–1.07(2H,m), 1.10–1.32(3H,m), 1.35–1.48(1H,bS), 1.54–1.92(5H,m), 1.93–2.05(1H,m), 2.39–2.48(1H,m), 2.60–2.72(3H,m), 2.84–2.96(2H,m), 3.44(1H,t,J=8.5 Hz), 3.66(3H,S), 3.83–3.96(2H,m), 5.12(1H,dd,J=14.2, 7.3 Hz), 5.55–5.69(2H,m), 6.76(1H,t,J=7.6 Hz), 6.94–7.02(2H,m) MASS (EI method, m/e): 400 (M+) High resolution mass spectrum Calcd. (C₂₄H₃₂O₅, M+): 400.2250 Found (M+): 400.2237

15-cyclohexyl-15-epi-2,5,6,7,16,17,18,19,20-nonanor-4,8-inter-m-phenylene PGI₂ methyl ester m.p. 107.0°–108.0° C. (Recrystallization Solvent: ethyl acetate:n-hexane=3:1) IR (KBr method): 3300, 2980, 2920, 2850, 1735, 1600, 1480, 1450, 1420, 1360, 1350, 1330, 1310, 1260, 1220, 1210, 1180, 1160, 1130, 1095, 1080, 1065, 1050, 1040, 1000, 975, 960, 910, 890, 870, 860, 840, 815, 790, 780, 765, 745, 660, 560, 530, 500, 490 cm⁻¹ NMR (400 MHz, CDCl₃, δ): 0.95–1.08(2H,m), 1.08–1.32(3H,m), 1.37–1.48(1H,bS), 1.64–1.92(5H,m), 1.96–2.05(1H,m), 2.46–2.55(1H,m), 2.57–2.72(3H,m), 2.83–2.96(2H,m), 3.49(1H,t,J=8.3 Hz), 3.66(3H,s), 3.86–3.98(2H,m), 5.11–5.19(1H,m), 5.60–5.72(2H,m), 6.77(1H,t,J=7.3 Hz), 6.97(1H,d,J=7.3 Hz), 7.01(1H,d,J=7.3 Hz) MASS (EI method, m/e): 400 (M+) High resolution mass spectrum Calcd. (C₂₄H₃₂O₅, M+): 400.2250 Found (M+): 400.2263

EXAMPLE 15

15-cyclohexyl-2,5,6,7,16,17,18,19,20-nonanor-4,8-inter-m-phenylene PGI₂ (60)

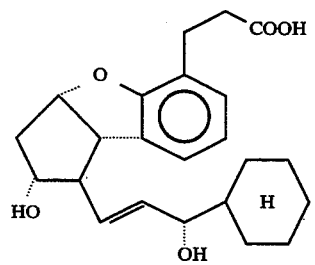

(60)

In 10 ml of methanol, 96.2 mg of 15-cyclohexyl-2,5,6,7,16,17,18,19,20-nonanor-4,8-inter-m-phenylene PGI₂ methyl ester, 11-acetate was dissolved. To this solution, 2.0 ml of 1N sodium hydroxide was added and the resulting mixture was stirred overnight at room temperature. The pH of the thus obtained reaction mixture was adjusted to 4 by adding 1N hydrochloric acid. To the mixture, 30 ml of water was added and the resultant was extracted with ethyl acetate (30 ml×3). The organic layers were combined, washed with water and brine and concetrated to obtain 187 mg (yield 99%) of 15-cyclohexyl-2,5,6,7,16,17,18,19,20-nonanor-4,8-inter-m-phenylene PGI₂ as a pure product.

The structure of this product was confirmed by the following data. m.p. 125.5°–127.0° C. (Recrystallization Solvent: acetone:n-hexane=10:1) IR (KBr method): 3410, 2920, 2850, 1700, 1600, 1480, 1450, 1405, 1370, 1345, 1310, 1260, 1220, 1190, 1169, 1120, 1100, 1075, 1030, 1000, 980, 960, 890, 860, 765, 740, 700, 650, 600 cm⁻¹ NMR (400 MHz, DMSO-d₆, δ): 0.92–1.07(2H,m), 1.10–1.32(3H,m), 1.34–1.45(1H,m), 1.62–1.82(4H,m), 1.87–1.99(2H,m), 2.27–2.38(1H,m), 2.57–2.73(3H,m), 2.81–2.93(2H,m), 3.39(1H,t,J=9.0 Hz), 3.75–3.89(2H,m), 5.09(1H,dd,J=15.1, 7.3 Hz), 5.52–5.63(2H,m), 6.74(1H,t,J=7.3 Hz), 6.95(1H,d,J=7.3 Hz), 6.98(1H,d,J=7.3 Hz) MASS (EI method, m/e): 386 (M+) High resolution mass spectrum Calcd. (C₂₃H₃₀O₅, M+): 386.2013 Found (M+): 386.2064

EXAMPLE 16

16-cyclohexyl-2,5,6,7,17,18,19,20-octanor-4,8-inter-m-pehnylene PGI₂ methyl ester (61) and 15-epimer thereof (62)

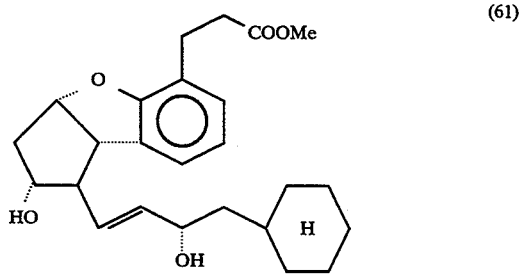

(61)

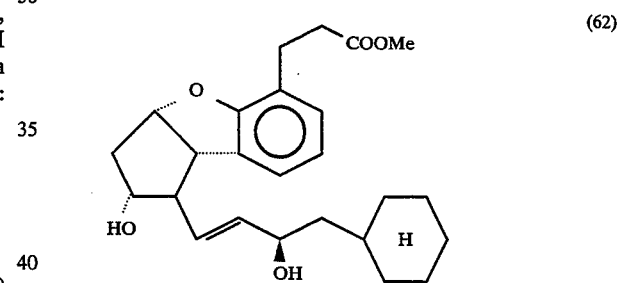

(62)

In 60 ml of methanol, 1.17 g (2.58 mmol) of 16-cyclohexyl-15-oxo-2,5,6,7,17,18,18,20-octanor-4,8-inter-m-phenylene PGI₂ methyl ester, 11-acetato was dissolved. To this stirred solution was added 964 mg (2.58 mmol) of cerium chloride heptahydrate and then 147 mg (3.87 mmol) of sodium borohydride under cooling in iced water and the resulting mixture was stirred for 10 minutes. To the thus obtained reaction mixture, 20 ml of saturated aqueous sodium hydrogen carbonate solution was added and the resulting mixture was concentrated. To the residue, 30 ml of water and 100 ml of ethyl acetate were added and the mixture was filtered. The precipitate was washed with ethyl acetate (30 ml×3). The organic layers were combined, washed once with 30 ml each of water and brine, dried over anhydrous sodium sulfate and concentrated to obtain 1.14 g of an oily product. The thus obtained oily product was dissolved in 250 ml of anhydrous methanol. To this solution, 0.12 ml (0.63 mmol) of 5.22N sodium methoxide was added under argon atmosphere and under stirring at room temperature, and the resulting mixture was stirred for 3 hours at room temperature. To the thus obtained reaction mixture, 0.05 ml of acetic acid was added and the mixture was concentrated. To the residue, 20 ml of water was added and the resultant was extracted with ethyl acetate (50 ml×2). The organic layers were combined, washed once with 20 ml each of water and brine, dried over anhydrous sodium sulfate and concentrated. The thus obtained residue was purified by column chromatography (Lobar column commercially available from Merck & Co., Inc., eluant; ethyl acetate:cyclohexane=2:1) to firstly obtain 494 mg (yield 47.7%) of 16-cyclohexyl-15-epi-2,5,6,7,17,18,19,20-octanor-4,8-inter-m-phenylene PGI$_2$ methyl ester having low polarity. Then 421 mg (yield 40.7%) of 16-cyclohexyl-2,5,6,7,17,18,19,20-octanor-4,8-inter-m-phenylene PGI$_2$ methyl ester was obtained from high polar fractions.

The structures of these products were confirmed by the following data.

16-cyclohexyl-2,5,6,7,17,18,19,20-octanor-4,8-inter-m-phenylene PGI$_2$ methyl ester m.p. 94.8°–95.5° C. (Recrystallization Solvent:ethyl acetate:n-hexane=2:1) IR (KBr method): 3370, 2920, 2840, 1730, 1595, 1440, 1340, 1325, 1290, 1250, 1185, 1170, 1150, 1090, 1080, 1030, 1010, 960, 885, 830, 785, 760, 740, 615 cm$^{-1}$ NMR (400 MHz, CDCl$_3$, $\delta$): 0.9–1.85(15H,m), 1.98(1H,ddd,J=4.9, 8.5, 13.7 Hz), 2.42(1H,q,J=8.5 Hz), 2.6–2.7(3H,m), 2.85–2.95(2H,m), 3.43(1H,t,J=8.5 Hz), 3.66(3H,s), 3.92(1H,dt,J=5.9, 8.5 Hz), 4.24(1H,q,J=6.5 Hz), 5.12(1H,ddd,J=4.9, 7.3, 8.5 Hz), 5.58(1H,dd,J=6.5, 15.2 Hz), 5.64(1H,dd,J=8.5, 15.2 Hz), 6.76(1H,t,J=7.3 Hz), 6.96(1H,d,J=7.3 Hz), 6.98(1H,d,J=7.3 Hz) MASS (EI method, m/e): 414 (M+)

| Element Analysis | C | H |
|---|---|---|
| Calcd. (C$_{25}$H$_{34}$O$_5$) | 72.43 | 8.27 |
| Found | 72.43 | 8.33 |

16-cyclohexyl-15-epi-2,5,6,7,17,18,19,20-octanor-4,8-inter-m-phenylene PGI$_2$ methyl ester m.p. 77.2°–78.5° C. (Recrystallization Solvent:ethyl acetate:n-hexane=2:1) IR (KBr method): 3350, 2920, 2850, 1735, 1600, 1480, 1450, 1420, 1365, 1350, 1260, 1220, 1210, 1180, 1165, 1090, 1070, 1040, 1000, 970, 950, 930, 865, 845, 780, 770, 745, 660 cm$^{-1}$ NMR (400 MHz, CDCl$_3$, $\delta$): 0.9–1.9(15H,m), 2.02(1H,ddd,J=4.9, 7.8, 13.7 Hz), 2.45–2.55(1H,m), 2.55–2.7(3H,m), 2.85–3.0(2H,m), 3.5(1H,t,J=8.4 Hz), 3.66(3H,s), 3.9–4.0(1H,m), 4.2–4.3(1H,m), 5.16(1H,ddd,J=4.9, 7.3, 8.4 Hz), 5.6–5.75(2H,m), 6.77(1H,t,J=7.3 Hz), 6.97(1H,d,J=7.3 Hz), 7.01(1H,d,J=7.3 Hz) MASS (EI method, m/e): 414 (M+)

| Element Analysis | C | H |
|---|---|---|
| Calcd. (C$_{25}$H$_{34}$O$_5$) | 72.43 | 8.27 |
| Found | 72.50 | 8.34 |

EXAMPLE 17

16-cyclohexyl-2,5,6,7,17,18,19,20-octanor-4,8-inter-m-phenylene PGI$_2$ (63)

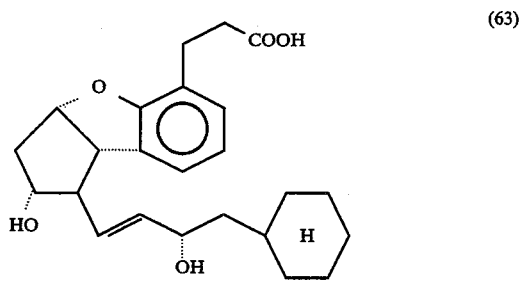

(63)

| Element Analysis | C | H |
|---|---|---|
| Calcd. (C$_{25}$H$_{34}$O$_5$) | 72.43 | 8.27 |
| Found | 72.50 | 8.34 |

In 25 ml of methanol, 317 mg (0.77 mmol) of 16-cyclohexyl-2,5,6,7,17,18,19,20-octanor-4,8-inter-m-phenylene PGI$_2$ methyl ester was dissolved. To this stirred solution, 6.2 ml (6.13 mmol) of 0.986N sodium hydroxide was added under cooling, and the resulting mixture was stirred 5 hours at room temperature. To the thus obtained reaction mixture, 6.2 ml (6.2 mmol) of 1N hydrochloric acid was added and the mixture was concentrated. To the thus obtained residue, 20 ml of water was added and the resultant was extracted with ethyl acetate (50 ml×2). The organic layers were combined, washed once with 10 ml each of water and brine, dried over anhydrous sodium sulfate and concetrated. The thus obtained residue was recrystallized from 1.0 ml of ethyl acetate and from 0.5 ml of n-hexane to obtain 234 mg (yield 76.3%) of 16-cyclohexyl-2,5,6,7,17,18,19,20-octanor-4,8-inter-m-phenylene PGI$_2$ as white crystals.

The structure of this product was confirmed by the following data. m.p. 135.5°–136.8° C. (Recrystallization Solvent:ethyl acetate:n-hexane=2:1) IR (KBr method): 3380, 2920, 2840, 1720, 1695, 1590, 1435, 1400, 1320, 1270, 1185, 1150, 1075, 1025, 955, 880, 850, 820, 755, 735, 610 cm$^{-1}$ NMR (400 MHz, CDCl$_3$, $\delta$): 0.9–1.85(13H,m), 1.95(1H,ddd,J=5.0, 8.6, 14.1 Hz), 2.36(1H,q,J=8.6 Hz), 2.55–2.8(3H,m), 2.8–3.0(2H,m), 3.39(1H,t,J=8.6 Hz), 3.88(1H,dt,J=6.1, 8.6 Hz), 4.21(1H,q,J=6.9 Hz), 5.09(1H,ddd,J=5.0, 7.3, 8.6 Hz), 3.5–5.2(2H,m), 5.53(1H,dd,J=6.9, 15.3 Hz), 5.59(1H,dd,J=8.6, 15.3 Hz), 6.74(1H,t,J=7.3 Hz), 6.93(1H,d,J=7.3 Hz), 6.97(1H,d,J=7.3 Hz) MASS (EI method, m/e): 400 (M+)

| Element Analysis | C | H |
|---|---|---|
| Calcd. (C$_{24}$H$_{32}$O$_5$) | 71.97 | 8.05 |
| Found | 71.77 | 8.05 |

EXAMPLE 18

16-cyclohexyl-15-epi-2,5,6,7,17,18,19,20-octanor-4,8-inter-m-phenylene PGI$_2$ (64)

(64)

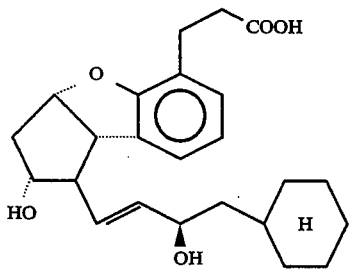

In 30 ml of methanol, 368 mg (0.89 mmol) of 16-cyclohexyl-15-epi-2,5,6,7,17,18,19,20-octanor-4,8-inter-m-phenylene PGI₂ methyl ester was dissolved. To this stirred solution, 7.2 ml (7.11 mmol) of 0.986N sodium hydroxide was added under cooling, and the resulting mixture was stirred 5 hours at room temperature. To the thus obtained reaction mixture, 7.2 ml (7.2 mmol) of 1N hydrochloric acid was added and the mixture was concentrated. To the thus obtained residue, 20 ml of water was added and the resultant was extracted with ethyl acetate (50 ml×2). The organic layers were combined, washed once with 10 ml each of water and brine, dried over anhydrous sodium sulfate and concetrated. The thus obtained residue was recrystallized from 1 ml of ethyl acetate and from 0.5 ml of n-hexane to obtain 274 mg (yield 77%) of 16-cyclohexyl-15-epi-2,5,6,7,17,18,19,20-octanor-4,8-inter-m-phenylene PGI₂ as colorless crystals.

The structure of this product was confirmed by the following data. m.p. 119.7°–120.9° C. (Recrystallization Solvent:ethyl acetate:n-hexane=2:1) IR (KBr method): 3300, 2950, 2840, 1720, 1650, 1590, 1470, 1440, 1380, 1340, 1250, 1210, 1180, 1135, 1080, 1050, 1035, 990, 960, 935, 915, 890, 850, 825, 780, 740, 635, 610 cm⁻¹ NMR (400 MHz, CDCl₃, δ): 0.8–1.85(13H,m), 1.99(1H,ddd,J=4.9, 8.1, 15.7 Hz), 2.4–2.5(1H,m), 2.55–2.8(3H,m), 2.8–3.0(2H,m), 3.47(1H,t,J=8.4 Hz), 3.94(1H,dt,J=5.9, 8.1 Hz), 4.2–4.3(1H,m), 4.5–5.0(2H,m), 5.13(1H,ddd,J=4.9, 7.3, 8.4 Hz), 5.6–5.75(2H,m), 6.76(1H,t,J=7.3 Hz), 6.95–7.05(2H,m) MASS (EI method, m/e): 400 (M+)

| Element Analysis | C | H |
|---|---|---|
| Calcd. (C₂₄H₃₂O₅) | 71.97 | 8.05 |
| Found | 71.79 | 8.02 |

EXAMPLE 19

17-cyclohexyl-16,16-dimethyl-2,5,6,7,18,19,20-heptanor-4,8-inter-m-phenylene PGI₂ methyl ester (65) and 15-epimer thereof (66)

(65)

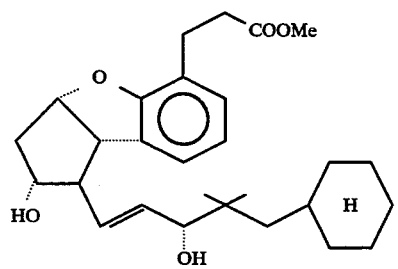

(66)

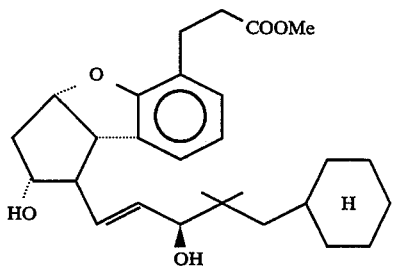

In 20 ml of methanol, 1.3262 g (2.67 mmol) of 17-cyclohexyl-16,16-dimethyl-15-oxo-2,5,6,7,18,19,20-heptanor-4,8-inter-m-phenylene PGI₂ methyl ester, 11-acetate was dissolved and then 1.194 g (3.20 mmol) of cerium trichloride heptahydrate was dissolved therein. To the stirred mixture, 56.2 mg (1.34 mmol) of sodium borohydride was added under cooling in iced water. After stirring the resulting mixture for 10 minutes, 25 ml of saturated aqueous sodium hydrogen carbonate solution was added thereto and the resulting mixture was stirred for 10 minutes at room temperature. The thus obtained reaction mixture was filtered under suction through Celite and the residue was washed with 200 ml of ethyl acetate. After concentrating the filtrate, the thus obtained residue was extracted with ethyl acetate (20 ml×3). The organic layers were combined, washed with 50 ml of brine, dried over anhydrous sodium sulfate (15 g) and concentrated to obtain 1.4202 g of an oily product.

Then the thus obtained oily product was subjected to azeotropic distillation with benzene and the resultant was dissolved in 20 ml of anhydrous methanol. To this solution, 0.05 ml (0.267 mmol) of 5.22N sodium methoxide was added and the resulting mixture was stirred for 2 hours under argon atmosphere at room temperature. To the thus obtained reaction mixture, 0.1 ml of acetic acid was added. After concentrating the mixture, 15 ml of water was added to the residue and the resultant was extracted with ethyl acetate (15 ml×3). The organic layers were combined, washed with 40 ml of brine, dried over anhydrous sodium sulfate (15 g) and concentrated to obtain 1.3177 g of an oily product. The thus obtained oily product was purified by column chromatography (silica gel, eluant; ethyl acetate:cyclohexane=1:1) to firstly obtain 558.0 mg (1.22 mmol) of 17-cyclohexyl-16,16-dimethyl-15-epi-2,5,6,7,18,19,20-heptanor-4,8-inter-m-phenylene PGI₂ methyl ester having low polarity (yield 46%). This product was recrystallized from ethyl acetate/cyclohexane (1:1) to obtain colorless needle-shaped crystals. Then 565.6 mg (1.24 mmol) of 17-cyclohexyl-16,16-dimethyl-2,5,6,7,18,19,20-heptanor-4,8-inter-m-phenylene PGI₂ methyl ester was obtained from high polar fractions (yield 47%). This product was recrystallized from ethyl/cyclohexane (1:1) to obtain colorless needle-shaped crystals.

The structures of these products were confirmed by the following data.

17-cyclohexyl-16,16-dimethyl-2,5,6,7,18,19,20-heptanor-4,8-inter-m-phenylene PGI₂ methyl ester m.p. 107°–107.5° C. IR (KBr method): 3350, 2920, 2850, 1732, 1592, 1441, 1361, 1330, 1292, 1263, 1190, 1168, 1095, 1088, 1031, 1014, 992, 965, 950, 884, 860, 743, 615 cm⁻¹ NMR (400 MHz, CDCl₃, δ): 0.90(3H,s), 0.92(3H,s), 0.95–1.42(8H,m), 1.55–1.84(7H,m), 1.94–2.03(1H,m), 2.41–2.52(1H,m), 2.58–2.71(3H,m), 2.85–2.96(2H,m), 3.47(1H,t,J=8.3 Hz), 3.66(3H,s), 3.81–3.86(1H,m), 3.92–3.97(1H,m), 5.11–5.20(1H,m), 5.61–5.72(2H,m), 6.76(1H,t,J=7.33 Hz), 6.95–7.01(2H,m) MASS (EI method, m/e): 456 (M+) High resolution mass spectrum Calcd. ($C_{28}H_{40}O_5$, M+) 456.2876 Found (M+) 456.2845

17-cyclohexyl-16,16-dimethyl-15-epi-2,5,6,7,18,19,20-heptanor-4,8-inter-m-phenylene $PGI_2$ methyl ester m.p. 108.5°–109° C. IR (KBr method): 3300, 2910, 2850, 1725, 1660, 1590, 1439, 1360, 1339, 1303, 1265, 1220, 1192, 1182, 1144, 1055, 1019, 980, 952, 891, 863, 835, 806, 760, 740, 700, 615 cm$^{-1}$ NMR (400 MHz, CDCl$_3$, δ): 0.90(3H,s), 0.92(3H,s), 0.96–1.42(8H,m), 1.48–1.78(7H,m), 1.98–2.05(1H,m), 2.51–2.57(1H,m), 2.59–2.72(3H,m), 2.84–2.97(2H,m), 3.51(1H,t,J=8.3 Hz), 3.66(3H,s), 3.84–3.99(1H,m), 3.93–4.00(1H,m), 5.12–5.19(1H,m), 5.63–5.77(2H,m), 6.77(1H,t,J=7.33 Hz), 6.98(1H,d,J=7.33 Hz), 7.01(1H,d,J=7.33 Hz) MASS (EI method, m/e): 456 (m+) High resolution mass spectrum Calcd. ($C_{28}H_{40}O_5$, M+) 456.2876 Found (M+) 456.2904

EXAMPLE 20

17-cyclohexyl-16,16-dimethyl-2,5,6,7,18,19,20-heptanor-4,8-inter-m-phenylene $PGI_2$ (67)

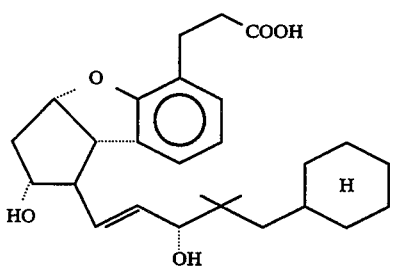

(67)

In 10 ml of methanol, 330 mg (0.724 mmol) of 17-cyclohexyl-16,16-dimethyl-2,5,6,7,18,19,20-heptanor-4,8-inter-m-phenylene $PGI_2$ methyl ester was dissolved. To this solution, 2 ml (2.17 mmol) of 1.06N aqueous sodium hydroxide solution was added and the resulting mixture was stirred 2 hours under argon atmosphere at room temperature. After concentrating the thus obtained reaction mixture, 3 ml of 1N hydrochloric acid was added and then 10 ml of water was added. The resulting mixture was extracted with ethyl acetate (10 ml×3). The organic layers were combined, washed with 20 ml of brine, dried over anhydrous sodium sulfate (10 g) and concetrated to quantitatively obtain 320.0 mg (0.724 mmol) of 17-cyclohexyl-16,16-dimethyl-2,5,6,7,18,19,20-heptanor-4,8-inter-m-phenylene $PGI_2$ as a pure product. This product was recrystallized from ethyl acetate/hexane (1:1) to obtain colorless needle-shaped crystals.

The structure of this product was confirmed by the following data. m.p. 154.5°–155.5° C. IR (KBr method): 3400 (3650–2200), 2916, 2850, 1691, 1591, 1445, 1341, 1282, 1260, 1195, 1062, 1019, 990, 958, 921, 882, 853, 823, 804, 782, 763, 743 cm$^{-1}$ NMR (400 MHz, 10% DMSO-d$_6$-CDCl$_3$, δ): 0.89(3H,s), 0.92(3H,s), 0.94–1.43(8H,m), 1.59–1.79(5H,m), 1.88–1.99(1H,m), 2.31–2.39(1H,m), 2.58–2.72(3H,m), 2.84–2.93(2H,m), 3.37–3.42(1H,m), 3.77(1H,d,J=7.82 Hz), 3.82–3.89(1H,m), 3.5–4.3(3H,brs), 5.07–5.16(1H,m), 5.56–5.68(2H,m), 6.74(1H,t,J=7.32 Hz), 6.95(1H,d,J=7.32 Hz), 6.99(1H,d,J=7.32 Hz) MASS (EI method, m/e): 442 (M+) High resolution mass spectrum Calcd. ($C_{27}H_{38}O_5$, M+): 442.2719 Found (M+): 442.2721

EXAMPLE 21

17-cyclohexyl-16,16-dimethyl-15-epi-2,5,6,7,18,19,20-heptanor-4,8-inter-m-phenylene $PGI_2$ (68)

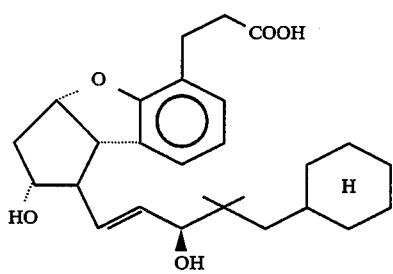

(68)

In 10 ml of methanol, 332 mg (0.728 mmol) of 17-cyclohexyl-16,16-dimethyl-15-epi-2,5,6,7,18,19,20-heptanor-4,8-inter-m-phenylene $PGI_2$ methyl ester was dissolved. To this solution, 2 ml (2.18 mmol) of 1.06N aqueous sodium hydroxide solution was added and the resulting mixture was stirred 2 hours under argon atmosphere at room temperature. After concentrating the reaction mixture, 3 ml of 1N hydrochloric acid was added thereto and then 10 ml of water was added. The mixture was extracted with ethyl acetate (10 ml×3). The organic layers were combined, washed with 20 ml of brine, dried over anhydrous sodium sulfate (10 g) and concetrated to obtain 321.4 mg (0.728 mmol) of 17-cyclohexyl-16,16-dimethyl-15-epi-2,5,6,7,18,19,20-heptanor-4,8-inter-m-phenylene $PGI_2$ as a pure product. This compound was recrystallized from THF/cyclohexane (1:1) to obtain colorless needle-shaped crystals.

The structure of this product was confirmed by the following data. m.p. 163°–164.5° C. IR (KBr method): 3300 (3700–2200), 2910, 2850, 1698, 1591, 1442, 1361, 1335, 1256, 1184, 1145, 1093, 1061, 1015, 994, 961, 890, 861, 742 cm$^{-1}$ NMR (400 MHz, 10% DMSO-d$_6$-CDCl$_3$, δ): 0.91(3H,s), 0.93(3H,s), 0.94–1.43(8H,m), 1.57–1.77(5H,m), 1.93–2.02(1H,m), 2.40–2.50(1H,m), 2.58–2.69(3H,m), 2.83–2.92(2H,m), 3.47(1H,t,J=8.3 Hz), 3.83–3.86(1H,m), 3.92–3.98(1H,m), 3.8–4.6(3H,brs), 5.10–5.18(1H,m), 5.69–5.80(2H,m), 6.75(1H,t,J=7.33 Hz), 6.97–7.02(2H,m) MASS (EI method, m/e): 442 (M+) High resolution mass spectrum Calcd. ($C_{27}H_{28}O_5$, M+) 442.2719 Found (M+) 442.2726

EXAMPLE 22

15-phenyl-2,5,6,7,16,17,18,19,20-nonanor-4,8-inter-m-phenylene $PGI_2$ methyl ester (69) and 15-epimer thereof (70)

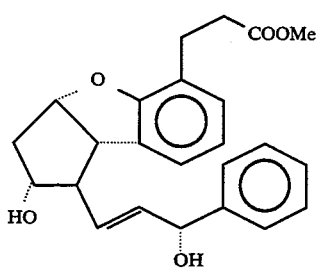

(69)

-continued

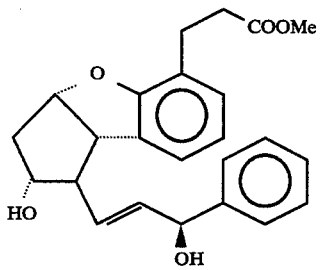
(70)

In 40 ml of methanol, 1.9953 g of 15-phenyl-15-oxo-2,5,6,7,16,17,18,18,20-nonanor-4,8-inter-m-phenylene PGI$_2$ methyl ester, 11-acetate was dissolved and then 2.571 g of cerium chloride heptahydrate was dissolved therein. To this stirred solution, 209 mg of sodium borohydride was added under cooling in iced water, and the resulting mixture was stirred for 10 minutes. To the thus obtained reaction mixture, 20 ml of saturated aqueous sodium hydrogen carbonate solution was added and the resulting mixture was concentrated. To the residue, 50 ml of water and the resultant was extracted with ethyl acetate (40 ml×3). The organic layers were combined, washed once with 60 ml each of water and brine, dried over anhydrous sodium sulfate and concentrated to obtain 2.0855 g of an oily product. The thus obtained residue was dissolved in 20 ml of methanol. To this solution, 0.04 ml of 4.89N sodium methoxide was added and the resulting mixture was stirred for 15 minutes at room temperature. To the thus obtained reaction mixture, 0.1 ml of acetic acid was added. After concentrating the mixture, 40 ml of water was added to the residue and the resultant was extracted with ethyl acetate (40 ml×3). The organic layers were combined, washed with 100 ml each of water and brine, dried over anhydrous sodium sulfate and concentrated to obtain 1.6987 g of an oily product. The thus obtained oily product was purified by column chromatography (Lobar column Type B commercially available from Merck & Co., Inc., eluant; ethyl acetate:cyclohexane=6:1) to firstly obtain 733.9 mg (yield 40.5%) of 15-phenyl-15-epi-2,5,6,7,16,17,18,19,20-nonanor-4,8-inter-m-phenylene PGI$_2$ methyl ester having low polarity. Then 774.8 mg (yield 42.8%) of 15-phenyl-2,5,6,7,16,17,18,19,20-nonanor-4,8-inter-m-phenylene PGI$_2$ methyl ester was obtained from high polar fractions.

The structures of these products were confirmed by the following data.

15-phenyl-2,5,6,7,16,17,18,19,20-nonanor-4,8-inter-m-phenylene PGI$_2$ methyl ester m.p. 117.5°–118° C. (Recrystallization Solvent:ethyl acetate:cyclohexane=2:1) IR (KBr method): 3255, 2902, 1730, 1590, 1446, 1424, 1360, 1260, 1224, 1198, 1164, 1105, 1064, 1038, 1005, 988, 956, 921, 884, 860, 786, 763, 754, 743, 703, 554 cm$^{-1}$ NMR (400 MHz, CDCl$_3$, δ): 1.95–2.02(1H,m), 2.34–2.35(1H,m), 2.40–2.42(1H,m), 2.43–2.52(1H,m), 2.58–2.68(3H,m), 2.82–2.93(2H,m), 3.47(1H,t,J=8.43 Hz), 3.65(3H,s), 3.93–4.00(1H,m), 5.08–5.17(1H,m), (1H,m), 5.23–5.28(1H,m), 5.75–5.87(2H,m), 6.71(1H,t,J=7.33 Hz), 6.88(1H,d,J=7.33 Hz), 6.95(1H,d,J=7.33 Hz), 7.27–7.41(5H,m) MASS (EI method, m/e): 394 (M$^+$)

| Element Analysis | C | H |
|---|---|---|
| Calcd. (C$_{24}$H$_{26}$O$_5$) | 73.08 | 6.64 |
| Found | 72.97 | 6.56 |

15-phenyl-15-epi-2,5,6,7,16,17,18,19,20-nonanor-4,8-inter-m-phenylene PGI$_2$ methyl ester m.p. 119.5° C. (Recrystallization Solvent:ethyl acetate:cyclohexane=5:1) IR (KBr method): 3320, 2951, 2948, 2930, 2905, 1738, 1690, 1619, 1442, 1359, 1290, 1263, 1245, 1193, 1148, 1070, 972, 959, 926, 864, 859, 840, 768, 746, 709, 626 cm$^{-1}$ NMR (400 MHz, CDCl$_3$, δ): 1.80–1.82(1H,m), 1.98–2.08(2H,m), 2.51–2.69(4H,m), 2.83–2.94(2H,m), 3.53(1H,t,J=8.24 Hz), 3.65(3H,s), 3.95–4.01(1H,m), 5.13–5.18(1H,m), 5.24–5.27(1H,m), 5.77–5.89(2H,m), 6.74(1H,t,J=7.33 Hz), 6.95–6.98(2H,m), 7.28–7.41(5H,m) MASS (EI method m/e): 394 (M$^+$)

| Element Analysis | C | H |
|---|---|---|
| Calcd. C$_{24}$H$_{26}$O$_5$) | 73.08 | 6.64 |
| Found | 72.95 | 6.70 |

EXAMPLE 23

15-phenyl-2,5,6,7,16,17,18,19,20-nonanor-4,8-inter-m-phenylene PGI$_2$ (71)

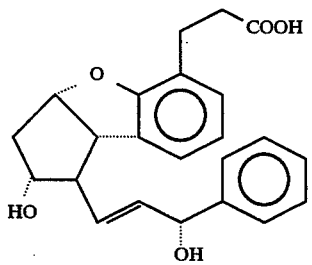
(71)

In 14 ml of methanol, 304.4 mg of 15-phenyl-2,5,6,7,16,17,18,19,20-nonanor-4,8-inter-m-phenylene PGI$_2$ methyl ester was dissolved. To this solution, 3.86 ml of 1N sodium hydroxide was added and the resulting mixture was stirred 1 hour at room temperature. To the thus obtained reaction mixture, 3.86 ml of 1N hydrochloric acid was added and then 70 ml of water was added and the resultant was extracted with ethyl acetate (40 ml×3). The organic layers were combined, washed once with 70 ml each of water and brine, dried over anhydrous sodium sulfate and concetrated to obtain 292.4 mg (yield 100%) of the captioned compound as a pure product.

The structure of this product was confirmed by the following data. m.p. 124°–125° C. (Recrystallization Solvent:ethyl acetate:cyclohexane=2:1) IR (KBr method): 3410 (3660–2100), 2960, 2930, 1695, 1590, 1442, 1298, 1243, 1208, 1184, 1107, 1068, 1035, 1002, 951, 858, 742, 698 cm$^{-1}$ NMR (400 MHz, CDCl$_3$, δ): 1.98–2.05(1H,m), 2.50–2.77(5H,m), 2.81–2.97(3H,m), 3.49(1H,t,J=8.06 Hz), 3.96–4.01(1H,m), 5.10–5.15(1H,m), 5.23–5.27(1H,m), 5.75–5.87(2H,m), 6.71(1H,t,J=7.33 Hz), 6.95(1H,d,J=7.33 Hz), 6.90(1H,d,J=7.33 Hz), 7.27–7.41(5H,m) MASS (EI method, m/e): 380 (M$^+$) High resolution mass spectrum Calcd. (C$_{23}$H$_{24}$O$_5$, M$^+$) 380.1624 Found (M$^+$) 380.1617

EXAMPLE 24

16-phenyl-2,5,6,7,17,18,19,20-octanor-4,8-inter-m-phenylene PGI₂ methyl ester (72) and 15-epimer thereof (73)

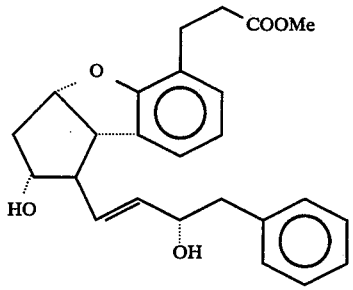
(72)

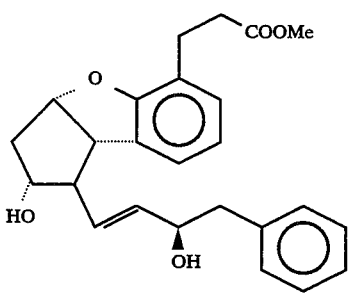
(73)

In 50 ml of methanol, 1.30 g (2.90 mmol) of 16-phenyl-15-oxo-2,5,6,7,17,18,18,20-octanor-4,8-inter-m-phenylene PGI₂ methyl ester, 11-acetate was dissolved. To this solution, 1.41 g (3.77 mmol) of cerium chloride heptahydrate was dissolved and the mixture was cooled down to 0° C. To the mixture, 132 mg (3.48 mmol) of sodium borohydride was added. After stirring the mixture for 10 minutes at 0° C., to the thus obtained reaction mixture, 15 ml of saturated aqueous sodium hydrogen carbonate solution was added and the resulting mixture was concentrated. To the residue, 30 ml of ethyl acetate was added and the precipitate was removed by filtration. The precipitate was washed 3 times with ethyl acetate and the filtrates were combined, washed with water and with brine, dried over anhydrous magnesium sulfate and concentrated to obtain 1.32 g of an oily product. The thus obtained oily product was dissolved in 20 ml of anhydrous methanol. To this solution, 0.15 ml (0.74 mmol) of 4.89N sodium methoxide was added and the resulting mixture was stirred for 1.5 hours at room temperature. The pH of the thus obtained reaction mixture was adjusted to 7 by adding acetic acid. After concentrating the mixture, the residue was dissolved in ethyl acetate and this solution was washed with saturated aqueous sodium hydrogen carbonate solution and with brine, dried over and concentrated to obtain 1.08 g of an oily product. The thus obtained oily product was purified by column chromatography (Lobar column Type B commercially available from Merck & Co., Inc., eluant; ethyl acetate:cyclohexane=5:1) to firstly obtain 615 mg (yield 52%) of 16-phenyl-15-epi-2,5,6,7,17,18,19,20-octanor-4,8-inter-m-phenylene PGI₂ methyl ester having low polarity. Then 393 mg (yield 33%) of 16-phenyl-2,5,6,7,17,18,19,20-octanor-4,8-inter-m-phenylene PGI₂ methyl ester was obtained from high polar fractions.

The structures of these products were confirmed by the following data.

16-phenyl-2,5,6,7,17,18,19,20-octanor-4,8-inter-m-phenylene PGI₂ methyl ester m.p. 127°–127.5° C. (ethyl acetate) IR (KBr method): 3300, 3040, 2975, 2940, 2910, 1730, 1600, 1480, 1455, 1440, 1370, 1330, 1310, 1265, 1185, 1155, 1100, 1070, 1045, 975, 950, 890, 860, 810, 790, 750, 700, 620, 530, 500 cm⁻¹ NMR (400 MHz, CDCl₃, δ): 1.91(1H,ddd,J=5.6, 8.8, 13.7 Hz), 2.33(1H,q,J=8.8 Hz), 2.45(1H,br.s), 2.5–2.8(4H,m), 2.8–3.0(4H,m), 3.31(1H,t,J=8.8 Hz), 3.66(3Hs), 3.80(1H,dt,J=6.0, 8.8 Hz), 4.35(1H,q,J=6.4 Hz), 5.05(1H,ddd,J=5.6, 7.3, 8.8 Hz), 5.54(1H,dd,J=8.8, 15.2 Hz), 5.60(1H,dd,J=6.4, 15.2 Hz), 6.7–6.8(2H,m), 6.96(1H,dd,J=1.5, 6.8 Hz), 7.15–7.4(5H,m) MASS (EI method, m/e): 408 (M+)

| Element Analysis | C | H |
|---|---|---|
| Calcd. C₂₅H₂₈O₅) | 73.51 | 6.91 |
| Found | 73.21 | 6.91 |

16-phenyl-15-epi-2,5,6,7,17,18,19,20-octanor-4,8-inter-m-phenylene PGI₂ methyl ester IR (liquid film method): 3400, 3030, 2950, 1730, 1600, 1450, 1370, 1260, 1200, 1100, 1070, 1030, 865, 745, 700 cm⁻¹ NMR (400 MHz, CDCl₃, δ): 1.76(1H,d,J=4.4 Hz), 1.85(1H,d,J=3.4 Hz), 1.95(1H,ddd,J=5.2, 8.4, 13.7 Hz), 2.42(1H,q,J=8.4 Hz), 2.5–2.9(3H,m), 2.8–3.0(4H,m), 3.41(1H,t,J=8.4 Hz), 3.66(3H,s), 3.80(1H,dt,J=5.9, 8.4 Hz), 4.39(1H,q,J=6.1 Hz), 5.10(1H,ddd,J=5.2, 7.3, 8.4 Hz), 5.59(1H,dd,J=8.4, 15.6 Hz), 5.68(1H,dd,J=6.1, 15.6 Hz), 6.76(1H,t,J=7.1 Hz), 6.9–7.0(2H,m), 7.2–7.4(5H,m) MASS (EI method, m/e): 408 (M+) High resolution mass spectrum Calcd. (C₂₅H₂₈O₅, M+) 408.1915 Found (M+) 408.1926

EXAMPLE 25

16-phenyl-2,5,6,7,17,18,19,20-octanor-4,8-inter-m-phenylene PGI₂ (74)

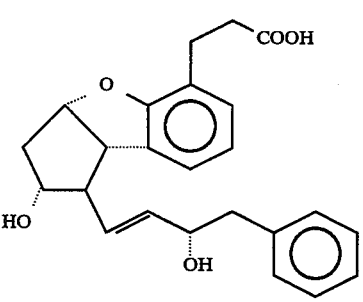
(74)

In 15 ml of methanol, 248 mg (0.61 mmol) of 16-phenyl-2,5,6,7,17,18,19,20-octanor-4,8-inter-m-phenylene PGI₂ methyl ester was dissolved. To this solution, 3 ml of 1N sodium hydroxide was added and the resulting mixture was stirred 3 hours at room temperature. The thus obtained reaction mixture was concentrated and water was added to the residue. The pH of the mixture was adjusted to 4 by adding 1N hydrochloric acid and the resultant was extracted 3 times with ethyl acetate. The organic layers were combined, washed with water and with brine, dried over and concetrated to obtain 223 mg of crude crystals. The thus obtained crude crystals were recrystallized from 3 ml of ethyl acetate to obtain 208 mg of 16-phenyl-2,5,6,7,17,18,19,20-octanor-4,8-inter-m-phenylene PGI$_2$ (yield 87%).

The structure of this product was confirmed by the following data. m.p. 153°–153.8° C. IR (KBr method): 3400, 3030, 2975, 2940, 1695, 1600, 1450, 1420, 1350, 1300, 1250, 1190, 1160, 1100, 1070, 1030, 1000, 970, 950, 880, 860, 830, 800, 750, 745, 700, 600, 540, 510 cm$^{-1}$ NMR (400 MHz, DMSO-d$_6$, δ): 1.65(1H,ddd,J=6.0, 9.9, 12.8 Hz), 2.09(1H,q,J=7.4 Hz), 2.4–2.6(3H,m), 2.65–2.75(3H,m), 2.80(1H,dd,J=6.8, 13.2 Hz), 3.2–3.5(1H,m), 3.6–3.8(1H,m), 4.15–4.3(1H,m), 4.7–4.9(2H,m), 5.0–5.1(1H,m), 5.49(1H,dd,J=5.9, 15.2 Hz), 5.55(1H,dd,J=7.4, 15.2 Hz), 6.6–6.7(2H,m), 6.9–7.0(1H,m), 7.1–7.3(5H,m) MASS (EI method, m/e): 394 (M$^+$)

| Element Analysis | C | H |
|---|---|---|
| Calcd. C$_{24}$H$_{26}$O$_5$) | 73.07 | 6.64 |
| Found | 72.82 | 6.61 |

EXAMPLE 26

16-phenyl-15-epi-2,5,6,7,17,18,19,20-octanor-4,8-inter-m-phenylene PGI$_2$ (75)

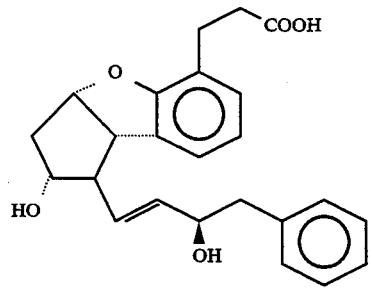
(75)

In 20 ml of methanol, 372 mg (0.91 mmol) of 16-phenyl-15-epi-2,5,6,7,17,18,19,20-octanor-4,8-inter-m-phenylene PGI$_2$ methyl ester was dissolved. To this solution, 4.5 ml of 1N sodium hydroxide was added and the resulting mixture was stirred 3 hours at room temperature. The thus obtained reaction mixture was concentrated and 5 ml of water was added to the residue. Then the pH of the mixture was adjusted to 4 by adding 1N hydrochloric acid and the resultant was extracted 3 times with ethyl acetate. The organic layers were combined, washed with water and with brine, dried over and concetrated to obtain 355 mg of 16-phenyl-15-epi-2,5,6,7,17,18,19,20-octanor-4,8-inter-m-phenylene PGI$_2$ (yield 99%).

The structure of this product was confirmed by the following data. m.p. 107°–108° C. (Recrystallization Solvent:ethyl acetate:cyclohexane) IR (KBr method): 3260, 2975, 2940, 2860, 1725, 1650, 1600, 1450, 1390, 1355, 1330, 1260, 1230, 1185, 1140, 1090, 1060, 1040, 995, 965, 940, 890, 860, 785, 770, 750, 730, 695, 660, 620, 590, 570, 555, 520, 460 cm$^{-1}$ NMR (400 MHz, CDCl$_3$, δ): 1.95(1H,ddd,J=5.5, 7.9, 13.7 Hz), 2.42(1H,q,J=7.9 Hz), 2.55(1H,dt,J=7.9, 13.7 Hz), 2.6–2.8(2H,m), 2.8–3.0(4H,m), 3.42(1H,t,J=7.9 Hz), 3.81(1H,q,J=7.9 Hz), 4.39(1H,q,J=6.1 Hz), 5.09(1H,dt,J=5.5, 7.9 Hz), 5.57(1H,dd,J=7.9, 1.5.4 Hz), 5.66(1H,dd,J=6.1, 15.4 Hz), 6.76(1H,t,J=7.7 Hz), 6.96(1H,d,J=7.7 Hz), 6.98(1H,d,J=7.7 Hz), 7.15–7.4(5H,m) MASS (EI method, m/e): 394 (M$^+$)

| Element Analysis | C | H |
|---|---|---|
| Calcd. C$_{24}$H$_{26}$O$_5$) | 73.07 | 6.64 |
| Found | 73.01 | 6.61 |

EXAMPLE 27

17-phenyl-2,5,6,7,18,19,20-heptanor-4,8-inter-m-phenylene PGI$_2$ methyl ester (76) and 15-epimer thereof (77)

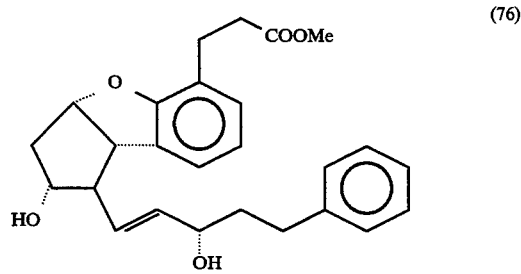
(76)

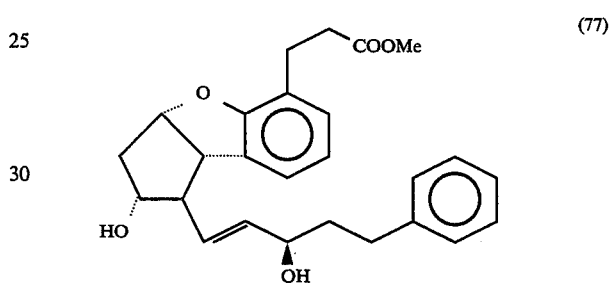
(77)

In 60 ml of methanol, 1.15 g (2.49 mmol) of 17-phenyl-15-oxo-2,5,6,7,18,18,20-heptanor-4,8-inter-m-phenylene PGI$_2$ methyl ester, 11-acetate was dissolved. To this stirred solution, 390 mg (2.49 mmol) of cerium chloride heptahydrate was dissolved and then 142 mg (3.74 mmol) of sodium borohydride was added under cooling iced water. The resulting mixture was stirred for 10 minutes. To the thus obtained reaction mixture, 20 ml of saturated aqueous sodium hydrogen carbonate solution was added and the resulting mixture was concentrated. To the thus obtained residue, 30 ml of water and 100 ml of ethyl acetate were added and the resultant was filtered. The precipitate was washed with ethyl acetate (30 ml×3). The organic layers were combined, washed once with 30 ml each of water and brine, dried over anhydrous sodium sulfate and concentrated to obtain 1.10 g of an oily product. Then the thus obtained oily product was dissolved in 25 ml of anhydrous methanol. Under argon atmosphere and under stirring at room temperature, 0.114 ml (0.59 mmol) of 5.22N sodium methoxide was added thereto and the resulting mixture was stirred for 3 hours at room temperature. To the thus obtained reaction mixture, 0.05 ml of acetic acid was added and the resultung mixture was concentrated. To the residue, 20 ml of water was added and the resultant was extracted with ethyl acetate (50 ml×2). The organic layers were combined, washed once with 20 ml each of water and brine, dried over anhydrous sodium sulfate and concentrated. The thus obtained residue was purified by column chromatography (Lobar column Type B commercially available from Merck & Co., Inc., eluant; ethyl acetate:cyclohexane=2:1) to firstly obtain 432 mg (yield 43.2%) of 17- phenyl-15-epi-2,5,6,7,18,19,20-heptanor-4,8-inter-m-phenylene PGI₂ methyl ester having low polarity. Then 383 mg (yield 38.3%) of 17-phenyl-2,5,6,7,18,19,20-heptanor-4,8-inter-m-phenylene PGI₂ methyl ester was obtained from high polar fractions.

The structures of these products were confirmed by the following data.

17-phenyl-2,5,6,7,18,19,20-heptanor-4,8-inter-m-phenylene PGI₂ methyl ester m.p. 86.4°–87.6° C. (Recrystallization Solvent:ethyl acetate:n-hexane=2:1) IR (KBr method): 3400, 3020, 2925, 2850, 1730, 1595, 1470, 1440, 1365, 1260, 1230, 1180, 1150, 1090, 1070, 1020, 970, 950, 905, 860, 820, 740, 695 cm⁻¹ NMR (400 MHz, CDCl₃, δ): 1.8–2.1(4H,m), 2.1–2.2(1H,m), 2.4–2.5(1H,m), 2.6–2.85(5H,m), 2.85–3.0(2H,m), 3.46(1H,t,J=8.8 Hz), 3.66(3H,s), 3.8–4.0(1H,m), 4.1–4.2(1H,m), 5.13(1H,ddd,J=5.4, 7.3, 8.8 Hz), 5.6–5.8(2H,m), 6.76(1H,t,J=7.4 Hz), 6.98(2H,d,J=7.4 Hz), 7.1–7.4(5H,m) MASS (EI method, m/e): 422 (M+)

| Element Analysis | C | H |
|---|---|---|
| Calcd. (C₂₆H₃₀O₅) | 73.91 | 7.16 |
| Found | 74.03 | 7.05 |

17-phenyl-15-epi-2,5,6,7,18,19,20-heptanor-4,8-inter-m-phenylene PGI₂ methyl ester m.p. 71.8°–72.7° C. (Recrystallization Solvent:ethyl acetate:n-hexane=2:1) IR (KBr method): 3350, 3020, 2960, 2920, 2860, 1730, 1595, 1490, 1445, 1415, 1355, 1300, 1250, 1200, 1170, 1150, 1090, 1060, 1030, 965, 890, 855, 840, 760, 740, 715, 700 cm⁻¹ NMR (400 MHz, CDCl₃, δ): 1.65–1.7(1H,m), 1.8–1.85(1H,m), 1.85–1.95(2H,m), 2.01(1H,ddd,J=4.9, 8.3, 13.7 Hz), 2.45–2.55(1H,m), 2.6–2.85(5H,m), 2.85–3.0(2H,m), 3.49(1H,t,J=8.5 Hz), 3.66(3H,s), 3.9–4.0(1H,m), 4.15–4.25(1H,m), 5.15(1H,ddd,J=4.9, 7.3, 8.5 Hz), 5.65–5.75(2H,m), 6.77(1H,t,J=7.3 Hz), 6.95–7.05(2H,m), 7.2–7.4(5H,m) MASS (EI method, m/e): 422 (M+)

| Element Analysis | C | H |
|---|---|---|
| Calcd. (C₂₆H₃₀O₅) | 73.91 | 7.16 |
| Found | 74.13 | 7.00 |

EXAMPLE 28

17-phenyl-2,5,6,7,18,19,20-heptanor-4,8-inter-m-phenylene PGI₂ (78)

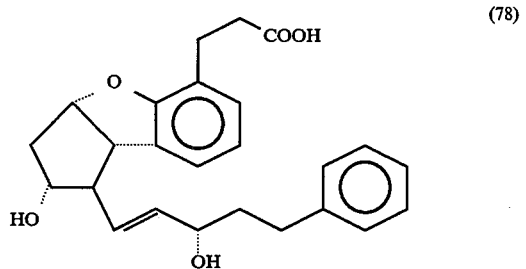

(78)

In 20 ml of methanol, 282 mg (0.668 mmol) of 17-phenyl-2,5,6,7,18,19,20-heptanor-4,8-inter-m-phenylene PGI₂ methyl ester was dissolved. To this stirred solution, 5.42 ml (5.35 mmol) of 0.986N sodium hydroxide was added under cooling in iced water, and the resulting mixture was stirred 5 hours at room temperature. To the thus obtained reaction mixture, 5.5 ml (5.5 mmol) of 1N hydrochloric acid was added and the mixture was concentrated. To the thus obtained residue, 20 ml of water was added and the resultant was extracted with ethyl acetate (50 ml×2). The organic layers were combined, washed once with 10 ml each of water and brine, dried over anhydrous sodium sulfate and concetrated. The thus obtained residue was recrystallized from 1 ml of ethyl acetate and from 0.5 ml of n-hexane to obtain 165 mg (yield 60.5%) of 17-phenyl-2,5,6,7,18,19,20-heptanor-4,8-inter-m-phenylene PGI₂ as colorless crystals.

The structure of this product was confirmed by the following data. m.p. 122.6°–123.1° C. (Recrystallization Solvent:ethyl acetate:n-hexane=2:1) IR (liquid film method): 3350, 3020, 2920, 1700, 1590, 1485, 1440, 1400, 1335, 1250, 1210, 1185, 1145, 1060, 1015, 995, 965, 880, 855, 830, 750, 695, 660 cm⁻¹ NMR (400 MHz, CDCl₃, δ): 1.75–2.0(3H,m), 2.37(1H,q,J=8.5 Hz), 2.55–2.8(5H,m), 2.8–3.0(2H,m), 3.38(1H,t,J=8.5 Hz), 3.86(1H,dt,J=6.3, 8.5 Hz), 4.13(1H,q,J=6.5 Hz), 5.07(1H,ddd,J=5.4, 7.3, 8.5 Hz), 4.0–5.2(2H,m), 5.5–5.65(2H,m), 6.74(1H,t,J=7.5 Hz), 6.94(1H,d,J=7.5 Hz), 6.97(1H,d,J=7.5 Hz), 7.15–7.35(5H,m) MASS (EI method, m/e): 408 (M+) High resolution mass spectrum Calcd. (C₂₅H₂₈O₅, M+) 408.1937 Found (M+) 408.1914

EXAMPLE 29

17-phenyl-15-epi-2,5,6,7,18,19,20-heptanor-4,8-inter-m-phenylene PGI₂ (79)

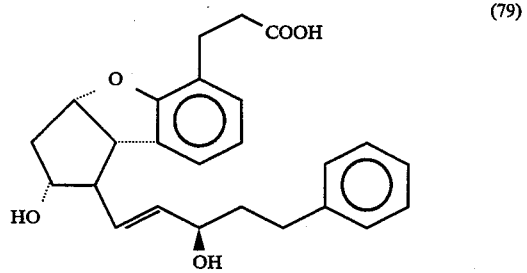

(79)

In 25 ml of methanol, 347 mg (0.822 mmol) of 17-phenyl-15-epi-2,5,6,7,18,19,20-heptanor-4,8-inter-m-phenylene PGI₂ methyl ester was dissolved. To this stirred solution, 6.7 ml (6.6 mmol) of 0.986N sodium hydroxide was added under cooling in iced water, and the resulting mixture was stirred 5 hours at room temperature. To the thus obtained reaction mixture, 6.6 ml (6.6 mmol) of 1N hydrochloric acid was added and the mixture was concentrated. To the thus obtained residue, 20 ml of water was added and the resultant was extracted with ethyl acetate (50 ml×2). The organic layers were combined, washed once with 10 ml each of water and brine, dried over anhydrous sodium sulfate and concetrated. The thus obtained residue was recrystallized from 1.5 ml of ethyl acetate and from 0.5 ml of n-hexane to obtain 295 mg (yield 88.0%) of 17-phenyl-15-epi-2,5,6,7,18,19,20-heptanor-4,8-inter-m-phenylene PGI₂ as colorless crystals.

The structure of this product was confirmed by the following data. m.p. 120.6°–121.3° C. (Recrystallization Solvent:ethyl acetate:n-hexane=2:1) IR (KBr method): 3400, 2920, 2850, 1725, 1640, 1590, 1445, 1380, 1350, 1320, 1255, 1225, 1180, 1140, 1090, 1055, 1035, 945, 890, 745, 700 cm⁻¹ NMR (400 MHz, CDCl₃, δ):

1.4–1.8(2H,m), 1.85–1.95(2H,m), 2.0–2.1(1H,m), 2.45–2.55(1H,m), 2.61(1H,ddd,J=6.1, 7.3, 13.7 Hz), 2.65–3.0(6H,m), 3.50(1H,t,J=8.4 Hz), 3.97(1H,dt,J=6.1, 7.5 Hz), 4.15–4.25(1H,m), 5.16(1H,ddd,J=4.9, 7.3, 8.4 Hz), 5.65–5.75(2H,m), 6.78(1H,t,J=7.3 Hz), 6.95–7.05(2H,m), 7.2–7.4(5H,m) MASS (EI method, m/e): 408 (M+)

| Element Analysis | C | H |
|---|---|---|
| Calcd. (C$_{25}$H$_{28}$O$_0$) | 73.51 | 6.91 |
| Found | 73.67 | 6.84 |

EXAMPLE 30

16,16-dimethyl-17-phenyl-2,5,6,7,18,19,20-heptanor-4,8-inter-m-pehnylene PGI$_2$ methyl ester (80) and 15-epimer thereof (81)

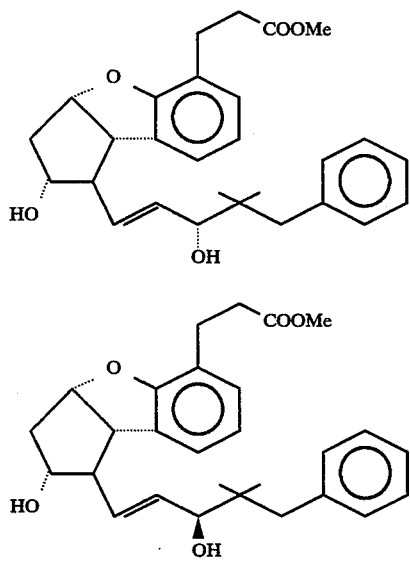

In 20 ml of methanol, 1.165 g (2.373 mmol) of 16,16-dimethyl-15-oxo-17-phenyl-2,5,6,7,18,18,20-heptanor-4,8-inter-m-phenylene PGI$_2$ methyl ester, 11-acetate was dissolved and then 1.33 g (3.569 mmol) of cerium trichloride heptahydrate was dissolved. To this stirred solution, 0.11 g (2.848 mmol) of sodium borohydride was added under cooling in iced water. After stirring the resulting mixture for 20 minutes, saturated aqueous sodium hydrogen carbonate solution was added thereto and the resulting mixture was stirred for 15 minutes. The thus obtained mixture was filtered through Celite and washed with ethyl acetate. The solvent was evapolated under reduced pressure. To the residue, 10 ml of distilled water was added and the resultant was extracted with ethyl acetate. The extrate was washed with brine, dried over anhydrous sodium sulfate. Ethyl acetate was evapolated under reduced pressure to obtain 1.69 g of an oily product. Then the thus obtained oily product was subjected to azeotropic distillation with benzene (25 ml×3) and the resultant was dissolved in 20 ml of anhydrous methanol. To this solution, 0.045 ml (0.237 mmol) of 5.22N sodium methoxide was added at room temperature and the resulting mixture was stirred for 3 hours at room temperature. To the thus obtained reaction mixture, 1 ml of acetic acid was added. After the solvent was evapolated under reduced pressure, 10 ml of water was added to the residue and the resultant was extracted with ethyl acetate. The extrate was washed with brine and dried over anhydrous sodium sulfate. The solvent was evapolated under reduced pressure to obtain a colorless oily product. The thus obtained product was purified by column chromatography (Lobar column, Type B commercially available from Merck & Co., Inc., eluant; ethyl acetate:cyclohexane=1:1) to firstly obtain 0.5196 g (1.157 mmol, yield 48.8%) of 16,16,-dimethyl-17-phenyl-15-epi-2,5,6,7,18,19,20-heptanor-4,8-inter-m-phenylene PGI$_2$ methyl ester having low polarity. Then 0.4469 g (0.9948 mmol, yield 42%) of 16,16-dimethyl-17-phenyl-2,5,6,7,18,19,20-heptanor-4,8-inter-m-phenylene PGI$_2$ methyl ester was obtained from high polar fractions. These compounds were recrystallized from n-hexane/ethyl acetate to obtain colorless crystals.

The structures of these products were confirmed by the following data.

16,16-dimethyl-17-phenyl-2,5,6,7,18,19,20-heptanor-4,8-inter-m-phenylene PGI$_2$ methyl ester m.p. 111.5°–113° C. IR (liquid film method): 3420, 3100, 3090, 3040, 2980, 2950, 2900, 1740, 1600, 1502, 1460, 1430, 1378, 1302, 1260, 1158, 1098, 1070, 1040, 1002, 970, 955, 900, 890, 865, 840, 780, 765, 745, 705 cm$^{-1}$ NMR (400 MHz, CDCl$_3$, δ): 0.85(3H,s), 0.93(3H,s), 1.56(2H,s), 1.87–2.05(1H,m), 2.48–2.54(2H,m), 2.61–2.67(3H,m), 2.77–2.81(1H,m), 2.88–2.91(2H,m), 3.44–3.48(1H,m), 3.66(3H,s), 3.84–3.86(1H,m), 3.92–3.98(1H,m), 5.10–5.16(1H,m), 5.61–5.78(2H,m), 6.74–6.78(1H,m), 6.98–7.00(2H,m), 7.19–7.31(5H,m) MASS (EI method, m/e): 450 (M+) High resolution mass spectrum Calcd. (C$_{28}$H$_{34}$O$_5$, M+) 450.2406 Found (M+) 450.2425

16,16-dimethyl-17-phenyl-15-epi-2,5,6,7,18,19,20-heptanor-4,8-inter-m-phenylene PGI$_2$ methyl ester m.p. 89°–91° C. IR (liquid film method): 3420, 3040, 2980, 2880, 1740, 1602, 1499, 1458, 1375 1365, 1305, 1255, 1195, 1180, 1160, 1095, 1075, 1039, 1005, 980, 960, 865, 770, 750, 710 cm$^{-1}$ NMR (400 MHz, CDCl$_3$, δ): 0.84(3H,s), 0.93(3H,s), 2.60(2H,brs), 1.98–2.10(1H,m), 2.51–2.56(2H,m), 2.58–2.66(3H,m), 2.77–2.81(1H,m), 2.87–2.95(2H,m), 3.48–3.52(1H,m), 3.66(3H,s), 3.86–3.87(1H,m), 3.92–3.95(1H,m), 5.12–5.17(1H,m), 5.65–5.80(2H,m), 6.75–6.79(1H,m), 6.98–7.02(2H,m), 7.16–7.30(5H,m) MASS (EI method, m/e): 450 (M+) High resolution mass spectrum Calcd. (C$_{28}$H$_{34}$O$_5$, M+) 450.2406 Found (M+) 450.2378

EXAMPLE 31

16,16-dimethyl-17-phenyl-2,5,6,7,18,19,20-heptanor-4,8-inter-m-phenylene PGI$_2$ (82)

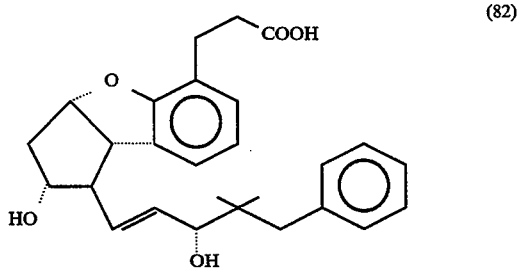

In 10 ml of methanol, 0.1691 g (0.376 mmol) of 16,16-dimethyl-17-phenyl-2,5,6,7,18,19,20-heptanor-4,8-inter-m-phenylene PGI$_2$ methyl ester was dissolved and then 1.0 ml of 1.06N sodium hydroxide was added. After stirring the resulting mixture for 6 hours under argon atmosphere at room temperature, methanol was evapolated under reduced pressure. To the thus obtained residue, 5 ml of water was added and the pH of the mixture was adjusted to 2 by adding 1N hydrochloric acid. The resultant was extracted with ethyl acetate (15 ml×3). The extract was washed with brine, dried over anhydrous sodium sulfate. Ethyl acetate was evapolated under reduced pressure and then the resultant was dried under reduced pressure to obtain 0.147 g (0.337 mmol) of 16,16-dimethyl-17-phenyl-2,5,6,7,18,19,20-heptanor-4,8-inter-m-phenylene PGI$_2$ with a 90% yield. The thus obtained crude crystals were recrystallized from n-hexane/ethyl acetate to obtain colorless crystals.

The structure of this product was confirmed by the following data. m.p. 131.5°–132.5° C. IR (KBr method): 3420, 3030, 2970, 2940, 2880, 1700, 1600, 1460, 1420, 1385, 1365, 1320, 1290, 1250, 1160, 1075, 1025, 1000, 985, 965, 930, 900, 860, 830, 780, 750, 740, 730, 705 cm$^{-1}$ NMR (400 MHz, CDCl$_3$, δ): 0.85(3H,s), 0.92(3H,s), 1.96–2.02(1H,m), 2.44–2.54(3H,m), 2.59–2.71(3H,m), 2.73–2.95(4H,m), 3.42–3.46(1H,m), 3.83–3.85(1H,m), 3.90–3.96(1H,m), 5.09–5.14(1H,m), 5.59–5.76(2H,m), 6.74–6.78(1H,m), 6.96–7.00(2H,m), 7.20–7.31(5H,m) MASS (E I method, m/e): 436 (M+) High resolution mass spectrum Calcd. (C$_{27}$H$_{32}$O$_5$, M+) 436.2249 Found (M+) 436.2261

EXAMPLE 32 d-17-phenyl-2,5,6,7,18,19,20-heptanor-4,8-inter-m-phenylene PGI$_2$ methyl ester (83) and 15-epimer thereof (84)

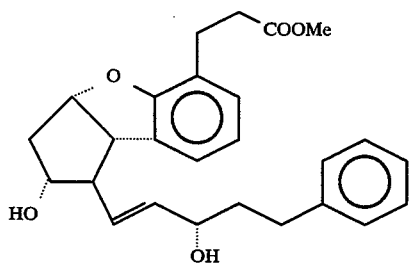
(83)

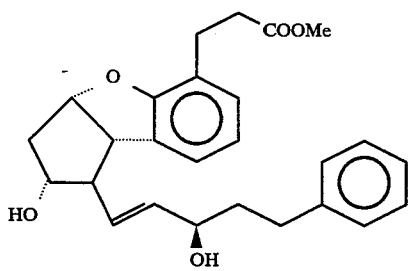
(84)

In 40 ml of methanol, 740 mg (1.6 mmol) of d-17-phenyl-15-oxo-2,5,6,7,18,19,20-heptanor-4,8-inter-m-phenylene PGI$_2$ methyl ester, 11-acetate was dissolved and then 597 mg (1.6 mmol) of cerium trichloride heptahydrate was added. Further, to this stirred mixture, 91 mg (2.4 mmol) of sodium borohydride was added under cooling in iced water and the resulting mixture was stirred for 10 minutes. To the thus obtained reaction mixture, 10 ml of saturated aqueous sodium hydrogen carbonate solution was added and the resulting mixture was filtered. The precipitate was washed with ethyl acetate (10 ml×5) and the filtrates were combined followed by being concentrated. To the thus obtained residue, 70 ml of ethyl acetate was added and the mixture was washed once with 20ml each of water and brine, dried over anhydrous sodium sulfate and concentrated. Then the thus obtained residue was subjected to azeotropic distillation with benzene (10 ml×2) to obtain 727 mg of an oily product. Then the thus obtained oily product was dissolved in 30 ml of anhydrous methanol under argon atmosphere. To this solution, 0.075 ml (0.393 mmol) of 5.22N sodium methoxide was added under stirring and the resulting mixture was stirred for 3 hours at room temperature. The obtained reaction mixture was neutralized with acetic acid and the resulting mixture was concentrated. The thus obtained reaction mixture, 20 ml of water was added and the resultant was extracted with ethyl acetate (50 ml×2). The ethyl acetate layers were washed once with 20 ml each of water and brine, dried over anhydrous sodium sulfate and concentrated. The thus obtained residue was purified by Lobar column (silica gel, commercially available from Merck & Co., Inc., eluant; ethyl acetate:cyclohexane=2:1) to firstly obtain 256 mg (0.61 mmol, yield 38.6%) of d-17-phenyl-15-epi-2,5,6,7,18,19,20-heptanor-4,8-inter-m-phenylene PGI$_2$ methyl ester from low polar fractions as colorless crystals. Then 282 mg (0.67 mmol, yield 42.6%) of d-17-phenyl-2,5,6,7,18,19,20-heptanor-4,8-inter-m-phenylene PGI$_2$ methyl ester was obtained from high polar fractions as an oily product.

The structures of these products were confirmed by the following data.

d-17-phenyl-2,5,6,7,18,19,20-heptanor-4,8-inter-m-phenylene PGI$_2$ methyl ester [α]$_D^{25}$=+96.34° (C=1.23, MeOH) IR (liquid film method): 3350, 3020, 2925, 2850, 1725, 1595, 1450, 1250, 1190, 1060, 1025, 965, 885, 855, 830, 740, 695 cm$^{-1}$ NMR (400MHz, CDCl$_3$, δ): 1.8–2.2(5H,m), 2.4–2–5(1H,m), 2.6–2.8(5H,m), 2.8–3.0(2H,m), 3.46(1H,t,J=8.3 Hz), 3.66(3H,S), 3.9–4.0(1H,m), 4.1–4.3(1H,m), 5.1–5.3(1H,m), 5.6–5.8(2H,m), 6.76(1H,t,J=7.6 Hz), 6.9–7.0(2H,m), 7.1–7.4(5H,m) MASS (EI method, m/e): 422 (M+) High resolution mass spectrum Calcd. (C$_{26}$H$_{30}$O$_5$, M+) 422.2093 Found (M+) 422.2106 d-17-phenyl-15-epi-2,5,6,7,18,19,20-heptanor-4,8-inter-m-phenylene PGI$_2$ methyl ester

[α]$_D^{25}$=+77.56° (C=1.11, MeOH) m.p. 85.4° C.–86.3° C. (Recrystallization Solvent:ethyl acetate:n-hexane=2:1) IR (KBr method): 3380, 3020, 2930, 2975, 1730, 1590, 1425, 1340, 1270, 1250, 1220, 1170, 1140, 1065, 1040, 975, 880, 860, 820, 765, 740, 695 cm$^{-1}$ NMR (400 MHz, CDCl$_3$, δ): 1.5–1.7(1H,m), 1.7–1.8(1H,m), 1.8–1.95(2H,m), 1.95–2.1(1H,m), 2.4–2.55(1H,m), 2.55–2.85(5H,m), 2.85–3.0(2H,m), 3.49(1H,t,J=8.1 Hz), 3.66(3H,S), 3.9–4.0(1H,m), 4.1–4.3(1H,m), 5.1–5.2(1H,m), 5.6–5.8(2H,m), 6.76(1H,t,J=7.4 Hz), 6.98(1H,d,J=7.4 Hz), 7.00(1H,d,J=7.4 Hz), 7.2–7.4(5H,m) MASS (EI method, m/e): 422 (M+) High resolution mass spectrum Calcd. (C$_{26}$H$_{30}$O$_5$, M+) 422.2093 Found (M+) 422.2085

EXAMPLE 33 d-17-phenyl-2,5,6,7,18,19,20-heptanor-4,8-inter-m-phenylene PGI$_2$ (85)

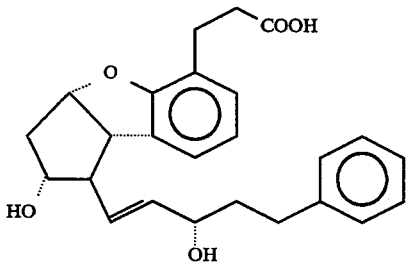

(85)

In 20 ml of methanol, 214 mg (0.507 mmol) of d-17-phenyl-2,5,6,7,18,19,20-heptanor-4,8-inter-m-phenylene PGI$_2$ methyl ester was dissolved. To this stirred solution, 5 ml (5 mmol) of 1N sodium hydroxide was added under cooling in iced water, and the resulting mixture was stirred 5 hours at room temperature. The thus obtained reaction mixture was neutralized with 1N hydrochloric acid and the mixture was concentrated. To the thus obtained residue, 20 ml of water was added and the resultant was extracted with ethyl acetate (50 ml×2). Ethyl acetate layers were washed once with 20 ml each of water and brine, dried over anhydrous sodium sulfate and concetrated. The thus obtained residue was recrystallized from 2 ml of ethyl acetate and from 4 ml of n-hexane to obtain 156 mg (0.38 mmol, yield 75.4%) of d-17-phenyl-2,5,6,7,18,19,20-heptanor-4,8-inter-m-phenylene PGI$_2$ as colorless crystals.

The structure of this product was confirmed by the following data. $[\alpha]_D^{25} = +102.93°$ (C=1.124, MeOH) m.p. 89.3° C.-90.8° C. (Recrystallization Solvent:ethyl acetate:n-hexane=1:2) IR (KBr method): 3300, 3020, 2925, 1685, 1590, 1440, 1400, 1255, 1190, 1150, 1110, 1090, 1060, 1030, 965, 945, 880, 855, 830, 760, 740, 710, 690 cm$^{-1}$ NMR (400 MHz, CDCl$_3$, δ): 1.7–1.9(1H,m), 1.9–2.0(2H,m), 2.36(1H,q,J=8.0 Hz), 2.5–2.8(5H,m), 2.5–3.0(2H,m), 3.37(1H,t,J=8.5 Hz), 3.4–4.5(3H,m), 3.84(1H,q,J=8.0 Hz), 4.12(1H,q,J=6.5 Hz), 5.0–5.1(1H,m), 5.5–5.7(2H,m), 6.73(1H,t,J=7.2 Hz), 6.92(1H,d,J=7.2 Hz), 6.96(1H,d,J=7.2 Hz), 7.1–7.25(3H,m), 7.25–7.4(2H,m) MASS (EI method, m/e): 408 (M+) High resolution mass spectrum Calcd. (C$_{25}$H$_{28}$O$_5$, M+) 408.1936 Found (M+) 408.1948

EXAMPLE 34 d-17-phenyl-15-epi-2,5,6,7,18,19,20-heptanor-4,8-inter-m-phenylene PGI$_2$ (86)

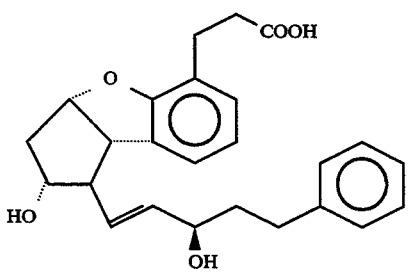

(86)

In 20 ml of methanol, 197 mg (0.47 mmol) of d-17-phenyl-15-epi-2,5,6,7,18,19,20-heptanor-4,8-inter-m-phenylene PGI$_2$ methyl ester was dissolved. To this stirred solution, 4.7 ml (4.7 mmol) of 1N sodium hydroxide was added under cooling in iced water, and the resulting mixture was stirred 5 hours at room temperature. The thus obtained reaction mixture was neutralized with 1N hydrochloric acid was added to neutralize the same and the mixture was concentrated. To the thus obtained residue, 20 ml of water was added and the resultant was extracted with ethyl acetate (50 ml×2). Ethyl acetate layers were washed once with 20 ml each of water and brine, dried over anhydrous sodium sulfate and concetrated. The thus obtained residue was recrystallized from 2.5 ml of ethyl acetate and from 2.5 ml of n-hexane to obtain 129 mg (0.316 mmol, yield 67.3%) of d-17-phenyl-15-epi-2,5,6,7,18,19,20-heptanor-4,8-inter-m-phenylene PGI$_2$ as colorless crystals.

The structure of this product was confirmed by the following data. $[\alpha]_D^{25} = +86.71°$ (C=1.054, MeOH) m.p. 122.0°–123.2° C. (Recrystallization Solvent:ethyl acetate:n-hexane=1:1) IR (KBr method): 3420, 3030, 2930, 1700, 1590, 1445, 1300, 1250, 1190, 1060, 1030, 970, 940, 915, 890, 865, 795, 740, 700 cm$^{-1}$ NMR (400 MHz, CDCl$_3$, δ): 1.8–2.1(3H,m), 2.4–2.6(11H,m), 3.46(1H,t,J=8.0 Hz), 3.93(1H,q,J=7.0 Hz), 4.1–4.2(1H,m), 5.0–5.2(1H,m), 5.6–5.8(2H,m), 6.75(1H,t,J=7.3 Hz), 6.98(2H,t,J=7.3 Hz), 7.1–7.25(3H,m), 7.25–7.4(2H,m) MASS (EI method, m/e): 408 (M+) High resolution mass spectrum Calcd. (C$_{25}$H$_{28}$O$_6$, M+) 408.1936 Found (M+) 408.1915

EXAMPLE 35 d-15-p-chlorophenyl-2,5,6,7,16,17,18,19,20-nonanor-4,8-inter-m-phenylene PGI$_2$ methyl ester (87) and 15-epimer thereof (88)

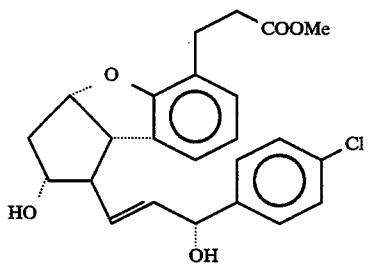

(87)

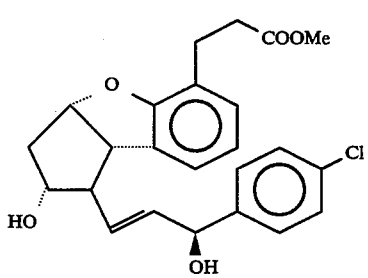

(88)

In 40 ml of methanol, 793 mg (1.69 mmol) of d-15-p-chlorophenyl-15-oxo-2,5,6,7,16,17,18,19,20-nonanor-4,8-inter-m-phenylene PGI$_2$ methyl ester was dissolved and then 630.5 mg (1.69 mmol) of cerium trichloride heptahydrate was dissolved. Further, to the stirred mixture, 80 mg (2.11 mmol) of sodium borohydride was added slowly and the resulting mixture was atirred for 20 minutes. To the thus obtained reaction mixture, 10 ml of saturated aqueous sodium hydrogen carbonate solution was added and the resulting mixture was filtered. The precipitate was washed with ethyl acetate (10 ml×5) and the filtrates were combined followed by being concentrated. To the thus obtained residue, 20 ml of water was added and the resultant was extracted with ethyl acetate (50 ml×2). Ethyl acetate layers were washed once with 20 ml each of water and brine, dried over anhydrous sodium sulfate and concentrated. Then the thus residue was subjected to azeotropic distillation with benzene (10 ml×2) to obtain 786 mg of an oily product. Then to the thus obtained oily product, 0.08 ml (0.42 mmol) of 5.22N sodium methoxide in methanol was added under argon atmosphere and the resuling mixture was stirred for 14 hours at room temperature. The thus obtained reaction mixture was neutralized with acetic acid and the resultant was concentrated. To the thus obtained residue, 20 ml of water was added and the resultant was extracted with ethyl acecate (50 ml×2). Ethyl acetate layers were washed once with 20 ml each of water and brine, dried over anhydrous sodium sulfate and concetrated. The thus obtained residue was purified by Lobar column (silica gel, commercially available from Merck & Co., Inc., eluant; ethyl acetate:-cyclohexane=2:1) to firstly obtain 279 mg (0.65 mmol, yield 39%) of d-15-p-chlorophenyl-15-epi-2,5,6,7,16,17,18,19,20-nonanor-4,8-inter-m-phenylene $PGI_2$ methyl ester from low polar fractions as white crystals. Then 235 mg (0.59 mmol, yield 35.3%) of d-15-p-chlorophenyl-2,5,6,7,16,17,18,19,20-nonanor-4,8-inter-m-phenylene $PGI_2$ methyl ester was obtained from high polar fractions.

The structures of these products were confirmed by the following data.

d-15-p-chlorophenyl-2,5,6,7,16,17,18,19,20,-nonanor-4,8-inter-m-phenylene $PGI_2$ methyl ester $[\alpha]_D^{25} = +124.41°$ (C=1.356, MeOH) m.p. 114.6°-116.1° C. (Recrystallization Solvent:ethyl acetate:n-hexane=1:3) IR (KBr method): 3370, 2975, 2930, 2870, 1730, 1590, 1470, 1440, 1390, 1360, 1280, 1265, 1230, 1180, 1140, 1100, 1070, 1020, 970, 950, 920, 860, 810, 790, 740, 715 cm$^{-1}$ NMR (400 MHz, CDCl$_3$, δ): 1.9-2.1(2H,m), 2.29(1H,d,J=3.4 Hz), 2.4-2.7(4H,m), 2.8-3.0(2H,m), 3.47(1H,t,J=8.3 Hz), 3.65(3H,S), 3.9-4.1(1H,m), 5.0-5.2(1H,m), 5.2-5.3(1H,m), 5.7-5.9(2H,m), 6.73(1H,t,J=7.3 Hz), 6.88(1H,d,J=7.3 Hz), 6.96(1H,d,J=7.3 Hz), 7.3-7.4(4H,m), MASS (EI method, m/e): 428 (M+) High resolution mass spectrum Calcd. (C$_{24}$H$_{25}$O$_5$Cl, M+) 428.1391 Found (M+) 428.1398 d-15-p-chlorophenyl-15-epi-2,5,6,7,16,17,18,19,20-nonanor-4,8-inter-m-phenylene $PGI_2$ methyl ester $[\alpha]_D^{25} = +106.46°$ (C=1.176, MeOH ) m.p. 122.0°-123.3° C. (Recrystallization Solvent:ethyl acetate:n-hexane=3:8) IR (KBr method): 3500, 2950, 1725, 1600, 1490, 1450, 1400, 1255, 1150, 1095, 1035, 1010, 980, 960, 945, 885, 850, 820, 800, 760, 740, 720 cm$^{-1}$ NMR (400 MHz, CDCl$_3$, δ): 1.76(1H,d,J=5.9 Hz), 1.9-2.1(2H,m), 2.5-2.7(4H,m), 2.8-3.0(2H,m), 3.51(1H,t,J=8.3 Hz), 3.65(3H,S), 3.9-4.1(1H,m), 5.0-5.2(1H,m), 5.2-5.3(1H,m), 5.7-5.9(2H,m), 6.75(1H,t,J=8.1 Hz), 6.9-7.0(2H,m), 7.3-7.4(4H,m) MASS (EI method, m/e): 428 (M+) High resolution mass spectrum Calcd. (C$_{24}$H$_{25}$ClO$_5$, M+) 428.1391 Found (M+) 428.1383

EXAMPLE 36 d-15-p-chlorophenyl-2,5,6,7,16,17,18,19,20-nonanor-4,8-inter-m-phenylene $PGI_2$ (89)

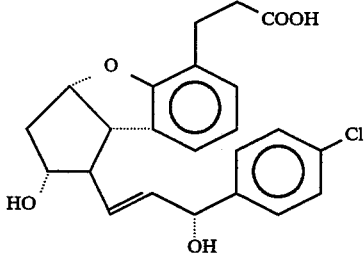

(89)

In 30 ml of methanol, 221.2 mg (0.52 mmol) of d-15-p-chlorophenyl-2,5,6,7,16,17,18,19,20-nonanor-4,8-inter-m-phenylene $PGI_2$ methyl ester was dissolved. To this stirred solution, 7.42 ml (7.42 mmol) of 1N sodium hydroxide was added under cooling in iced water. The resulting mixture was stirred 5 hours at room temperature and concentrated. To the concentrate, 40 ml of water was added and the mixture was neutralized by adding 1N hydrochloric acid. The resulting mixture was extracted with ethyl acetate (50 ml×2). Ethyl acetate layers were washed once with 20 ml each of water and brine, dried over anhydrous sodium sulfate and concetrated. The thus obtained residue was recrystallized from 2 ml of ethyl acetate and from 4 ml of n-hexane to obtain 178 mg (0.43 mmol, yield 82.6%) of d-17-p-chlorophenyl-2,5,6,7,16,17,18,19,20-nonanor-4,8-inter-m-phenylene $PGI_2$ as colorless crystals.

The structure of this product was confirmed by the following data. $[\alpha]_D^{25} = +122.05°$ (C=1.052, MeOH) m.p. 100.3°-101.5° C. (Recrystallization Solvent:ethyl acetate:n-hexane=1:2) IR (KBr method): 3400, 2920, 1700, 1590, 1445, 1400, 1255, 1190, 1085, 1060, 1030, 1005, 960, 855, 760, 740 cm$^{-1}$ NMR (400 MHz, CDCl$_3$, δ): 1.5-2.7(3H,m), 1.9-2.1(1H,m), 2.40(1H,q,J=8.1 Hz), 2.5-2.7(3H,m), 2.8-3.0(2H,m), 3.43(1H,t,J=8.8 Hz), 3.8-4.0(1H,m), 5.0-5.2(1H,m), 5.19(1H,d,J=5.9 Hz), 5.7-5.9(2H,m), 6.71(1H,t,J=7.1 Hz), 6.86(1H,d,J=7.1 Hz), 6.97(1H,d,J=7.1 Hz), 7.2-7.4(4H,m) MASS (EI method, m/e): 414 (M+) High resolution mass spectrum Calcd. (C$_{23}$H$_{23}$ClO$_5$, M+) 414.1234 Found (M+) 414.1238

EXAMPLE 37 d-15-p-chlorophenyl-15-epi-2,5,6,7,16,17,18,19,20-nonanor-4,8-inter-m-phenylene $PGI_2$ (90)

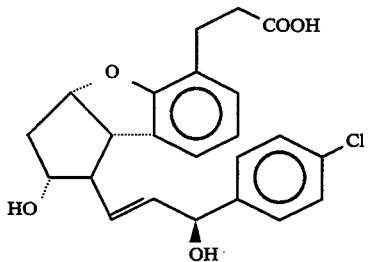

(90)

In 40 ml of methanol, 218 mg (0.51 mmol) of d-15-p-chlorophenyl-15-epi-2,5,6,7,16,17,18,19,20-nonanor-4,8-inter-m-phenylene $PGI_2$ methyl ester was dissolved. To this stirred solution, 8.6 ml (8.6 mmol) of 1N sodium hydroxide was added under cooling in iced water, and the resulting mixture was stirred 3 hours at room temperature. The thus obtained reaction mixture was concentrated and 20 ml of water was added thereto. The mixture was neutralized by adding 8.6 ml (8.6 mmol) of 1N hydrochloric acid and the thus obtained mixture was extracted with ethyl acetate (50 ml×2). Ethyl acetate layers were washed once with 20 ml each of water and saturated saline, dried over anhydrous sodium sulfate and concetrated. The thus obtained residue was recrystallized from 3 ml of ethyl acetate and from 5 ml of n-hexane to obtain 97 mg (0.23 mmol, yield 45.9%) of d-15-p-chlorophenyl-2,5,6,7,16,17,18,19,20-nonanor-4,8-inter-m-phenylene PGI$_2$.

The structure of this product was confirmed by the following data. $[\alpha]_D^{25} = +109.17$ (C=0.676, MeOH) m.p. 100.3°–101.5° C. (Recrystallization Solvent:ethyl acetate:n-hexane=3:5 IR (KBr method): 370, 2980, 2950, 1715, 1600, 1490, 1450, 1410, 1340, 1260, 1190, 1085, 1010, 970, 940, 850, 830, 740 cm$^{-1}$ NMR (400 MHz, CDCl$_3$, δ): 1.5–2.7(3H,m), 1.9–2.1(1H,m), 2.47(1H,q,J=7.8 Hz), 2.5–3.7(3H,m), 2.8–3.0(2H,m), 3.46(1H,t,J=8.6 Hz), 3.8–4.0(1H,m), 5.0–5.2(1H,m), 5.21(1H,d,J=5.9 Hz), 5.74(1H,dd,J=15.9, 7.8 Hz), 5.83(1H,dd,J=15.9, 5.9 Hz), 6.73(1H,t,J=7.6 Hz), 6.94(1H,d,J=7.6 Hz), 6.98(1H,d,J=7.6 Hz), 7.2–7.4(4H,m) MASS (EI method, m/e): 414 (M$^+$) Hith resolution mass spectrum Calcd. (C$_{23}$H$_{23}$ClO$_5$, M$^+$) 414.1234 Found (M$^+$) 414.1253

EXAMPLE 38 d-16-(R)-methyl-17-phenyl-2,5,6,7,18,19,20-heptanor-4,8-inter-m-phenylene PGI$_2$ (91) and 15-epimer thereof (92)

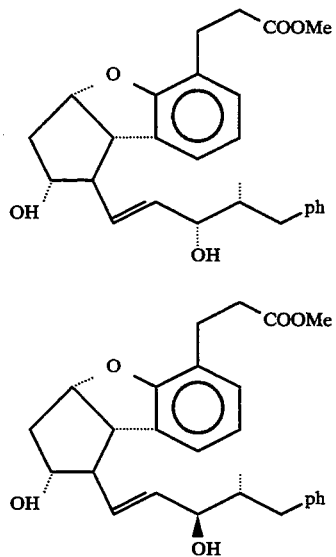

In 50 ml of methanol, 963.6 mg (2.02 mmol) of d-16-(R)-methyl-15-oxo-17-phenyl-2,5,6,7,18,19,20-heptanor-4,8-inter-m-phenylene PGI$_2$ methyl ester, 11-acetate was dissolved and then 753 mg (2.02 mmol) of cerium trichloride heptahydrate was dissolved. To this stirred solution, 42.6 mg (1.13 mmol) of sodium borohydride was added at 0° C. and the resulting mixture was stirred 40 minutes. To the thus obtained reaction mixture, 20 ml of water was added and the solvent was evaporated. Then the generated precipitate was removed by filtration through High Flow Super Cell and washed with ethyl acetate. After separating ethyl acetate layer, water layer was extracted with ethyl acetate (40 ml×3). Then ethyl acetate layers were combined, washed with 30 ml of brine, dried over anhydrous sodium sulfate and concetrated to obtain an oily product. The thus obtained oily product was subjected to azeotropic distillation with THF (6 ml×2) and was dried under reduced pressure. The residue was dissolved in 40 ml of anhydrous methanol. To this solution, 0.02 ml (0.10 mmol) of 5.22N sodium methoxide was added and the resulting mixture was stirred at room temperature under argon atmosphere overnight. To the thus obtained reaction mixture, acetic acid was added to attain pH 7 and the resulting mixture was concentrated. To the concentrate, 20 ml of water was added and the resultant was extracted with ethyl acetate (30 ml×4). Then ethyl acetate layers were washed with 50 ml of brine, dried over anhydrous sodium sulfate and concentrated to obtain an oily product. The thus obtained oily product was purified by column chromatography (silica gel, eluant; ethyl acetate:cyclohexane=2:1) to obtain 354.5 mg (0.812 mmol, yield 40.2%) of d-16-(R)-methyl-17-phenyl-15-epi-2,5,6,7,18,19,20-heptanor-4,8-inter-m-phenylene PGI$_2$ methyl ester from low polar fractions. Then 387.2 mg (0.887 mmol, yield 43.9%) of d-16-(R)-methyl-17-phenyl-2,5,6,7,18,19,20-heptanor-4,8-inter-m-phenylene PGI$_2$ methyl ester was obtained from high polar fractions.

The structures of these products were confirmed by the following data.

d-16-(R)-methyl-17-phenyl-2,5,6,7,18,19,20-heptanor-4,8-inter-m-phenylene PGI$_2$ methyl ester $[\alpha]_D^{20} = +109.67°$ (C=1.13, MeOH) IR (liquid film method): 3380, 3040, 2940, 1736, 1602, 1493, 1473, 1369, 1346, 1303, 1258, 1198, 1178, 1158, 1068, 1050, 1003, 968, 910, 890, 861, 743, 705 cm$^{-1}$ NMR (400MHz, CDCl$_3$, δ): 0.90(3H,d,J=6.83 Hz), 1.53–2.15(4H,m), 2.30–2.52(2H,m), 2.57–2.61(3H,m), 2.83–2.95(3H,m), 3.40–3.48(1H,m), 3.66(3H,S), 3.88–3.96(1H,m), 4.06–4.14(1H,m), 5.08–5.16(1H,m), 5.62–5.72(2H,m), 6.75(1H,t,J=7.33 Hz), 6.96(1H,d,J=1.96 Hz), 6.98(1H,d,J=1.95 Hz), 7.16–7.24(2H,m), 7.24–7.32(3H,m) MASS (EI method, m/e): 436 (M$^+$) High resolution mass spectrum Calcd. (C$_{27}$H$_{32}$O$_5$, M$^+$) 436.2250 Found (M$^+$) 436.2257 d-16-(R)-methyl-17-phenyl-15-epi-2,5,6,7,18,19,20-heptanor-4,8-inter-m-phenylene PGI$_2$ methyl ester $[\alpha]_D^{20} = +55.70°$ (C=0.964, MeOH ) IR (liquid film method): 3385, 3020, 2925, 1726, 1598, 1489, 1466, 1366, 1300, 1255, 1190, 1150, 1065, 1025, 967, 906, 864, 859, 739, 699 cm$^{-1}$ NMR (400 MHz, CDCl$_3$, δ): 0.88(3H,d,J=6.84 Hz), 1.53–1.78(2H,brm), 1.92–2.10(2H,m), 2.37–2.45(1H,m), 2.50–2.59(1H,m), 2.59–2.72(3H,m), 2.83–2.96(3H,m), 3.51(1H,t,J=8.30 Hz), 3.66(3H,S), 3.93–4.02(1H,m), 4.02–4.08(1H,m), 5.13–5.20(1H,m), 5.67–5.77(2H,m), 6.74–7.01(1H,m), 6.98(1H,d,J=7.33 Hz), 7.01(1H,d,J=7.33 Hz), 7.15–7.24(2H,m), 7.24–7.32(3H,m) MASS (EI method, m/e): 436 (M$^+$) High resolution mass spectrum Calcd. (C$_{27}$H$_{32}$O$_5$, M$^+$) 436.2250 Found (M$^+$) 436.2264

EXAMPLE 39 d-16-(R)-methyl-17-phenyl-2,5,6,7,18,19,20-heptanor-4,8-inter-m-phenylene PGI$_2$ (93)

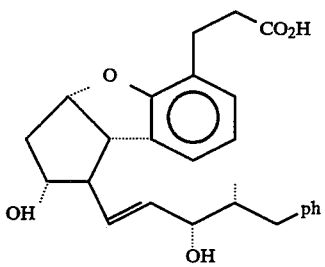

(93)

In 30 ml of methanol, 232.6 mg (0.533 mmol) of d-16-(R)-methyl-17-phenyl-2,5,6,7,18,19,20-heptanor-4,8-inter-m-phenylene PGI$_2$ methyl ester was dissolved. To this solution, 6.40 ml (6.40 mmol) of 1N sodium hydroxide was added and resulting mixture was stirred overnight under argon atmosphere at room temperature. The pH of the thus obtained reaction mixture was adjusted to 1 by adding 1N hydrochloric acid and then methanol was evaporated. To the residue, 10 ml of water was added and the resultant was extracted with ethyl acetate (20 ml×4). Then ethyl acetate layers were washed with water (10 ml) and with brine (20 ml), dried over anhydrous sodium sulfate and concetrated to obtain 225.2 mg of d-16-(R)-methyl-17-phenyl-2,5,6,7,18,19,20-heptanor-4,8-inter-m-phenylene PGI$_2$ as a pure product (yield 100%).

The structure of this product was confirmed by the following data. $[\alpha]_D^{20} = +110.57°$ (C=1.02, MeOH) m.p. <30° IR (KBr method): 3350, 2920, 2870, 2825, 1703, 1598, 1493, 1448, 1403, 1368, 1338, 1255, 1188, 1151, 1053, 1028, 1001, 965, 888, 858, 836, 763, 741, 700, 613, 503 cm$^{-1}$ NMR (400 MHz, CDCl$_3$, δ): 0.88(3H,d,J=6.83 Hz), 1.83-2.02(2H,m), 2.28-2.47(2H,m), 2.55-2.75(3H,m), 2.80-2.97(3H,m), 3.37-3.44(1H,m), 3.85-3.93(1H,m), 4.00-4.10(1H,m), 4.30-5.50(2H,brs), 5.05-5.13(1H,m), 5.57-5.69(2H,m), 6.73(1H,t,J=7.32 Hz), 6.93(1H,d,J=7.32 Hz), 6.97(1H,d,J=7.32 Hz), 7.14-7.34(5H,m) MASS (EI method, m/e): 422 (M+) High resolution mass spectrum Calcd. (C$_{26}$H$_{30}$O$_5$, M+) 422.2094 Found (M+) 422.2107

EXAMPLE 40 d-16-(R)-methyl-17-phenyl-15-epi-2,5,6,7,18,19,20-heptanor-4,8-inter-m-phenylene PGI$_2$ (94)

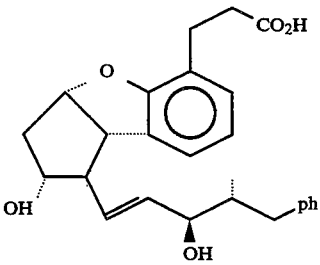

(94)

In 30 ml of methanol, 238.2 mg (0.546 mmol) of d-16-(R)-methyl-17-phenyl-15-epi-2,5,6,7,18,19,20-heptanor-4,8-inter-m-phenylene PGI$_2$ methyl ester was dissolved. To this solution, 6.44 ml (6.44 mmol) of 1N sodium hydroxide was added and the resulting mixture was stirred overnight under argon atmosphere at room temperature. The pH of the thus obtained reaction mixture was adjusted to 1 by adding 1N hydrochloric acid and then methanol was evaporated. To the residue, 10 ml of water was added and the resultant was extracted with ethyl acetate (20 ml×4). Then ethyl acetate layers were washed with water (10 ml) and with brine (20 ml), dried over anhydrous sodium sulfate and concetrated to obtain 230.70 mg of d-16-(R)-methyl-17-phenyl-15-epi-2,5,6,7,18,19,20-heptanor-4,8-inter-m-phenylene PGI$_2$ as a pure product (yield 100%).

The structure of this product was confirmed by the following data. $[\alpha]_D^{20} = +64.84°$ (C=0.0990, MeOH) m.p. <30° IR (KBr method): 3400, 3030, 2965, 2925, 1706, 1598, 1493, 1448, 1401, 1371, 1338, 1253, 1188, 1153, 1063, 1033, 1003, 967, 885, 857, 792, 740, 700, 607, 522 cm$^{-1}$ NMR (400 MHz, CDCl$_3$, δ): 0.88(3H,d,J=6.84 Hz), 1.92-2.07(2H,m), 2.35-2.45(1H,m), 2.48-2.77(4H,m), 2.82-2.98(3H,m), 3.45-3.53(1H,m), 3.00-4.00(2H,brs), 3.97(1H,dd,J=13.67, 7.8 Hz), 4.02-4.07(1H,m), 5.02-5.08(1H,m), 5.65-5.77(2H,m), 6.76(1H,t,J=7.33 Hz), 6.99(1H,d,J=7.33 Hz), 7.01(1H,d,J=7.33 Hz), 7.14-7.33(5H,m) MASS (EI method, m/e): 422 (M+) High resolution mass spectrum Calcd. (C$_{26}$H$_{30}$O$_5$, M+) 422.2093 Found (M+) 422.2094

EXAMPLE 41 d-16-(S)-methyl-17-phenyl-2,5,6,7,18,19,20-heptanor-4,8-inter-m-phenylene PGI$_2$ methyl ester (95) and 15-epimer thereof (96)

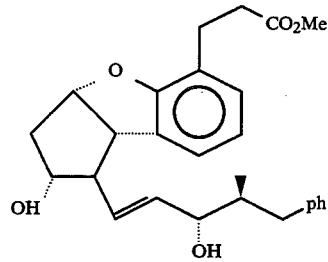

(95)

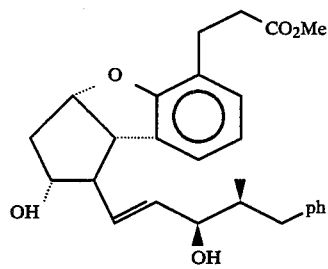

(96)

In 50 ml of methanol, 857.7 mg (1.80 mmol) of d-16-(S)-methyl-15-oxo-17,phenyl-2,5,6,7,18,19,20-heptanor-4,8-inter-m-phenylene PGI$_2$ methyl ester, 11-acetate was dissolved and then 671 mg (1.80 mmol) of cerium trichloride heptahydrate was dissolved. To this stirred solution, 41.1 mg (1.08 mmol) of sodium borohydride was added at 0° C. and the resulting mixture was stirred 1 hours. To the thus obtained reaction mixture, 10 ml of water was added and the solvent was evaporated. Then the generated precipitate was removed by filtration through High Flow Super Cell and washed with ethyl acetate. After separating ethyl acetate layer, water layer was extracted with ethyl acetate (20 ml×3). Then ethyl acetate layers were combined, washed with 30 ml of brine, dried over anhydrous sodium sulfate and concetrated to obtain an oily product. The thus obtained oily product was subjected to azeotropic distillation with THF (20 ml×2) and the residue was dried under reduced pressure. The residue was dissolved in 40 ml of anhydrous methanol. To this solution, 0.05 ml (0.261 mmol) of 5.22N sodium methoxide was added and the resulting mixture was stirred under argon atmosphere at room temperature overnight. To the thus obtained reaction mixture, acetic acid was added to attain pH 7 and the resulting mixture was concentrated. To the concentrate, 10 ml of water was added and the resultant was extracted with ethyl acetate (20 ml×3). Then ethyl acetate layers were washed with 50 ml of brine, dried over anhydrous sodium sulfate and concentrated to obtain an oily product. The thus obtained oily product was purified by column chromatography (silica gel, eluant; ethyl acetate:cyclohexane=2:1) to obtain 400.8 mg (0.918 mmol, yield 51.0%) of d-16-(S)-methyl-17-phenyl-15-epi-2,5,6,7,18,19,20-heptanor-4,8-inter-m-phenylene PGI₂ methyl ester from low polar fractions. Then 246.6 mg (0.565 mmol, yield 31.4%) of d-16-(S)-methyl-17-phenyl-2,5,6,7,18,19,20-heptanor-4,8-inter-m-phenylene PGI₂ methyl ester was obtained from high polar fractions.

The structures of these products were confirmed by the following data.

d-16-(S)-methyl-17-phenyl-2,5,6,7,18,19,20-heptanor-4,8 -inter-m-phenylene PGI₂ methyl ester m.p. 128°–128.5° C. (Recrystallization Solvent:ethyl acetate:cyclohexane) $[\alpha]_D^{20}= +113.28°$ (C=1.00, MeOH) IR (KBr method): 3510, 3460, 2955, 2895, 2870, 1691, 1601, 1455, 1441, 1417, 1378, 1323, 1295, 1273, 1266, 1188, 1153, 1101, 1078, 1048, 1016, 1001, 986, 953, 916, 888, 866, 843, 833, 791, 765, 706, 671, 626, 608, 558, 528 cm⁻¹ NMR (400 MHz, CDCl₃, δ): 0.87(3H,d,J=6.84 Hz), 1.58(2H,brs), 1.80–2.20(2H,m), 2.37–2.54(2H,m), 2.58–2.72(3H,m), 2.85–2.95(3H,m), 3.47(1H,t,J=8.30 Hz), 3.66(3H,S), 3.90–4.05(2H,m), 5.10–5.18(1H,m), 5.63–5.73(2H,m), 6.76(1H,t,J=7.33 Hz), 6.96–7.01(2H,m), 7.15–7.32(5H,m) MASS (EI method, m/e): 436 (M+) High resolution mass spectrum Calcd. (C₂₇H₃₂O₅, M+) 436.2250 Found (M+) 436.2271 d-16-(S)-methyl-17-phenyl-15-epi-2,5,6,7,18,19,20-heptanor-4,8-inter-m-phenylene PGI₂ methyl ester $[\alpha]_D^{20}= +65.91°$ (C=1.02, MeOH) IR (liquid film method): 3375, 3015, 2945, 2915, 2855, 1720, 1590, 1443, 1360, 1290, 1247, 1183, 1167, 1145, 1055, 1020, 961, 881, 853, 838, 736, 696, 658 cm⁻¹ NMR (400 MHz, CDCl₃, δ): 0.91(3H,d,J=6.84 Hz), 1.55–2.08(4H,m), 2.40–2.56(2H,m), 2.58–2.71(3H,m), 2.82–2.95(3H,m), 3.47–3.53(1H,m), 3.66(3H,s), 3.91–3.98(1H,m), 4.08–4.16(1H,m), 5.11–5.18(1H,m), 5.64–5.75(2H,m), 6.73–6.80(1H,m), 6.97(1H,d,J=7.33 Hz), 7.01(1H,d,J=7.33 Hz), 7.14–7.23(3H,m), 7.23–7.32(2H,m) MASS (EI method, m/e): 436 (M+) High resolution mass spectrum Calcd. (C₂₇H₃₂O₅, M+) 436.2250 Found (M+) 436.2231

EXAMPLE 42 d-16-(S)-methyl-17-phenyl-2,5,6,7,18,19,20-heptanor-4,8-inter-m-phenylene PGI₂ (97)

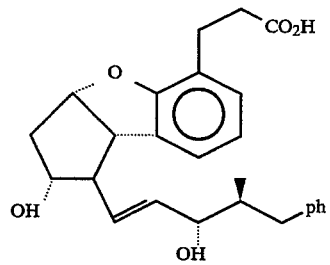

In 20 ml of methanol, 170.4 mg (0.390 mmol) of d-16-(S)-methyl-17-phenyl-2,5,6,7,18,19,20-heptanor-4,8-inter-m-phenylene PGI₂ methyl ester was dissolved. To this solution, 3.2 ml (3.20 mmol) of 1N sodium hydroxide was added and the resulting mixture was stirred overnight under argon atmosphere at room temperature. The pH of the thus obtained reaction mixture was adjusted to 4 by adding 1N hydrochloric acid and then methanol was evaporated. To the residue, 10 ml of water was added and the resultant was extracted with ethyl acetate (20 ml×4). Then ethyl acetate layers were washed with water (10 ml) and with brine (20 ml), dried over anhydrous sodium sulfate and concetrated to obtain 165.0 mg of d-16-(S)-methyl-17-phenyl-2,5,6,7,18,19,20-heptanor-4,8-inter-m-phenylene PGI₂ as a pure product (yield 100%).

The structure of this product was confirmed by the following data. m.p. 131.0°–131.5° C. (Recrystallization Solvent:ethyl acetate:cyclohexane) $[\alpha]_D^{20}= +116.38°$ (C=1.00, MeOH) IR (KBr method): 3475, 3365, 3830, 2945, 1688, 1600, 1448, 1406, 1375, 1333, 1293, 1260, 1245, 1213, 1198, 1150, 1102, 1068, 1043, 1030, 1008, 965, 950, 915, 860, 815, 785, 748, 700, 605, 525 cm⁻¹ NMR (400 MHz, CDCl₃, δ): 0.86(3H,d,J=6.83 Hz), 1.89–2.06(2H,m), 2.34–2.50(2H,m), 2.57–2.76(3H,m), 2.80–3.00(3H,m), 3.44(1H,t,J=8.30 Hz), 3.87–4.03(2H,m), 5.08–5.15(1H,m), 5.59–5.70(2H,m), 6.75(1H,t,J=7.33 Hz), 6.98(2H,t,J=7.33 Hz), 7.13–7.32(5H,m) MASS (EI method, m/e): 422 (M+) High resolution mass spectrum Calcd. (C₂₆H₃₀O₅, M+) 422.2093 Found (M+) 422.2083

EXAMPLE 43 d-16-(S)-methyl-17-phenyl-15-epi-2,5,6,7,18,19,20-heptanor-4,8-inter-m-phenylene PGI₂ (98)

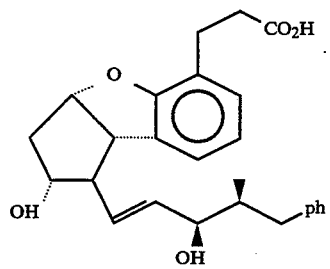

In 20 ml of methanol, 162.2 mg (0.372 mmol) of d-16-(S)-methyl-17-phenyl-15-epi-2,5,6,7,18,19,20-heptanor-4,8-inter-m-phenylene PGI₂ methyl ester was dissolved. To this solution, 1.10 ml (1.10 mmol) of 1N sodium hydroxide was added and the resulting mixture was stirred overnight under argon atmosphere at room temperature. The pH of the thus obtained reaction mixture was adjusted to 4 by adding 1N hydrochloric acid and then methanol was evaporated. To the residue, 10 ml of water was added and the resultant was extracted with ethyl acetate (20 ml×4). Then ethyl acetate layers were washed with water (10 ml) and with brine (20 ml), dried over anhydrous sodium sulfate and concetrated to obtain 157.2 mg of d-16-(S)-methyl-17-phenyl-15-epi-2,5,6,7,18,19,20-heptanor-4,8-inter-m-phenylene PGI$_2$ as a pure product (yield 100%).

The structure of this product was confirmed by the following data. m.p. 133.5°-134.0° C. (Recrystallization Solvent:ethyl acetate:cyclohexane) $[\alpha]_D^{20} = +72.12°$ (C=1.00, MeOH) IR (KBr method): 3350, 3015, 2955, 2885, 1688, 1596, 1488, 1446, 1403, 1366, 1341, 1318, 1289, 1262, 1219, 1189, 1152, 1116, 1104, 1054, 1027, 986, 974, 964, 924, 894, 875, 857, 829, 784, 766, 744, 699, 667, 644, 614, 544, 507, 484 cm$^{-1}$ NMR (400 MHz, CDCl$_3$-DMSO-d$_6$, δ): 0.89(3H,dd,J=6.83, 1.47 Hz), 1.83-1.98(2H,m), 2.34-2.47(2H,m), 2.52-2.68(5H,m), 2.68-3.40(5H,m), 3.45(1H,t,J=8.79 Hz), 3.83-3.93(1H,m), 4.03-4.12(1H,m), 5.06-5.13(1H,m), 5.64-5.81(2H,m), 6.73(1H,td,J=7.33, 1.95 Hz), 6.97(1H,d,J=7.32 Hz), 7.03(1H,d,J=7.32 Hz), 7.13-7.31(5H,m) MASS (EI method, m/e): 422 (M+) High resolution mass spectrum Calcd. (C$_{26}$H$_{30}$O$_5$, M+) 422.2093 Found (M+) 422.2083

EXAMPLE 44

2,5,6,7-tetranor-17-oxa-4,8-inter-m-pehnylene PGI$_2$ methyl ester (99) and 15-epimer thereof (100)

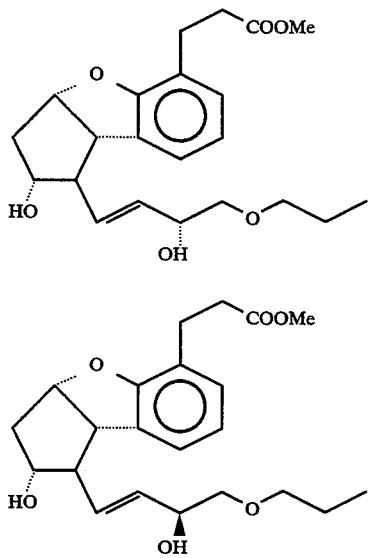

In 10 ml of methanol, 672 mg of 15-oxo-2,5,6,7-tetranor-17-oxa-4,8-inter-m-phenylene PGI$_2$ methyl ester, 11-acetate was dissolved and then 870 mg of cerium trichloride heptahydrate was added. To the stirred mixture, 59 mg of sodium borohydride was added under cooling in iced water and the resulting mixture was stirred for 20 minutes. To the thus obtained reaction mixture, 10 ml of saturated aqueous sodium hydrogen carbonate solution was added and the resulting mixture was concentrated. To the residue, 30 ml of water was added and the resultant was extracted with ethyl acetate (50 ml×3). The organic layers were combined, washed with water and with brine, dried over anhydrous sodium sulfate and concentrated to obtain 621 mg of an oily product. Then the thus obtained oily product was dissolved in 10 ml of anhydrous methanol. To this solution, 54 μl of 5.22N sodium methoxide was added and the resulting mixture was stirred for 2.5 hours at room temperature under argon atmosphere. To the thus obtained reaction mixture, acetic acid was added to attain pH 4 and the resultung mixture was concentrated. To the concentrate, 30 ml of water was added and the resultant was extracted with ethyl acetate (30 ml×3). The organic layers were combined, washed with water and with brine, dried over anhydrous sodium sulfate and concentrated to obtain 539 mg of an oily product. The thus obtained oily product was purified by column chromatography (Lobar column Type B commercially available from Merck & Co., Inc., eluant; ethyl acetate:cyclohexane=8:1) to firstly obtain 227 mg (yield 41%) of 15-epi-2,5,6,7-tetranor-17-oxa-4,8-inter-m-phenylene PGI$_2$ methyl ester having low polarity. Then 177 mg (yield 32%) of 2,5,6,7-tetranor-17-oxa-4,8-inter-m-phenylene PGI$_2$ methyl ester was obtained from high polar fractions.

The structures of these products were confirmed by the following data.

2,5,6,7-tetranor-17-oxa-4,8-inter-m-phenylene PGI$_2$ methyl ester m.p. 81.5°-83.0° C. (Recrystallization Solvent:ethyl acetate:n-hexane=5:7) IR (KBr method): 3350, 3050, 3030, 2975, 2950, 2900, 2850, 1735, 1715, 1600, 1480, 1455, 1445, 1425, 1380, 1365, 1300, 1285, 1270, 1255, 1240, 1195, 1180, 1160, 1140, 1120, 1100, 1080, 1065, 1055, 1025, 1000, 970, 960, 890, 870, 840, 820, 780, 750, 700, 560, 500 cm$^{-1}$ NMR (400 MHz, CDCl$_3$, δ): 0.94 (3H,t,J=7.3 Hz), 1.58-1.70(2H,m), 1.95-2.07(1H,m), 2.35-2.41(1H,bs), 2.46(1H,q,J=16.1 Hz, 7.3 Hz), 2.58-2.70(3H,m), 2.80(1H,bs), 2.85-2.93(2H,m), 3.31-3.38(1H,m), 3.42-3.55(4H,m), 3.66(3H,s), 3.91-3.98(1H,bs), 4.32-4.40(1H,bs), 5.10-5.18(1H,m), 5.54-5.63(1H,m), 5.75-5.84(1H,m), 6.75(1H,t,J=7.3 Hz), 6.97(2H,d,J=7.3 Hz) MASS (EI method, m/e): 390 (M+) High resolution mass spectrum Calcd. (C$_{22}$H$_{30}$O$_6$, M+) 390.2024 Found (M+) 390.2031

15-epi-2,5,6,7-tetranor-17-oxa-4.8-inter-m-phenylene PGI$_2$ methyl ester m.p. 99.0°-100.0° C. (Recrystallization Solvent:ethyl acetate:n-hexane=6:7) IR (KBr method): 3500, 3400, 2960, 2950, 2900, 2860, 2800, 1740, 1600, 1480, 1450, 1440, 1425, 1360, 1345, 1330, 1300, 1290, 1260, 1235, 1190, 1175, 1150, 1120, 1100, 1070, 1035, 1020, 1000, 980, 950, 890, 860, 850, 840, 820, 795, 770, 750, 700, 620, 600, 530, 510, 480, 440, 400 cm$^{-1}$ NMR (400 MHz, CDCl$_3$, δ): 0.94(3H,t,J=7.5 Hz), 1.59-1.62(2H,m), 1.96-2.07(2H,m), 2.50(1H,q,J=7.8 Hz), 2.56-2.72(2H,m), 3.30-3.38(1H,m), 3.41-3.55(4H,m), 3.66(3H,s), 3.91-4.00(1H,bs), 4.32-4.40(1H,bs), 5.10-5.19(1H,m), 5.57-5.67(1H,m), 5.76-5.86(1H,m), 6.76(1H,t,J=7.5 Hz), 6.94-7.04(2H,m) MASS (EI method, m/e): 390 (M+) High resolution mass spectrum Calcd. (C$_{22}$H$_{30}$O$_6$, M+) 390.2042 Found (M+) 390.2056

EXAMPLE 45

2,5,6,7-tetranor-17-oxa-4,8-inter-m-phenylene PGI$_2$ (101)

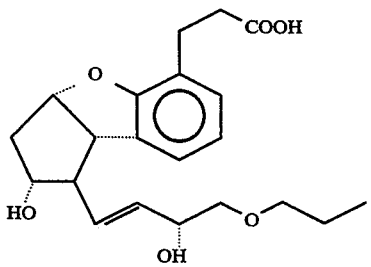

(101)

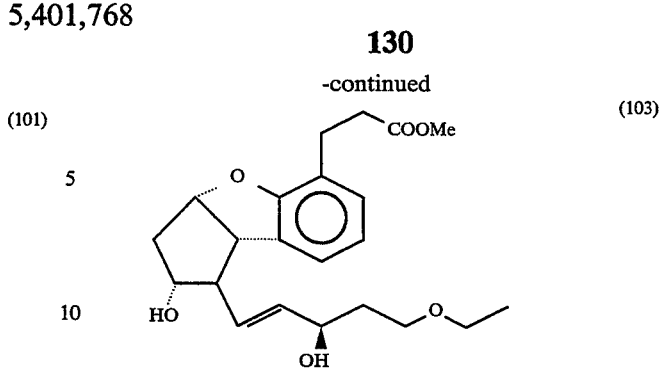

(103)

In 5 ml of methanol, 113 mg of 2,5,6,7-tetranor-17-oxa-4,8-inter-m-phenylene PGI₂ methyl ester was dissolved. To this solution, 1.5 ml of 1N sodium hydroxide was added and resulting mixture was stirred overnight at room temperature. The pH of the thus obtained reaction mixture was adjusted to 4 by adding 1N hydrochloric acid. To the mixture, 30 ml of water was added and the resulting mixture was extracted with ethyl acetate (30 ml×3). The organic layers were combined, washed with water and with brine, dried over anhydrous sodium sulfate and concetrated to obtain 107 mg of 2,5,6,7-tetranor-4,8-inter-m-phenylene PGI₂ as a pure product (yield 98%).

The structure of this product was confirmed by the following data. m.p. 112.5°–114.5° C. (Recrystallization Solvent:ethyl acetate:n-hexane=2:1) IR (KBr method): 3440, 3050, 2960, 2940, 2880, 2800, 1695, 1595, 1480, 1450, 1440, 1415, 1380, 1360, 1350, 1315, 1290, 1250, 1220, 1190, 1170, 1160, 1120, 1105, 1075, 1050, 1040, 1005, 980, 945, 920, 900, 860, 840, 820, 790, 765, 740, 700, 620, 600, 560, 520, 500, 460, 400 cm⁻¹ NMR (400 MHz, CDCl₃, δ): 0.94(3H,t,J=7.5 Hz), 1.57–1.69(2H,m), 1.95–2.06(1H,m), 2.45(1H,q,J=8.3 Hz), 2.68–2.75(3H,m), 2.81–2.98(2H,m), 3.32–3.39(1H,m), 3.42–3.54(4H,m), 3.90–3.99(1H,m), 4.31–4.40(1H,bs), 5.08–5.18(1H,m), 5.53–5.62(1H,m), 5.75–5.84(1H,m), 6.76(1H,t,J=7.3 Hz) MASS (EI method, m/e): 376 (M+) High resolution mass spectrum Calcd. (C₂₁H₂₈O₆, M+) 376.1886 Found (M+) 376.1879

EXAMPLE 46

2,5,6,7-tetranor-18-oxa-4,8-inter-m-phenylene PGI₂ methyl ester (102) and 15-epimer thereof (103)

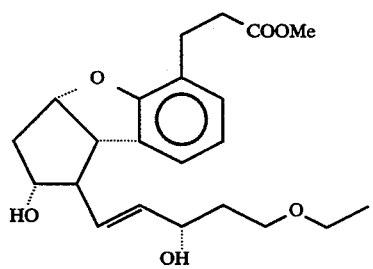

(102)

In 60 ml of methanol, 1.14 g (2.65 mmol) of 15-oxo-2,5,6,7-tetranor-18-oxa-4,8-inter-m-phenylene PGI₂ methyl ester, 11-acetate was dissolved and under cooling in iced water, 990 mg (2.65 mmol) of cerium trichloride heptahydrate was dissolved. Further, to this solution, 15 mg (3.98 mmol) of sodium borohydride was added and the resulting mixture was stirred for 10 minutes. To the thus obtained reaction mixture, 20 ml of saturated aqueous sodium hydrogen carbonate solution was added and the resulting mixture was concentrated. To the thus obtained residue, 30 ml of water and 100 ml of ethyl acetate were added and the resultant was filtered. The precipitate was washed with ethyl acetate (30 ml×3), The organic layers were combined, washed once with 30 ml each of water and brine, dried over anhydrous sodium sulfate and concentrated to obtain 1.04 g of an oily product. Then 1.04 g of the thus obtained oily product was dissolved in 25 ml of anhydrous methanol. To this stirred solution, 0.117 ml (0.613 mmol) of 5.22N sodium methoxide was added and the resulting mixture was stirred for 3 hours under argon atmosphere at room temperature. To the thus obtained reaction mixture, 0.05 ml of acetic acid was added and the resulting mixture was concentrated. To the residue, 20 ml of water was added and the resultant was extracted with ethyl acetate (50 ml×2). The organic layers were combined, washed once with 20 ml each of water and brine, dried over anhydrous sodium sulfate and concentrated. The thus obtained residue was purified by Lobar column (silica gel, eluant; ethyl acetate:-cyclohexane=2:1) to firstly obtain 451 mg (yield 47.2%) of 15-epi-2,5,6,7-tetranor-18-oxa-4,8-inter-m-phenylene PGI₂ methyl ester having low polarity. Then 430 mg (yield 45%) of 2,5,6,7-tetranor-18-oxa-4,8-inter-m-phenylene PGI₂ methyl ester was obtained from high polar fractions.

The structures of these products were confirmed by the following data.

15-epi-2,5,6,7-tetranor-18-oxa-4,8-inter-m-phenylene PGI₂ methyl ester

IR (liquid film method): 3400, 2970, 2930, 2860, 1730, 1595, 1450, 1370, 1350, 1300, 1255, 1190, 1150, 1100, 1065, 1030, 970, 920, 885, 860, 840, 780, 760, 740 cm⁻¹ NMR (400 MHz, CDCl₃, δ): 1.22(3H,t,J=7.1 Hz), 1.75–1.9(2H,m), 2.00(1H,ddd,J=4.9, 8.5, 13.7 Hz), 2.05–2.1(1H,m), 2.49(1H,q,J=8.0 Hz), 2.55–2.75(3H,m), 2.85–2.95(2H,m), 3.35–3.4(1H,m), 3.45–3.55(3H,m), 3.6–3.75(2H,m), 3.66(3H,s), 3.9–4.0(1H,m), 4.3–4.4(1H,m), 5.15(1H,ddd,J=4.9, 7.3, 8.8 Hz), 5.67(1H,dd,J=4.9, 15.4 Hz), 5.74(1H,dd,J=8.0, 15.4 Hz), 6.76(1H,t,J=7.5 Hz), 6.97(1H,d,J=7.5 Hz), 7.01(1H,d,J=7.5 Hz) MASS (m/e): 390 (M+) High resolution mass spectrum Calcd. (C₂₂H₃₀O₆, M+) 390.2042 Found (M+) 390.2047

2,5,6,7-tetranor-18-oxa-4,8-inter-m-phenylene PGI₂ methyl ester m.p. 62.3°–63.2° C. (Recrystallization Solvent:ethyl acetate:cyclohexane=2:1) IR (KBr method): 3370, 2970, 2930, 2870, 1730, 1595, 1445, 1375, 1325, 1295, 1250, 1185, 1175, 1155, 1130, 1120, 1100, 1085, 1060, 1030, 1005, 960, 940, 910, 890, 875, 860, 830, 790, 760, 730, 620 cm⁻¹ NMR (400 MHz, CDCl₃, δ) 1.22(3H,t,J=6.8 Hz), 1.8–1.9(2H,m), 1.98(1H,ddd,J=5.4, 8.8, 13.7 Hz), 2.4–2.5(2H,m), 2.6–2.7(3H,m), 2.85–2.95(2H,m), 3.4–3.55(4H,m), 3.6–3.75(2H,m), 3.66(3H,s), 3.9–4.0(1H,m), 5.13(1H,ddd,J=5.4, 7.3, 8.8 Hz), 5.64(1H,dd,J=5.5, 15.5 Hz), 5.71(1H,dd,J=7.8, 15.5 Hz), 6.75(1H,t,J=7.3 Hz), 6.97(2H,d,J=7.3 Hz) MASS (m/e): 390 (M+)

| Element Analysis | C | H |
|---|---|---|
| Calcd. C₂₂H₃₀O₆ | 67.67 | 7.74 |
| Found | 67.56 | 7.69 |

EXAMPLE 47

2,5,6,7-tetranor-18-oxa-4,8-inter-m-phenylene PGI₂ (104)

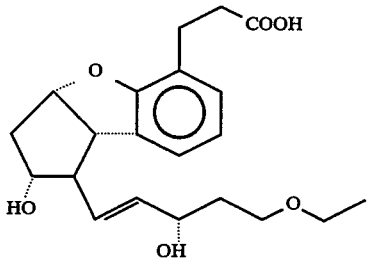

(104)

In 30 ml of methanol, 334 mg (0.86 mmol) of 2,5,6,7-tetranor-18-oxa-4,8-inter-m-phenylene PGI₂ methyl ester was dissolved. To this stirred solution, 6.95 ml (6.85 mmol) of 0.986N sodium hydroxide was added under cooling in iced water, and the resulting mixture was stirred 5 hours at room temperature. To the thus obtained reaction mixture, 7 ml (7 mmol) of 1N hydrochloric acid was added and the mixture was concentrated. To the thus obtained residue, 20 ml of water was added and the resultant was extracted with ethyl acetate (50 ml×2). The organic layers were combined, washed once with 10 ml each of water and brine, dried over anhydrous sodium sulfate and concetrated. The thus obtained residue was recrystallized from 1.0 ml of ethyl acetate and from 0.4 ml of n-hexane to obtain 164 mg (yield 51%) of 2,5,6,7-tetranor-18-oxa-4,8-inter-m-phenylene PGI₂ as colorless crystals.

The structure of this product was confirmed by the following data. m.p. 96.3°–97.1° C. (Recrystallization Solvent:ethyl acetate:n-hexane=2:1) IR (KBr method): 3380, 2970, 2925, 2860, 1710, 1595, 1450, 1370, 1350, 1240, 1190, 1150, 1090, 1060, 1040, 1000, 965, 930, 780, 760, 740 cm⁻¹ NMR (CDCl₃, δ): 1.21(3H,s), 1.75–1.9(2H,m,1.96(H,ddd,J=5.1, 9.0, 13.4 Hz), 2.40(1H,q,J=8.3 Hz), 2.6–2.75(3H,m), 2.8–3.0(2H,m), 3.42(1H,t,J=8.3 Hz), 3.51(2H,q,J=7.1 Hz), 3.55–3.7(2H,m), 3.85–4.0(1H,m), 4.3–4.4(1H,m), 4.4–5.4(2H,m), 5.0–5.1(1H,m), 5.59(1H,dd,J=6.0, 15.4 Hz), 5.67(1H,dd,J=8.3, 15.4 Hz), 6.74(1H,t,J=7.5 Hz), 6.94(1H,d,J=7.5 Hz), 6.96(1H,d,J=7.5 Hz) MASS (m/e): 376 (M+)

| Element Analysis | C | H |
|---|---|---|
| Calcd. (C₂₁H₂₈O₆) | 67.00 | 7.50 |
| Found | 66.85 | 7.58 |

EXAMPLE 48

15-epi-2,5,6,7-tetranor-18-oxa-4,8-inter-m-phenylene PGI₂ (105)

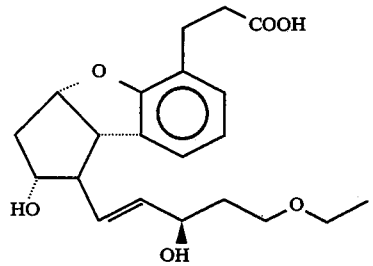

(105)

In 30 ml of methanol, 369 mg (0.95 mmol) of 15-epi-2,5,6,7-tetranor-18-oxa-4,8-inter-m-phenylene PGI₂ methyl ester was dissolved. To this stirred solution, 8.6 ml (8.5 mmol) of 0.986N sodium hydroxide was added under cooling in iced water, and the resulting mixture was stirred 5 hours at room temperature. To the thus obtained reaction mixture, 8.5 ml (8.5 mmol) of 1N hydrochloric acid was added and the mixture was concentrated. To the thus obtained residue, 20 ml of water was added and the resultant was extracted with ethyl acetate (50 ml×2). The organic layers were combined, washed once with 10 ml each of water and brine, dried over anhydrous sodium sulfate and concetrated. The thus obtained residue was recrystallized from 1.0 ml of ethyl acetate and from 0.4 ml of n-hexane to obtain 273 mg (yield 76.8%) of 15-epi-2,5,6,7-tetranor-18-oxa-4,8-inter-m-phenylene PGI₂ as colorless crystals.

The structure of this product was confirmed by the following data. m.p. 111.2°–111.5° C. (Recrystallization Solvent:ethyl acetate:n-hexane=2:1) IR (KBr method): 3330, 2970, 2925, 2870, 1590, 1445, 1375, 1320, 1260, 1160, 1120, 1080, 1020, 980, 855, 790, 745 cm⁻¹ NMR (400 MHz, CDCl₃, δ): 1.22(3H,s), 1.75–1.9(2H,m), 2.0–2.1(1H,m), 2.49(1H,q,J=7.8 Hz), 2.55–2.8(3H,m), 2.8–3.0(2H,m), 3.45–3.6(3H,m), 3.6–3.8(2H,m), 3.9–4.0(1H,m), 3.1–4.2(2H,m), 4.3–4.4(1H,m), 5.1–5.2(1H,m), 5.65(1H,dd,J=4.9, 15.1 Hz), 5.74(1H,dd,J=7.8, 15.1 Hz), 6.76(1H,t,J=7.3 Hz), 6.98(1H,d,J=7.3 Hz), 7.02(1H,d,J=7.3 Hz) MASS (m/e): 376 (M+)

| Element Analysis | C | H |
|---|---|---|
| Calcd. (C₂₁H₂₈O₆) | 67.00 | 7.50 |
| Found | 66.92 | 7.57 |

EXAMPLE 49

16,16-dimethyl-2,5,6,7-tetranor-18-oxa-4,8-inter-m-phenylene PGI₂ methyl ester (106) and 15-epimer thereof (107)

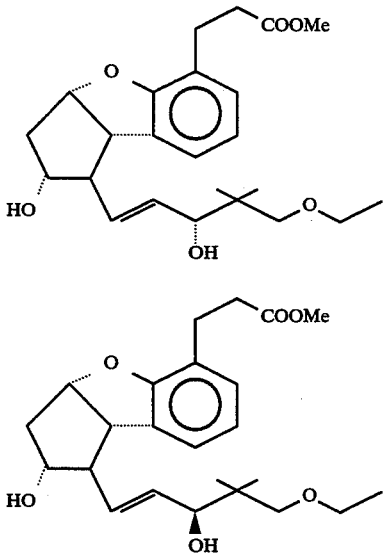

(106)

(107)

In 50 ml of methanol, 1.05 g (2.29 mmol) of 16,16-dimethyl-15-oxo-2,5,6,7-tetranor-18-oxa-4,8-inter-m-phenylene PGI$_2$ methyl ester, 11-acetate was dissolved. To this solution, 915 mg (2.46 mmol) of cerium trichloride heptahydrate was added and then 138 mg (3.64 mmol) of sodium borohydride was added slowly under cooling in iced water. After stirring the resulting mixture for 10 minutes, to the thus obtained reaction mixture, 15 ml of saturated aqueous sodium hydrogen carbonate solution was added. After filtering the mixture, the filtrate was concentrated. To the thus obtained residue, 30 ml of water was added and the resultant was extracted once with 100 ml of ethyl acetate. The ethyl acetate layer was washed once with 20 ml each of water and brine, dried over anhydrous sodium sulfate and concentrated to obtain 1.03 g of an oily product. Then the thus obtained oily product was dissolved in 30 ml of anhydrous methanol under argon atmosphere. To this stirred solution, 0.115 ml (0.6 mmol) of 5.22N sodium methoxide was added and the resulting mixture was stirred for 14 hours at room temperature. The thus obtained reaction mixture was neutralized with acetic acid and the resultung mixture was concentrated. To the concentrate, 20 ml of water was added and the resultant was extracted with ethyl acetate (10 ml×2). The ethyl acetate layers were washed once with 20 ml each of water and brine, dried over anhydrous sodium sulfate and concentrated. The thus obtained residue was purified by column chromatography (silica gel, Lobar column Type B commercially available from Merck & Co., Inc., eluant; ethyl acetate:cyclohexane=2:1) to firstly obtain 449 mg (1.07 mmol, yield 48%) of 16,16-dimethyl-15-epi-2,5,6,7-tetranor-18-oxa-4,8-inter-m-phenylene PGI$_2$ methyl ester from low polar fractions. Then 445 mg (1.06 mmol, yield 47.5%) of 16,16-dimehtyl-2,5,6,7-tetranor-18-oxa-4,8-inter-m-phenylene PGI$_2$ methyl ester was obtained from high polar fractions.

The structures of these products were confirmed by the following data.

16,16-dimethyl-2,5,6,7-tetranor-18-oxa-4,8-inter-m-phenylene PGI$_2$ methyl ester IR (liquid film method): 3410, 2970, 2870, 1730, 1595, 1450, 1360, 1250, 1190, 1100, 1065, 1030, 1000, 965, 880, 855, 830, 750 cm$^{-1}$ NMR (400 MHz, CDCl$_3$, δ): 0.92(3H,s), 0.947(3H,s), 1.20(3H,t,J=7.1 Hz), 1.9-2.1(1H,m), 2.4-2.6(2H,m), 2.8-3.0(2H,m), 3.29(1H,d,J=8.8 Hz), 3.37(1H,d,J=8.8 Hz), 3.4-3.6(3H,m), 3.66(3H,s), 3.9-4.1(3H,m), 5.0-5.2(1H,m), 5.6-5.8(2H,m), 6.76(1H,t,J=7.3 Hz), 6.97(2H,d,J=7.3 Hz) MASS (EI method, m/e): 418 (M$^+$) High resolution mass spectrum Calcd. (C$_{24}$H$_{34}$O$_6$, M$^+$) 418.2355 Found (M$^+$) 418.2341

16,16-dimethyl-15-epi-2,5,6,7-tetranor-18-oxa-4,8-inter-m-phenylene PGI$_2$ methyl ester IR (liquid film method): 3400, 2960, 2860, 1720, 1590, 1440, 1360, 1250, 1190, 1095, 1020, 970, 880, 860, 830, 750 cm$^{-1}$ NMR (400 MHz, CDCl$_3$, δ): 0.928(3H,s), 0.933(3H,s), 1.23(3H,t,J=7.1 Hz), 1.8-2.1(1H,m), 1.9-2.1(1H,m), 2.53(1H,q,J=7.3 Hz), 2.5-2.8(3H,m), 2.8-3.0(2H,m), 3.3(1H,d,J=8.8 Hz), 3.4(1H,d,J=8.8 Hz), 3.4-3.6(3H,m), 3.66(3H,s), 3.8-4.1(3H,m), 5.1-5.2(1H,m), 5.6-5.8(2H,m), 6.77(1H,t,J=7.2 Hz), 6.97(1H,d,J=7.2 Hz), 7.03(1H,d,J=7.2 Hz) MASS (EI method, m/e): 418 (M$^+$) High resolution mass spectrum Calcd. (C$_{24}$H$_{34}$O$_6$, M$^+$) 418.2355 Found (M$^+$) 418.2340

EXAMPLE 50

16,16-dimethyl-2,5,6,7-tetranor-18-oxa-4,8-inter-m-phenylene PGI$_2$ (108)

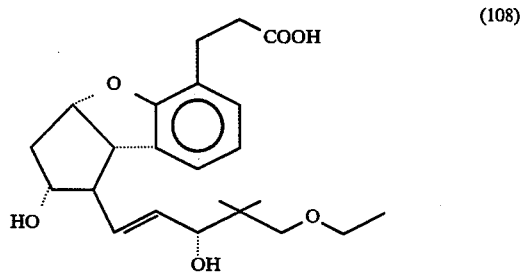

(108)

In 20 ml of methanol, 275 mg (0.66 mmol) of 16,16-dimethyl-2,5,6,7-tetranor-18-oxa-4,8-inter-m-phenylene PGI$_2$ methyl ester was dissolved. To this stirred solution, 5.3 ml (5.3 mmol) of 1N sodium hydroxide was added under cooling in iced water, and the resulting mixture was stirred 14 hours at room temperature. The thus obtained reaction mixture was neutralized by adding 1N hydrochloric acid and the mixture was concentrated. To the concentrate, 10 ml of water was added and the resultant was extracted with ethyl acetate (60 ml×2). The ethyl acetate layers were washed once with 10 ml each of water and brine, dried over anhydrous sodium sulfate and concetrated. The thus obtained residue was recrystallized from 3 ml of ethyl acetate and from 4 ml of n-hexane to obtain 238 mg (0.59 mmol) of 16,16-dimethyl-2,5,6,7-tetranor-18-oxa-4,8-inter-m-phenylene PGI$_2$ as colorless crystals (yield 89.5%).

The structure of this product was confirmed by the following data. m.p. 119.2°-120.9° C. (Recrystallization Solvent:ethyl acetate:n-hexane=3:4) IR (KBr method): 3400, 2960, 2920, 2850, 1695, 1590, 1450, 1410, 1280, 1260, 1240, 1200, 1085, 1065, 1010, 995, 965, 915, 850, 820, 800, 780, 740 cm$^{-1}$ NMR (400 MHz, CDCl$_3$, δ): 0.92(3H,s), 0.95(3H,s), 1.21(3H,t,J=7.1 Hz), 1.9-2.1(1H,m), 2.4-2.6(1H,m), 2.6-2.8(3H,m), 2.8-3.0(2H,m), 3.29(1H,d,J=9.0 Hz), 3.37(1H,d,J=9.0 Hz), 2.0-3.3(3H,m), 3.4-3.6(3H,m), 3.9-4.0(2H,m), 5.1-5.2(1H,m), 5.6-5.8(2H,m), 6.76(1H,t,J=7.6 Hz), 6.9-7.1(2H,m) MASS (EI method, m/e): 404 (M$^+$)

High resolution mass spectrum Calcd. ($C_{23}H_{32}O_6$, M+) 404.2199 Found (M+) 404.2191

EXAMPLE 51

16,16-dimethyl-15-epi-2,5,6,7-tetranor-18-oxa-4,8-inter-m-phenylene $PGI_2$ (109)

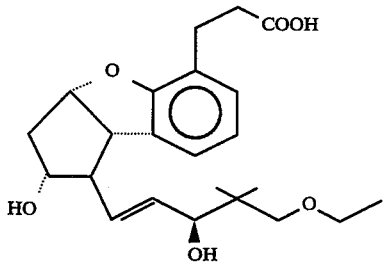
(109)

In 25 ml of methanol, 280 mg (0.67 mmol) of 16,16-dimethyl-15-epi,2,5,6,7-tetranor-18-oxa-4,8-inter-m-phenylene $PGI_2$ methyl ester was dissolved. To this solution, 5.4 ml (5.4 mmol) of 1N sodium hydroxide was added under cooling in iced water and the resulting mixture was stirred 4 hours at room temperature. The thus obtained reaction mixture was concentrated and 15 ml of water was added thereto. The mixture was neutralized by adding 1N hydrochloric acid and the mixture was extracted with ethyl acetate (50 ml×2). The ethyl acetate layers were washed once with 15 ml each of water and brine, dried over anhydrous sodium sulfate and concetrated to obtain 271 mg (0.67 mmol) of 16,16-dimethyl-15-epi-2,5,6,7-tetranor-18-oxa-4,8-inter-m-phenylene $PGI_2$ as a colorless oily product (yield 100%).

The structure of this product was confirmed by the following data. IR (liquid film method): 3400, 2960, 2870, 1705, 1590, 1440, 1250, 1210, 1190, 1090, 1060, 1030, 970, 860, 750 cm$^{-1}$ NMR (400MHz, CDCl$_3$, δ): 0.923(3H,s), 0.932(3H,s), 1.22(3H,t,J=7.1 Hz), 1.9–2.1(1H,m), 2.52(1H,q,J=7.3 Hz), 2.5–2.8(3H,m), 2.8–3.0(2H,m), 3.30(1H,d,J=8.8 Hz), 3.38(1H,d,J=8.8 Hz), 3.4–3.6(3H,m), 3.9–4.0(1H,m), 4.0(1H,d,J=4.9 Hz), 5.1–5.2(1H,m), 5.6–5.8(2H,m), 6.77(1H,t,J=7.4 Hz), 6.98(1H,d,J=7.4 Hz), 7.03(1H,d,J=7.4 Hz) MASS (EI method, m/e): 404 (M+) High resolution mass spectrum Calcd. ($C_{23}H_{32}O_6$, M+) 404.2199 Found (M+) 404.2199

EXAMPLE 52

16,16-dimethyl-20a-homo-2,5,6,7-tetranor-18-oxa-4,8-inter-m-phenylene $PGI_2$ methyl ester (110) and 15-epimer thereof (111)

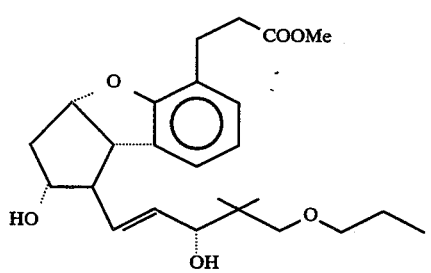
(110)

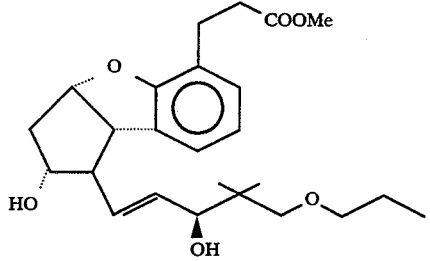
(111)

In 20 ml of methanol, 1.3624 g (2.89 mmol) of 16,16-dimethyl-20a-homo-15-oxo-2,5,6,7-tetranor-18-oxa-4,8-inter-m-phenylene $PGI_2$ methyl ester, 11-acetate was dissolved and then 1.6131 g (4.33 mmol) of cerium trichloride heptahydrate was dissolved. To this stirred solution, 107.1 mg (3.46 mmol) of sodium borohydride was added under cooling in iced water. After stirring the resulting mixture for 10 minutes, 20 ml of saturated aqueous sodium hydrogen carbonate solution was added thereto and the resulting mixture was stirred for 10 minutes at room temperature. The thus obtained reaction mixture was filterted through Celite and the precipitate was washed with 150 ml of ethyl acetate. After concentrating the filtrate, the residue was extracted with ethyl acetate (30 ml×3). The organic layers were combined, washed with 70 ml of brine, dried over anhydrous sodium sulfate (30 g) and concentrated to obtain 1.26 g of an oily product. Then the thus obtained oily product was subjected to azeotropic distillation with benzene (15 ml×3) and the resultant was dissolved in 30 ml of anhydrous methanol. To this solution, 0.06 ml (0.29 mmol) of 5.22N sodium methoxide was added and the resulting mixture was stirred for 3 hours under argon atmosphere at room temperature. To the thus obtained reaction mixture, 0.1 ml of acetic acid was added. After concentrating the mixture, 10 ml of water was added to the residue and the resultant was extracted with ethyl acetate (10 ml×3). The organic layers were combined, washed with 30 ml of brine, dried over anhydrous sodium sulfate (15 g) and concentrated to obtain 1.2112 g of an oily product. The thus obtained oily product was purified by column chromatography (silica gel, eluant; ethyl acetate:cyclohexane=3:1) to firstly obtain 547.1 mg (1.27 mmol) of 16,16,-dimethyl-15-epi-20a-homo-2,5,6,7-tetranor-18-oxa-4,8-inter-m-phenylene $PGI_2$ methyl ester having low polarity with a 44% yield. Then 492.3 mg (1.14 mmol) of 16,16-dimethyl-20a-homo-2,5,6,7-tetranor-18-oxa-4,8-inter-m-phenylene $PGI_2$ methyl ester was obtained from high polar fractions with a 40% yield.

The structures of these products were confirmed by the following data.

16,16-dimethyl-20a-homo-2,5,6,7-tetranor-18-oxa-4,8-inter-m-phenylene $PGI_2$ methyl ester IR (liquid film method): 3380, 2951, 2860, 1728, 1595, 1445, 1360, 1296, 1254, 1191, 1095, 1032, 1002, 968, 885, 861, 835, 743 cm$^{-1}$ NMR (400 MHz, CDCl$_3$, δ): 0.91–0.97(3H,m), 0.93(3H,s), 0.95(3H,S), 1.55–1.64(2H,m), 1.96–2.03(1H,m), 2.45–2.51(2H,m), 2.61–2.67(3H,m), 2.87–2.91(2H,m), 3.29–3.43(4H,m), 3.48(1H,t,J=8.3 Hz), 3.66(3H,S), 3.92–3.98(2H,m), 4.01–4.03(1H,m), 5.11–5.16(1H,m), 5.62–5.77(2H,m), 6.75(1H,t,J=7.3 Hz), 6.97(2H,d,J=7.3 Hz) MASS (EI method, m/e): 432 (M+) High resolution mass spectrum Calcd. ($C_{25}H_{36}O_6$, M+) 432.2512 Found (M+) 432.2519

16,16-dimetyl-15-epi-20a-homo-2,5,6,7-tetranor-18-oxa-4,8-inter-m-phenylene PGI₂ methyl ester IR (liquid film method): 3400, 2951, 2860, 1725, 1593, 1444, 1362, 1297, 1251, 1190, 1146, 1093, 1031, 972, 884, 862, 835, 743 cm⁻¹ NMR (400 MHz, CDCl₃, δ): 0.91–0.97(3H,m), 0.94(6H,s), 1.56–1.65(2H,m), 1.88(1H,brs), 1.98–2.04(1H,m), 2.50–2.56(1H,m), 2.59–2.68(3H,m), 2.87–2.92(2H,m), 3.29–3.42(4H,m), 3.52(1H,t,J=8.3 Hz), 3.66(3H,s), 3.93–4.02(3H,m), 5.13–5.18(1H,m), 5.62–5.76(2H,m), 6.77(1H,t,J=7.3 Hz), 6.97(1H,d,J=7.3 Hz), 7.03(1H,d,J=7.3 Hz) MASS (EI method, m/e): 432 (M+) High resolution mass spectrum Calcd. (C₂₅H₃₆O₆, M+) 432.2512 Found (M+) 432.2508

EXAMPLE 53

16,16-dimethyl-20a-homo-2,5,6,7-tetranor-18-oxa-4,8-inter-m-phenylene PGI₂ (112)

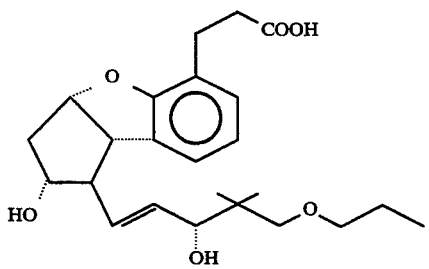

(112)

In 12 ml of methanol, 309.9 mg (0.72 mmol) of 16,16-dimethyl-20a-homo-2,5,6,7-tetranor-18-oxa-4,8-inter-m-phenylene PGI₂ methyl ester was dissolved. To this solution, 2.3 ml (2.16 mmol) of 0.92N sodium hydroxide was added and resulting mixture was stirred overnight under argon atmosphere at room temperature. To the thus obtained reaction mixture, 2.6 ml of 1N hydrochloric acid was added and then 15 ml of water was added thereto and the mixture was extracted with ethyl acetate (15 ml×2). The organic layers were combined, washed with 40 ml of brine, dried over anhydrous sodium sulfate (15 g) and concetrated to obtain 299.1 mg (0.72 mmol) of 16,16-dimethyl-20a-homo-2,5,6,7-tetranor-18-oxa-4,8-inter-m-phenylene PGI₂ as a pure product (yield 100%). This product was recrystallized from ethyl acetate/cyclohexane (1:1) to quantitatively obtain colorless rhombic crystals.

The structure of this product was confirmed by the following data. m.p. 107.5°–108.5° C. IR (KBr method): 3375 (3625–2250), 2956, 2928, 2853, 1697, 1595, 1447, 1417, 1382, 1354, 1285, 1255, 1201, 1157, 1139, 1102, 1063, 1040, 1017, 983, 964, 921, 902, 850, 822, 802, 782, 762, 742, 642, 603 cm⁻¹ NMR (400 MHz, CDCl₃, δ): 0.90–0.97(3H,m), 0.92(3H,s), 0.94(3H,s), 1.55–1.64(2H,m), 1.96–2.04(1H,m), 2.44–2.52(1H,m), 2.59–2.74(3H,m), 2.83–2.98(2H,m), 3.28–3.43(4H,m), 3.47(1H,t,J=8.3 Hz), 3.91–4.00(2H,m), 2.8–4.6(3H,brs), 5.12–5.17(1H,m), 5.61–5.72(2H,m), 6.75(1H,t,J=7.3 Hz), 6.95–6.99(2H,m) MASS (EI method, m/e): 418 (M+) High resolution mass spectrum Calcd. (C₂₄H₃₄O₆, M+) 418.2356 Found (M+) 418.2385

EXAMPLE 54

16,16-dimethyl-15-epi-20a-homo-2,5,6,7-tetranor-18-oxa-4,8-inter-m-phenylene PGI₂ (113)

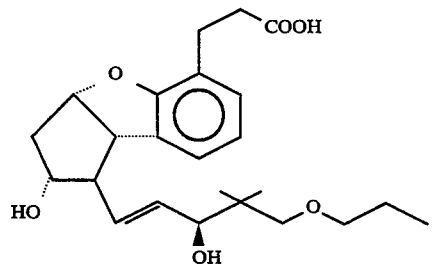

(113)

In 12 ml of methanol, 346.3 mg (0.81 mmol) of 16,16-dimethyl-15-epi-20a-homo-2,5,6,7-tetranor-18-oxa-4,8-inter-m-phenylene PGI₂ methyl ester was dissolved. To this solution, 2.64 ml (2.43 mmol) of 0.92N sodium hydroxide was added and resulting mixture was stirred overnight under argon atmosphere at room temperature. To the thus obtained reaction mixture, 3 ml of 1N hydrochloric acid was added and then 15 ml of water was added thereto and the mixture was extracted with ethyl acetate (15 ml×3). The organic layers were combined, washed with 40 ml of brine, dried over anhydrous sodium sulfate (15 g) and concetrated to quantitatively obtain 335.0 mg (0.81 mmol) of 16,16-dimethyl-15-epi-20a-homo-2,5,6,7-tetranor-18-oxa-4,8-inter-m-phenylene PGI₂ as a pure product.

The structure of this product was confirmed by the following data. IR (liquid film method): 3380 (3675–2250), 2951, 2860, 1702, 1592, 1444, 1404, 1381, 1257, 1187, 1149, 1092, 1024, 1000, 965, 944, 884, 861, 834, 741 cm⁻¹ NMR (400 MHz, CDCl₃, δ): 0.91–0.96(3H,m), 0.94(6H,s), 1.56–1.65(2H,m), 1.98–2.06(1H,m), 2.50–2.73(4H,m), 2.83–2.96(2H,m), 3.30–3.45(4H,m), 3.52(1H,t,J=8.3 Hz), 3.93–4.01(2H,m), 2.8–4.6(3H,brs), 5.13–5.19(1H,m), 5.64–5.76(2H,m), 6.77(1H,t,J=7.3 Hz), 6.98(1H,d,J=7.3 Hz), 7.01(1H,d,J=7.3 Hz) MASS (EI method, m/e): 418 (M+) High resolution mass spectrum Calcd. (C₂₄H₃₄O₆, M+) 418.2356 Found (M+) 418.2337

EXAMPLE 55

16-cyclopentyloxy-2,5,6,7,17,18,19,20-octanor-4,8-inter-m-phenylene PGI₂ methyl ester (114) and 15-epimer thereof (115)

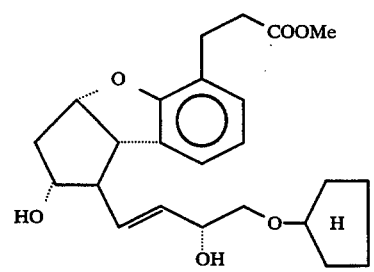

(114)

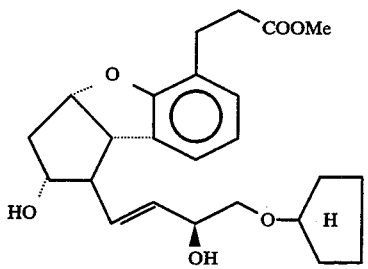

(115)

In 50 ml of methanol, 1.57 g (3.44 mmol) of 16-cyclopentyloxy-15-oxo-2,5,6,7,17,18,19,20-octanor-4,8-inter-m-phenylene PGI₂ methyl ester, 11-acetate was dissolved and then 1.67 g (4.47 mmol) of cerium trichloride heptahydrate was dissolved followed by being cooled to 0 C. To this solution, 156 mg (4.13 mmol) of sodium borohydride was added. After stirring the resulting mixture for 10 minutes at 0° C., 15 ml of saturated aqueous sodium hydrogen carbonate solution was added thereto and the resulting mixture was concentrated. Ethyl acetate was added to the residue and the resultant was filtered. The filtrate was washed with water and brine, dried and concentrated to obtain 1.40 g of an oily product. Then the thus obtained oily product was dissolved in anhydrous methanol. To this solution, 0.16 ml (0.84 mmol) of 5.22N sodium methoxide was added and the resulting mixture Was stirred for 2 hours at room temperature. To the thus obtained reaction mixture, acetic acid was added to attain pH 7 and the resultung mixture was concentrated. The residue was dissolved in ethyl acetate. This solution was washed with water and with brine, dried over anhydrous magnesium sulfate and concentrated to obtain 1.23 g of an oily product. The thus obtained oily product was purified by column chromatography (Lobar column commercially available from Merck & Co., Inc., eluant; ethyl acetate:cyclohexane=5:1) to firstly obtain 591 mg (yield 41%) of 16-cyclopentyloxy-15-epi-2,5,6,7,17,18,19,20-octanor-4,8-inter-m-phenylene PGI₂ methyl ester having low polarity. Then 509 mg (yield 36%) of 16-cyclopentyloxy-2,5,6,7,17,18,19,20-octanor-4,8-inter-m-phenylene PGI₂ methyl ester was obtained from high polar fractions.

The structures of these products were confirmed by the following data.

16-cyclopentyloxy-2,5,6,7,17,18,19,20-octanor-4,8-inter-m-phenylene PGI₂ methyl ester m.p. 71.5°-72.5° C. (Recrystallization Solvent:ethyl acetate:n-hexane) IR (KBr method): 3425, 2950, 2860, 1730, 1590, 1450, 1360, 1300, 1250, 1190, 1120, 1100, 1070, 1030, 1000, 980, 945, 900, 885, 860, 830, 780, 740, 620, 600, 550, 530, 500, 400, 330 cm⁻¹ NMR (400 MHz, CDCl₃, δ): 1.5–1.85(8H,m), 2.00(1H,ddd,J=5.3, 8.7, 13.8 Hz), 2.21(1H,d,J=4.9 Hz), 2.47(1H,q,J=8.2 Hz), 2.6–2.7(3H,m), 2.72(1H,d,J=2.9 Hz), 2.85–3.0(2H,m), 3.27(1H,dd,J=8.2, 9.2 Hz), 3.4–3.55(2H,m), 3.66(3H,s), 3.9–4.0(2H,m), 4.3–4.4(1H,m), 5.14(1H,ddd,J=5.3, 7.2, 9.2 Hz), 5.59(1H,dd,J=6.1, 15.4 Hz), 5.78(1H,dd,J=8.2, 15.4 Hz), 6.76(1H,t,J=7.3 Hz), 6.972(1H,d,J=7.3 Hz), 6.982(1H,d,J=7.3 Hz) MASS (EI method, m/e): 416 (M+)

| Element Analysis | C | H |
|---|---|---|
| Calcd. (C₂₄H₃₂O₆) | 69.21 | 7.74 |
| Found | 69.21 | 7.76 |

16-cyclopentyloxy-15-epi-2,5,6,7,17,18,19,20-octanor-4,8-inter-m-phenylene PGI₂ methyl ester m.p. 106°-107° C. (Recrystallization Solvent:ethyl acetate:n-hexane) IR (KBr method): 3530, 2960, 1730, 1600, 1450, 1370, 1350, 1300, 1270, 1250, 1200, 1180, 1130, 1090, 1050, 1010, 980, 950, 900, 890, 860, 700, 600, 520, 480 NMR (400 MHz, CDCl₃, δ): 1.5–1.9 (8H,m), 1.85(1H,d,J=4.9 Hz), 2.01(1H,ddd,J=5.1, 8.5, 13.7 Hz), 2.49(1H,q,J=8.1 Hz), 2.6–2.75(4H,m), 2.85–3.0(2H,m), 3.28(1H,dd,J=8.1, 9.2 Hz), 3.45–3.55(2H,m), 3.66(3H,s), 3.9–4.0(2H,m), 4.25–4.35(1H,m), 5.15(1H,ddd,J=5.1, 7.2, 9.2 Hz), 5.62(1H,dd,J=5.6, 5.6 Hz), 5.81(1H,ddd,J=1.4, 8.1, 15.6 Hz), 6.77(1H,t,J=7.6 Hz), 6.97(1H,d,J=7.6 Hz), 7.01(1H,d,J=7.6 Hz) MASS (EI method, m/e): 416 (M+)

| Element Analysis | C | H |
|---|---|---|
| Calcd. (C₂₄H₃₂O₆) | 69.21 | 7.74 |
| Found (M+) | 69.16 | 7.78 |

EXAMPLE 56

16-cyclopentyloxy-2,5,6,7,17,18,19,20-octanor-4,8-inter-m-phenylene PGI₂ (116)

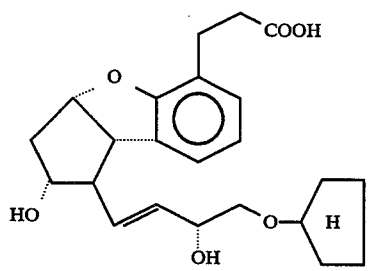

(116)

In 15 ml of methanol, 250 mg (0.60 mmol) of 16-cyclopentyloxy-2,5,6,7,17,18,19,20-octanor-4,8-inter-m-phenylene PGI₂ methyl ester was dissolved. To this solution, 3 ml of 1N sodium hydroxide was added and resulting mixture was stirred 24 hours at room temperature. The thus obtained reaction mixture was concentrated and water was added to the residue. Then 1N hydrochloric acid was added to attain pH 4 and the resultant was extracted with ethyl acetate. The organic layer was washed with brine, dried and concetrated to obtain 244 mg of crude crystals. The thus obtained crude crystals were recrystallized from ethanol to obtain 185 mg of 16-cyclopentyloxy-2,5,6,7,17,18,19,20-octanor-4,8-inter-m-phenylene PGI₂ (yield 77%).

The structure of this product was confirmed by the following data. m.p. 147°-147.5° C. IR (KBr method): 3400, 2950, 2870, 1695, 1600, 1450, 1435, 1410, 1380, 1350, 1310, 1250, 1210, 1190, 1110, 1100, 1080, 1050, 1030, 1000, 980, 950, 900, 860, 790, 765, 740, 690, 600, 555, 510, 400 cm⁻¹ NMR (400 MHz, DMSO-d₆, δ): 1.4–1.8(9H,m), 2.14(1H,q,J=8.3 Hz), 2.4–2.6(3H,m), 2.65–2.80(2H,m), 3.2–3.5(3H,m), 3.7–3.8(1H,m), 4.05–4.15(1H,m), 4.7–4.9(1H,m), 4.9–5.0(1H,m), 5.05(1H,q,J=7.5 Hz), 5.50(1H,dd,J=6.3, 15.2 Hz), 5.71(1H,dd,J=8.3, 15.2 Hz), 6.70(1H,t,J=7.3 Hz), 6.95(1H,brd,J=7.3 Hz), 6.97(1H,brd,J=7.3 Hz) MASS: 402 (M+)

| Element Analysis | C | H |
|---|---|---|
| Calcd. ($C_{23}H_{30}O_6$) | 68.63 | 7.51 |
| Found | 68.28 | 7.57 |

EXAMPLE 57

16-cyclopentyloxy-15-epi-2,5,6,7,17,18,19,20-octanor-4,8-inter-m-phenylene $PGI_2$ (117)

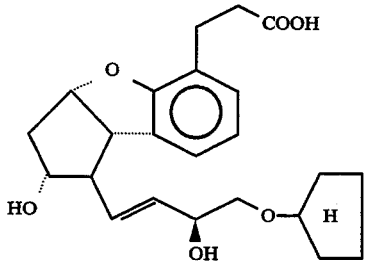
(117)

In 15 ml of methanol, 300 mg (0.72 mmol) of 16-cyclopentyloxy-15-epi-2,5,6,7,17,18,19,20-octanor-4,8-inter-m-phenylene $PGI_2$ methyl ester was dissolved. To this solution, 4 ml of 1N sodium hydroxide was added and resulting mixture was stirred 24 hours at room temperature. The thus obtained reaction mixture was concentrated and water was added to the residue. Then 1N hydrochloric acid was added to attain pH 4 and the resultant was extracted with ethyl acetate. The organic layers were washed with brine, dried and concetrated to obtain 261 mg of crude crystals. The thus obtained crude crystals were recrystallized from ethanol-ethyl acetate-cyclohexane to obtain 174 mg of 16-cyclopentyloxy-15-epi-2,5,6,7,17,18,19,20-octanor-4,8-inter-m-phenylene $PGI_2$ (yield 60%).

The structure of this product was confirmed by the following data. m.p. 143°–144° C. IR (KBr method): 3530, 3270, 2960, 1730, 1600, 1455, 1370, 1345, 1330, 1310, 1280, 1250, 1180, 1155, 1090, 1040, 1015, 970, 940, 900, 870, 840, 790, 770, 750, 720, 600, 490, 450, 400 cm$^{-1}$ NMR (400 MHz, DMSO-$d_6$, δ): 1.4–1.8(9H,m), 2.15(1H,q,J=8.5 Hz), 2.45–2.6(3H,m), 2.7–2.8(2H,m), 3.27(2H,d,J=5.9 Hz), 3.39(1H,t,J=8.5 Hz), 3.7–3.8(1H,m), 3.9–4.0(1H,m), 4.05–4.15(1H,m), 4.8–4.9(1H,m), 5.05(1H,q,J=8.5 Hz), 5.53(1H,dd,J=5.4, 15.5 Hz), 5.74(1H,dd,J=8.5, 15.5 Hz), 6.70(1H,t,J=7.8 Hz), 6.95(1H,d,J=7.8 Hz), 6.97(1H,d,J=7.8 Hz) MASS (EI method, m/e): 402 (M+)

| Element Analysis | C | H |
|---|---|---|
| Calcd. ($C_{23}H_{30}O_6$) | 68.63 | 7.51 |
| Found | 68.43 | 7.55 |

EXAMPLE 58

16-phenoxy-2,5,6,7,17,18,19,20-octanor-4,8-inter-m-pehnylene $PGI_2$ methyl ester (118) and 15-epimer thereof (119)

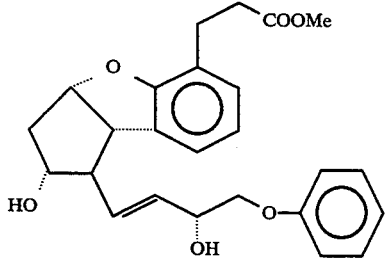
(118)

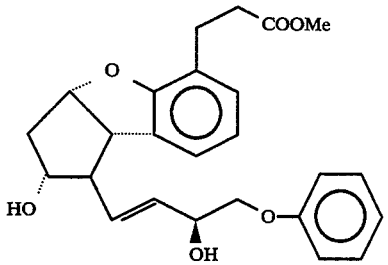
(119)

In 50 ml of methanol, 1.25 g (2.69 mmol) of 15-oxo-6-phenoxy-2,5,6,7,17,18,19,20-octanor-4,8-inter-m-phenylene $PGI_2$ methyl ester, 11-acetate was dissolved and then 1.30 g (3.50 mmol) of cerium trichloride heptahydrate was dissolved followed by being cooled down to 0° C. To this solution, 122 mg (3.23 mmol) of sodium borohydride was added. After stirring the resulting mixture for 10 minutes at 0° C., 15 ml of saturated aqueous sodium hydrogen carbonate solution was added thereto and the resulting mixture was concentrated. Ethyl acetate was added to the residue and the resultant was filtered. The solid was washed with ethyl acetate and the filtrates were combined. This solution was washed with water and with brine, dried and concentrated to obtain 1.20 g of an oily product. Then the thus obtained oily product was dissolved in 20 ml of anhydrous methanol. To this solution, 0.13 ml (0.68 mmol) of 5.22N sodium methoxide was added and the resulting mixture was stirred for 2 hours at room temperature. To the thus obtained reaction mixture, acetic acid was added to attain pH 7 and the resultung mixture was concentrated. The residue was dissolved in ethyl acetate. This solution was washed with saturated aqueous sodium hydrogen carbonate solution and with saturated saline, dried over anhydrous magnesium sulfate and concentrated. The thus obtained residue was purified by column chromatography (silica gel, eluant; acetonitril:-methylene chloride=1:3) to firstly obtain 378 mg (yield 33%) of 16-phenoxy-15-epi-2,5,6,7,17,18,19,20-octanor-4,8-inter-m-phenylene $PGI_2$ methyl ester having low polarity. Then 317 mg (yield 28%) of 16-phenoxy-2,5,6,7,17,18,19,20-octanor-4,8-inter-m-phenylene $PGI_2$ methyl ester was obtained from high polar fractions.

The structures of these products were confirmed by the following data.

16-phenoxy-2,5,6,7,17,18,19,20-octanor-4,8-inter-m-phenylene $PGI_2$ methyl ester IR (liquid film method): 3400, 2920, 1730, 1600, 1490, 1450, 1240, 1070, 1035, 970, 890, 860, 750, 690 cm$^{-1}$ NMR (400 MHz, CDCl$_3$, δ): 2.00(1H,ddd,J=5.1, 9.0, 13.9 Hz), 2.36(1H,d,J=4.9 Hz), 2.48(1H,q,J=8.6 Hz), 2.6–2.75(3H,m), 2.80(1H,d,J=3.4 Hz), 2.85–3.0(2H,m), 3.47(1H,t,J=8.6 Hz), 3.66(3H,s), 3.93(1H,dd,J=7.8, 9.3 Hz), 3.9–4.0(1H,m), 4.03(1H,dd,J=3.9, 9.3 Hz), 4.5–4.6(1H,m), 5.13(1H,ddd,J=5.1, 7.3, 8.6 Hz), 5.69(1H,dd,J=6.8, 15.4 Hz), 5.88(1H,dd,J=8.6, 15.4 Hz), 6.74(1H,t,J=7.3 Hz), 6.85–7.0(5H,m), 7.2–7.35(2H,m) MASS (EI method, m/e): 424 (M+) High resolution mass spectrum Calcd. ($C_{25}H_{28}O_6$, M+) 424.1904 Found (M+) 424.1895
16-phenoxy-15-epi-2,5,6,7,17,18,19,20-octanor-4,8-inter-m-phenylene PGI$_2$ methyl ester m.p. 130°–130.5° C. (Recrystallization Solvent:ethyl acetate) IR (KBr method): 3290, 2920, 1735, 1600, 1580, 1490, 1450, 1440, 1360, 1310, 1290, 1230, 1200, 1170, 1150, 1080, 1035, 970, 950, 890, 870, 860, 840, 760, 740, 700, 520 cm$^{-1}$ NMR (400 MHz, CDCl$_3$, δ): 1.85(1H,d,J=5.5 Hz), 2.03(1H,ddd,J=5.14, 8.4, 13.6 Hz), 2.5–2.6(2H,m), 2.6–2.75(3H,m), 2.85–3.0(2H,m), 3.53(1H,t,J=8.3 Hz), 3.66(3H,s), 3.92(1H,dd,J=7.8, 9.3 Hz), 3.95–4.05(1H,m), 4.06(1H,dd,J=3.4, 9.3 Hz), 4.55–4.65(1H,m), 5.16(1H,ddd,J=5.1, 7.2, 8.4 Hz), 5.73(1H,dd,J=5.6, 15.5 Hz), 5.91(1H,dd,J=8.4, 15.5 Hz), 6.76(1H,t,J=7.3 Hz), 6.9–7.1(5H,m), 7.3–7.4(2H,m) MASS (m/e): 424 (M+)

| Element Analysis | C | H |
|---|---|---|
| Calcd. ($C_{25}H_{28}O_6$) | 70.74 | 6.65 |
| Found (m+) | 70.66 | 6.58 |

EXAMPLE 59

16-phenoxy-2,5,6,7,17,18,19,20-octanor-4,8-inter-m-phenylene PGI$_2$ (120)

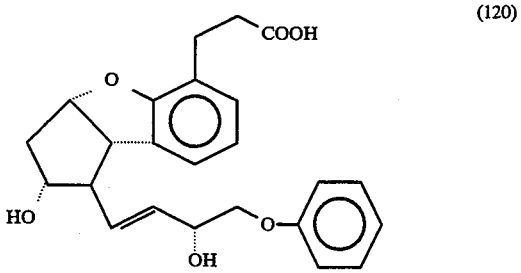

(120)

In 15 ml of methanol, 248 mg (0.58 mmol) of 16-phenoxy-2,5,6,7,17,18,19,20-octanor-4,8-inter-m-phenylene PGI$_2$ methyl ester was dissolved. To this solution, 3 ml of 1N sodium hydroxide was added and the resulting mixture was stirred for 18 hours at room temperature. The thus obtained reaction mixture was concentrated and water was added to the residue. Then 3N hydrochloric acid was added to attain pH 4 and the resultant was extracted with ethyl acetate. The organic layers were washed with water and with brine, dried and concentrated to obtain 231 mg of crude crystals. The thus obtained crude crystals were recrystallized from ethyl acetate-cyclohexane to obtain 185 mg of 16-phenoxy-2,5,6,7,17,18,19,20-octanor-4,8-inter-m-phenylene PGI$_2$ (yield 78%).

The structure of this product was confirmed by the following data. m.p. 150°–150.5° C. IR (KBr method): 3570, 3460, 2940, 1730, 1600, 1590, 1495, 1450, 1400, 1380, 1335, 1285, 1250, 1200, 1170, 1080, 1050, 1030, 1010, 975, 940, 900, 860, 840, 800, 750, 700, 580, 550, 520, 440 cm$^{-1}$ NMR (400 MHz, DMSOd$_6$, δ): 1.69(1H,ddd,J=5.9, 9.8, 12.7 Hz), 2.15–2.25(1H,m), 2.45–2.6(3H,m), 3.3–3.4(1H,m), 2.71(2H,t,J=7.6 Hz), 3.7–3.85(1H,m), 3.91(2H,t,J=5.9 Hz), 4.3–4.4(1H,m), 4.8–4.9(1H,m), 5.06(1H,m), 5.2–5.3(1H,m), 5.62(1H,dd,J=5.9, 15.5 Hz), 5.83(1H,dd,J=7.6, 15.5 Hz), 6.64(1H,t,J=7.6 Hz), 6.9–7.0(5H,m), 7.29(1H,d,J=7.3 Hz), 7.31(1H,d,J=8.3 Hz) MASS (EI method, m/e): 410 (M+)

| Element Analysis | C | H |
|---|---|---|
| Calcd. ($C_{24}H_{26}O_6$) | 70.23 | 6.39 |
| Found | 70.15 | 6.32 |

EXAMPLE 60

16-phenoxy-15-epi-2,5,6,7,17,18,19,20-octanor-4,8-inter-m-phenylene PGI$_2$ (121)

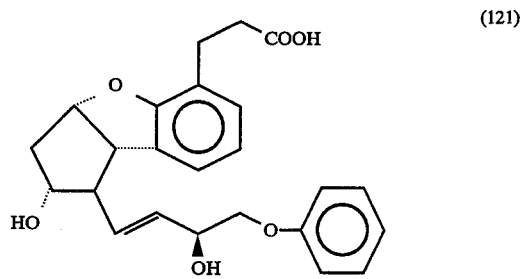

(121)

In 15 ml of methanol, 198 mg (0.47 mmol) of 16-phenoxy-15-epi-2,5,6,7,17,18,19,20-octanor-4,8-inter-m-phenylene PGI$_2$ methyl ester was dissolved. To this solution, 3 ml of 1N sodium hydroxide was added and the resulting mixture was stirred for 24 hours at room temperature. The thus obtained reaction mixture was concentrated and water was added to the residue. Then 3N hydrochloric acid was added to attain pH 4 and the resultant was extracted with ethyl acetate. The organic layers were washed with water and with brine, dried and concentrated to obtain 170 mg of crude crystals. The thus obtained crude crystals were recrystallized from ethanol to obtain 150 mg of 16-phenoxy-15-epi-2,5,6,7,17,18,19,20-octanor-4,8-inter-m-phenylene PGI$_2$ (yield 78%).

The structure of this product was confirmed by the following data. m.p. 170°–170.5° C. IR (KBr method): 3260, 3975, 2940, 2920, 2875, 1730, 1655, 1600, 1585, 1500, 1450, 1380, 1300, 1285, 1230, 1190, 1140, 1090, 1060, 1040, 970, 950, 900, 890, 860, 840, 755, 695, 650, 520, 470 cm$^{-1}$ NMR (400 MHz, DMSOd$_6$, δ): 1.69(1H,ddd,J=6.1, 10.0, 12.9 Hz), 2.1–2.25(1H,m), 2.4–2.6(3H,m), 2.71(2H,t,J=7.6 Hz), 3.2–3.4(1H,m), 3.7–3.8(1H,m), 3.89(1H,dd,J=6.8, 9.8 Hz), 3.94(1H,dd,J=4.4, 9.8 Hz), 4.3–4.4(1H,m), 4.8–4.9(1H,m), 5.06(1H,m), 5.2–5.3(1H,m), 5.66(1H,dd,J=5.7, 15.5 Hz), 5.85(1H,dd,J=8.0, 15.5 Hz), 6.67(1H,t,J=7.3 Hz), 6.9–7.0(5H,m), 7.29(1H,d,J=7.3 Hz), 7.31(1H,d,J=8.8 Hz) MASS (m/e): 410 (M+)

| Element Analysis | C | H |
|---|---|---|
| Calcd. ($C_{24}H_{26}O_6$) | 70.23 | 6.39 |
| Found | 70.27 | 6.28 |

EXAMPLE 61

16-methyl-16-phenoxy-2,5,6,7,18,19,20-heptanor-4,8-inter-m-phenylene PGI$_2$ methyl ester (122) and 15-epimer thereof (123)

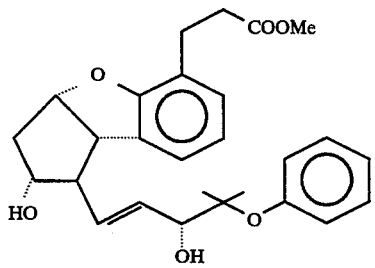
(122)

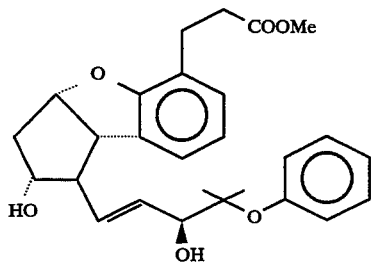
(123)

In 85 ml of methanol, 1.88 g (3.82 mmol) of 16-methyl-16-phenoxy-15-oxo-2,5,6,7,18,19,20-heptanor-4,8-inter-m-phenylene PGI$_2$ methyl ester, 11-acetate was dissolved and then 1.39 g (3.72 mmol) of cerium trichloride heptahydrate was added. Further, under cooling in iced water, 0.21 g (5.58 mmol) of sodium borohydride was added slowly thereto and the resulting mixture was stirred for 20 minutes. To the thus obtained reaction mixture, 20 ml of saturated aqueous sodium hydrogen carbonate solution was added. The resulting mixture was filtered and the filtrate was concentrated. To the thus obtained residue, 10 ml of water was added and the resultant was extracted with ethyl acetate (60 ml×1). Ethyl acetate layer was washed once with 10 ml each of water and brine, dried over anhydrous sodium sulfate and concetrated to obtain 1.84 g of an oily product. Then the thus obtained oily product was dissolved in 50 ml of anhydrous methanol under argon atmosphere. To this solution, 0.173 ml (0.906 mmol) of 5.22N sodium methoxide was added under stirring and the resulting mixture was stirred for 14 hours at room temperature. The thus obtained reaction mixture was neutralized with acetic acid and concentrated. To the thus obtained residue, 10 ml of water was added and the resultant was extracted with ethyl acetate (50 ml×2). Ethyl acetate layers were washed once with 10 ml each of water and brine, dried over anhydrous sodium sulfate and concentrated. The thus obtained residue was purified by Lobarr column (silica gel, commercially available from Merck & Co., Inc., eluant; ethyl acetate:cyclohexane=2:1) to obtain 647 mg (1.43 mmol, yield 37.5%) of 16-methyl-16-phenoxy-15-epi-2,5,6,7,18,19,20-heptanor-4,8-inter-m-phenylene PGI$_2$ methyl ester from low polar fractions. Then 618 mg (1.37 mmol, yield 35.7%) of 16-methyl-16-phenoxy-2,5,6,7,18,19,20-heptanor-4,8-inter-m-phenylene PGI$_2$ methyl ester was obtained from high polar fractions.

The structures of these products were confirmed by the following data.

16-methyl-16-phenoxy-2,5,6,7,18,19,20-heptanor-4,8-inter-m-phenylenePGI$_2$ methyl ester m.p. 124.5°–126.1° C. (Recrystallization Solvent:ethyl acetate:n-hexane=4:3) IR (KBr method): 3500, 3400, 2960, 1710, 1590, 1480, 1440, 1360, 1320, 1280, 1260, 1215, 1190, 1145, 1090, 1065, 1020, 975, 950, 880, 860, 830, 780, 740, 690 cm$^{-1}$ NMR (400 MHz, CDCl$_3$, δ): 1.25(3H,s), 1.26(3H,s), 1.9–2.1(1H,m), 2.3–2.5(1H,m), 2.52(1H,q,J=8.3 Hz), 2.6–2.7(3H,m), 2.8–3.0(2H,m), 3.0–3.2(1H,m), 3.49(1H,t,J=8.3 Hz), 3.66(3H,s), 3.9–4.1(1H,m), 4.1–4.3(1H,m), 5.1–5.2(1H,m), 5.72(1H,dd,J=15.4 Hz, 6.8 Hz), 5.83(1H,dd,J=15.4 Hz, 8.3 Hz), 6.75(1H,t,J=7.3 Hz), 6.9–7.0(4H,m), 7.05–7.15(1H,m), 7.2–7.4(2H,m) MASS (EI method, m/e): 452 (M$^+$)

| Element Analysis | C | H |
|---|---|---|
| Calcd. (C$_{24}$H$_{26}$O$_6$) | 71.66 | 7.13 |
| Found | 71.47 | 7.15 |

16-methyl-16-phenoxy-15-epi-2,5,6,7,18,19,20-heptanor-4,8-inter-m-phenylenePGI$_2$ methyl ester m.p. 95.3°–96.1° C. (Recrystallization Solvent:ethyl acetate:cyclohexane=1:1) IR (KBr method): 3370, 2970, 2850, 1730, 1590, 1480, 1420, 1370, 1360, 1290, 1250, 1225, 1190, 1125, 1100, 1070, 1030, 970, 950, 880, 860, 830, 780, 740, 695 cm$^{-1}$ NMR (400 MHz, CDCl$_3$, δ): 1.24(3H,s), 1.27(3H,s), 1.9–2.3(1H,m), 2.54(1H,q,J=8.2 Hz), 2.5–2.7(4H,m), 2.8–3.0(3H,m), 3.53(1H,t,J=8.2 Hz), 3.66(3H,s), 3.9–4.1(1H,m), 4.2–4.3(1H,m), 5.1–5.2(1H,m), 5.73(1H,dd,J=15.4, 5.9 Hz), 5.86(1H,ddd,J=15.4 Hz, 8.2 Hz, 1.0 Hz), 6.76(1H,t,J=7.6 Hz), 6.9–7.0(4H,m), 7.1–7.2(1H,m), 7.2–7.4(2H,m) MASS (EI method, m/e): 452 (M$^+$)

| Element Analysis | C | H |
|---|---|---|
| Calcd. (C$_{27}$H$_{32}$O$_6$) | 71.66 | 7.13 |
| Found | 71.43 | 7.19 |

EXAMPLE 62

16-methyl-16-phenoxy-2,5,6,7,18,19,20-heptanor-4,8-inter-m-phenylene PGI$_2$ (124)

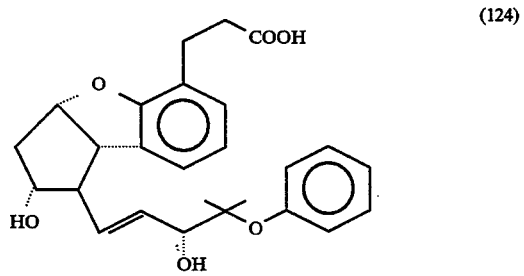
(124)

In 30 ml of methanol, 300 mg (0.66 mmol) of 16-methyl-1 6-phenoxy-2,5,6,7,18,19,20-heptanor-4,8-inter-m-phenylene PGI$_2$ methyl ester was dissolved. To this stirred solution, 1N sodium hydroxide was added under cooling in iced water, and the resulting mixture was stirred for 14 hours at room temperature. The thus obtained reaction mixture was concentrated and 10 ml of water was added to the residue. Then the mixture was neutralized with 1N hydrochloric acid and the resultant was extracted with ethyl acetate (50 ml×2).

The ethyl acetate layers were combined, washed with water (10 ml×1) and with brine (10 ml×1), dried over anhydrous sodium sulfate and concentrated. The thus obtained residue was recrystallized from 2 ml of ethyl acetate and from 1.5 ml of n-hexane to obtain 274 mg (0.626 mmol) of 16-methyl-16-phenoxy-2,5,6,7,18,19,20-heptanor-4,8-inter-m-phenylene PGI$_2$ (yield 94.3%) as colorless crystals.

The structure of this product was confirmed by the following data. m.p. 154.5°–155.6° C. (Recrystallization Solvent:ethyl acetate:n-hexane=4:3) IR (KBr method): 3360, 2970, 2870, 1700, 1590, 1480, 1470, 1375, 1250, 1220, 1190, 1150, 1120, 1090, 1065, 1030, 1000, 960, 910, 880, 860, 830, 780, 740, 695 cm$^{-1}$ NMR (400 MHz, DMSO-d$_6$, δ): 1.17(3H,s), 1.24(3H,s), 1.6–1.8(1H,m), 2.1–2.3(1H,m), 2.4–2.6(3H,m), 2.71(2H,t,J=7.6 Hz), 3.42(1H,t,J=9.0 Hz), 3.7–3.8(1H,m), 4.0–4.1(1H,m), 4.8–4.9(1H,m), 5.0–5.1(2H,m), 5.6–5.9(2H,m), 6.69(1H,t,J=7.3 Hz), 6.9–7.1(5H,m), 7.29(2H,t,J=7.8 Hz) MASS (EI method, m/e): 438 (M$^+$) High resolution mass spectrum Calcd. (C$_{26}$H$_{30}$O$_6$, M$^+$) 438.2042 Found (M$^+$) 438.2028

EXAMPLE 63

16-methyl-16-phenoxy-15-epi-2,5,6,7,18,19,20-heptanor-4,8-inter-m-phenylene PGI$_2$ (125)

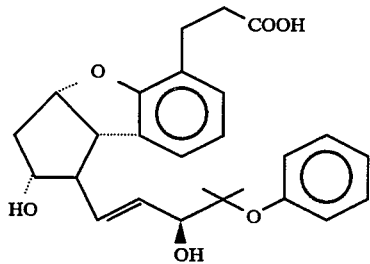

(125)

In 30 ml of methanol, 300 mg (0.664 mmol) of 16-methyl-16-phenoxy-15-epi-2,5,6,7,18,19,2 0-heptanor-4,8-inter-m-phenylene PGI$_2$ methyl ester was dissolved. To this stirred solution, 5.15 ml (5.15 mmol) of 1N sodium hydroxide was added under cooling in iced water, and the resulting mixture was stirred for 14 hours at room temperature. The thus obtained reaction mixture was concentrated and 10 ml of water was added to the residue. The resultant was extracted with ethyl acetate (50 ml×1). Ethyl acetate layers was washed with water (10 ml×1) and with brine (10 ml×1), dried over anhydrous sodium sulfate and concentrated. The thus obtained residue was recrystallized from 2 ml of ethyl acetate and from 1.5 ml of n-hexane to obtain 241 mg (0.55 mmol) of 16-methyl-16-phenoxy-15-epi-2,5,6,7,18,19,20-heptanor-4,8-inter-m-phenylene PGI$_2$ (yield 82.9%) as colorless crystals.

The structure of this product was confirmed by the following data. m.p. 103.5°–105.0° C. (Recrystallization Solvent:ethyl acetate:n-hexane=4:3) IR (KBr method): 3400, 2970, 2920, 1695, 1590, 1480, 1445, 1360, 1250, 1220, 1190, 1060, 1030, 980, 950, 870, 850, 770, 740, 695 cm$^{-1}$ NMR (400 MHz, DMSO-d$_6$, δ): 1.15(3H,s), 1.24(3H,s), 1.6–1.8(1H,m), 2.1–2.3(1H,m), 2.4–2.6(3H,m), 2.72(2H,t,J=7.8 Hz), 3.43(1H,t,J=9 Hz), 3.7–3.8(1H,m), 4.0–4.1(1H,m), 4.8–4.9(1H,m), 5.0–5.2(2H,m), 5.6–5.9(2H,m), 6.70(1H,t,J=7.6 Hz), 6.9–7.1(5H,m), 7.2–7.4(2H,m) MASS (EI method, m/e): 438 (M$^+$)

| Element Analysis | C | H |
|---|---|---|
| Calcd. (C$_{26}$H$_{30}$O$_6$) | 71.21 | 6.90 |
| Found | 71.20 | 6.89 |

EXAMPLE 64 d-16-(R)-methyl-16-phenoxy-2,5,6,7,17,18,19,20-octanor-4,8-inter-m-phenylene PGI$_2$ methyl ester (126) and 15-epimer thereof (127)

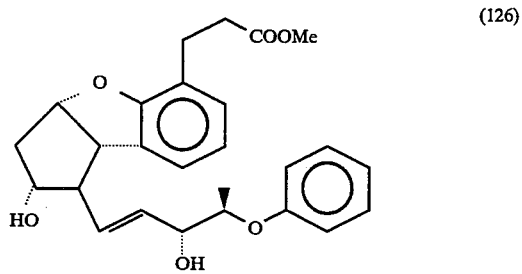

(126)

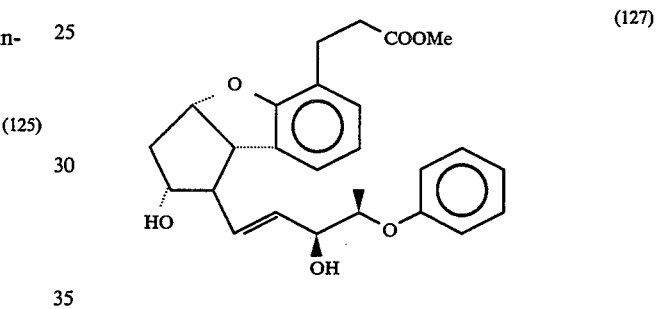

(127)

In 40 ml of methanol, 763 mg (1.6 mmol) of d-16-(R)-methyl-16-phenoxy-15-oxo-2,5,6,7,17,18,19,20-octanor-4,8-inter-m-phenylene PGI$_2$ methyl ester, 11-acetate was dissolved and then 662 mg (1.77 mmol) of cerium trichloride heptahydrate was added under stirring. Further, under cooling in iced water, 74 mg (1.95 mmol) of sodium borohydride was added slowly thereto and the resulting mixture was stirred for 20 minutes. To the thus obtained reaction mixture, 9 ml of saturated aqueous sodium hydrogen carbonate solution was added. The resulting mixture was filtered and the precipitate was washed with ethyl acetate (20 ml×3). The filtrates were combined and concentrated. To the thus obtained residue, 10 ml of ethyl acetate was added and the mixture was washed once with 30 ml each of water and brine, dried over anhydrous sodium sulfate and concetrated. The concentrate was subjected azeotropic distillation with benzene (10 ml×2) to obtain an oily product. Then the thus obtained oily product was dissolved in 40 ml of anhydrous methanol under argon atmosphere. To this solution, 0.083 ml (0.44 mmol) of 5.22N sodium methoxide was added under stirring and the resulting mixture was stirred for 2.5 hours at room temperature. The thus obtained reaction mixture was neutralized with acetic acid same and the mixture was concentrated. To the thus obtained residue, 20 ml of water was added and the resultant was extracted with ethyl acetate (50 ml×2). Ethyl acetate layers were washed once with 20 ml of water and with 30 ml of brine, dried over anhydrous sodium sulfate and concentrated. The thus obtained residue was purified by Lobar column (silica gel, commercially available from Merck & Co., Inc., eluant; ethyl acetate:cyclohexane=2:1) to obtain 95.5 mg (0.22 mmol, yield 13.6%) of d-16-(R)-methyl-16-phenoxy-15-epi-2,5,6,7,17,18,19,20-octanor-4,8-inter-m-phenylene PGI$_2$ methyl ester from low polar fractions. Then 437 mg (1 mmol, yield 62.5%) of d-16-(R)-methyl-16-phenoxy-2,5,6,7,17,18,19,20-octanor-4,8-inter-m-phenylene PGI$_2$ methyl ester was obtained from high polar fractions.

The structures of these products were confirmed by the following data.

d-16-(R)-methyl-16-phenoxy-2,5,6,7,17,18,19,20-octanor-4,8-inter-m-phenylene PGI$_2$ methyl ester $[\alpha]_D^{20} = +96.47°$ (C=1.306, MeOH) m.p. 88.5°-90.1° C. (Recrystallization Solvent;ethyl acetate:n-hexane=1:2) IR (KBr method): 3380, 2960, 2925, 2860, 1715, 1590, 1485, 1445, 1360, 1230, 1180, 1090, 1065, 1050, 1010, 970, 950, 920, 860, 740, 690 cm$^{-1}$ NMR (400 MHz, CDCl$_3$, δ): 1.30(3H,d,J=6.4 Hz), 1.9–2.1(1H,m), 2.4–2.6(2H,m), 2.5–2.7(3H,m), 2.8–3.0(3H,m), 3.47(1H,t,J=8.6 Hz), 3.66(3H,s), 3.9–4.1(1H,m), 4.1–4.4(2H,m), 5.0–5.2(1H,m), 5.65(1H,dd,J=15.2, 6.8 Hz), 5.84(1H,dd,J=15.2, 8.6 Hz), 6.73(1H,t,J=7.3 Hz), 6.8–7.0(5H,m), 7.2–7.4(2H,m) MASS (EI method, m/e): 438 (M$^+$) High resolution mass spectrum Calcd. (C$_{26}$H$_{30}$O$_6$, M$^+$) 438.2042 Found (M$^+$) 432.2031 d-16-(R)-methyl-16-phenoxy-15-epi-2,5,6,7,17,18,19,20-octnanor-4,8-inter-m-phenylenePGI$_2$ methyl ester $[\alpha]_D^{20} = +70.15°$ (C=1.19, MeOH) IR (liquid film method): 3370, 2920, 1715, 1590, 1480, 1460, 1360, 1230, 1190, 1055, 1020, 965, 880, 850, 745, 690 cm$^{-1}$ NMR (400 MHz, CDCl$_3$, δ): 1.31(3H,d,J=6.35 Hz), 1.7–1.8(1H,m), 1.9–2.1(1H,m), 2.25(1H,d,J=4.9 Hz), 2.54(1H,q,J=8.0 Hz), 2.5–2.7(3H,m), 2.8–3.0(2H,m), 3.52(1H,t,J=8.0 Hz), 3.66(3H,s), 3.9–4.1(1H,m), 4.1–4.5(2H,m), 5.1–5.2(1H,m), 5.73(1H,dd,J=14.8, 5.7 Hz), 5.85(1H,dd,J=14.8, 8.0 Hz), 6.75(1H,d,J=7.6 Hz), 6.8–7.1(5H,m), 7.23–7.4(2H,m) MASS (EI method, m/e): 438 (M$^+$) High resolution mass spectrum Calcd. (C$_{26}$H$_{30}$O$_6$, M$^+$) 438.2042 Found (M$^+$) 438.2033

EXAMPLE 65 d-16-(R)-methyl-16-phenoxy-2,5,6,7,17,18,19,20-octanor-4,8-inter-m-phenylene PGI$_2$ (128)

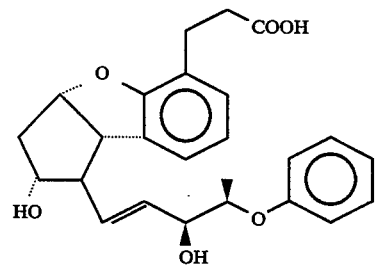

(128)

In 50 ml of methanol, 373 mg (0.85 mmol) of d-16-(R)-methyl-16-phenoxy-2,5,6,7,17,18,19,20-octanor-4,8-inter-m-phenylene PGI$_2$ methyl ester was dissolved. To this stirred solution, 8.5 ml (8.5 mmol) of 1N sodium hydroxide was added under cooling in iced water, and the resulting mixture was stirred for 3 hours at room temperature. The thus obtained reaction mixture was concentrated and 30 ml of water was added to the residue. This mixture was neutralized with 1N hydrochloric acid and the resultant was extracted with ethyl acetate (50 ml×2). The ethyl acetate layers were combined, washed with water (30 ml×1) and with brine (20 ml×1), dried over anhydrous sodium sulfate and concentrated. The thus obtained residue was recrystallized from 4 ml of ethyl acetate and from 8 ml of n-hexane to obtain 307 mg (0.72 mmol) of d-16-(R)-methyl-16-phenoxy-2,5,6,7,17,18,19,20-octanor-4,8-inter-m-phenylene PGI$_2$ (yield 85.2%) as colorless crystals.

The structure of this product was confirmed by the following data. $[\alpha]_D^{20} = +96.15°$ (C=0.624, MeOH) m.p. 94.8°-96.5° C. (Recrystallization Solvent:ethyl acetate:n-hexane=1:2) IR (KBr method): 3380, 2970, 2920, 1700, 1590, 1485, 1445, 1230, 1170, 1060, 965, 910, 855, 745, 690 cm$^{-1}$ NMR (400 MHz, CDCl$_3$, δ): 1.30(3H,d,J=6.7 Hz), 1.9–2.1(1H,m), 2.3–3.4(3H,m), 2.47(1H,q,J=8.3 Hz), 2.5–3.0(5H,m), 3.47(1H,t,J=8.3 Hz), 3.9–4.0(1H,m), 4.21(1H,t,J=6.7 Hz), 4.2–4.4(1H,m), 5.0–5.2(1H,m), 5.64(1H,dd,J=15.1, 6.7 Hz), 5.83(1H,dd,J=15.1, 8.3 Hz), 6.74(1H,t,J=7.3 Hz), 6.9–7.0(5H,m), 7.2–7.4(2H,m) MASS (EI method, m/e): 424 (M$^+$) High resolution mass spectrum Calcd. (C$_{25}$H$_{28}$O$_6$, M$^+$) 424.1886 Found (M$^+$) 424.1893

EXAMPLE 66 d-16-(R)-methyl-16-phenoxy-15-epi-2,5,6,7,17,18,19,20-octanor-4,8-inter-m-phenylene PGI$_2$ (129)

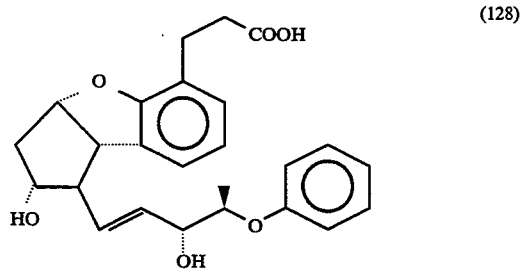

(129)

In 10 ml of methanol, 90.0 mg (0.205 mmol) of d-16-(R)-methyl-16-phenoxy-15-epi-2,5,6,7,17,18,19,20-octanor-4,8-inter-m-phenylene PGI$_2$ methyl ester was dissolved. To this solution, 2.05 ml (2.05 mmol) of 1N sodium hydroxide was added under cooling in iced water and the resulting mixture was stirred for 4 hours at room temperature. The thus obtained reaction mixture was concentrated and 10 ml of water was added to the residue. Then this mixture was neutralized with 1N hydrochloric acid and the resultant was extracted with ethyl acetate (50 ml×2). The ethyl acetate layers were washed with water (20 ml×1) and with brine (20 ml×1), dried over anhydrous sodium sulfate and concentrated to obtain 83.1 mg (0.196 mmol) of d-16-(R)-methyl-16-phenoxy-15-epi-2,5,6,7,17,18,19,20-octanor-4,8-inter-m-phenylene PGI$_2$ (yield 92.6%) as colorless and transparent oily product.

The structure of this product was confirmed by the following data. $[\alpha]_D^{20} = +71.47°$ (C=0.61, MeOH) IR (liquid film method): 3350, 2970, 2920, 1700, 1590, 1480, 1440, 1370, 1230, 1060, 960, 880, 855, 825, 790, 750,690 cm$^{-1}$ NMR (400 MHz, CDCl$_3$, δ): 1.30(3H,d,J=6.7 Hz), 1.9–2.1(1H,m), 2.3–3.4(3H,m), 2.47(1H,q,J=8.3 Hz), 2.5–3.0(5H,m), 3.47(1H,t,J=8.3 Hz), 3.9–4.0(1H,m), 4.21(1H,t,J=6.7 Hz), 4.2–4.4(1H,m), 5.0–5.2(1H,m), 5.64(1H,dd,J=15.1, 6.7 Hz), 5.83(1H,dd,J=15.1, 8.3 Hz), 6.74(1H,t,J=7.3 Hz), 6.9–7.0(5H,m), 7.2–7.4(2H,m), MASS (EI method, m/e): 424 (M$^+$) High resolution mass spectrum Calcd. (C$_{25}$H$_{28}$O$_6$, M$^+$) 424.1886 Found (M$^+$) 424.1899

EXAMPLE 67 d-16-(S)-methyl-16-phenoxy-2,5,6,7,17,18,19,20-octanor-4,8-inter-m-phenylene PGI₂ methyl ester (130) and 15-epimer thereof (131)

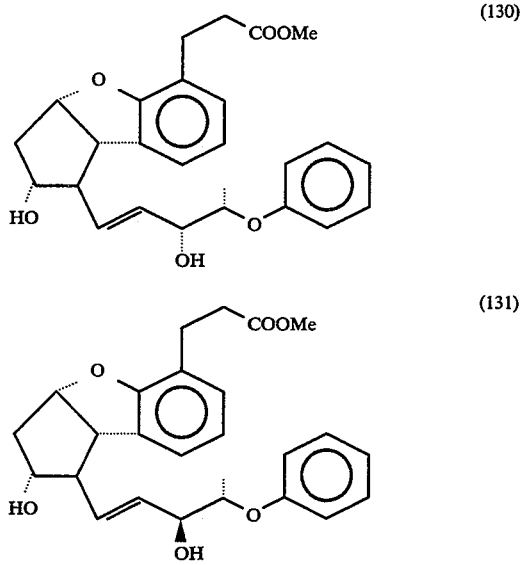

In 40 ml of methanol, 850 mg (1.78 mmol) of d-16-(S)-methyl-16-phenoxy-15-oxo-2,5,6,7,17,18,19,20-octanor-4,8-inter-m-phenylene PGI₂ methyl ester, 11-acetate was dissolved and then 663 mg (1.78 mmol) of cerium trichloride heptahydrate was dissolved under stirring. Further, under cooling in iced water, 67.3 mg (1.78 mmol) of sodium borohydride was added slowly thereto and the resulting mixture was stirred for 20 minutes. To the thus obtained reaction mixture, 10 ml of saturated aqueous sodium hydrogen carbonate solution was added. The resulting mixture was filtered and the precipitate was washed with ethyl acetate (10 ml×5). The filtrates were combined and concentrated. To the thus obtained residue, 30 ml of water was added and the resultant was extracted with ethyl acetate (100 ml×1). The organic layer was washed once with 30 ml each of water and brine, dried over anhydrous sodium sulfate and concetrated. The concentrate was subjected azeotropic distillation with benzene (10 ml×2) to obtain 843 mg of an oily product. Then the thus obtained oily product was dissolved in anhydrous methanol under argon atmosphere. To this solution, 0.05 ml (0.264 mmol) of 5.22N sodium methoxide was added under stirring and the resulting mixture was stirred for 2 hours at room temperature. The thus obtained reaction mixture was neutralized with acetic acid and the mixture was concentrated. To the thus obtained residue, 20 ml of water was added and the resultant was extracted with ethyl acetate (50 ml×2). Ethyl acetate layers were washed once with 20 ml of water and with 20 ml of brine, dried over anhydrous sodium sulfate and concentrated. The thus obtained residue was purified by Lobar column (silica gel, commercially available from Merck & Co., Inc., eluant; ethyl acetate:cyclohexane=2:1) to obtain 555 mg (1.27 mmol, yield 72%) of d-16-(S)-methyl-16-phenoxy-15-epi-2,5,6,7,17,18,19,20-octanor-4,8-inter-m-phenylene PGI₂ methyl ester from low polar fractions as an oily product. Then 49.5 mg of d-16-(S)-methyl-16-phenoxy-2,5,6,7,17,18,19,20-octanor-4,8-inter-m-phenylene PGI₂ methyl ester was obtained from high polar fractions as colorless crystals. Then 555 mg (1.27 mmol) of d-16-(S)-methyl-16-phenoxy-15-epi-2,5,6,7,17,18,19,20-octanor-4,8-inter-m-phenylene PGI₂ methyl ester was dissolved in 10 ml of methylenechloride. To this solution, 4.96 g (57 mmol) of manganese dioxide was added under stirring and the resulting mixture was stirred for 24 hours at room temperature. The thus obtained reaction mixture was filtered through High Flow Super Cell and the generate solid was washed with ethyl acetate (20 ml×8). The filtrates were combined and concentrated. The thus obtained residue was purified by Lobar column (silica gel, commercially available from Merck & Co., Inc., eluant; ethyl acetate:cyclohexane=1:1) to obtain 425 mg of an oily product. Then 375 mg (0.86 mmol) of the thus obtained oily product was dissolved in methanol. In this solution, 318 mg (0.86 mmol) of cerium trichloride heptahydrate was dissolved under stirring. Then under cooling in iced water, 25.9 mg (0.69 mmol) of sodium boron hydride was added slowly thereto and the resulting mixture was stirred for 20 minutes. To the thus obtained reaction mixture, 10 ml of saturated aqueous sodium hydrogen carbonate solution was added. The resulting mixture was filtered and inorganic materials were washed with ethyl acetate (10 ml×5). The filtrates were combined and concentrated. To the thus obtained residue, 30 ml of water was added and the resultant was extracted with ethyl acetate (100 ml×1). The ethyl acetate layer was washed once with 30 ml each of water and brine, dried over anhydrous sodium sulfate and concetrated. The thus obtained residue was purified by Lobar column (silica gel, commercially available from Merck Co., Inc., eluant; ethyl acetate:cyclohexane=2:1) to obtain 44.6 mg of crystals. The thus obtained crystals were combined with the previously obtained compound of d-16-(S)-methyl-16-phenoxy-2,5,6,7,17,18,19,20-octanor-4,8-inter-m-phenylene PGI₂ methyl ester (49.5 mg) and the crystals were recrystallized from 2 ml of ethyl acetate and from 4 ml of n-hexane to obtain 47.6 mg (0.11 mmol) of d-16-(S)-methyl-16-phenoxy-2,5,6,7,17,18,19,20-octanor-4,8-inter-m-phenylene PGI₂ methyl ester as colorless crystals (yield 6.2%).

The structures of these products were confirmed by the following data.

d-16-(S)-methyl-16-phenoxy-2,5,6,7,17,18,19,20-octanor-4,8-inter-m-phenylene PGI₂ methyl ester $[\alpha]_D^{20}=+108.73°$ (C=0.882, MeOH) m.p. 122.0°–123.0° C. (Recrystallization Solvent:ethyl acetate:n-hexane=1:2) IR (KBr method): 3430, 3030, 2920, 2880, 1725, 1700, 1590, 1485, 1445 1365, 1335, 1295, 1265, 1240, 1180, 1135, 1080, 1010, 960, 940, 870, 850, 825, 735, 690 cm⁻¹ NMR (400 MHz, CDCl₃, δ): 1.30(3H,d,J=6.4 Hz), 1.9–2.1(2H,m), 2.3–2.4(1H,m), 2.53(1H,q,J=8.1 Hz), 2.6–2.7(3H,m), 2.8–3.0(2H,m), 3.50(1H,t,J=8.1 Hz), 3.66(3H,s), 3.9–4.1(1H,m), 4.3–4.5(2H,m), 5.1–5.2(1H,m), 5.73(1H,dd,J=15.4, 6.1 Hz), 5.82(1H,dd,J=15.4, 8.1 Hz), 6.72(1H,t,J=8.1 Hz), 6.9–7.0(5H,m), 7.2–7.4(2H,m) MASS (EI method, m/e): 438 (M⁺) High resolution mass spectrum Calcd. (C₂₆H₃₀O₆, M⁺) 438.2042 Found (M⁺) 438.2063 d-16-(S)-methyl-16-phenoxy-15-epi-2,5,6,7,17,18,19,20-octanor-4,8-inter-m-phenylenePGI₂ methyl ester $[\alpha]_D^{20}=+77.99$ (C=0.868, MeOH) IR (liquid film method): 3400, 2970, 2920, 1715, 1590, 1485, 1445, 1370, 1230, 1190, 1170, 1060, 970, 920, 880, 855, 750, 690 cm⁻¹ NMR (400 MHz, CDCl₃, δ): 1.30(3H,d,J=5.9 Hz), 1.7–1.8(1H,m), 1.9–2.1(1H,m), 2.55(1H,q,J=7.6

Hz), 2.6–2.7(4H,m), 2.8–3.0(2H,m), 3.53(1H,t,J=8.3 Hz), 3.66(3H,s), 3.96(3H,s), 3.9–4.1(1H,m), 4.2–4.4(2H,m), 5.1–5.2(1H,m), 5.71(1H,dd,J=14.9, 5.9 Hz), 5.88(1H,dd,J=14.9, 7.6 Hz), 6.71(1H,t,J=7.3 Hz), 6.9–7.1(5H,m), 7.2–7.4(2H,m) MASS (EI method, m/e): 438 (M+) High resolution mass spectrum Calcd. ($C_{26}H_{30}O_6$, M+) 438.2042 Found (M+) 438.2022

EXAMPLE 68 d-16-(S)-methyl-16-phenoxy-2,5,6,7,17,18,19,20-octanor-4,8-inter-m-phenylene $PGI_2$ (132)

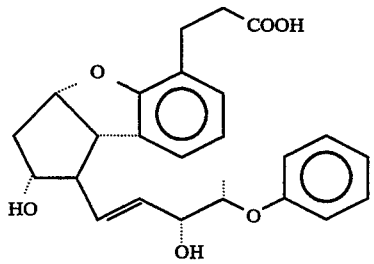

(132)

In 6 ml of methanol, 44 mg (0.1 mmol) of d-16-(S)-methyl-16-phenoxy-2,5,6,7,17,18,19,20-octanor-4,8-inter-m-phenylene $PGI_2$ methyl ester was dissolved. To this stirred solution, 1 ml (1 mmol) of 1N sodium hydroxide was added under cooling in iced water, and the resulting mixture was stirred for 14 hours at room temperature. The thus obtained reaction mixture was concentrated and 5 ml of water was added to the residue. Then this mixture was neutralized with 1N hydrochloric acid and the resultant was extracted with ethyl acetate (50 ml×2). The ethyl acetate layers were washed with water (20 ml×1) and with brine (20 ml×1), dried over anhydrous sodium sulfate and concentrated to obtain 41.3 mg (0.097 mmol) of d-16-(S)-methyl-16-phenoxy-2,5,6,7,17,18,19,20-octanor-4,8-inter-m-phenylene $PGI_2$ (yield 97.4%) as an oily product.

The structure of this product was confirmed by the following data. $[\alpha]_D^{20} = +115.37°$ (C=0.826, MeOH) IR (liquid film method): 3420, 2970, 2920, 1700, 1590, 1490, 1450, 1370, 1240, 1075, 1060, 1020, 1000, 965, 940, 880, 860, 740, 690 cm$^{-1}$ NMR (400 MHz, CDCl$_3$, δ): 1.30(3H,d,J=5.9 Hz), 1.8–3.3(2H,m), 1.9–2.1(1H,m), 2.49(1H,q,J=8.1 Hz), 2.5–2.8(3H,m), 2.8–3.0(2H,m), 3.47(1H,t,J=8.1 Hz), 3.3–4.8(1H,m), 3.9–4.0(1H,m), 4.35(1H,dd,J=6.5, 3.4 Hz), 4.4–4.5(1H,m), 5.0–5.2(1H,m), 5.71(1H,dd,J=15.5, 6.5 Hz), 5.8(1H,dd,J=15.5, 8.1 Hz), 6.71(1H,t,J=7.3 Hz), 6.9–7.1(5H,m), 7.2–7.4(2H,m) MASS (EI method, m/e): 424 (M+) High resolution mass spectrum Calcd. ($C_{25}H_{28}O_6$, M+) 424.1886 Found (M+) 424.1884

EXAMPLE 69 d-16-(S)-methyl-16-phenoxy-15-epi-2,5,6,7,17,18,19,20-octanor-4,8-inter-m-phenylene $PGI_2$ (133)

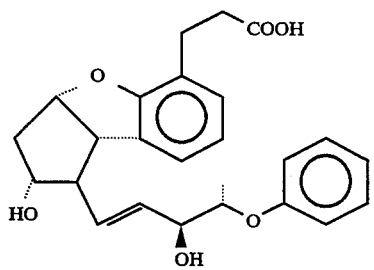

(133)

In 40 ml of methanol, 381 mg (0.87 mmol) of d-16-(S)-methyl-16-phenoxy-15-epi-2,5,6,7,17,18,19,20-octanor-4,8-inter-m-phenylene $PGI_2$ methyl ester was dissolved. To this stirred solution, 8.7 ml (8.7 mmol) of 1N sodium hydroxide was added under cooling in iced water, and the resulting mixture was stirred for 5 hours at room temperature. The thus obtained reaction mixture was concentrated and 30 ml of water was added to the residue. Under cooling in iced water, the mixture was neutralized with 1N hydrochloric acid and the resultant was extracted with ethyl acetate (50 ml×2). The ethyl acetate layers were washed with water (30 ml×1) and with brine (30 ml×1), dried over anhydrous sodium sulfate and concentrated to obtain 341 mg (0.8 mmol) of d-16-(S)-methyl-16-phenoxy-15-epi-2,5,6,7,17,18,19,20-octanor-4,8-inter-m-phenylene $PGI_2$ (yield 92.4%) as an oily product.

The structure of this product was confirmed by the following data. $[\alpha]_D^{20} = +75.39°$ (C=0.89, MeOH) IR (liquid film method): 3370, 3010, 2970, 2925, 1700, 1590, 1485, 1445, 1370, 1230, 1060, 970, 920, 880, 855, 750, 690, 660 cm$^{-1}$ NMR (400 MHz, CDCl$_3$, δ): 1.30(3H,d,J=5.9 Hz), 1.9–2.1(1H,m), 2.1–3.6(3H,m), 2.53(1H,q,J=7.6 Hz), 2.5–2.8(3H,m), 2.8–3.0(2H,m), 3.52(1H,t,J=8.3 Hz), 3.9–4.1(1H,m), 4.2–4.4(2H,m), 5.1–5.2(1H,m), 5.70(1H,dd,J=15.3, 5.9 Hz), 5.87(1H,dd,J=15.3, 8.3 Hz), 6.71(1H,t,J=7.6 Hz), 6.9–7.1(5H,m), 7.2–7.4(2H,m) MASS (EI method, m/e): 424 (M+) High resolution mass spectrum Calcd. ($C_{25}H_{28}O_6$, M+) 424.1886 Found (M+) 424.1913

EXAMPLE 70 d-16-methyl-16-phenoxy-2,5,6,7,18,19,20-heptanor-4,8-inter-m-phenylene $PGI_2$ methyl ester (134) and 15-epimer thereof (135)

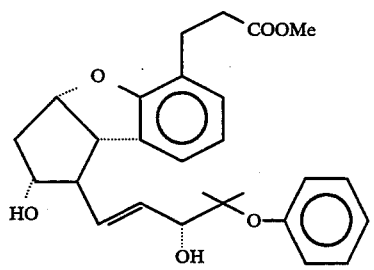

(134)

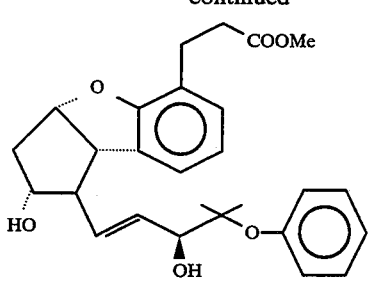

In 250 ml of methanol, 17.52 g (35.61 mmol) of d-16-methyl-16-phenoxy-15-oxo-2,5,6,7,18,19,20-heptanor-4,8-inter-m-phenylene PGI$_2$ methyl ester, 11-acetate was dissolved and then 19.9 g (53.41mmol) of cerium trichloride heptahydrate was dissolved. Further, under cooling in iced water and under stirring, 1.35 g (35.61 mmol) of sodium borohydride was added thereto. After stirring the resulting mixture for 10 minutes, 150 ml of saturated aqueous sodium hydrogen carbonate solution was added thereto and the resulting mixture was stirred for 20 minutes. The thus obtained reaction mixture was filtered under suction through Celite and the filtrate was concentrated and then the residue was extracted with ethyl acetate (150 ml×3). The organic layers were combined, washed with 300 ml of brine, dried over anhydrous sodium sulfate (30 g) and concentrated to obtain 18.42 g of an oily product. The thus obtained oily product was subjected to azeotropic distillation with benzene (20 ml×3) and the resultant was dissolved in 125 ml of anhydrous methanol. To this solution, 0.68 ml (3.56 mmol) of 5.22N sodium methoxide was added and the resulting mixture was stirred for 1.5 hours under argon atmosphere at room temperature. To the thus obtained reaction mixture, 0.8 ml of acetic acid was added and the mixture was concentrated. To the residue, 100 ml of water was added and the resultant was extracted with ethyl acetate (100 ml×3). The organic layers were combined, washed with 250 ml of saturated saline, dried over anhydrous sodium sulfate (30 g) and concentrated to obtain 17.82 g of an oily product. The thus obtained oily product was purified by column chromatography (silica gel, eluant; ethyl acetate:cyclohexane=2:1) to obtain 7.7173 g (17.07 mmol, yield 47.9%) of d-16-methyl-16-phenoxy-15-epi-2,5,6,7,18,19,20-heptanor-4,8-inter-m-phenylene PGI$_2$ methyl ester having low polarity. Then 6.980.5 g (15.44 mmol, yield 43.4%) of d-16-methyl-16-phenoxy-2,5,6,7,18,19,20-heptanor-4,8-inter-m-phenylene PGI$_2$ methyl ester was obtained from high polar fractions. These products were recrystallized from ethyl acetate to obtain colorless needle-shaped crystals.

The structures of these products were confirmed by the following data.

d-16-methyl-16-phenoxy-2,5,6,7,18,19,20-heptanor-4,8-inter-m-henylenePGI$_2$ methyl ester m.p. 104°–105° $[\alpha]_D^{20}=+118.21°$ (C=0.906, MeOH) IR (KBr method): 3510, 3405, 2920, 2905, 1714, 1667, 1584, 1482, 1442, 1380, 1362, 1342, 1322, 1283, 1262, 1227, 1184, 1174, 1144, 1125, 1105, 1088, 1065, 1030, 1015, 977, 952, 915, 883, 865, 838, 823, 785, 746, 699, 625, 605, 585, 548, 538, 520, 474, 439 cm$^{-1}$ NMR (400 MHz, CDCl$_3$, δ): 1.25(3H,s), 1.26(3H,s), 1.95–2.06(1H,m), 2.30–2.41(1H,brs), 2.48–2.58(1H,m), 2.59–2.70(3H,m), 2.83–2.97(2H,m), 3.03–3.12(1H,brs), 3.49(1H,t,J=8.24 Hz), 3.66(3H,s), 3.92–4.02(1H,m), 4.17–4.24(1H,m), 5.11–5.19(1H,m), 5.71(1H,dd,J=15.26, 7.02 Hz), 5.83(1H,dd,J=15.26, 8.24 Hz), 6.75(1H,t,J=7.32 Hz), 6.92–7.02(4H,m), 7.10–7.14(1H,m), 7.24–7.34(2H,m) MASS (EI method, m/e): 452 (M+) High resolution mass spectrum Calcd. (C$_{27}$H$_{32}$O$_6$, M+) 452.2199 Found (M+) 452.2190 d-16-methyl-16-phenoxy-15-epi-2,5,6,7,18,19,20-heptanor-4,8-inter-m-phenylenePGI$_2$ methyl ester $[\alpha]_D^{20}=+64.64°$ (C=1.072, MeOH) IR (liquid film method): 3400, 2970, 2930, 1722, 1587, 1482, 1444, 1362, 1250, 1222, 1193, 1124, 1045, 1024, 970, 881, 861, 834, 783, 744, 701 cm$^{-1}$ NMR (400 MHz, CDCl$_3$, δ): 1.24(3H,s), 1.26(3H,s), 1.5–1.8(1H,brs), 1.98–2.08(1H,m), 2.51–2.71(4H,m), 2.84–2.95(2H,m), 2.9–3.1(1H,brs), 3.51–3.58(1H,m), 3.66(3H,s), 3.97–4.03(1H,m), 4.20–4.23(1H,m), 5.13–5.20(1H,m), 5.72–5.79(1H,m), 5.83–5.92(1H,m), 6.76(1H,t,J=7.32 Hz), 6.93–7.04(4H,m), 7.10–7.16(1H,m), 7.25–7.33(2H,m) MASS (EI method, m/e): 452 (M+) High resolution mass spectrum CalCd. (C$_{27}$H$_{32}$O$_6$, M+) 452.2199 Found (M+) 452.2204

EXAMPLE 71 d-16-methyl-16-phenoxy-2,5,6,7,18,19,20-heptanor-4,8-inter-m-phenylene PGI$_2$ (136)

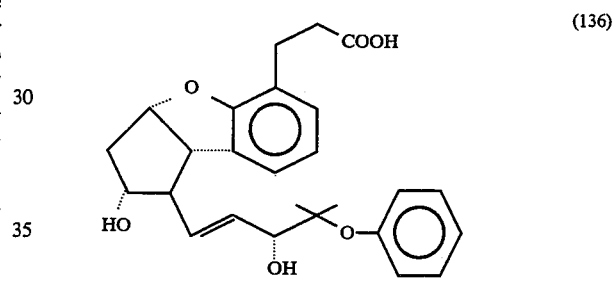

In 200 ml of methanol, 5.01 g (11.08 mmol) of d-16-methyl-16-phenoxy-2,5,6,7,18,19,20-heptanor-4,8-inter-m-phenylene PGI$_2$ methyl ester was dissolved. To this solution, 33.25 ml (33.25 mmol) of 1N sodium hydroxide was added and the resulting mixture was stirred overnight under argon atmosphere at room temperature. The thus obtained reaction mixture was concentrated. To the concentrate, 34.5 ml of 1N hydrochloric acid was added under cooling in iced water and then the resultant was extracted with ethyl acetate (70 ml×3). The organic layers were combined, washed with 150 ml of brine, dried over anhydrous sodium sulfate (40 g) and concentrated to quantitatively obtain 4.8528 g (11.08 mmol) of d-16-methyl-16-phenoxy-2,5,6,7,18,19,20-heptanor-4,8-inter-m-phenylene PGI$_2$ as a pure product. The thus obtained product was recrystallized from ethyl acetate/n-hexane (5:1) to obtain colorless needle-shaped crystals.

The structure of this product was confirmed by the following data. m.p. 125°–125.5° $[\alpha]_D^{20}=+122.84°$ (C=0.998, MeOH) IR (KBr method): 3375 (3650–2200), 3050, 2975, 2916, 1703, 1590, 1481, 1442, 1380, 1361, 1323, 1300, 1287, 1267, 1248, 1229, 1207, 1150, 1129, 1068, 1038, 1020, 980, 958, 907, 886, 868, 839, 824, 786, 766, 744, 702, 584, 486, 446 cm$^{-1}$ NMR (400 MHz, CDCl$_3$, δ): 1.24(3H,s), 1.25(3H,s), 1.98–2.08(1H,m), 2.0–4.5(3H,brs), 2.46–2.53(1H,m), 2.62–2.77(3H,m), 2.85–3.00(2H,m), 3.47(1H,t,J=8.3 Hz), 3.93–3.99(1H,m), 5.10–5.18(1H,m), 5.69(1H,dd,J=15.63, 6.83 Hz), 5.81(1H,dd,J=15.63, 8.3

Hz), 6.75(1H,t,J=7.33 Hz), 6.92–7.03(4H,m), 7.10–7.15(1H,m), 7.26–7.34(2H,m) MASS (EI method, m/e): 438 (M+) High resolution mass spectrum Calcd. (C26H30O6, M+) 438.2043 Found (M+) 438.2021

EXAMPLE 72 d-16-methyl-16-phenoxy-15-epi-2,5,6,7,18,19,20-heptanor-4,8-inter-m-phenylene PGI2 (137)

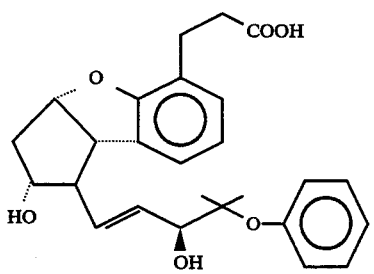
(137)

In 8 ml of methanol, 241.8 mg (0.535 mmol) of d-16-methyl-16-phenoxy-15-epi-2,5,6,7,18,19,20-heptanor-4,8-inter-m-phenylene PGI2 methyl ester was dissolved. To this solution, 1.6 ml (1.60 mmol) of 1N sodium hydroxide was added and the resulting mixture was stirred for 4 hours under argon atmosphere at room temperature. To the thus obtained reaction mixture, 2 ml of 1N hydrochloric acid was added and then 15 ml of water was added and the resultant was extracted with ethyl acetate (15 ml×3). The organic layers were combined, washed with 40 ml of brine, dried over anhydrous sodium sulfate (10 g) and concentrated to quantitatively obtain 234.2 mg (0.353 mmol) of d-16-methyl-16-phenoxy-15-epi-2,5,6,7,18,19,20-heptanor-4,8-inter-m-phenylene PGI2 as a pure product.

The structure of this product was confirmed by the following data. $[\alpha]_D^{20}$= +66.73° (C=0.920, MeOH) IR (liquid film method): 3400 (3650–2100), 2975, 2930, 1705, 1590, 1483, 1444, 1364, 1222, 1190, 1127, 1064, 1039, 965, 945, 910, 880, 860, 830, 780, 741, 700 cm$^{-1}$ NMR (400 MHz, CDCl3, δ): 1.24(3H,s), 1.25(3H,s), 1.98–2.09(1H,m), 2.2–4.5(3H,brs), 2.50–2.78(4H,m), 2.82–2.97(2H,m), 3.50–3.57(1H,m), 3.93–4.03(1H,m), 4.19–4.24(1H,m), 5.10–5.21(1H,m), 5.73(1H,dd,J=6.11, 15.38 Hz), 5.85(1H,dd,J=8.55, 15.38 Hz), 6.75(1H,t,J=7.32 Hz), 6.93–7.07(4H,m), 7.09–7.18(1H,m), 7.23–7.35(2H,m) MASS (EI method, m/e): 438 (M+) High resolution mass spectrum Calcd. (C26H30O6, M+) 438.3043 Found (M+) 438.2057

EXAMPLE 73 sodium salt of d-16-methyl-16-phenoxy-2,5,6,7,18,19,20-heptanor-4,8-inter-m-phenylene PGI2

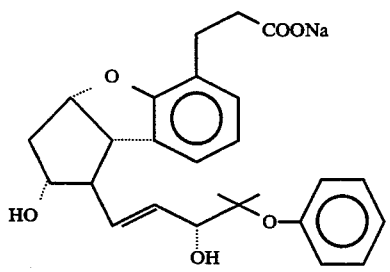
(138)

In 30 ml of 70% ethanol solution, 2.9897 g (6.8176 mmol) of d-16-methyl-16-phenoxy-2,5,6,7,18,19,20-heptanor-4,8-inter-m-phenylene PGI2 was dissolved. To this solution, firstly 60.312 ml of 0.017N sodium hydroxide was added and then 6.7696 ml of 0.1007N saturated aqueous sodium hydrogen carbonate solution was added. Further, to the thus obtained reaction mixture, 100 ml of anhydrous ethanol was added and the mixture was left to stand overnight in a refrigerator.

The thus obtained reaction mixture was filtered through membrane filter (regenerated cellose, Type TM-4P, 0.2 μm) under reduced pressure at 0°–5° C. and the resultant was concentrated to about 5 g. The thus obtained residue was dissolved in 10 ml of distilled water and this solution was freeze-dried for 4 hours and 20 minutes. The residue was adissolved in 12 ml of distilled water and freeze-dried for 5 hours. The thus obtained salts was pulverized under argon atmosphere and then dried under reduced pressure to obtain 3.0915 g (6.7132 mmol) of sodium salt of d-16-methyl-16-phenoxy-2,5,6,7,18,19,20-heptanor-4,8-inter-m-phenylene PGI2 with a 98.5% yield.

The structure of this product was confirmed by the following data. $[\alpha]_D^{20}$= +120.0° (C=0.992, MeOH) IR (KBr method): 3375 (3700–2000), 2960, 2920, 1552, 1480, 1441, 1400, 1334, 1282, 1220, 1182 1150, 1124, 1090, 1062, 1022, 1000, 963, 855, 828, 777, 740, 699 cm$^{-1}$ NMR (400 MHz, D2O, δ): 1.22(3H,s), 1.24(3H,s), 1.81–1.94(1H,m), 2.28–2.37(1H,m), 2.37–2.51(2H,m), 2.64–2.75(1H,m), 2.75–2.88(2H,m), 3.23–3.38(1H,m), 3.89–3.99(1H,m), 4.12–4.22(1H,m), 5.02–5.11(1H,m), 5.61–5.70(2H,m), 6.67–6.79(1H,m), 5.86–6.95(1H,m), 6.99–7.12(3H,m), 7.12–7.22(1H,m), 7.27–7.42(2H,m) MASS (CI method, m/e): 461 (M+ +1) High resolution mass spectrum Calcd. (C26H29O6Na, M+-Na) 437.1964 Found (M+-Na) 437.1968

EXAMPLE 74

3-decarboxy-3-hydroxymethyl-16,16-dimethyl-2,5,6,7-tetranor-4,8-inter-m-phenylene PGI2 (139)

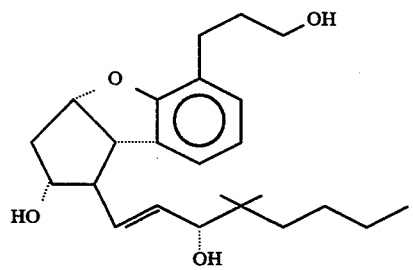
(139)

In 5 ml of anhydrous toluene, 62 mg of 16,16-dimethyl-2,5,6,7-tetranor-4,8-inter-m-phenylene PGI2 methyl ester was dissolved. To this solution, 0.5 ml of diisobutyl aluminium hydride (DIBAH) was added under argon atmosphere at −78° C. and the resulting mixture was stirred for an hour at the same temperature. To the thus obtained reaction mixture, 5 ml of saturated aqueous ammonium chloride solution was added and the resulting mixture was stirred for 10 minutes at room temperature. Further, 10 ml of water was added thereto and the resultant was extracted with ethyl acetate (10 ml×3). The organic layers were combined, washed once with 30 ml each of water and brine, dried over anhydrous sodium sulfate. Then the solvent was evaporated to obtain 68.3 mg of an oily product. The thus obtained oily product was purified by Lobar column (Type B commercially available from Merck & Co., Inc., eluant; ethyl acetate:cyclohexane=3:1) to obtain 38.1 mg of 3-decarboxy-3-hydroxymethyl-16,16-dimethyl-2,5,6,7-tetranor-4,8-inter-m-phenylene PGI$_2$ (yield 66%).

The structure of this product was confirmed by the following data. m.p. 113°–113.5° (ethyl acetate:n-hexane=3:10) IR (liquid film method): 3350, 2950, 2925, 2852, 1598, 1444, 1379, 1359, 1340, 1295, 1254, 1190, 1060, 1021, 964, 882, 860, 830, 739 cm$^{-1}$ NMR (400 MHz, CDCl$_3$, δ): 0.82–0.95(3H,m), 0.87(3H,s), 0.90(3H,s), 1.15–1.38(6H,m), 1.69–1.93(3H,m), 1.93–2.02(1H,m), 2.08–2.37(1H,m), 2.40–2.48(1H,m), 2.62–2.75(3H,m), 2.76–2.96(1H,m), 3.42–3.48(1H,m), 3.52–3.63(2H,m), 3.81–3.86(1H,m), 3.88–3.96(1H,m), 5.11–5.15(1H,m), 5.58–6.70(2H,m), 6.79(1H,t,J=7.33 Hz), 6.94–6.98(2H,m) MASS (EI method, m/e): 388 (M+) High resolution mass spectrum Calcd. (C$_{24}$H$_{36}$O$_4$, M+) 388.2613 Found (M+) 388.2636

EXAMPLE 75 d-3-decarboxy-3-hydroxymethyl-16-methyl-16-phenoxy-2,5,6,7,18,19,20-heptanor-4,8-inter-m-phenylene PGI$_2$ (140)

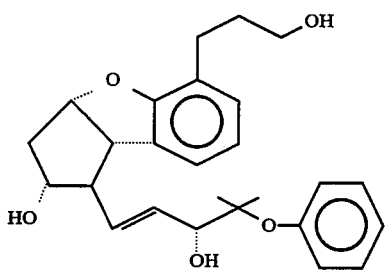

(140)

In 3 ml of anhydrous toluene, 140 mg (0.31 mmol) of d-16-methyl-16-phenoxy-2,5,6,7,18,19,20-heptanor-4,8-inter-m-phenylene PGI$_2$ methyl ester was dissolved. To this solution, 1.03 ml (1.55 mmol) of diisobutyl aluminium hydride was added under argon atmosphere at −78° C. and the resulting mixture was stirred for 20 minutes. Then the mixture was allowed to 0° C. and was stirred for 10 minutes. The thus obtained reaction mixture, 5 ml of saturated aqueous ammonium chloride solution was added and then 5 ml of 1N hydrochloric acid was added. The mixture was extracted with ethyl acetate (10 ml×3). The organic layers were combined, washed with 25 ml of brine, dried over anhydrous sodium sulfate (10 g) and concentrated to obtain 142.9 mg of an oily product. The thus obtained oily product was purified by column chromatograpy (silica gel, eluant; acetonitrile) to obtain 128.6 mg (0.3 mmol) of d-3-decarboxy-3-hydroxymethyl-16-methyl-16-phenoxy-2,5,6,7,18,19,20-heptanor-4,8-inter-m-phenylene PGI$_2$ as colorless oily product (yield of 97.8%).

The structure of this product was confirmed by the following data. [α]$_D^{20}$=+103.11° (C=0.418, MeOH) IR (liquid film method): 3350, 2970, 2930, 1691, 1586, 1481, 1443, 1362, 1250, 1220, 1184, 1152, 1125, 1063, 1023, 968, 910, 882, 861, 831, 781, 740, 700 cm$^{-1}$ NMR (400 MHz, CDCl$_3$, δ): 1.25(3H,s), 1.26(3H,s), 1.4–2.3(3H,brs), 1.76–1.93(2H,m), 1.96–2.07(1H,m), 2.50–2.58(1H,m), 2.60–2.76(3H,m), 3.50–3.63(3H,m), 3.98–4.05(1H,m), 4.18–4.23(1H,m), 5.10–5.18(1H,m), 5.72(1H,dd,J=8.55, 15.62 Hz), 5.72(1H,dd,J=6.84, 15.62 Hz), 6.78(1H,t,J=7.33 Hz), 6.93–7.02(4H,m), 7.11–7.18(1H,m), 7.24–7.34(2H,m) MASS (EI method, m/e): 424 (M+) High resolution mass spectrum Calcd. (C$_{26}$H$_{32}$O$_5$, M+) 424.2250 Found (M+) 424.2269

EXAMPLE 76

16-methyl-16-phenoxy-2,5,6,7,18,19,20-heptanor-13,14-dihydro-4,8-inter-m-phenylene PGI$_2$ methyl ester (141)

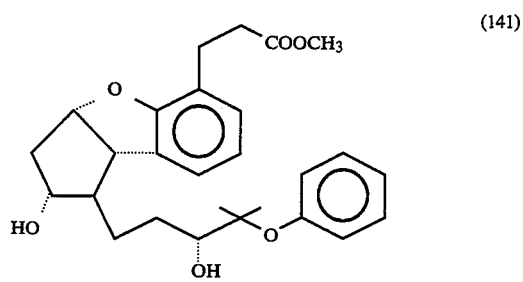

(141)

In 10 ml of ethyl acetate, 118.2 mg (0.262 mmol) of 16-methyl-16-phenyl-2,5,6,7,18,19,20-heptanor-4,8-inter-m-phenylene PGI$_2$ methyl ester was dissolved under argon atmosphere. To this solution, 35 mg of 10% palladium-carbon was added and the atmosphere was substituted with hydrogen, followed by being stirred for an hour at room temperature under normal pressure. The thus obtained reaction mixture was filtered through Celite under reduced pressure to remove palladium-carbon. The filtrate was concentrated and the residue was purified by column chromatography (Lobar column, Type B commercially available from Merck & Co., Inc., eluant; cyclohexane:ethyl acetate=1:3) to obtain 102.9 mg (0.227 mmol) of 16-methyl-16-phenoxy-2,5,6,7,18,19,20-heptanor-13,14-dihydro-4,8-inter-m-phenylene PGI$_2$ methyl ester with a 87% yield.

The structure of this product was confirmed by the following data. IR (liquid film method): 3430, 3090, 3050, 2990, 2970, 2940, 2890, 1745, 1600, 1490, 1455, 1385, 1370, 1300, 1265, 1260, 1230, 1200, 1190, 1155, 1145, 1095, 1075, 1055, 1030, 990, 965, 915, 885, 870, 840, 790, 750, 705 cm$^{-1}$ NMR (400 MHz, CDCl$_3$, δ): 1.23(6H,s), 1.59–1.85(6H,m), 2.04–2.16(2H,m), 2.43–2.50(1H,m), 2.59–2.70(2H,m), 2.82–2.93(2H,m), 3.42–3.49(1H,m), 3.65–3.70(4H,m), 4.02–4.07(1H,m), 5.19–5.24(1H,m), 6.76–6.80(1H,m), 6.95–7.00(3H,m), 7.08–7.15(2H,m), 7.26–7.31(3H,m) MASS (EI method, m/e): 454 (M+) High resolution mass spectrum Calcd. (C$_{27}$H$_{34}$O$_6$, M+) 454.2355 Found (M+) 454.2364

EXAMPLE 77

16-methyl-16-phenoxy-2,5,6,7,18,19,20-heptanor-13,14-dihydro-4,8-inter-m-phenylene PGI$_2$ (142)

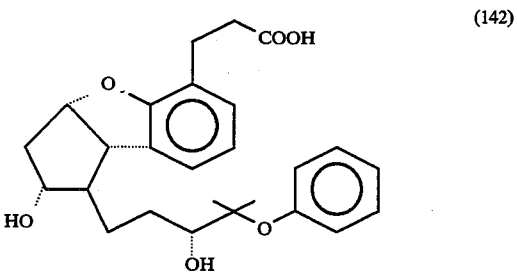

(142)

In 20 ml of methanol, 70 mg (0.154 mmol) of 16-methyl-16-phenoxy-2,5,6,7,18,19,20-heptanor-13,14-dihydro-4,8-inter-m-phenylene PGI$_2$ methyl ester was dissolved. To this solution, 0.46 ml of 1N sodium hydroxide was added and the resulting mixture was left to stand overnight at room temperature. Methanol was evaporated under reduced pressure and 10 ml of water was added to the residue. The resultant as extracted with ethyl acetate. Then 1N hydrochloric acid was added to water layer to attain pH 2. The resultant was extracted with ethyl acetate and the thus obtained extract was washed with brine, dried over anhydrous sodium sulfate. The solvent was evaporated under reduced pressure to obtain 57.1 mg (0.130 mmol) of 16-methyl-16-phenoxy-2,5,6,7,18,19,20-heptanor-13,14-dihydro-4,8-inter-m-phenylene PGI$_2$ with a 84% yield. This product was recrystallized from n-hexane/ethyl acetate to obtain colorless crystals.

The structure of this product was confirmed by the following data. m.p. 160°–161° C. IR (KBr method): 3425, 3070, 3045, 2990, 2955, 2940, 2870, 1704, 1603, 1598, 1495, 1455, 1450, 1420, 1405, 1385, 1375, 1365, 1350, 1325, 1315, 1280, 1235, 1210, 1155, 1138, 1110, 1075, 1045, 1035, 970, 955, 940, 918, 883, 855, 835, 822, 802, 790, 770, 750, 732, 700, 610, 580, 538, 477 cm$^{-1}$ NMR (400 MHz, CDCl$_3$, δ): 1.23(6H,s), 1.61–1.82(5H,m), 2.08–2.17(3H,m), 2.41–2.48(1H,m), 2.62–2.76(2H,m), 2.84–2.96(2H,m), 3.42–3.46(1H,m), 3.67–3.69(1H,m), 4.04–4.08(1H,m), 5.20–5.25(1H,m), 6.77–6.81(1H,m), 6.96–6.99(3H,m), 7.07–7.14(2H,m), 7.25–7.31(3H,m) MASS (EI method, m/e): 440 (M$^+$) High resolution mass spectrum Calcd. (C$_{26}$H$_{32}$O$_6$, M$^+$) 440.2198 Found (M$^+$) 440.2169

EXAMPLE 78

Cytoprotection

According to the method by A. Robert (Gartroerterolegy, 77(3), 443 (1979)), 30 minutes after oral administration of the compound, 0.2N NaOH was administered orally to the animals. After an hour, the animal was sacrified by chloroform anesthesia and the stomack was removed and fixed in 5% formalin solution. After fixation, the stomack was cut along the great curvature. A total length of blooding spot appearing on the corpus of stomack was measured and served as the ulcer index. When the ulcer index of the control group is taken as 100%, the dose of the compound by which the ulcer index decreased to 50% is designated as ED$_{50}$.

The results of evaluation of activity of the compound of the present invention by this method were summarized in Table 1.

TABLE 1

| Cytoprotention | |
|---|---|
| Compound | ED$_{50}$ (μg/kg) |
| 42 | 48.6 |
| 48 | 2.30 |
| 51 | 0.46 |
| 54 | 0.86 |
| 60 | 6.79 |
| 71 | 1.50 |
| 101 | 78.9 |
| 108 | 3.50 |
| 120 | 4.56 |
| 124 | 3.0 |

EXAMPLE 79

Gastric acid secretion-inhibiting action by pylorus ligation

According to the Shay's method (Gastroeuterology 5, 43 (1945)), median section was performed on abdomen of the rat under ether anesthesia and pylorus was ligated with thread. At the same time, the compound was injected into duodenum and then the incision was closed. After 5 hours, the abdomen was incised again and whole stomach was removed after ligating esophagus. The great curvature of the stomack was incised and the content was transferred to a graduated centrifuge tube. After centrifugation at 3000 rpm for 10 minutes, the volume of the gastric juice was measured. A part of the supernatant was sampled and was titrated with 0.1N NaOH until the pH became 7 using pH star (commercially available from Radio Meter Co., Ltd.). The ED$_{50}$ is defined as the average of 5 animals in a group of the dose of the compound by which the volume of the gestic acid (ml) is decreaseed to 50% of that of the control group, and as the average of 5 animals in a group of the dose of the Compound by which the level of the acid (mEq/ml) is decreased to that of the control group.

The results of evaluation of activity of the compound of the present invention were summarized in Table 2.

TABLE 2

| Gastric Acid Secretion-Inhibiting Action | | |
|---|---|---|
| | ED$_{50}$ (mg/kg) | |
| Compound | Gastric Acid | Volume of Gastric Juice |
| 42 | 3.80 | 4.60 |
| 48 | 0.63 | 6.30 |
| 51 | 0.21 | 0.36 |
| 54 | 0.11 | 0.015 |
| 60 | 2.39 | 1.19 |
| 71 | 0.034 | 0.045 |
| 101 | 0.90 | 1.40 |
| 108 | 2.02 | >10 |
| 120 | 0.11 | 0.30 |
| 124 | 0.19 | 0.75 |

EXAMPLE 80

Gastric acid secretion-inhibiting action

Male SD rat was incised in the abdomen under urethane anesthesia to open a hole at lumen of stomach. A double cannula was inserted from the hole and physiological saline was perfused in the stomack. The gastric acid flowed out was monitored by a pH meter (M. Chosh, H. Schild Br.J. Pharmacol 13, 54 (1958)). When the pH of the gastric acid was stabilized to about 4 after stimulation with continuous injection of pentagastrin at a rate of 0.05 μg/kg/min, the compound was injected through the femoral vein. As an index of the gastric acid secretion-inhibiting effect was measured using area enclosed by the curve from the point at which the pH started to increase by the gastric acid secretion-inhibiting effect to the point at which the pH is come back to the baseline. The relative effectiveness of gastric acid secretion-inhibiting effect of a compound was expressed when the value of PGE$_2$ is 1, and the effectiveness of each compound was compared.

The results of evaluation of activity of the compound of the present invention were summarized in Table 3.

TABLE 3

Gastric Acid Secretion-Inhibiting Action

| Compound | Relative Effectiveness to PGE$_2$ |
|---|---|
| PGE$_2$ | 1 |
| 42 | 3.6 |
| 45 | 3.5 |
| 51 | 35 |
| 54 | 6.1 |
| 60 | 1.3 |
| 71 | 7.1 |
| 101 | 4.9 |
| 108 | 7.0 |
| 120 | 54 |
| 124 | 62 |

EXAMPLE 81

Platelet aggregation-inhibiting action

Blood taken from human median cubital vein was centrifuged at 800 rpm for 10 minutes and the upper part was collected as platelet-rich plasma (PRP). PRP was put into small test tubes and adenosine-2-phosphate (ADP) was added thereto (final concentration of 10 μM) to induce platelet aggregation. The degree of platelet aggregation was measured as the change of turbidity determined by using a platelet aggregation measuring apparatus (commercially available from Rikadenki Co., Ltd., Tokyo). The compound was added 1 minute before the addition of ADP. The concentration which inhibits 50% aggregation was designated as IC$_{50}$.

The results of evaluation of the activity of the compound of the present invention were summarized in Table 4.

TABLE 4

Platelet aggregation-Inhibiting Action

| Compound | IC$_{50}$ (ng/ml) |
|---|---|
| 42 | 5.8 |
| 48 | 1000 |
| 51 | 11.0 |
| 54 | 3.2 |
| 60 | 3.8 |
| 71 | 2.85 |
| 101 | 48.0 |
| 108 | (—) |
| 120 | 1000 |
| 124 | (—) |

EXAMPLE 82

Hypotensive effect

Under chloralose anesthesia, catheter was inserted to carotid arteries of Wistar rat (male). The catheter was connected to a polygraph via pressure transducer to measure the pressure of carotid arteries. The compound was injected via catheter connected to a femoral articles. The dose which may reduce the blood pressure by 25 mmHg from the dose-response curve was designated as ED$_{25}$. The effectiveness of each compound was compared based on it.

The results of evaluation of the activity of the compound of the present invention were summarized in Table 5.

TABLE 5

Hypotensive effect

| Compound | ED$_{25}$ mmHg (μg/kg) |
|---|---|
| 42 | 0.46 |
| 48 | 0.84 |
| 51 | 0.11 |
| 54 | 0.78 |
| 60 | 0.17 |
| 71 | 0.26 |
| 101 | 1.50 |
| 108 | — |
| 120 | 0.51 |
| 124 | 1.30 |

Reference Example 40 d-16,16-dimethyl-15-oxo-2,5,6,7,20-pentanor-18-oxa-4,8-inter-m-phenylene PGI$_2$ methyl ester, 11-acetate (143)

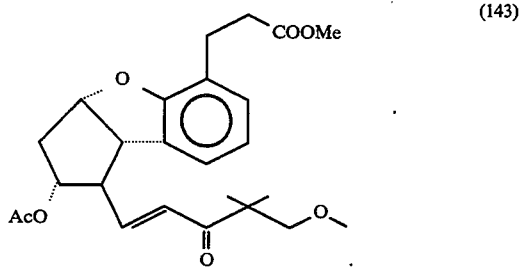

The same procedure as in Reference Example 13 to 39 was repeated except that d-2α-acetoxy-1β-hydroxymethyl-3aβH,8bβH-2,3,3a,8b-tetrahydro-5-1H-cyclopenta[b]benzofuran propionic acid methyl ester (1.8 g, 5.38 mmol) (synthetic method thereof was explained in Reference Example 12) and dimethyl 3,3-dimethyl-2-oxo-5-oxa-hexyl phosphonate (1.93 g, 8.07 mmol) were employed as reactants to obtain the captioned product (2.03 g, 4.57 mmol) having the following physical properties with a 85.0% yield. [α]$_D^{25}$ = +92.09° (C=0.722, CHCl$_3$) IR (liquid film method): 2930, 1740, 1690, 1600, 1450, 1390, 1370, 1320, 1300, 1240, 1200, 1110, 1060, 1010, 980, 930, 850, 750 cm$^{-1}$ NMR (90 MHz, CDCl$_3$, δ): 1.17(6H,s), 1.77(3H,s), 1.9–2.3(1H,m), 2.4–3.1(6H,m), 3.33(3H,s), 3.41(2H,s), 3.6–3.8(4H,m), 4.85–5.4(2H,m), 6.4–7.1(5H,m) MASS (EI method, m/e): 444 (M+) High resolution mass spectrum Calcd. (C$_{25}$H$_{32}$O$_7$, M+) 444.2148 Found (M+) 444.2149

Reference Example 41 d-16,16-dimethyl-15-oxo-20a,20b-dihomo-2,5,6,7-tetranor-18-oxa-4,8-inter-m-phenylene PGI$_2$ methyl ester, 11-acetate (144)

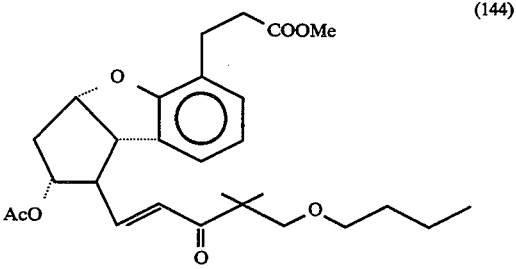

The same procedure as in Reference Example 13 to 39 was repeated except that d-2α-acetoxy-1β-hydroxymethyl-3aβH,8bβH-2,3,3a,8b-tetrahydro-5-1H-cyclopenta[b]benzofuran propionic acid methyl ester (1.2 g, 3.59 mmol) (synthetic method thereof was explained in Reference Example 12) and dimethyl 3,3-dimethyl-2-oxo-5-oxa-nonyl phosphonate (1.51 g, 5.39 mmol) were employed as reactants to obtain the captioned product (1.41 g, 2.90 mmol) having the following physical properties with a 80.8% yield. [α]$_D^{25}$=+81.12° (C=0.784, CHCl$_3$) IR (liquid film method): 2950, 2930, 2870, 1740, 1690, 1630, 1600, 1450, 1370, 1320, 1300, 1240, 1110, 1060, 1010, 980, 950, 850, 750 cm$^{-1}$ NMR (90 MHz, CDCl$_3$, δ): 0.8–1.0(3H,m), 1.16(6H,s), 1.2–1.6(4H,m), 1.75(3H,s), 1.9–2.2(1H,m), 2.4–3.1(6H,m), 3.3–3.5(4H,m), 3.5–3.8(4H,m), 4.8–5.4(2H,m), 6.4–7.1(5H,m) MASS (EI method, m/e): 486 (M+) High resolution mass spectrum Calcd. (C$_{28}$H$_{32}$O$_7$, M+) 486.2618 Found (M+) 486.2663

Reference Example 42 d-15-cycloheptyl-15-oxo-2,5,6,7,16,17,18,19,20-nonanor-4,8-inter-m-phenylene PGI$_2$ methyl ester, 11-acetate (145)

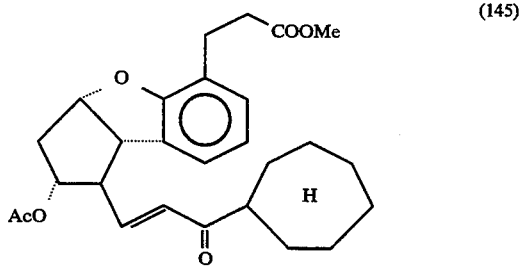

(145)

The same procedure as in Reference Example 13 to 39 was repeated except that d-2α-acetoxy-1β-hydroxymethyl-3aβH,8bβH-2,3,3a,8b-tetrahydro-5-1H-cyclopenta[b]benzofuran propionic acid methyl ester (1 g, 2.99 mmol) (synthetic method thereof was explained in Reference Example 12) and dimethyl 4-cycloheptyl-3-oxo-ethyl phosphonate (1.11 g, 4.49 mmol) were employed as reactants to obtain the captioned product (1.25 g, 2.74 mmol) having the following physical properties with a 92% yield. [α]$_D^{20}$=+81.14° (C=3.304, EtOH ) IR (liquid film method): 3220, 2920, 2860, 1739, 1690, 1670, 1630, 1550, 1480, 1455, 1420, 1370, 1320, 1300, 1239, 1195, 1155, 1130, 1050, 1025, 990, 950, 920, 890, 850, 830, 780, 745 cm$^{-1}$ NMR (400 MHz, CDCl$_3$, δ): 1.26–1.32(2H,m), 1.37–1.79(11H,m), 1.78(3H,s), 2.14(1H,ddd,J=11.23, 5.86, 3.42), 2.57–2.68(2H,m), 2.70–2.74(1H,m), 2.83–2.91(2H,m), 2.93–2.98(1H,m), 3.63–3.69(4H,m), 5.00(1H,q,J=5.86), 5.26(1H,ddd,J=9.16, 7.07, 3.41), 6.23–6.28(1H,m), 6.74–6.80(2H,m), 6.80–7.00(2H,m) MASS (EI method, m/e): 454 (M+)

Reference Example 43 d-15-cyclooctyl-15-oxo-2,5,6,7,16,17,18,19,20-nonanor-4,8-inter-m-phenylene PGI$_2$ methyl ester, 11-acetate (146)

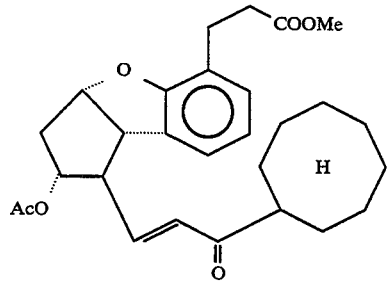

(146)

The same procedure as in Reference Example 13 to 39 was repeated except that d-2α-acetoxy-1β-hydroxymethyl-3aαH,8bβH-2,3,3a,8b-tetrahydro-5-1H-cyclopenta[b]benzofuran propionic acid methyl ester (1.0 g, 2.99 mmol) (synthetic method thereof was explained in Reference Example 12) and dimethyl 2-cyclooctyl-2-oxo-ethyl phosphonate (1.41 g, 5.39 mmol) were employed as reactants to obtain the captioned product (0.946 g, 2.02 mmol) having the following physical properties with a 67.5% yield. [α]$_D^{20}$=+102.57° (C=0.70, MeOH) IR (liquid film method): 3025, 2920, 2860, 1730, 1690, 1645, 1625, 1590, 1450, 1365, 1320, 1300, 1240, 1190, 1170, 1060, 980, 950, 850, 750 cm$^{-1}$ NMR (400 MHz, CDCl$_3$, δ): 1.4–1.7(10H,m), 1.57(3H,s), 1.7–2.0(4H,m), 2.1–2.2(1H,m), 2.5–2.7(3H,m), 2.7–2.8(1H,m), 2.89(2H,t,J=7.6 Hz), 2.9–3.0(1H,m), 3.67(3H,s), 3.6–3.8(1H,m), 5.00(1H,d,J=5.9 Hz), 5.2–5.3(1H,m), 6.25(1H,dd,J=15.6, 0.98 Hz), 6.773(1H,t,J=7.7 Hz), 6.774(1H,dd,J=15.6, 8.3 Hz), 6.98(2H,t,J=7.7 Hz) MASS (EI method, m/e): 468 (M+)

Reference Example 44 d-15-(p-methylphenyl)-15-oxo-2,5,6,7,16,17,18,19,20-nonanor-4,8-inter-m-phenylene PGI$_2$ methyl ester, 11-acetate (147)

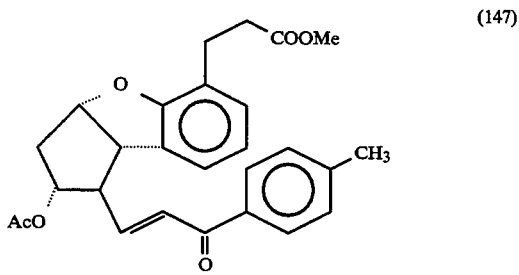

(147)

The same procedure as in Reference Example 13 to 39 was repeated except that d-2α-acetoxy-1β-hydroxymethyl-3aβH,8bβH-2,3,3a,8b-tetrahydro-5-1H-cyclopenta[b]benzofuran propionic acid methyl ester (1.0 g, 2.99 mmol) (synthetic method thereof was explained in Reference Example 12) and dimethyl 2-(p-methylphenyl)-2-oxo-ethyl phosphonate (1.31 g, 5.38 mmol) were employed as reactants to obtain the captioned product (1.05 g, 2.34 mmol) having the following physical properties with a yield of 78.4%. [α]$_D^{25}$=+106.92° (C=1.14, MeOH) IR (liquid film method): 3020, 2950, 1730, 1665, 1620, 1445, 1370, 1330, 1230, 1180, 1065, 1010, 980, 950, 850, 810, 750 cm$^{-1}$ NMR (400 MHz, CDCl$_3$, δ): 1.78(3H,s), 2.1–2.3(1H,m), 2.43(3H,s), 2.6–2.8(3H,m), 2.91(2H,t,J=7.6 Hz), 3.07(1H,q,J=6.2 Hz), 3.68(3H,s), 3.75(1H,dd,J=8.5, 6.2

Hz), 5.07(1H,q,J=6.1 Hz), 5.2–5.4(1H,m), 6.77(1H,t,J=7.5 Hz), 6.9–7.1(4H,m), 7.29(2H,d,J=8.1 Hz), 7.87(2H,d,J=8.1 Hz) MASS (EI method, m/e): 448 (M+)

Reference Example 45 d-15-(m-fluorophenyl)-15-oxo-2,5,6,7,16,17,18,19,20-nonanor-4,8-inter-m-phenylene PGI₂ methyl ester, 11-acetate (148)

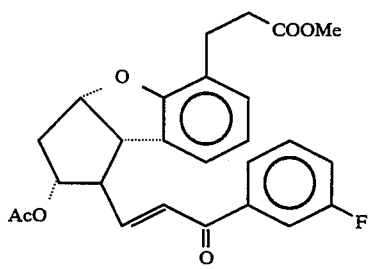
(148)

The same procedure as in Reference Example 13 to 39 was repeated except that d-2α-acetoxy-1β-hydroxymethyl-3aβH,8bβH-2,3,3a,8b-tetrahydro-5-1H-cyclopenta[b]benzofuran propionic acid methyl ester (1.0 g, 2.99 mmol) (synthetic method thereof was explained in Reference Example 12) and dimethyl 2-(m-fluorophenyl)-2-oxo-ethyl phosphonate (1.32 g, 5.38 mmol) were employed as reactants to obtain the captioned product (0.805 g, 1.78 mmol) having the following physical properties with a 59.5% yield. [α]$_D^{25}$ = +120.60° (C=1.33, MeOH) IR (liquid film method): 3070, 3020, 2960, 1730, 1670, 1620, 1585, 1485, 1440, 1370, 1300, 1230, 1190, 1170, 1065, 980, 950, 890, 850, 790, 750 cm⁻¹ NMR (400 MHz, CDCl₃, δ): 1.80(3H,s), 2.1–2.2(1H,m), 2.6–2.8(3H,m), 2.91(2H,t,J=7.6 Hz), 3.07(1H,q,J=6.7 Hz), 3.68(3H,s), 3.74(1H,dd,J=8.5, 6.1 Hz), 5.07(1H,q,J=6.1 Hz), 5.1–5.2(1H,m), 6.79(1H,t,J=7.5 Hz), 6.9–7.1(4H,m), 7.2–7.4(1H,m), 7.48(1H,dt,J=8.0, 5.6 Hz), 7.6–7.7(1H,m), 7.73(1H,d,J=8.0 Hz) MASS (EI method, m/e): 452 (M+)

Reference Example 46 d-15-(p-fluorophenyl)-15-oxo-2,5,6,7,16,17,18,19,20-nonanor-4,8-inter-m-phenylene PGI₂ methyl ester, 11-acetate (149)

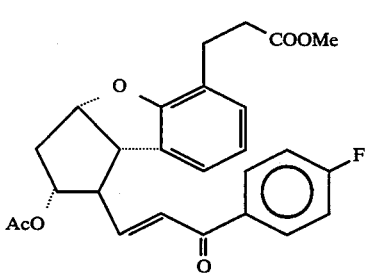
(149)

The same procedure as in Reference Example 13 to 39 was repeated except that d-2α-acetoxy-1β-hydroxymethyl-3aβH,8bβH-2,3,3a,8b-tetrahydro-5-1H-cyclopenta[b]benzofuran propionic acid methyl ester (1.2 g, 3.59 mmol) (synthetic method thereof was explained in Reference Example 12) and dimethyl 2-(p-fluorophenyl)-2-oxo-ethyl phosphonate (1.33 g, 5.39 mmol) were employed as reactants to obtain the captioned product (1.22 g, 2.70 mmol) having the following physical properties with a 75.3% yield. [α]$_D^{25}$ = +105.3° (C=0.994, CHCl₃) IR (liquid film method): 2970, 1740, 1680, 1630, 1605, 1515, 1460, 1380, 1240, 1165, 1075, 985, 840, 755 cm⁻¹ NMR (90 MHz, CDCl₃, δ): 1.79(3H,s), 2.0–3.2(7H,m), 3.68(3H,s), 3.6–3.9(1H,m), 4.9–5.4(2H,m), 6.6–7.3(7H,m), 7.9–8.1(2H,m) MASS (EI method, m/e): 452 (M+)

Reference Example 47 d-15-(o-fluorophenyl)-15-oxo-2,5,6,7,16,17,18,19,20-nonanor-4,8-inter-m-phenylene PGI₂ methyl ester, 11-acetate (150)

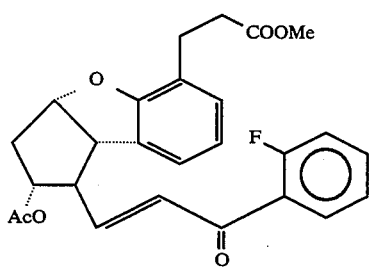
(150)

The same procedure as in Reference Example 13 to 39 was repeated except that d-2α-acetoxy-1β-hydroxymethyl-3aβH,8bβH-2,3,3a,8b-tetrahydro-5-1H-cyclopenta[b]benzofuran propionic acid methyl ester (1.00 g, 2.99 mmol) (synthetic method thereof was explained in Reference Example 12) and dimethyl 2-(o-fluorophenyl)-2-oxo-ethyl phosphonate (1.10 g, 4.49 mmol) were employed as reactants to obtain the captioned product (794.5 mg, 1.75 mmol) having the following physical properties with a 59% yield. [α]$_D^{20}$ = +98.76° (C=0.972, MeOH) IR (liquid film method): 3070, 2960, 2870, 1750, 1680, 1630, 1490, 1460, 1380, 1315, 1250, 1080, 990, 960, 875, 860, 790, 755, 655 cm⁻¹ NMR (400 MHz, CDCl₃, δ): 1.80(3H,s), 2.12–2.18(1H,m), 2.65(2H,t,J=7.3 Hz), 2.64–2.72(1H,m), 2.90(2H,t,J=7.3 Hz), 3.05(1H,dd,J=6.1, 14.0 Hz), 3.68(3H,s), 3.74(1H,dd,J=6.1, 8.5 Hz), 5.05(1H,m), 5.27(1H,m), 6.78(1H,t,J=7.3 Hz), 6.86–7.03(4H,m), 7.13–7.17(1H,m), 7.23–7.28(1H,m), 7.50–7.56(1H,m), 7.76–7.80(1H,m) MASS (EI method, m/e): 452 (M+)

Reference Example 45 d-15-(3,4-difluorophenyl)-15-oxo-2,5,6,7,16,17,18,19,20-nonanor-4,8-inter-m-phenylene PGI₂ methyl ester, 11-acetate (151)

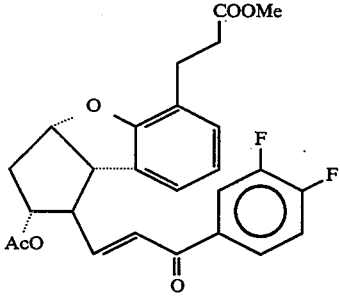
(151)

The same procedure as in Reference Example 13 to 39 was repeated except that d-2α-acetoxy-1β-hydroxymethyl-3aβH,8bβH-2,3,3a,8b-tetrahydro-5-1H-cyclopenta[b]benzofuran propionic acid methyl ester (1.00 g, 2.99 mmol) (synthetic method thereof was explained in Reference Example 12) and dimethyl 2-(3,4-difluorophenyl)-2-oxo-ethyl phosphonate (1.18 g, 4.49 mmol) were employed as reactants to obtain the captioned product (427.8 mg, 0.94 mmol) having the following physical properties with a 32% yield. $[\alpha]_D^{24}=+94.70°$ (C=0.434, MeOH) IR (liquid film method): 3070, 2950, 1740, 1680, 1625, 1610, 1525, 1455, 1440, 1370, 1295, 1250, 1210, 1170, 1110, 1070, 995, 955, 855, 830, 770, 750 cm$^{-1}$ NMR (400 MHz, CDCl$_3$, δ): 1.80(3H,S), 2.16-2.19(1H,m), 2.63-2.73(3H,m), 2.91(2H,t,J=7.6 Hz), 3.06(1H,dd,J=6.1, 14.0 Hz), 3.68(3H,s), 3.71-2.75(1H,m), 5.07(1H,m), 5.28(1H,m), 6.79(1H,t,J=7.6 Hz), 6.95-7.05(4H,m), 7.25-7.32(1H,m), 7.73-7.84(2H,m) MASS (EI method, m/e): 470 (M+)

Reference Example 49 d-15-(2,6-difluorophenyl)-15-oxo-2,5,6,7,16,17,18,19,20-nonanor-4,8-inter-m-phenylene PGI$_2$ methyl ester, 11-acetate (152)

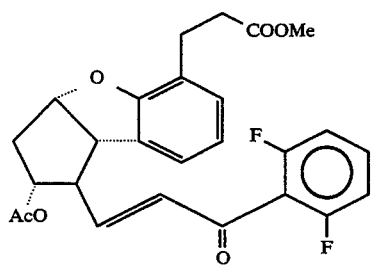

(152)

The same procedure as in Reference Example 13 to 39 was repeated except that d-2α-acetoxy-1β-hydroxymethyl-3aβH,8bβH-2,3,3a,8b-tetrahydro-5-1H-cyclopenta[b]benzofuran propionic acid methyl ester (1.2 g, 3.59 mmol) (synthetic method thereof was explained in Reference Example 12) and dimethyl 2-(2,6-difluorophenyl)-2-oxo-ethyl phosphonate (1.43 g, 5.39 mmol) were employed as reactants to obtain the captioned product (1.18 g, 2.51 mmol) having the following physical properties with a 71.4% yield. $[\alpha]_D^{20}=+100.27°$ (C=1.466, CHCl$_3$) IR (liquid film method): 2960, 1735, 1660, 1620, 1595, 1465, 1370, 1240, 1095, 1060, 1000, 945, 850, 790, 745 cm$^{-1}$ NMR (400 MHz, CDCl$_3$, δ): 1.80(3H,s), 2.14(1H,ddd,J=14.4, 6.7, 4.0 Hz), 2.6-2.7(3H,m), 2.90(2H,t,J=7.3 Hz), 3.02(1H,q,J=7.3 Hz), 3.67(3H,s), 3.65-3.75(1H,m), 5.01(1H,q,J=6.4 Hz), 5.25(1H,ddd,J=8.6, 7.3, 4.0 Hz), 6.52(1H,dd,J=15.9, 1.0 Hz), 6.76(1H,dd,J=15.9, 8.2 Hz), 6.79(1H,t,J=7.6 Hz), 6.95-7.05(4H,m), 7.4-7.5(1H,m) MASS (EI method, m/e): 470 (M+)

Reference Example 50 d-15-(m-trifluoromethylphenyl)-15-oxo-2,5,6,7,16,17,18,19,20-nonanor-4,8-inter-m-phenylene PGI$_2$ methyl ester, 11-acetate (153)

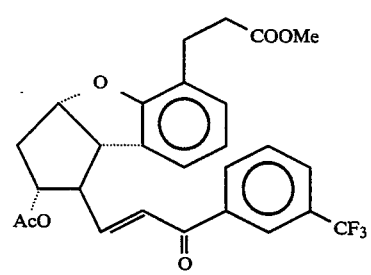

(153)

The same procedure as in Reference Example 13 to 39 was repeated except that d-2α-acetoxy-1β-hydroxymethyl-3aβH,8bβH-2,3,3a,8b-tetrahydro-5-1H-cyclopenta[b]benzofuran propionic acid methyl ester (1 g, 2.99 mmol) (synthetic method thereof was explained in Reference Example 12) and dimethyl 3-oxo-4-(m-trifluoromethylphenyl)ethyl phosphonate (1.0 g, 2.99 mmol) were employed as reactants to obtain the captioned product (0.89 g, 1.77 mmol) having the following physical properties with a 59% yield. $[\alpha]_D^{20}=+108.76°$ (C=0.124, MeOH) IR (liquid film method): 2930, 1750, 1600, 1480, 1450, 1410, 1390, 1335, 1310, 1280, 1270, 1250, 1190, 1165, 1120, 1100, 1088, 1020, 1002, 980, 950, 860, 805, 740, 700 cm$^{-1}$ NMR (100 MHz, CDCl$_3$, δ): 1.77(3H,s), 1.98-2.05(1H,m), 2.50-2.72(4H,m), 2.81-3.02(2H,m), 3.46(1H,t,J=8.30 Hz), 3.60(3H,s), 4.95-5.03(1H,m), 5.20-5.25(1H,m), 6.58-6.62(1H,m), 6.75-6.97(4H,m), 7.46-7.66(4H,m) MASS (EI method, m/e): 502 (M+)

Reference Example 51 d-15-(o-chlorophenyl)-15-oxo-2,5,6,7,16,17,18,19,20-nonanor-4,8-inter-m-phenylene PGI$_2$ methyl ester, 11-acetate (154)

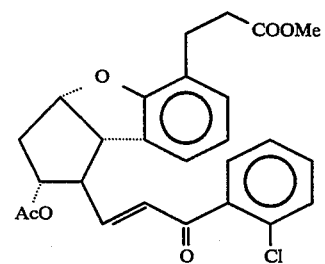

(154)

The same procedure as in Reference Example 13 to 39 was repeated except that d-2α-acetoxy-1β-hydroxymethyl-3aβH,8bβH-2,3,3a,8b-tetrahydro-5-1H-cyclopenta[b]benzofuran propionic acid methyl ester (1.0 g, 2.99 mmol) (synthetic method thereof was explained in Reference Example 12) and dimethyl 2-(o-chlorophenyl)-2-oxo-ethyl phosphonate (1.16 g, 5.11 mmol) were employed as reactants to obtain the captioned product (1.01 g, 2.16 mmol) having the following physical properties with a 72.1% yield. $[\alpha]_D^{20}=+129.36°$ (C=1.10, MeOH) IR (liquid film method): 3020, 2930, 1730, 1655, 1615, 1590, 1450, 1430, 1370, 1295, 1230, 1100, 1060, 1030, 970, 950, 850, 750 cm$^{-1}$ NMR (400 MHz, CDC$_3$, δ): 1.79(3H,s), 2.1-2.3(1H,m), 2.6-2.8(3H,m), 2.89(2H,t,J=7.8 Hz), 3.03(1H,q,J=6.9 Hz), 3.67(3H,s), 3.6-3.8(1H,m), 5.01(1H,q,J=6.9 Hz), 5.2-5.3(1H,m), 6.59(1H,d,J=15.6 Hz), 6.71(1H,dd,J=15.6, 6.9 Hz), 6.78(1H,t,J=7.5 Hz), 6.99(2H,d,J=7.5 Hz), 7.3–7.5(4H,m) MASS (EI method, m/e): 468 (M+)

Reference Example 52 d-15-(2,6-dichlorophenyl)-15-oxo-2,5,6,7,16,17,18,19,20-nonanor-4,8-inter-m-phenylene PGI₂ methyl ester, 11-acetate (155)

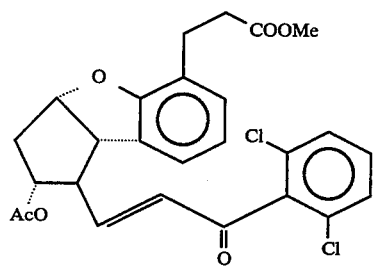
(155)

The same procedure as in Reference Example 13 to 39 was repeated except that d-2α-acetoxy-1β-hydroxymethyl-3aβH,8bβH-2,3,3a,8b-tetrahydro-5-1H-cyclopenta[b]benzofuran propionic acid methyl ester (1.0 g, 2.99 mmol) (synthetic method thereof was explained in Reference Example 12) and dimethyl 2-(2,6-dichlorophenyl)-2-oxo-ethyl phosphonate (1.5 g, 5.05 mmol) were employed as reactants to obtain the captioned product (0.62 g, 1.24 mmol) having the following physical properties with a 41.4% yield. $[\alpha]_D^{20}=+149.67°$ (C=1.516, MeOH) IR (liquid film method): 3000, 2930, 1730, 1660, 1580, 1550, 1445, 1425, 1360, 1230, 1185, 1120, 1055, 1000, 970, 940, 840, 780, 750 cm⁻¹ NMR (400 MHz, CDCl₃, δ): 1.80(3H,s), 2.0–2.2(1H,m), 2.5–2.7(3H,m), 2.89(2H,t,J=7.8 Hz), 3.00(1H,q,J=7.3 Hz), 3.67(3H,s), 3.6–3.8(1H,m), 4.99(1H,q,J=7.3 Hz), 5.1–5.3(1H,m), 6.36(1H,d,J=15.6 Hz), 6.53(1H,dd,J=15.6, 7.3 Hz), 6.78(1H,t,J=7.6 Hz), 6.97(1H,d,J=7.6 Hz), 7.00(1H,d,J=7.6 Hz), 7.3–7.5(3H,m) MASS (EI method, m/e): 502 (M+)

Reference Example 53 d-15-(p-nitrophenyl)-15-oxo-2,5,6,7,16,17,18,19,20-nonanor-4,8-inter-m-phenylene PGI₂ methyl ester, 11-acetate (156)

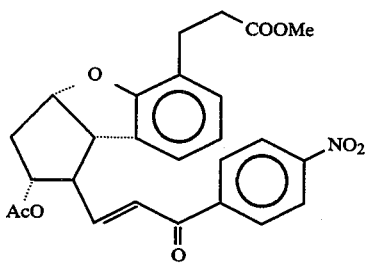
(156)

The same procedure as in Reference Example 13 to 39 was repeated except that d-2β-acetoxy-1β-hydroxymethyl-3aβH,8bβH-2,3,3a,8b-tetrahydro-5-1H-cyclopenta[b]benzofuran propionic acid methyl ester (1.80 g, 5.38 mmol) (synthetic method thereof was explained in Reference Example 12) and dimethyl 2-(p-nitrophenyl)-2-oxo-ethyl phosphonate (2.35 g, 8.61 mmol) were employed as reactants to obtain the captioned product (889 mg, 1.86 mmol) having the following physical properties with a 34.5% yield. $[\alpha]_D^{25}=+118.27°$ (C=0.788, MeOH) IR (liquid film method): 3030, 2950, 1730, 1680, 1620, 1600, 1530, 1480, 1450, 1350, 1320, 1300, 1240, 1110, 1060, 1020, 1010, 980, 950, 850, 750, 700, 670 cm⁻¹ NMR (400 MHz, CDCl₃, δ): 1.82(3H,s), 2.21(1H,ddd,J=3.9, 6.5, 14.7 Hz), 2.6–2.8(3H,m), 2.91(2H,t,J=7.8 Hz), 3.08(1H,q,J=6.5 Hz), 3.68(3H,s), 3.73(1H,dd,J=6.5, 8.6 Hz), 5.09(1H,q,J=6.5 Hz), 5.29(1H,ddd,J=3.9, 7.3, 8.6 Hz), 6.79(1H,t,J=7.3 Hz), 6.95–7.1(4H,m), 8.09(2H,d,J=8.8 Hz), 8.35(2H,d,J=8.8 Hz) MASS (EI method, m/e): 479 (M+) High resolution mass spectrum Calcd. (C₂₆H₂₅O₈, M+) 479.1580 Found (M+) 479.1573

EXAMPLE 83 d-16,16-dimethyl-2,5,6,7,20-pentanor-18-oxa-4,8-inter-m-phenylene PGI₂ methyl ester (157) and 15-epimer thereof (158)

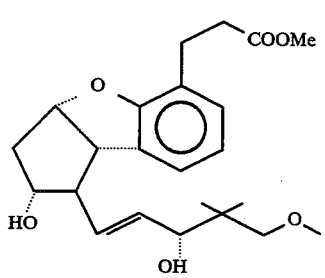
(157)

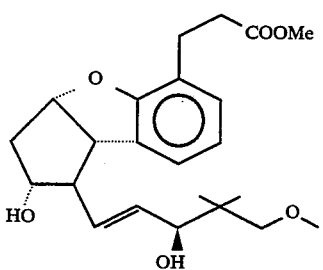
(158)

In 80 ml of methanol, 1.82 g (4.1 mmol) of d-16,16-dimethyl-15-oxo-2,5,6,7,20-pentanor-18-oxa-4,8-inter-m-phenylene PGI₂ methyl ester, 11-acetate was dissolved and then 1.83 g (4.9 mmol) of cerium trichloride heptahydrate was added. Further, under cooling in iced water, 124 mg (3.3 mmol) of sodium borohydride was added thereto and the resulting mixture was stirred for 10 minutes. To the thus obtained reaction mixture, 20 ml of saturated aqueous sodium hydrogen carbonate solution was added. The resulting mixture was filtered and the precipitate was washed with ethyl acetate (20 ml×3). The filtrates were combined and concentrated. To the thus obtained residue, 100 ml of ethyl acetate was added and the mixture was washed once with 30 ml each of water and brine, dried over anhydrous magnesium sulfate and concetrated. Then the residue was subjected to azeotropic distillation with benzene (15 ml×2) and then the resultant was dissolved in 50 ml of anhydrous methanol under argon atmosphere. To this solution, 0.23 ml (1.20 mmol) of 5.22N sodium methoxide in methanol was added and the resulting mixture was stirred for 3 hours at room temperature. The thus obtained reaction mixture was neutralized with acetic acid and the mixture was concentrated. To the thus obtained residue, 20 ml of water was added and the resultant was extracted with ethyl acetate (50 ml×2). Ethyl acetate layers were washed once with 20 ml each of water and brine, dried over anhydrous magnesium sulfate and concentrated. The thus obtained residue was purified by Lobar column (silica gel, commercially available from Merck & Co., Inc., eluant; ethyl acetate:-cyclohexane=2:1) to firstly obtain 733 mg (1.81 mmol, yield of 44.3%) of d-16,16-dimethyl-15-epi-2,5,6,7,20-pentanor-18-oxa-4,8-inter-m-phenylene PGI$_2$ methyl ester from low polar fractions. Then 707 mg (1.75 mmol, yield of 42.7%) of d-16,16-dimethyl-2,5,6,7,20-pentanor-18-oxa-4,8-inter-m-phenylene PGI$_2$ methyl ester was obtained from high polar fractions.

The structures of these products were confirmed by the following data.

d-16,16-dimethyl-2,5,6,7,20-pentanor-18-oxa-4,8-inter-m-phenylenePGI$_2$ $[\alpha]_D^{25}=+98.51°$ (C=0.606, MeOH) IR (liquid film method): 3400, 2950, 2930, 1740, 1600, 1480, 1450, 1360, 1300, 1260, 1200, 1100, 1070, 1040, 1000, 970, 920, 890, 860, 840, 750 cm$^{-1}$ NMR (400 MHz, CDCl$_3$, δ): 0.92(3H,s), 0.94(3H,s), 1.5–1.9(1H,m), 1.99(1H,ddd,J=5.4, 8.8, 13.7 Hz), 2.45–2.55(1H,m), 2.6–2.7(3H,m), 2.85–2.95(2H,m), 3.25(1H,d,J=8.8 Hz), 3.33(1H,d,J=8.8 Hz), 3.35(3H,s), 3.48(1H,t,J=8.6 Hz), 3.6–3.7(1H,m), 3.66 (3H,s), 3.9–4.0(2H,m), 5.14(1H,ddd,J=5.4, 7.3, 8.6 Hz), 5.6–5.75(2H,m), 6.76(1H,t,J=7.7 Hz), 6.97(2H,d,J=7.7 Hz) MASS (EI method, m/e): 404 (M+) High resolution mass spectrum Calcd. (C$_{23}$H$_{32}$O$_6$, M+) 404.2199 Found (M+) 404.2224 d-16,16-dimethyl-15-epi-2,5,6,7,20-pentanor-18-oxa-4,8-inter-m-phenylenePGI$_2$ $[\alpha]_D^{25}=+69.54°$ (C=0.614, MeOH) IR (liquid film method): 3420, 2960, 2930, 1730, 1600, 1480, 1450, 1400, 1370, 1300, 1260, 1200, 1100, 1030, 970, 920, 890, 860, 840, 750 cm$^{-1}$ NMR (400 MHz, CDCl$_3$, δ): 0.93(6H,s), 1.85–1.95(1H,m), 2.01(1H,ddd,J=4.9, 8.3, 13.7 Hz), 2.5–2.6(1H,m), 2.6–2.7(3H,m), 2.85–2.95(2H,m), 3.26(1H,d,J=8.8 Hz), 3.33(1H,d,J=8.8 Hz), 3.36(3H,s), 3.45–3.6(2H,m), 3.66(3H,s), 3.9–4.0(2H,m), 5.16(1H,ddd,J=4.9, 7.1, 8.8 Hz), 5.65–5.8(2H,m), 6.77(1H,t,J=7.4 Hz), 6.98(1H,d,J=7.4 Hz), 7.03(1H,d,J=7.4 Hz) MASS (EI method, m/e): 404 (M+) High resolution mass spectrum Calcd. (C$_{23}$H$_{32}$O$_6$, M+) 404.2199 Found (M+) 404.2214

EXAMPLE 84 d-16,16-dimethyl-2,5,6,7,20-pentanor-18-oxa-4,8-inter-m-phenylene PGI$_2$ (159)

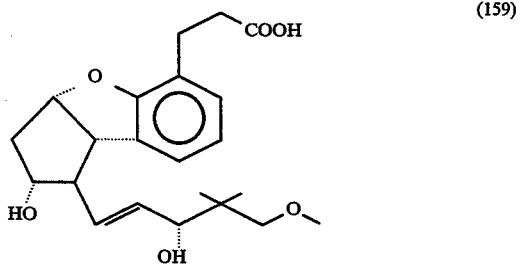

(159)

In 25 ml of methanol, 384 mg (0.95 mmol) of d-16,16-dimethyl-2,5,6,7,20-petanor-18-oxa-4,8-inter-m-phenylene PGI$_2$ methyl ester was dissolved under argon atmosphere. To this solution, 5 ml (5 mmol) of 1N sodium hydroxide was added under cooling in iced water and the resulting mixture was stirred for 5 hours at room temperature. The thus obtained reaction mixture was concentrated and 15 ml of water was added to the residue. Then 1N hydrochloric acid was added to neutralize the mixture and the resultant was extracted with ethyl acetate (60 ml, 20 ml×2). The ethyl acetate layers were washed with water (30 ml) and with brine (30 ml), dried over anhydrous magnesium sulfate and concentrated to obtain 367 mg (0.94 mmol) of d-16,16-dimethyl-2,5,6,7,20-pentanor-18-oxa-4,8-inter-m-phenylene PGI$_2$ (yield 99.1%) as a pure product.

The structure of this product was confirmed by the following data. $[\alpha]_D^{25}=+99.86°$ (C=0.754, MeOH) IR (liquid film method): 3380, 2960, 2930, 1710, 1600, 1480, 1450, 1400, 1360, 1340, 1260, 1190, 1150, 1100, 1030, 1000, 970, 920, 890, 860, 840, 750 cm$^{-1}$ NMR (400 MHz, CDCl$_3$, δ): 0.92(3H,s), 0.94(3H,s), 1.99(1H,ddd,J=5.2, 8.8, 13.7 Hz), 2.4–2.5(1H,m), 2.6–2.75(3H,m), 2.8–2.9(2H,m), 3.24(1H,d,J=9.3 Hz), 3.33(1H,d,J=9.3 Hz), 3.35(3H,s), 3.45(1H,t,J=8.7 Hz), 3.9–4.0(2H,m), 5.12(1H,ddd,J=5.2, 7.3, 8.7 Hz), 5.6–5.7(2H,m), 6.76(1H,t,J=7.3 Hz), 6.95–7.05(2H,m) MASS (EI method, m/e): 390 (M+) High resolution mass spectrum Calcd. (C$_{22}$H$_{30}$O$_6$, M+) 390.2042 Found (M+) 390.2029

EXAMPLE 85 d-16,16-dimethyl-15-epi-2,5,6,7,20-pentanor-18-oxa-4,8-inter-m-phenylene PGI$_2$ (160)

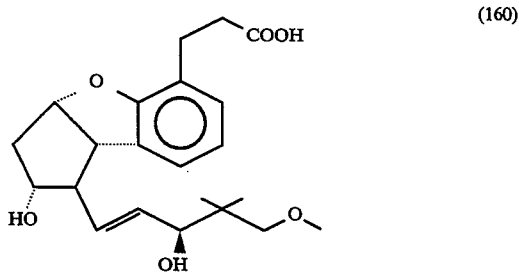

(160)

In 25 ml of methanol, 409 mg (1.01 mmol) of d-16,16-dimethyl-15-epi-2,5,6,7,20-pentanor-18-oxa-4,8-inter-m-phenylene PGI$_2$ methyl ester was dissolved under argon atmosphere. To this solution, 4 ml (4 mmol) of 1N sodium hydroxide was added under cooling in iced water and the resulting mixture was stirred for 5 hours at room temperature. The thus obtained reaction mixture was concentrated and 15 ml of water was added to the residue. Then the mixture was neutralized with 1N hydrochloric acid and the resultant was extracted with ethyl acetate (60 ml, 20 ml×2). The ethyl acetate layers were washed with water (30 ml) and with saturated saline (30 ml), dried over anhydrous magnesium sulfate and concentrated to obtain 374 mg (0.96 mmol) of d-16,16-dimethyl-15-epi-2,5,6,7,20-pentanor-18-oxa-4,8-inter-m-phenylene PGI$_2$ (yield 95.0%) as a pure product.

The structure of this product was confirmed by the following data. $[\alpha]_D^{25}=+75.72°$ (c=0.762, MeOH) m.p. 119.5°–120.5° C. (Recrystllization Solvent:ethyl acetate:n-hexane) IR (KBr method): 3430, 3320, 2960, 2870, 1700, 1600, 1480, 1450, 1420, 1400, 1370, 1330, 1300, 1270, 1250, 1200, 1150, 1100, 1090, 1070, 1040, 1030, 1000, 990, 980, 960, 920, 910, 890, 860, 840, 820, 800, 760, 740, 700, 620, 600, 550, 530, 500, 480, 460, 440 cm$^{-1}$ NMR (400 MHz, CDCl$_3$, δ): 0.93(6H,s), 2.01(1H,ddd,J=4.9, 8.3, 13.7 Hz), 2.52(1H,q,J=8.1 Hz), 2.55–2.75(3H,m), 2.85–2.95(2H,m), 3.25(1H,d,J=8.8 Hz), 3.34(1H,d,J=8.8 Hz), 3.36(3H,s), 3.52(1H,t,J=8.1 Hz), 3.9–4.0(2H,m), 5.15(1H,ddd,J=4.9, 7.3, 8.1 Hz), 5.6–5.75(2H,m), 6.77(1H,t,J=7.3 Hz), 6.98(1H,d,J=7.3 Hz), 7.03(1H,d,J=7.3 Hz) MASS (EI method, m/e): 390 (M+) High resolution mass spectrum Calcd. ($C_{22}H_{30}O_6$, M+) 390.2042 Found (M+) 390.2032

EXAMPLE 86 d-16,16-dimethyl-20a,20b-dihomo-2,5,6,7-tetranor-18-oxa-4,8-inter-m-phenylene PGI$_2$ methyl ester (161) and 15-epimer thereof (162)

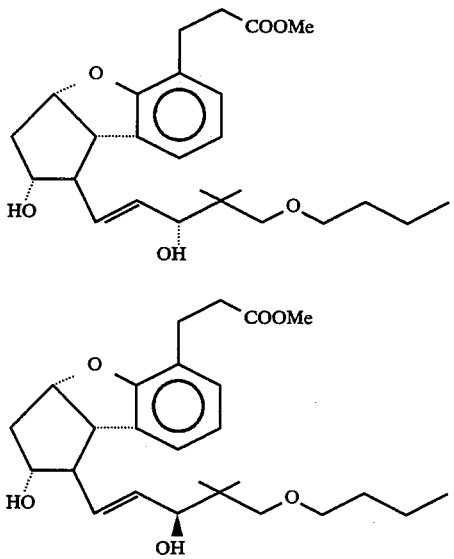

The same procedure as in Example 83 was repeated except that d-16,16-dimethyl-15-oxo-20a,20b-dihomo-2,5,6,7-tetranor-18-oxa-4,8-inter-m-phenylene PGI$_2$ methyl ester, 11-acetate (1.29 g, 2.65 mmol) was employed as a reactant to obtain the captioned compound (Compound (161) (522 mg, 1.17 mmol) and Compound (162) (537 mg, 1.20 mmol)) with a yield of 44.2% and 45.4%, respectively, which have the following physical properties. $[\alpha]_D^{25}=+95.64°$ (C=0.712, MeOH) IR (liquid film method): 3400, 2960, 2930, 2870, 1740, 1600, 1450, 1360, 1300, 1260, 1190, 1100, 1070, 1040, 1000, 970, 890, 860, 840, 750 cm$^{-1}$ NMR (400 MHz, CDCl$_3$, δ): 0.9–1.0(9H,m), 1.3–1.45(2H,m), 1.5–1.65(2H,m), 2.00(1H,ddd,J=5.3, 8.5, 13.7 Hz), 2.25–2.35(1H,m), 2.45–2.55(1H,m), 2.6–2.7(3H,m), 2.85–2.95(2H,m), 3.29(1H,d,J=8.8 Hz), 3.35(1H,d,J=8.8 Hz), 3.4–3.55(3H,m), 3.66(3H,s), 3.9–4.0(3H,m), 5.14(1H,ddd,J=5.3, 7.3, 8.8 Hz), 5.6–5.75(2H,m), 6.76(1H,t,J=7.3 Hz), 6.95–7.05(2H,m) MASS (EI method, m/e): 446 (M+) High resolution mass spectrum Calcd. ($C_{26}H_{38}O_6$, M+) 446.2668 Found (M+) 446.2675
d-16,16-dimethyl-15-epi-20a,20b-dihomo-2,5,6,7-tetranor-18-oxa-4,8-inter-m-phenylenePGI$_2$ $[\alpha]_D^{25}=+64.07°$ (C=0.760, MeOH) IR (liquid film method): 3420, 2960, 2940, 2880, 1740, 1600, 1460, 1370, 1300, 1260, 1200, 1160, 1100, 1070, 1040, 980, 890, 860, 840, 750 cm$^{-1}$ NMR (400 MHz, CDCl$_3$, δ): 0.85–1.0(9H,m), 1.35–1.45(2H,m), 1.55–1.65(2H,m), 1.8–1.9(1H,m), 2.02(1H,ddd,J=4.9, 8.3, 13.7 Hz), 2.53(1H,q,J=8.2 Hz), 2.6–2.75(3H,m), 2.85–2.95(2H,m), 3.30(1H,d,J=8.8 Hz), 3.36(1H,d,J=8.8 Hz), 3.4–3.5(2H,m), 3.53(1H,t,J=8.1 Hz), 3.66(3H,s), 3.9–4.05(3H,m), 5.16(1H,ddd,J=4.9, 7.3, 8.1 Hz), 5.65–5.75(2H,m), 6.77(1H,t,J=7.3 Hz), 6.97(1H,d,J=7.3 Hz), 7.03(1H,d,J=7.3 Hz) MASS (EI method, m/e): 446 (M+) High resolution mass spectrum Calcd. ($C_{26}H_{38}O_6$, M+) 446.2668 Found (M+) 446.2689

EXAMPLE 87 d-16,16-dimethyl-20a,20b-dihomo-2,5,6,7-tetranor-18-oxa-4,8-inter-m-phenylene PGI$_2$ (163)

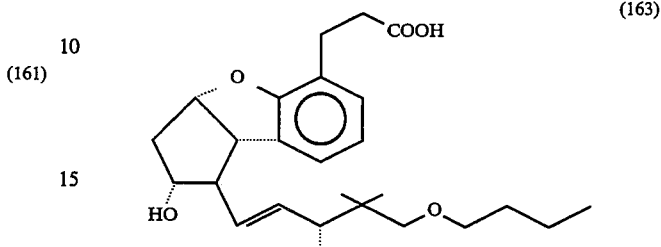

The same procedure as in Example 84 was repeated except that d-16,16-dimethyl-20a,20b-dihomo-2,5,6,7-tetranor-18-oxa-4,8-inter-m-phenylene PGI$_2$ methyl ester (351 mg, 0.79 mmol) was employed as a reactant to obtain the captioned compound (314 mg, 0.73 mmol) having the following physical properties with a 92.4% yield. $[\alpha]_D^{25}=+92.47°$ (C=0.784, MeOH) IR (liquid film method): 3380, 2950, 2930, 2870, 1720, 1600, 1450, 1410, 1380, 1360, 1260, 1190, 1150, 1100, 1040, 1000, 970, 890, 860, 830, 750 cm$^{-1}$ NMR (400MHz, CDCl$_3$, δ): 0.85–1.0(9H,m), 1.3–1.4(2H,m), 1.5–1.6(2H,m), 1.99(1H,ddd,J=5.4, 8.8, 13.7 Hz), 2.4–2.5(1H,m), 2.6–2.75(3H,m), 2.85–2.95(2H,m), 3.29(1H,d,J=9.0 Hz), 3.36(1H,d,J=9.0 Hz), 3.4–3.5(3H,m), 3.9–4.0(2H,m), 5.1–5.2(1H,m), 5.6–5.7(2H,m), 6.75(1H,t,J=7.6 Hz), 6.9–7.0(2H,m) MASS (EI method, m/e): 432 (M+) High resolution mass spectrum Calcd. ($C_{25}H_{36}O_6$, M+) 432.2512 Found (M+) 432.2507

EXAMPLE 88 d-16,16-dimethyl-15-epi-20a,20b-dihomo-2,5,6,7-tetranor-18-oxa-4,8-inter-m-phenylene PGI$_2$ (164)

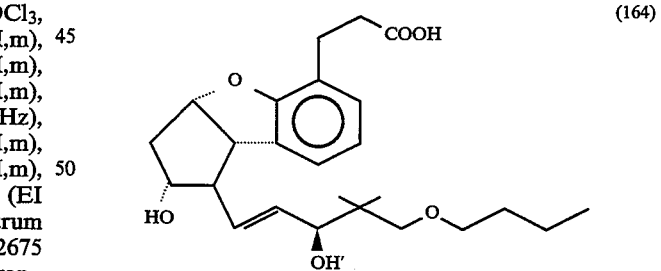

The same procedure as in Example 85 was repeated except that d-16,16-dimethyl-15-epi-20a,20b-dihomo-2,5,6,7-tetranor-18-oxa-4,8-inter-m-phenylene PGI$_2$ methyl ester (339 mg, 0.76 mmol) was employed as a reactant to obtain the captioned compound (317 mg, 0.73 mmol) having the following physical properties with a 96.6% yield. $[\alpha]_D^{25}=+62.11°$ (C=0.784, MeOH) IR (liquid film method): 3390, 2950, 2860, 1710, 1600, 1450, 1380, 1360, 1250, 1190, 1150, 1100, 1030, 1000, 970, 890, 860, 840, 750, 660 cm$^{-1}$ NMR (400 MHz, CDCl$_3$, δ): 0.9–1.0(9H,m), 1.35–1.45(2H,m), 1.55–1.65(2H,m), 2.01(1H,ddd,J=4.9, 8.3, 13.7 Hz), 2.5–2.75(4H,m), 2.85–2.95(2H,m), 3.30(1H,d,J=8.8 Hz), 3.37(1H,d,J=8.8 Hz), 3.4–3.5(2H,m), 3.52(1H,t,J=8.6 Hz), 3.9–4.0(2H,m), 5.16(1H,ddd,J=4.9, 6.8, 8.6 Hz), 5.6–5.8(2H,m), 6.77(1H,t,J=7.3 Hz), 6.98(1H,d,J=7.3 Hz), 7.03(1H,d,J=7.3 Hz) MASS (EI method, m/e): 432 (M+) High resolution mass spectrum Calcd. ($C_{25}H_{36}O_6$, M+) 432.2512 Found (M+) 432.2539

EXAMPLE 89 d-15-cycloheptyl-2,5,6,7,16,17,18,19,20-nonanor-4,8-inter-m-phenylene PGI$_2$ methyl ester (165) and 15-epimer thereof (166)

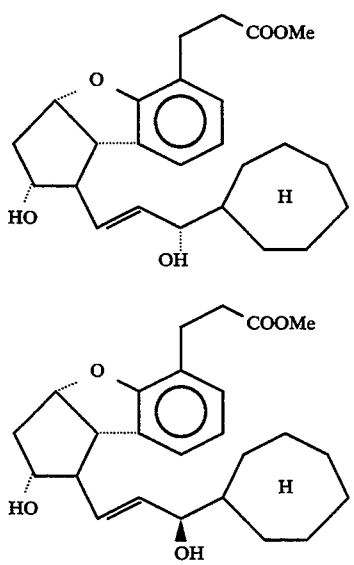

The same procedure as in Example 83 was repeated except that d-15-cycloheptyl-15-oxo-2,5,6,7,16,17,18,19,20-nonanor-4,8-inter-m-phenylene PGI$_2$ methyl ester, 11-acetate (1.23 g, 2.70 mmol) was employed as a reactant to obtain the captioned compounds (Compound (165) (0.41 g, 0.990 mmol) and Compound (166) (0.50 g, 1.208 mmol)) with a yield of 36% and 45%, respectively, which have the following physical properties.

d-15-cycloheptyl-2,5,6,7,16,17,18,19,20-nonanor-4,8-inter-phenylene PGI$_2$ methyl ester $[\alpha]_D^{20}$=+103.06° (C=0.196, MeOH) m.p. 87°–88° C. (Recrystallization Solvent:cyclohexane-ethyl acetate) IR (KBr method): 3470, 3420, 2930, 2870, 1715, 1600, 1480, 1455, 1420, 1400, 1350, 131.8, 1280, 1260, 1230, 1210, 1190, 1145, 1090, 1065, 1020, 1005, 995, 970, 945, 895, 880, 830, 800, 792, 740 cm$^{-1}$ NMR (400 MHz, CDCl$_3$, δ): 1.25–1.32(2H,m), 1.42–1.81(13H,m), 2.00(1H,ddd,J=13.66, 8.66, 5.00 Hz), 2.48–2.50(1H,m), 2.61–2.67(3H,m), 2.88–2.92(2H,m), 3.46–3.50(1H,m), 3.66(3H,s), 3.94–4.00(2H,m), 3.46–3.50(1Hm), 3.66(3H,s), 3.94–4.00(2Hm,), 5.15(1H,ddd,J=8.79, 7.32, 4.88 Hz), 5.62–5.65(2H,m), 6.77(1H,t,J=7.32 Hz), 6.97–7.00(2H,m) MASS (EI method, m/e): 414 (M+) High resolution mass spectrum Calcd. ($C_{25}H_{34}O_5$, M+) 414.2406 Found (M+) 414.2363 d-15-cycloheptyl-15-epi-2,5,6,7,16,17,18,19,20-nonanor-4,8-inter-m-phenylenePGI$_2$ methyl ester $[\alpha]_D^{20}$=+70.32° (C=0.546, MeOH) m.p. 94°–95.5° C. (Recrystallization Solvent:cyclohexane-ethyl acetate) IR (liquid film method): 3470, 3420, 2930, 2870, 1715, 1600, 1480, 1455, 1420, 1400, 1350, 1318, 1280, 1260, 1230, 1210, 1190, 1145, 1020, 1005, 995, 970, 945, 895, 880, 830, 800, 792, 740 cm$^{-1}$ NMR (400 MHz, CDCl$_3$, δ): 1.24–1.31(2H,m), 1.33–1.83(12H,m), 2.01(1H,ddd,J=13.18, 8.30, 4.88 Hz), 2.50(1H,q,J=7.32 Hz), 2.59–2.66(2H,m), 2.87–2.91(2H,m), 3.49(1H,t,J=8.30 Hz), 3.66(3H,s), 3.96–4.02(2H,m), 4.12(1H,q,J=7.32 Hz), 5.12–5.17(1H,m), 5.61–5.71(2H,m), 6.76(1H,t,J=7.57 Hz), 6.96–7.01(2H,m) MASS (EI method, m/e): 414 (M+) High resolution mass spectrum Calcd. ($C_{25}H_{34}O_5$, M+) 414.2406 Found (M+) 414.2387

EXAMPLE 90 d-15-cycloheptyl-2,5,6,7,16,17,18,19,20-nonanor-4,8-inter-m-phenylene PGI$_2$ (167)

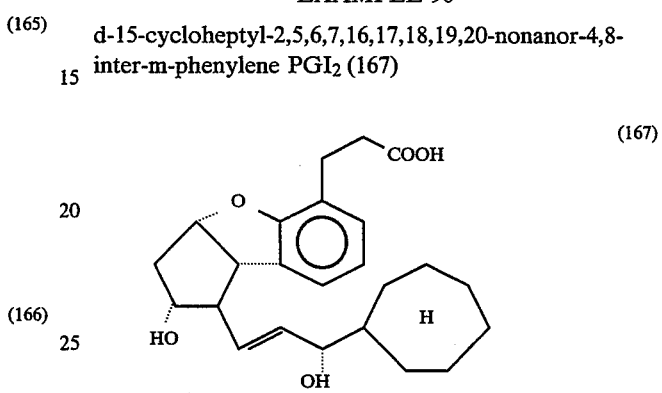

The same procedure as in Example 84 was repeated except that d-15-cycloheptyl-2,5,6,7,16,17,18,19,20-nonanor-4,8-inter-m-phenylene PGI$_2$ methyl ester (0.23 g, 0.555 mmol) was employed as a reactant to obtain the captioned compound (0.22 g, 0.55 mmol) having the following physical properties with a 99% yield. $[\alpha]_D^{20}$=+107.21° (C=0.194, MeOH) m.p. 117°–118° C. (Recrystallization Solvent:cyclohexane-ethyl acetate) IR (KBr method): 3400, 3050, 2930, 2870, 1712, 1600, 1480, 1450, 1400, 1330, 1305, 1283, 1270, 1250, 1190, 1180, 1075, 1040, 1005, 970, 910, 890, 862, 835, 770, 745 cm$^{-1}$ NMR (400 MHz, CDCl$_3$, δ): 1.20–1.31(2H,m), 1.40–1.65(7H,m), 1.60–1.83(4H,m), 1.98(1H,ddd,J=13.52, 8.47, 5.05 Hz), 2.43(1H,q,J=7.81 Hz), 2.58–2.74(2H,m), 2.82–2.98(2H,m), 3.44(1H,t,J=8.54 Hz), 3.89–3.98(2H,m), 5.11(1H,ddd,J=8.78, 7.07, 5.12 Hz), 5.54–5.65(2H,m), 6.76(1H,t,J=7.31 Hz), 6.95–7.00(2H,m) MASS (EI method, m/e): 400 (M+) High resolution mass spectrum Calcd. ($C_{24}H_{32}O_5$, M+) 400.2249 Found (M+) 400.2249

EXAMPLE 91 d-15-cyclooctyl-2,5,6,7,16,17,18,19,20-nonanor-4,8-inter-m-phenylene PGI$_2$ methyl ester (168) and 15-epimer thereof (169)

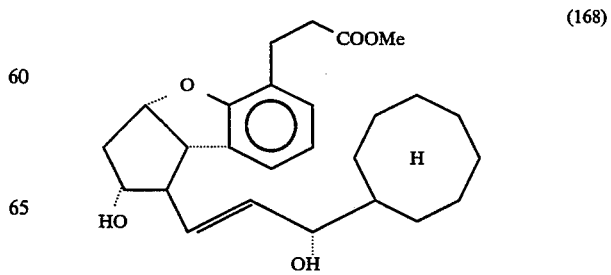

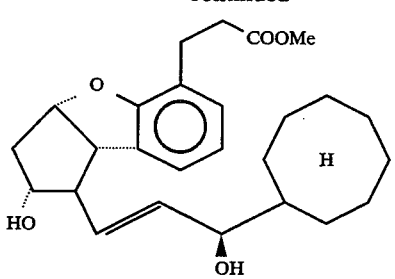

(169)

The same procedure as in Example 83 was repeated except that d-15-cyclooctyl-15-oxo-2,5,6,7,16,17,18,19,20-nonanor-4,8-inter-m-phenylene PGI₂ methyl ester, 11-acetate (0.91 g, 1.94 mmol) was employed as a reactant to obtain the captioned compounds (Compound (168)) (0.281 g, 0.660 mmol) and Compound (169) (0.345 g, 0.806 mmol)) with a yield of 34.0% and 41.5%, respectively, which have the following physical properties.

d-15-cyclooctyl-2,5,6,7,16,17,18,19,20-nonanor-4,8-inter-phenylene PGI₂ methyl ester $[\alpha]_D^{20}$= +105.75° (C=1.026, MeOH) m.p. 77.2°–77.9° C. (Recrystallization Solvent:ether:n-hexane=1:2) IR (KBr method): 3450, 2920, 2850, 1725, 1705, 1590, 1440, 1410, 1270, 1185, 1140, 1080, 1060, 1000, 945, 880, 850, 735 cm⁻¹ NMR (400 MHz, CDCl₃, δ): 1.2–1.4(2H,m), 1.4–1.8(13H,m), 1.8–2.1(2H,m), 2.2–2.4(2H,m), 2.5–2.8(3H,m), 2.8–3.0(2H,m), 3.45(1H,t,J=8.5 Hz), 3.66(3H,s), 3.8–4.0(2H,m), 5.1–5.2(1H,m), 5.5–5.7(2H,m), 6.76(1H,t,J=7.4 Hz), 6.96(1H,d,J=7.4 Hz), 6.97(1H,d,J=7.4 Hz) MASS (EI method, m/e): 428 (M+) High resolution mass spectrum Calcd. (C₂₆H₃₆O₅, M+) 428.2563 Found (M+) 428.2537 d-15-cyclooctyl-15-epi-2,5,6,7,16,17,18,19,20-nonanor-4,8-inter-m-phenylenePGI₂ methyl ester $[\alpha]_D^{20}$= +73.96° (C=1.256, MeOH) IR (liquid film method): 3400, 2910, 2850, 1705, 1590, 1440, 1400, 1330, 1270, 1240, 1190, 1095, 1080, 1030, 955, 850, 830, 810, 790, 735 cm⁻¹ NMR (400 MHz, CDCl₃, δ): 1.1–1.9(17H,m), 1.9–2.1(1H,m), 2.51(1H,q,J=7.3 Hz), 2.5–2.7(3H,m), 2.8–3.0(2H,m), 3.50(1H,t,J=8.3 Hz), 3.66(3H,s), 3.9–4.1(2H,m), 5.1–5.2(1H,m), 5.6–5.8(2H,m), 6.77(1H,t,J=7.4 Hz), 6.98(1H,d,J=7.4 Hz), 7.01(1H,d,J=7.4 Hz) MASS (EI method, m/e): 428 (M+) High resolution mass spectrum Calcd. (C₂₆H₃₆O₅, M+) 428.2563 Found (M+) 428.2555

EXAMPLE 92 d-15-cyclooctyl-2,5,6,7,16,17,18,19,20-nonanor-4,8-inter-m-phenylene PGI₂ (170)

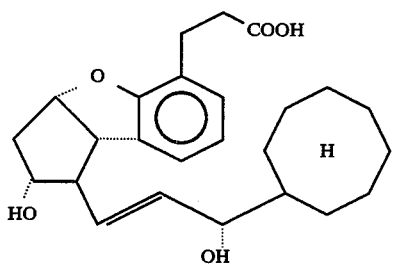

(170)

The same procedure as in Example 84 was repeated except that d-15-cyclooctyl-2,5,6,7,16,17,18,19,20-nonanor-4,8-inter-m-phenylene PGI₂ methyl ester (0.271 g, 0.633 mmol) was employed as a reactant to obtain the captioned compound (0.234 g, 0.56 mmol) having the following physical properties with a 88.5% yield.

$[\alpha]_D^{20}$= +100.98° (C=0.71, MeOH) m.p. 87.5°–89.2° C. (Recrystallization Solvent:ethyl acetate:n-hexane=1:2) IR (KBr method): 3400, 2920, 2850, 1710, 1590, 1445, 1400, 1330, 1270, 1240, 1185, 1095, 1075, 1030, 955, 910, 885, 850, 830, 790, 735 cm⁻¹ NMR (400 MHz, CDCl₃, δ): 1.2–1.4(2H,m), 1.4–1.8(16H,m), 1.9–2.1(1H,m), 2.48(1H,q,J=7.2 Hz), 2.5–2.8(3H,m), 2.8–3.0(2H,m), 3.46(1H,t,J=8.1 Hz), 3.9–4.0(2H,m), 5.1–5.2(1H,m), 5.5–5.7(2H,m), 6.75(1H,t,J=7.3 Hz), 6.97(2H,d,J=7.3 Hz) MASS (EI method, m/e): 414 (M+) High resolution mass spectrum Calcd. (C₂₅H₃₄O₅, M+) 414.2406 Found (M+) 414.2406

EXAMPLE 93 d-15-cyclooctyl-15-epi-2,5,6,7,16,17,18,19,20-nonanor-4,8-inter-m-phenylene PGI₂ (1.71)

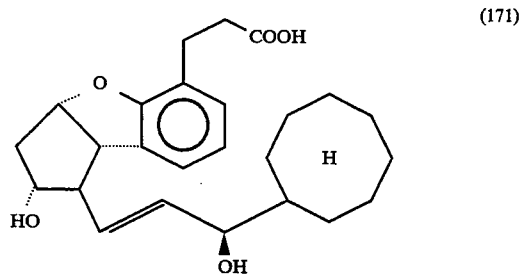

(171)

The same procedure as in Example 85 was repeated except that d-15-cyclopentyl-15-epi-2,5,6,7,16,17,18,19,20-nonanor-4,8-inter-m-phenylene PGI₂ methyl ester (0.335 g, 0.783 mmol) was employed as a reactant to obtain the captioned compound (0.306 g, 0.739 mmol) having the following physical properties with a 94.4% yield.

$[\alpha]_D^{20}$= +102.09° (C=0.698, MeOH) m.p. 126.0°–127.9° C. (Recrystallization Solvent:ethyl acetate:n-hexane=3:4) IR (KBr method): 3400, 2910, 2850, 1695, 1590, 1445, 1340, 1250, 1185, 1150, 1060, 1030, 1010, 955, 855, 830, 740 cm⁻¹ NMR (400 MHz, CDCl₃, δ): 1.2–1.4(2H,m), 1.4–1.9(13H,m), 1.9–2.1(1H,m), 2.50(1H,q,j=7.3 Hz), 2.5–2.8(3H,m), 2.8–3.0(2H,m), 3.49(1H,t,J=8.3 Hz), 3.9–4.1(2H,m), 5.1–5.2(1H,m), 5.5–5.8(2H,m), 6.77(1H,t,J=7.6 Hz), 6.99(1H,d,J=7.6 Hz), 7.00(1H,d,J=7.6 Hz) MASS (EI method, m/e): 414 (M+) High resolution mass spectrum Calcd. (C₂₅H₃₄O₅, M+) 414.2406 Found (M+) 414.2388

EXAMPLE 94 d-15-(p-methylpheny 1)-2,5,6,7,16,17,18,19,20-nonanor-4,8-inter-m-phenylene PGI₂ methyl ester (172) and 15-epimer thereof (173)

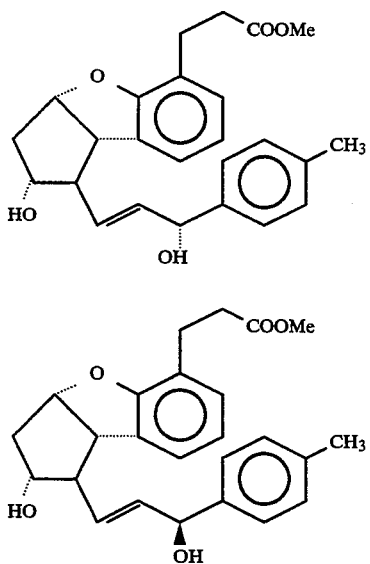

(172)

(173)

The same procedure as in Example 83 was repeated except that d-15-(p-methylphenyl)-15-oxo-2,5,6,7,16,17,18,19,20-nonanor-4,8-inter-m-phenylene PGI₂ methyl ester, 11-acetate (0.99 g, 2.21 mmol) was employed as a reactant to obtain the captioned compounds (Compound (172) (0.366 g, 0.898 mmol) and Compound (173) (0.38 g, 0.93 mmol)) with a yield of 40.6% and 42.3%, respectively, which have the following physical properties.

d-15-(p-methylphenyl)-2,5,6,7,16,17,18,19,20-nonanor-4,8-inter-phenylene PGI₂ methyl ester $[\alpha]_D^{25}$ = +124.05° (C=0.848, MeOH) m.p. 94.2°–96.0° C. (Recrystallization Solvent:ethyl acetate:n-hexane=2:3) IR (KBr method): 3390, 2930, 2870, 1730, 1450, 1360, 1265, 1230, 1180, 1140, 1100, 1070, 1040, 1020, 970, 955, 865, 805, 780, 745 cm⁻¹ NMR (400 MHz, CDCl₃, δ): 1.9–2.2(3H,m), 2.36(3H,s), 2.52(1H,q,J=7.8 Hz), 2.6–2.8(3H,m), 2.8–3.0(2H,m), 3.49(1H,t,J=7.8 Hz), 3.65(3H,s), 3.9–4.1(1H,m), 5.1–5.2(1H,m), 5.23(1H,d,J=5.3 Hz), 5.77(1H,dd,J=15.5, 7.5 Hz), 5.84(1H,dd,J=15.5, 5.3 Hz), 6.72(1H,t,J=7.6 Hz), 6.91(1H,d,J=7.6 Hz), 7.19(2H,d,J=7.6 Hz), 7.2–7.4(2H,m) MASS (EI method, m/e): 408 (M+) High resolution mass spectrum Calcd. (C₂₅H₂₈O₅, M+) 408.1937 Found (M+) 408.1936 d-15-(p-methylphenyl)-15-epi-2,5,6,7,16,17,18,19,20-nonanor-4,8-inter-m-phenylenePGI₂ methyl ester $[\alpha]_D^{25}$ = +110.84° (C=0.922, MeOH,) m.p. 107.8°–109.2° C. (Recrystallization Solvent:ethyl acetate:n-hexane=3:4) IR (KBr method): 3500, 2950, 1725, 1510, 1450, 1350, 1290, 1260, 1180, 1140, 1090, 1070, 1030, 965, 945, 885, 855, 810, 790, 745 cm⁻¹ NMR (400 MHz, CDCl₃, δ): 1.7–1.8(1H,m), 1.9–2.1(2H,m), 2.36(3H,s), 2.54(1H,q,J=7.7 Hz), 2.5–2.7(3H,m), 2.8–3.0(2H,m), 3.54(1H,t,J=7.7 Hz), 3.65(3H,s), 3.9–4.1(1H,m), 5.1–5.2(1H,m), 5.2–5.3(1H,m), 5.79(1H,dd,J=15.4, 7.7 Hz), 5.85(1H,dd,J=15.4, 5.0 Hz), 6.75(1H,t,J=8.0 Hz), 6.97(2H,t,J=8.0 Hz), 7.19(2H,d,J=8.1 Hz), 7.28(2H,d,J=8.1 Hz) MASS (EI method, m/e): 408 (M+) High resolution mass spectrum Calcd. (C₂₅H₂₈O₅, M+) 408.1937 Found (M+) 408.1959

EXAMPLE 95 d-15-(p-methylphenyl)-2,5,6,7,16,17,18,19,20-nonanor-4,8-inter-m-phenylene PGI₂ (174)

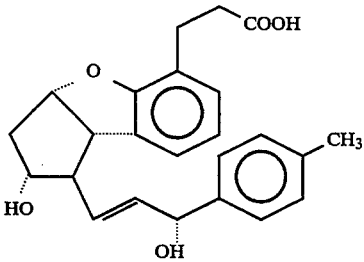

(174)

The same procedure as in Example 84 was repeated except that d-15-(p-methylphenyl)-2,5,6,7,16,17,18,19,20-nonanor-4,8-inter-m-phenylene PGI₂ methyl ester (0.29 g, 0.711 mmol) was employed as a reactant to obtain the captioned compound (0.182 g, 0.462 mmol) having the following physical properties with a 65% yield.

$[\alpha]_D^{25}$ = +128.25° (C=1.26, MeOH) m.p. 71.5°–73.0° C. (Recrystallization Solvent:ether) IR (KBr method): 3320, 3020, 2920, 1700, 1590, 1500, 1440, 1400, 1335, 1270, 1185, 1065, 1025, 980, 960, 940, 890, 855, 805, 780, 740 cm⁻¹ NMR (400 MHz, DMSO-d₆, δ): 1.6–1.8(1H,m), 2.16(1H,q,J=7.8 Hz), 2.29(3H,s), 2.4–2.6(3H,m), 2.70(2H,t,J=7.6 Hz), 3.3–3.4(1H,m), 3.7–3.8(1H,m), 4.83(1H,d,J=6.2 Hz), 5.0–5.1(2H,m), 5.35(1H,d,J=4.4 Hz), 5.62(1H,dd,J=15.5, 6.2 Hz), 5.73(1H,dd,J=15.5, 7.8 Hz), 6.65(1H,t,J=7.4 Hz), 6.80(1H,d,J=7.4 Hz), 6.92(1H,d,J=7.4 Hz), 7.15(2H,d,J=7.8 Hz), 7.25(2H,d,J=7.8 Hz), 12.0–12.1(1H,brs) MASS (EI method, m/e): 394 (M+) High resolution mass spectrum Calcd. (C₂₄H₂₆O₅, M+) 394.1780 Found (M+) 394.1779

EXAMPLE 96 d-15-(p-methylphenyl)-15-epi-2,5,6,7,16,17,18,19,20-nonanor-4,8-inter-m-phenylene PGI₂ (175)

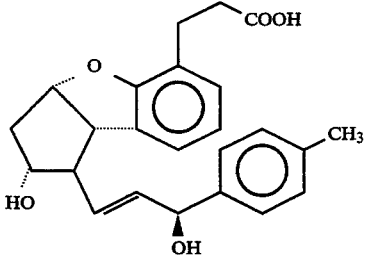

(175)

The same procedure as in Example 85 was repeated except that d-15-(p-methylphenyl)-15-epi-2,5,6,7,16,17,18,19,20-nonanor-4,8-inter-m-phenylene PGI₂ methyl ester (0.047 g, 0.115 mmol) was employed as a reactant to obtain the captioned compound (0.036 g, 0.091 mmol) having the following physical properties with a 79.1% yield.

$[\alpha]_D^{25}$ = +113.27° (C=0.422, MeOH) m.p. 147.0°–148.7° C. (Recrystallization Solvent:ethyl acetate:n-hexane=1:2) IR (KBr method): 3370, 2950, 2900, 1690, 1455, 1330, 1245, 1175, 1080, 1065, 1025, 995, 965, 930, 840, 800, 730 cm⁻¹ NMR (400 MHz, DMSO-d₆, δ):

1.6–1.8(1H,m), 2.16(1H,q,J=8.0 Hz), 2.29(3H,s), 2.4–2.6(3H,m,), 3.74(2H,t,J=6.1 Hz), 3.2–3.5(1H,m), 3.7–3.8(1H,m), 4.8(1H,d,J=6.4 Hz), 5.0–5.1(1H,m), 5.35(1H,d,J=4.4 Hz), 5.62(1H,dd,J=15.5, 6.4 Hz), 5.73(1H,dd,J=15.5, 8.0 Hz), 6.65(1H,t,J=7.5 Hz), 6.80(1H,d,J=7.5 Hz), 6.93(1H,d,J=7.5 Hz), 7.15(2H,d,J=8.1 Hz), 7.25(2H,d,J=8.1 Hz), 12.0–12.2(1H,brs) MASS (EI method, m/e): 394 (M+) High resolution mass spectrum Calcd. ($C_{24}H_{26}O_5$, M+) 394.1780 Found (M+) 394.1762

EXAMPLE 97 d-15-(m-fluorophenyl)-2,5,6,7,16,17,18,19,20-nonanor-4,8-inter-m-phenylene PGI$_2$ methyl ester (176) and 15-epimer thereof (177)

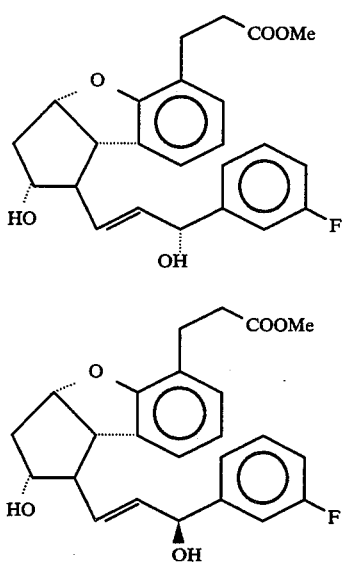

The same procedure as in Example 83 was repeated except that d-15-(m-fluorophenyl)-15-oxo-2,5,6,7,16,17,18,19,20-nonanor-4,8-inter-m-phenylene PGI$_2$ methyl ester, 11-acetate (0.805 g, 1.78 mmol) was employed as a reactant to obtain the captioned compounds (Compound (176) (0.319 g, 0.774 mmol) and Compound (177) (0.331 g, 0.803 mmol)) with a yield of 43.5% and 45.1%, respectively, which have the following physical properties.

d-15-(m-fluorophenyl)-2,5,6,7,16,17,18,19,20-nonanor-4,8-inter-m-phenylene PGI$_2$ methyl ester $[\alpha]_D^{25} = +120.78°$ (C=1.102, MeOH) IR (liquid film method): 3350, 2920, 1730, 1610, 1590, 1440, 1365, 1250, 1190, 1150, 1060, 1030, 960, 850, 830, 780, 740 cm$^{-1}$ NMR (400 MHz, CDCl$_3$, δ): 1.9–2.1(1H,m), 2.45(1H,q,J=7.8 Hz), 2.5–2.7(4H,m), 2.7–3.0(3H,m), 3.45(1H,t,J=8.6 Hz), 3.64(3H,s), 3.9–4.0(1H,m), 5.1–5.2(1H,m), 5.23(1H,d,J=5.49 Hz), 5.7–5.8(2H,m), 6.71(1H,t,J=7.4 Hz), 6.87(1H,d,J=7.4 Hz), 6.95(1H,d,J=7.4 Hz), 6.95(1H,d,J=7.4 Hz), 6.9–7.0(1H,m), 7.0–7.2(2H,m), 7.32(1H,dt,J=7.9, 5.8 Hz) MASS (EI method, m/e): 412 (M+) High resolution mass spectrum Calcd (C$_{24}$H$_{25}$O$_5$F, M+) 412.1686 Found (M+) 412.1703 d-15-(m-fluorophenyl)-15-epi-2,5,6,7,16,17,18,19,20-nonanor-4,8-inter-m-phenylenePGI$_2$ methyl ester $[\alpha]_D^{25} = +105.96°$ (C=1.040, MeOH) m.p. 84.0°–85.3° C. (Recrystallization Solvent:ether:n-hexnane=2:1) IR (KBr method): 3500, 2930, 2870, 1710, 1610, 1585, 1475, 1445, 1410, 1365, 1330, 1305, 1240, 1190, 1150, 1090, 1065, 1030, 995, 970, 950, 890, 850, 830, 775, 740, 690 cm$^{-1}$ NMR (400 MHz, CDCl$_3$, δ): 1.8–2.0(1H,m), 2.0–2.2(1H,m), 1.99(1H,d,J=4.9 Hz), 2.5–2.7(4H,m), 2.8–3.0(2H,m), 3.51(1H,t,J=8.2 Hz), 3.65(3H,s), 3.9–4.1(1H,m), 5.1–5.2(1H,m), 5.25(1H,s), 5.7–5.9(2H,m), 6.75(1H,t,J=7.5 Hz), 6.96(1H,d,J=7.5 Hz), 6.964(1H,d,J=7.5 Hz), 6.9–7.1(1H,m), 7.1–7.2(2H,m), 7.34(1H,dt,J=7.9, 6.1 Hz) MASS (EI method, m/e): 412 (M+) High resolution mass spectrum Calcd. (C$_{24}$H$_{25}$O$_5$F, M+) 412.1686 Found (M+) 412.1710

EXAMPLE 98 d-15-(m-fluorophenyl)-2,5,6,7,16,17,18,19,20-nonanor-4,8-inter-m-phenylene PGI$_2$ (178)

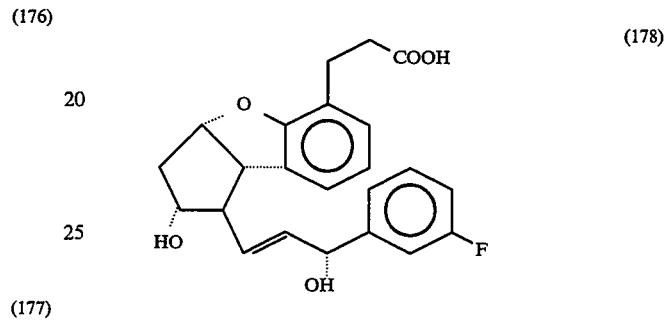

The same procedure as in Example 84 was repeated except that d-15-(m-fluorophenyl)-2,5,6,7,16,17,18,19,20-nonanor-4,8-inter-m-phenylene PGI$_2$ methyl ester (0.281 g, 0.682 mmol) was employed as a reactant to obtain the captioned compound (0.231 g, 0.58 mmol) having the following physical properties with a 85.1% yield. $[\alpha]_D^{25} = +115.84°$ (C=0.978, MeOH) m.p. 132°–134° C. (Recrystallization Solvent:ethyl acetate:n-hexane=3:2) IR (KBr method): 3460, 3350, 2990, 2930, 2880, 1700, 1610, 1585, 1480, 1440, 1335, 1295, 1240, 1180, 1150, 1090, 1060, 1025, 1000, 955, 940, 910, 880, 855, 830, 785, 755, 735, 690 cm$^{-1}$ NMR (400 MHz, CDCl$_3$, δ): 1.3–2.3(4H,m), 2.42(1H,q,J=8.1 Hz), 2.5–2.7(3H,m), 2.8–3.0(2H,m), 3.44(1H,t,J=8.7 Hz), 3.9–4.0(1H,m), 5.0–5.2(1H,m), 5.21(1H,d,J=6.1 Hz), 5.7–5.9(2H,m), 6.88(1H,d,J=7.5 Hz), 6.97(1H,d,J=7.5 Hz), 6.9–7.1(1H,m), 7.1–7.2(2H,m), 7.2–7.4(1H,m) MASS (EI method, m/e): 398 (M+) High resolution mass spectrum Calcd. (C$_{23}$H$_{23}$O$_5$F, M+) 398.1530 Found (M+) 398.1509

EXAMPLE 99 d-15-(m-fluorophenyl)-15-epi-2,5,6,7,16,17,18,19,20-nonanor-4,8-inter-m-phenylene PGI$_2$ (179)

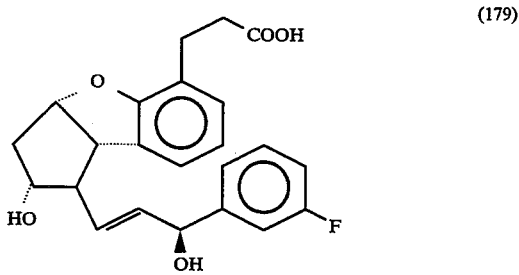

The same procedure as in Example 85 was repeated except that d-15-(m-fluorophenyl)-15-epi-2,5,6,7,16,17,18,19,20-nonanor-4,8-inter-m-phenylene PGI₂ methyl ester (0.266 g, 0.646 mmol) was employed as a reactant to obtain the captioned compound (0.199 g, 0.5 mmol) having the following physical properties with a 77.4% yield.

$[\alpha]_D^{25} = +90.76°$ (C=1.278, MeOH) m.p. 144.1°–145.5° C. (Recrystallization Solvent:ethyl acetate:n-hexane=3:2) IR (KBr method): 3360, 2920, 1700, 1605, 1580, 1470, 1440, 1330, 1280, 1240, 1180, 1120, 1090, 1060, 1030, 995, 960, 935, 870, 830, 780, 730, 690 cm⁻¹ NMR (400 MHzM, CDCl₃, δ): 1.9–2.1(1H,m), 2.4–2.8(4H,m), 2.8–3.0(2H,m), 3.52(1H,t,J=7.93 Hz), 3.98(1H,q,J=6.9 Hz), 5.1–5.2(1H,m), 5.2–5.3(1H,m), 5.7–5.9(2H,m), 6.75(1H,t,J=7.3 Hz), 6.9–7.1(3H,m), 7.1–7.2(2H,m), 7.3–7.4(1H,m) MASS (EI method, m/e): 398 (M⁺) High resolution mass spectrum Calcd. (C₂₃H₂₃O₅F, M⁺) 398.1530 Found (M⁺) 398.1524

EXAMPLE 100 d-15-(p-fluorophenyl)-2,5,6,7,16,17,18,19,20-nonanor-4,8-inter-m-phenylene PGI₂ methyl ester (180) and 15-epimer thereof (181)

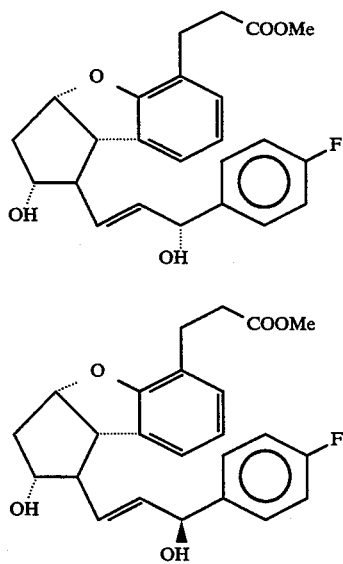

The same procedure as in Example 83 was repeated except that d-15-(p-fluorophenyl)-15-oxo-2,5,6,7,16,17,18,19,20-nonanor-4,8-inter-m-phenylene PGI₂ methyl ester, 11-acetate (1.10 g, 2.43 mmol) was employed as a reactant to obtain the captioned compounds (Compound (180) (390 mg, 0.946 mmol) Compound (181) (328 mg, 0.926 mmol)) with a yield of 38.9% and 38.1%, respectively, which have the following physical properties.

d-15-(p-fluorophenyl)-2,5,6,7,16,17,18,19,20-nonanor-4,8-inter-m-phenylene PGI₂ methyl ester $[\alpha]_D^{25} = +85.91°$ (C=1.008, CHCl₃) m.p. 120°–121° C. (Recrystallization Solvent:ethyl acetate:n-hexane) IR (KBr method): 3375, 2950, 1730, 1600, 1505, 1450, 1365, 1265, 1240, 1100, 1070, 980, 960, 870, 830, 820, 750 cm⁻¹ NMR (400 MHz, CDCl₃, δ): 1.99(1H,ddd,J=13.6, 8.9, 5.2 Hz), 2.4(1H,brs), 2.4–2.5(1H,m), 2.6–2.7(3H,m), 2.85–2.9(2H,m), 3.46(1H,t,J=8.2 Hz), 3.65(3H,s), 3.96(1H,dd,J=14.5, 8.2 Hz), 5.12(1H,ddd,J=9.0, 7.2, 5.2 Hz), 5.24–5.25(1H,m), 5.75–5.8(2H,m), 6.72(1H,t,J=7.3 Hz), 6.87(1H,d,J=7.3 Hz), 6.95(1H,d,J=7.3 Hz), 7.0–7.1(2H,m), 7.3–7.4(2H,m) MASS (EI method, m/e): 412 (M⁺)

d-15-(p-fluorophenyl-15-epi-2,5,6,7,16,17,18,19,20-nonanor-4,8-inter-m-phenylenePGI₂ methyl ester $[\alpha]_D^{25} = +94.12°$ (C=1.550, MeOH) IR (liquid film method): 3380, 2940, 1730, 1600, 1510, 1450, 1370, 1260, 1220, 1160, 1090, 1070, 1035, 975, 890, 860, 840, 745 cm⁻¹ NMR (400 MHz, CDCl₃, δ): 1.91(1H,brs), 2.01(1H,ddd,J=13.9, 7.9, 4.9 Hz), 2.53(1H,q,J=7.3 Hz), 2.6–2.7(3H,m), 2.85–2.95(2H,m), 3.48(1H,brs), 3.51(1H,t,J=8.2 Hz), 3.65(3H,s), 3.96(1H,dt,J=7.9, 6.1 Hz), 5.15(1H,ddd,J=8.9, 7.3, 4.8 Hz), 5.23(1H,d,J=5.2 Hz), 5.77(1H,dd,J=15.9, 7.6 Hz), 5.84(1H,dd,J=15.9, 5.2 Hz), 6.75(1H,t,J=7.3 Hz), 6.96(2H,dd,J=7.3, 3.1 Hz), 7.0–7.1(2H,m), 7.3–7.4(2H,m) MASS (EI method, m/e): 412 (M⁺)

EXAMPLE 101 d-15-(p-fluorophenyl)-2,5,6,7,16,17,18,19,20-nonanor-4,8-inter-m-phenylene PGI₂ (182)

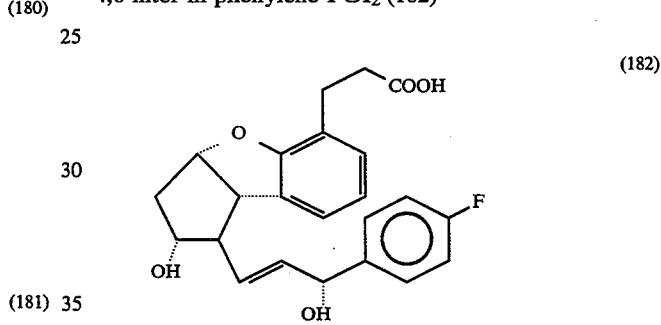

The same procedure as in Example 84 was repeated except that d-15-(p-fluorophenyl)-2,5,6,7,16,17,18,19,20-nonanor-4,8-inter-m-phenylene PGI₂ methyl ester (265 mg, 0.643 mmol) was employed as a reactant to obtain the captioned compound (202 mg, 0.508 mmol) having the following physical properties with a 78.9% yield.

$[\alpha]_D^{25} = +118.77°$ (C=0.90, MeOH) m.p. 139°–140° C. (Recrystallization Solvent:ethyl acetate:n-hexane) IR (KBr method): 3480, 3450–2500, 2940, 1710, 1600, 1505, 1450, 1330, 1270, 1230, 1190, 1160, 1100, 1080, 1000, 980, 830, 740, 580 cm⁻¹ NMR (400 MHz, DMSO-d₆, δ) 1.68(1H,ddd,J=13.2, 9.8, 5.9 Hz), 2.16(1H,q,J=8.2 Hz), 2.45–2.6(3H,m), 2.70(2H,t,J=7.6 Hz), 3.38(1H,t,J=9.0 Hz), 3.76(1H,dd,J=15.6, 9.3 Hz), 4.86(1H,brs), 5.04(1H,dd,J=15.6, 7.3 Hz), 5.1–5.15(1H,m), 5.50(1H,brs), 5.62(1H,dd,J=15.2, 6.4 Hz), 5.76(1H,dd,J=15.2, 7.8 Hz), 6.65(1H,t,J=7.3 Hz), 6.79(1H,d,J=7.3 Hz), 6.93(1H,d,J=7.3 Hz), 7.17(2H,t,J=9.3 Hz), 7.40(2H,dd,J=8.3, 5.8 Hz), 12.1(1H,brs) MASS (EI method, m/e): 398 (M⁺) High resolution mass spectrum Calcd. (C₂₃H₂₃O₅F, M⁺) 398.1529 Found (M⁺) 398.1516

EXAMPLE 102 d-15-(p-fluorophenyl)-15-epi-2,5,6,7,16,17,18,19,20-nonanor-4,8-inter-m-phenylene PGI₂ (183)

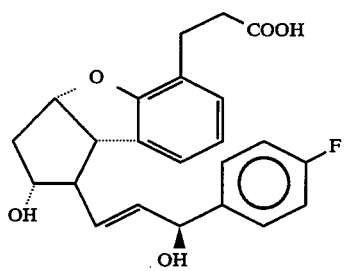

(183)

The same procedure as in Example 85 was repeated except that d-15-(p-fluorophenyl)-15-epi-2,5,6,7,16,17,18,19,20-nonanor-4,8-inter-m-phenylene PGI₂ methyl ester (280 mg, 0.680 mmol) was employed as a reactant to obtain the captioned compound (212 mg, 0.530 mmol) having the following physical properties with a 78.0% yield.

$[\alpha]_D^{25} = +97.09°$ (C=0.992, MeOH) m.p. 131.0°–132.8° C. (Recrystallization Solvent:ethyl acetate:n-hexane) IR (KBr method): 3500, 3400–2500, 2950, 2900, 1715, 1610, 1595, 1510, 1450, 1425, 1410, 1340, 1290, 1250, 1225, 1195, 1160, 1100, 1085, 1070, 975, 950, 860, 840, 740, 730, 600, 560, 480 cm⁻¹ NMR (400 MHz, CDCl₃, δ) 1.97(1H,ddd,J=13.7, 8.9, 5.2 Hz), 2.46(1H,q,J=8.2 Hz), 2.55–2.65(3H,m), 2.8–3.0(2H,m), 3.45(1H,t,J=8.6 Hz), 3.92(1H,dt,J=8.6, 5.8 Hz), 5.17(1H,ddd,J=9.2, 7.3, 4.9 Hz), 5.21(1H,d,J=5.5 Hz), 5.73(1H,dd,J=15.8, 7.9 Hz), 5.84(1H,dd,J=15.8, 5.5 Hz), 6.72(1H,t,J=7.3 Hz), 6.96(2H,dd,J=12.9, 7.3 Hz), 7.0–7.1(2H,m), 7.35–7.4(2H,m) MASS (EI method, m/e): 398 (M⁺) High resolution mass spectrum Calcd. (C₂₃H₂₃O₅F, M⁺) 398.1529 Found (M⁺) 398.1520

EXAMPLE 103 d-15-(o-fluorophenyl)-2,5,6,7,16,17,18,19,20-nonanor-4,8-inter-m-phenylene PGI₂ methyl ester (184)

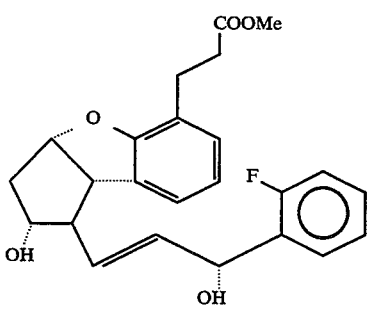

(184)

The same procedure as in Example 83 was repeated except that d-15-(o-fluorophenyl)-15-oxo-2,5,6,7,16,17,18,19,20-nonanor-4,8-inter-m-phenylene PGI₂ methyl ester, 11 acetate (730 mg, 1.59 mmol) was employed as a reactant to obtain the captioned compound (182.0 mg, 0.44 mmol) having the following physical properties with a 28% yield.

$[\alpha]_D^{20} = +121.45°$ (C=0.606, MeOH) m.p. 99.0°–99.5° C. (Recrystallization Solvent:ethyl acetate:cyclohexane) IR (KBr method): 3400, 2950, 1740, 1620, 1590, 1490, 1460, 1260, 1230, 1190, 1100, 1080, 1040, 960, 870, 760, 630 cm⁻¹ NMR (400 MHz, CDCl₃, δ) 1.64(2H,brs), 1.92–1.99(1H,m), 2.40–2.46(1H,m), 2.59–2.67(3H,m), 2.85–2.89(2H,m), 3.43(1H,t,J=8.5 Hz), 3.64(3H,s), 3.90–3.96(1H,m), 5.07–5.12(1H,m), 5.51–5.52(1H,m), 5.78–5.80(2H,m), 6.69(1H,d,J=7.3 Hz), 6.85(1H,d,J=7.3 Hz), 6.93(1H,d,J=7.3 Hz), 7.03–7.07(1H,m), 7.13–7.17(1H,m), 7.25–7.28(1H,m), 7.45–7.48(1H,m) MASS (EI method, m/e): 412 (M⁺) High resolution mass spectrum Calcd. (C₂₄H₂₅O₅F, M⁺) 412.1686 Found (M⁺) 412.1704

EXAMPLE 104 d-15-(o-fluorophenyl)-2,5,6,7,16,17,18,19,20-nonanor-4,8-inter-m-phenylene PGI₂ (185)

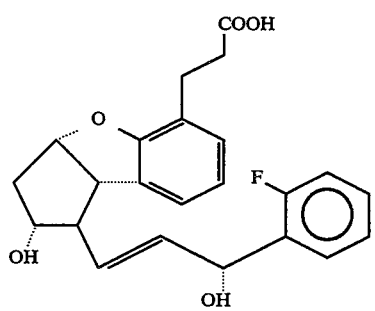

(185)

The same procedure as in Example 84 was repeated except that d-15-(o-fluorophenyl)-2,5,6,7,16,17,18,19,20-nonanor-4,8-inter-m-phenylene PGI₂ methyl ester (122.3 mg, 0.30 mmol) was employed as a reactant to obtain the captioned compound (94.3 mg, 0.24 mmol) having the following physical properties with a 80% yield.

$[\alpha]_D^{20} = +116.31°$ (C=0.570, MeOH) m.p. 135°–136° C. (Recrystallization Solvent:ethyl acetate:cyclohexane) IR (KBr method): 3480, 3390, 2950, 2880, 1715, 1590, 1490, 1450, 1400, 1340, 1305, 1280, 1220, 1200, 1190, 1100, 1080, 980, 830, 760, 740 cm⁻¹ NMR (400 MHz, 5% DMSO-d₆/CDCl₃, δ) 1.90–1.97(1H,m), 2.36(1H,q,J=8.3 Hz), 2.56–2.68(3H,m), 2.84–2.88(2H,m), 3.40(1H,t,J=8.8 Hz), 3.86–3.92(1H,m), 5.05–5.11(1H,m), 5.49(1H,d,J=5.9 Hz), 5.72–5.83(2H,m), 6.66(1H,t,J=7.3 Hz), 6.84(1H,d,J=7.3 Hz), 6.94(1H,d,J=7.3 Hz), 7.01–7.05(1H,m), 7.13–7.17(1H,m), 7.23–7.27(1H,m), 7.52–7.56(1H,m) MASS (EI method, m/e): 398 (M⁺) High resolution mass spectrum Calcd. (C₂₃H₂₃O₅F, M⁺) 398.1530 Found (M⁺) 398.1531

EXAMPLE 105 d-15-(3,4-difluorophenyl)-2,5,6,7,16,17,18,19,20-nonanor-4,8-inter-m-phenylene PGI₂ methyl ester (186) and 15-epimer thereof (187)

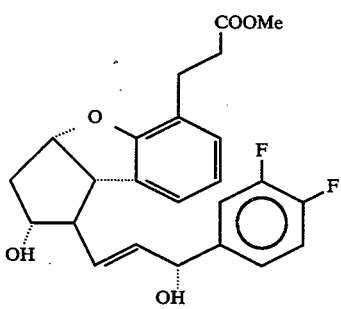

(186)

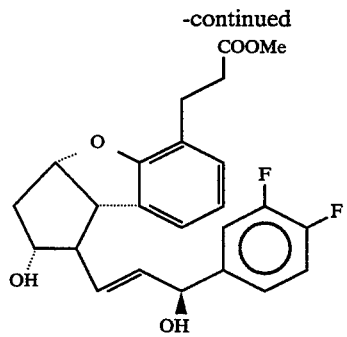

(187)

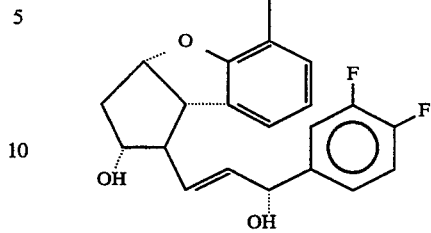

(188)

The same procedure as in Example 83 was repeated except that d-15-(3,4-difluorophenyl)-15-oxo-2,5,6,7,16,17,18,19,20-nonanor-4,8-inter-m-phenylene PGI₂ methyl ester, 11-acetate (427.8 mg, 0.94 mmol) was employed as a reactant to obtain the above-captioned compounds (Compound (186) (128.3 mg, 0.30 mmol) and Compound (187) (141.4 mg, 0.33 mmol)) with a yield of 32% and 35%, respectively, which have the following physical properties.

d-15-(3,4-difluorophenyl)-2,5,6,7,16,17,18,19,20-nonanor-4,8-inter-m-phenylene PGI₂ methyl ester $[\alpha]_D^{20} = +114.24°$ (C=0.688, MeOH) m.p. 100°–101° C. (Recrystallization Solvent:ethyl acetate:cyclohexane) IR (KBr method): 3390, 3300, 2950, 2870, 1740, 1615, 1600, 1515, 1450, 1435, 1370, 1330, 1305, 1290, 1250, 1210, 1190, 1150, 1110, 1080, 1030, 960, 870, 815, 780, 750, 630 cm⁻¹ NMR (400 MHz, CDCl₃, δ) 1.94–2.01(1H,m), 2.45(1H,q,J=8.2 Hz), 2.58–2.69(3H,m), 2.85–2.92(1H,m), 3.45(1H,t,J=8.6 Hz), 3.65(3H,s), 3.91–3.97(1H,m), 5.08–5.14(1H,m), 5.18(1H,d,J=6.4 Hz), 5.68–5.82(2H,m), 6.72(1H,t,J=7.3 Hz), 6.86(1H,d,J=7.3 Hz), 6.95(1H,d,J=7.3 Hz), 7.10–7.62(3H,m) MASS (EI method, m/e): 430 (M+) High resolution mass spectrum Calcd. (C₂₄H₂₄O₅F₂, M+) 430.1591 Found (M+) 430.1591 d-15-(3,4-difluorophenyl)-15-epi-2,5,6,7,16,17,18,19,20-nonanor-4,8-inter-m-phenylenePGI₂ methyl ester $[\alpha]_D^{20} = +98.19°$ (C=0.498, MeOH) m.p. 103°–104.5° C. (Recrystallization Solvent:ethyl acetate:cyclohexane) IR (KBr method): 3450, 3330, 2960, 2910, 1720, 1690, 1610, 1515, 1450, 1420, 1350, 1300, 1280, 1200, 1170, 1110, 1090, 1070, 1030, 1000, 890, 870, 855, 830, 770, 750, 640 cm⁻¹ NMR (400 MHz, CDCl₃, δ) 1.98–2.04(1H,m), 2.51–2.54(1H,m), 2.58–2.65(3H,m), 2.86–2.91(2H,m), 3.49(1H,t,J=8.6 Hz), 3.65(3H,s), 3.93–3.99(1H,m), 5.11–5.16(1H,m), 5.20(1H,d,J=4.3 Hz), 5.73–5.79(2H,m), 6.75(1H,t,J=7.6 Hz), 6.93–6.97(2H,m), 7.10–7.26(3H,m) MASS (EI method, m/e): 430 (M+) High resolution mass spectrum Calcd. (C₂₄H₂₄O₅F₂, M+) 430.1592 Found (M+) 430.1590

EXAMPLE 106 d-15-(3,4-difluorophenyl)-2,5,6,7,16,17,18,19,20-nonanor-4,8-inter-m-phenylene PGI₂ (188)

The same procedure as in Example 84 was repeated except that d-15-(3,4-difluorophenyl)-2,5,6,7,16,17,18,19,20-nonanor-4,8-inter-m-phenylene PGI₂ methyl ester (84.3 mg, 0.20 mmol) was employed as a reactant to obtain the captioned compound (64.4 mg, 0.15 mmol) having the following physical properties with a 79% yield.

$[\alpha]_D^{20} = +111.62°$ (C=0.628, MeOH) m.p. 93°–95° C. (Recrystallization Solvent:ethyl acetate:cyclohexane) IR (KBr method): 3500, 3400, 2950, 1710, 1620, 1515, 1450, 1345, 1280, 1250, 1210, 1200, 1150, 1115, 1090, 1070, 1040, 1010, 970, 950, 890, 825, 780, 750 cm⁻¹ NMR (400 MHz, 5% DMSO-d₆/CDCl₃, δ) 1.91–1.99(1H,m), 2.37(1H,q,J=8.6 Hz), 2.56–2.70(3H,m), 2.83–2.92(2H,m), 3.42(1H,td,J=9.0 Hz), 3.86–3.92(1H,m), 5.06–5.12(1H,m), 5.15(1H,d,J=7.0 Hz), 5.66–5.80(2H,m), 6.71(1H,t,J=7.3 Hz), 6.86(1H,d,J=7.3 Hz), 6.97(1H,d,J=7.3 Hz), 7.11–7.17(2H,m), 7.23–7.29(1H,m) MASS (EI method, m/e): 416 (M+) High resolution mass spectrum Calcd. (C₂₃H₂₂O₅F₂, M+) 416.1435 Found (M+) 416.1454

EXAMPLE 107 d-15-(3,4-difluorophenyl)-15-epi-2,5,6,7,16,17,18,19,20-nonanor-4,8-inter-m-phenylene PGI₂ (189)

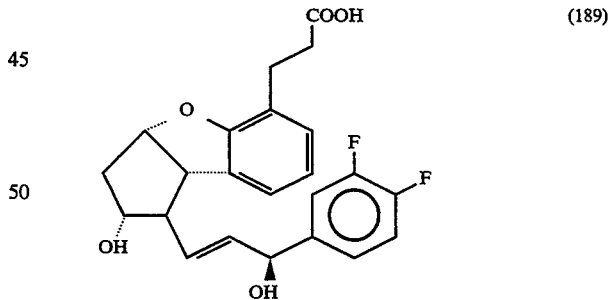

(189)

The same procedure as in Example 85 was repeated except that d-15-(3,4-difluorophenyl)-15-epi-2,5,6,7,16,17,18,19,20-nonanor-4,8-inter-m-phenylene PGI₂ methyl ester (90.0 mg, 0.21 mmol) was employed as a reactant to obtain the captioned compound (77.7 mg, 0.19 mmol) having the following physical properties with a 89% yield.

$[\alpha]_D^{20} = +99.33°$ (C=0.748, MeOH) m.p. 137°–138.5° C. (Recrystallization Solvent:ethyl acetate:cyclohexane) IR (KBr method): 3500, 3380, 2930, 1715, 1610, 1600, 1510, 1450, 1345, 1280, 1255, 1210, 1195, 1150, 1110, 1090, 1070, 1040, 970, 950, 890, 820, 780, 745 cm⁻¹ NMR (400 MHz, 5% DMSO-d₆/CDCl₃, δ) 1.93-2.05(1H,m), 2.44(1H,q,J=8.2 Hz), 2.56-2.67(3H,m), 2.81-2.92(2H,m), 3.43(1H,td,J=8.9 Hz), 3.87-3.93(1H,m), 5.06-5.11(1H,m), 5.17(1H,d,J=5.5 Hz), 5.69-5.84(2H,m), 6.73(1H,t,J=7.3 Hz), 6.93(1H,d,J=7.3 Hz), 6.97(1H,d,J=7.3 Hz), 7.09-7.18(2H,m), 7.24-7.29(1H,m) MASS (EI method, m/e): 416 (M+) High resolution mass spectrum Calcd. ($C_{23}H_{22}O_5F_2$, M+) 416.1435 Found (M+) 416.1432

EXAMPLE 108 d-15-(2,6-difluorophenyl)-2,5,6,7,16,17,18,19,20-nonanor-4,8-inter-m-phenylene PGI₂ methyl ester (199) and 15-epimer thereof (191)

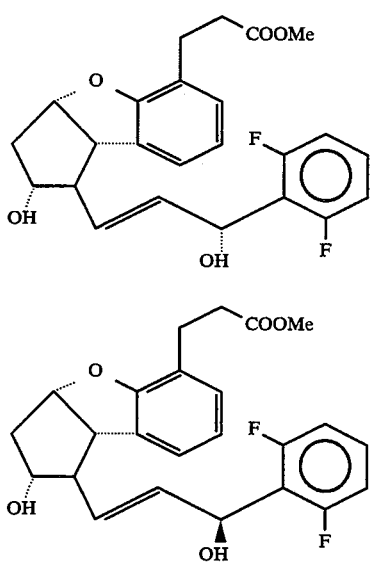

(190)

(191)

The same procedure as in Example 83 was repeated except that d-15-(2,6-difluorophenyl)-15-oxo-2,5,6,7,16,17,18,19,20-nonanor-4,8-inter-m-phenylene PGI₂ methyl ester, 11-acetate (1.05 g, 2.23 mmol) was employed as a reactant to obtain the captioned compounds (Compound (190) (351 mg, 0.815 mmol) Compound (191) (401 mg, 0.932 mmol)) with a yield of 36.5% and 41.7%, respectively, which have the following physical properties.

d-15-(2,6-difluorophenyl)-2,5,6,7,16,17,18,19,20-nonanor-4,8-inter-m-phenylene PGI₂ methyl ester $[\alpha]_D^{25} = +122.38°$ (C=0.956, MeOH) m.p. 87.5°-89.0° C. (Recrystallization Solvent:ethyl acetate:n-hexane) IR (KBr method): 3370, 2975, 2950, 2880, 1730, 1615, 1590, 1465, 1450, 1380, 1340, 1290, 1250, 1230, 1180, 1120, 1070, 1035, 990, 950, 860, 780, 750, 730, 710, 595, 560, 515 cm⁻¹ NMR (400 MHz, CDCl₃, δ) 2.00(1H,ddd,J=13.7, 8.8, 5.4 Hz), 2.51(1H,q,J=7.8 Hz), 2.6-2.7(3H,m), 2.85-2.9(2H,m), 3.46(1H,t,J=8.3 Hz), 3.65(3H,s), 3.96(1H,dd,J=14.0, 8.3 Hz), 5.13(1H,ddd,J=8.9, 7.0, 4.9 Hz), 5.6-5.65(1H,m), 5.76(1H,dd,J=15.6, 8.2 Hz), 6.02(1H,dd,J=15.6, 5.6 Hz), 6.72(1H,t,J=7.7 Hz), 6.8-7.0(4H,m), 7.25-7.3(1H,m) MASS (EI method, m/e): 430 (M+)
d-15-(2,6-difluorophenyl)-15-epi-2,5,6,7,16,17,18,19,20-nonanor-4,8-inter-m-phenylenePGI₂ methyl ester $[\alpha]_D^{20} = +65.68°$ (C=0.440, MeOH) IR (liquid film method): 3400, 2950, 1730, 1625, 1595, 1465, 1450, 1370, 1300, 1260, 1235, 1195, 1090, 1085, 1000, 890, 860, 845, 785, 765, 745 cm⁻¹ NMR (400 MHz, CDCl₃, δ) 1.82(1H,brs), 2.01(1H,ddd,J=13.7, 8.2, 4.9 Hz), 2.52(1H,q,J=7.9 Hz), 2.6-2.7(3H,m,), 2.85-2.95(2H,m), 3.51(1H,t,J=8.2 Hz), 3.65(3H,s), 3.9-4.0(1H,m), 5.14(1H,ddd,J=8.9, 7.0, 4.9 Hz), 5.62(1H,t,J=6.4 Hz), 5.78(1H,dd,J=15.6, 8.6 Hz), 6.00(1H,dd,J=15.6, 6.1 Hz), 6.75(1H,t,J=7.6 Hz), 6.91(1H,t,J=8.2 Hz), 6.98(1H,dd,J=13.7, 7.6 Hz), 7.2-7.3(1H,m)

EXAMPLE 109 d-15-(2,6-difluorophenyl)-2,5,6,7,16,17,18,19,20-nonanor-4,8-inter-m-phenylene PGI₂ (192)

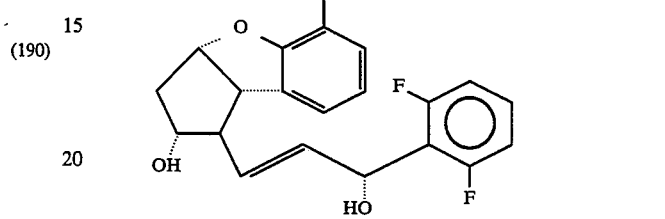

(192)

The same procedure as in Example 84 was repeated except that d-15-(2,6-difluorophenyl)-2,5,6,7,16,17,18,19,20-nonanor-4,8-inter-m-phenylene PGI₂ methyl ester (230 mg, 0.537 mmol) was employed as a reactant to obtain the captioned compound (165 mg, 0.396 mmol) having the following physical properties with a 74.2 yield.

$[\alpha]_D^{25} = +114.81°$ (C=0.844, MeOH) m.p. 108.5°-109.5° C. (Recrystallization Solvent:ethyl acetate:n-hexane) IR (KBr method): 3400, 3230, 3200-2200, 2975, 2940, 2900, 2640, 1720, 1615, 1590, 1470, 1450, 1360, 1320, 1300, 1260, 1230, 1190, 1150, 1080, 1070, 1035, 1000, 970, 900, 860, 790, 750, 615, 530, 455 cm⁻¹ NMR (400 MHz, DMSO-d₆, δ) 1.68(1H,ddd,J=12.7, 10.3, 6.3 Hz), 2.17(1H,dd,J=14.1, 8:8 Hz), 2.45-2.6(3H,m), 2.70(2H,t,J=7.8 Hz), 3.31(1H,t,J=9.3 Hz), 3.75(1H,dt,J=9.8, 5.9 Hz), 4.86(1H,brs), 5.02(1H,dt,J=8.3, 6.8 Hz), 5.45-5.5(1H,m), 5.64(1H,brs), 5.71(1H,dd,J=15.6, 7.8 Hz), 5.93(1H,dd,J=15.6, 6.4 Hz), 6.64(1H,t,J=7.3 Hz), 6.71(1H,d,J=7.3 Hz), 6.93(1H,d,J=6.8 Hz), 7.08(2H,t,J=8.3 Hz), 7.35-7.45(1H,m) MASS (EI method, m/e): 416 (M+) High resolution mass spectrum Calcd. ($C_{23}H_{22}O_5F_2$, M+) 416.1436 Found (M+) 416.1457

EXAMPLE 110 d-15-(2,6-difluorophenyl)-15-epi-2,5,6,7,16,17,18,19,20-nonanor-4,8-inter-m-phenylene PGI₂ (193)

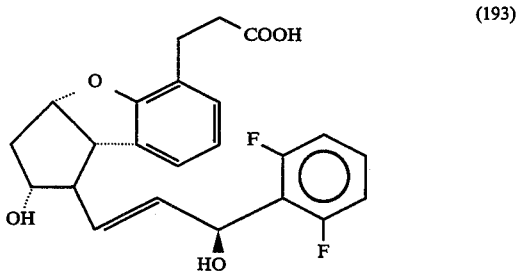

(193)

The same procedure as in Example 85 was repeated except that d-15-(2,6-difluorophenyl)-15-epi-2,5,6,7,16,17,18,19,20-nonanor-4,8-inter-m-phenylene PGI$_2$ methyl ester (300 mg, 0.700 mmol) was employed as a reactant to obtain the captioned compound (219 mg, 0.526 mmol) having the following physical properties with a 75.4% yield.

$[\alpha]_D^{27.5} = +82.70°$ (C=1.012, MeOH) m.p. 111.2°–113.0° C. (Recrystallization Solvent:ethyl acetate:n-hexane) IR (KBr method): 3390, 3300–2300, 3120, 2980, 2890, 1715, 1680, 1615, 1595, 1470, 1455, 1410, 1390, 1255, 1235, 1195, 1150, 1095, 1080, 1000, 980, 950, 850, 790, 750, 735, 570, 530, cm$^{-1}$ NMR (400 MHz, DMSO-D$_6$, δ) 1.66(1H,ddd,J=12.3, 10.3, 6.4 Hz), 2.16(1H,dd,J=16.1, 8.8 Hz), 2.45–2.6(3H,m), 2.71(2H,t,J=7.8 Hz), 3.44(1H,t,J=9.3 Hz), 3.74(1H,dt,J=9.8, 5.8 Hz), 4.81(1H,d,J=6.4 Hz), 5.06(1H,dt,J=9.3, 6.9 Hz), 5.45(1H,t,J=4.9 Hz), 5.65(1H,d,J=4.4 Hz), 5.81(1H,dd,J=15.6, 7.3 Hz), 5.88(1H,dd,J=15.6, 2.9 Hz), 6.71(1H,dd,J=7.3 Hz), 6.97(2H,t,J=7.8 Hz), 7.07(2H,t,J=8.3 Hz), 7.3–7.4(1H,m) MASS (EI method, m/e): 416 (M$^+$) High resolution mass spectrum Calcd. (C$_{23}$H$_{22}$O$_5$F$_2$, M$^+$) 416.1436 Found (M$^+$) 416.1447

EXAMPLE 111 d-15-(m-trifluoromethylphenyl)-2,5,6,7,16,17,18,19,20-nonanor-4,8-inter-m-phenylene PGI$_2$ methyl ester (194) and 15-epimer thereof (195)

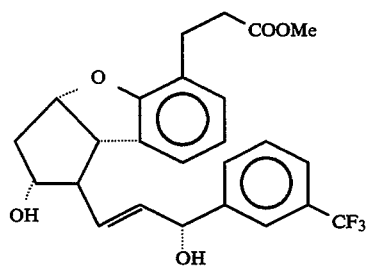
(194)

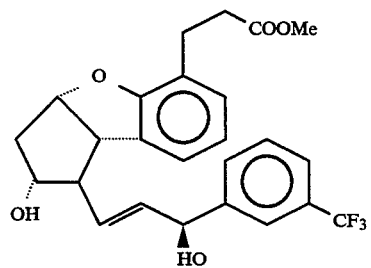
(195)

The same procedure as in Example 83 was repeated except that d-15-(m-trifluoromethylphenyl)-15-oxo-2,5,6,7,16,17,18,19,20-nonanor-4,8-inter-m-phenylene PGI$_2$ methyl ester, 11-acetate (0.90 g, 1.785 mmol) was employed as a reactant to obtain the captioned compounds (Compound (194) (0.264 g, 0.572 mmol) and Compound (195) (0.231 g, 0.500 mmol)) with a yield of 32% and 28%, respectively, which have the following physical characters.

d-15-(m-trifluoromethylphenyl)-15-oxo-2,5,6,7,16,17,18,19,20-nonanor-4,8-inter-m-phenylene PGI$_2$ methyl ester $[\alpha]_D^{20} = +110.78°$ (C=0.380, MeOH) m.p. 118.7°–119.3° C. (Recrystallization Solvent:cyclohexane-ethyl acetate) IR (KBr method): 3520, 2950, 1717, 1600, 1455, 1440, 1420, 1370, 1335, 1315, 1280, 1260, 1205, 1190, 1175, 1165, 1155, 1105, 1070, 1030, 1015, 1000, 970, 938, 920, 900, 887, 850, 825, 800, 790, 740, 700 cm$^{-1}$ NMR (400 MHz, CDCl$_3$, δ): 1.25–1.98(1H,m), 2.41(1H,q,J=8.55 Hz), 2.57–2.70(3H,m), 2.84–2.90(2H,m), 2.98(1H,bs), 3.31(1H,bs), 3.42(1H,t,J=8.85 Hz), 3.63(3H,S), 3.89–3.95(1H,m), 5.06–5.11(1H,m), 5.26(1H,d,J=7.02 Hz), 5.69–5.84(2H,m), 6.70(1H,t,J=7.32 Hz), 6.84(1H,d,J=7.32 Hz), 6.93(1H,d,J=7.32 Hz), 7.53–7.59(3H,m), 7.64(1H,S) MASS (EI method, m/e): 462 (M$^+$) High resolution mass spectrum Calcd. (C$_{25}$H$_{25}$O$_5$F$_3$, M$^+$) 462.1641 Found (M$^+$) 462.1649 d-15-(m-trifluoromethylphenyl)-15-epi2,5,6,7,16,17,18,19,20-nonanor-4,8-inter-m-phenylenePGI$_2$ methyl ester $[\alpha]_D^{20} = +108.69°$ (C=0.184, MeOH) m.p. 114.8°–116.4° C. (Recrystallization Solvent:cyclohexane-ethyl acetate) IR (KBr method): 3520, 2950, 1715, 1600, 1455, 1440, 1420, 1370, 1335, 1315, 1280, 1260, 1205, 1190, 1175, 1165, 1155, 1105, 1070, 1030, 1015, 1000, 970, 938, 920, 900, 887, 850, 825, 800, 790, 740 cm$^{-1}$ NMR (400 MHz, CDCl$_3$, δ) 2.00(2H,ddd,J=13.74, 8.55, 5.19 Hz), 2.42(1H,brs), 2.49–2.58(1H,m), 2.60–2.67(3H,m), 2.85–2.91(2H,m), 3.49(1H,t,J=8.24 Hz), 3.64(3H,s), 3.94–4.00(1H,m), 5.13(1H,ddd,J=8.85, 7.33, 4.88 Hz), 5.31(1H,brs), 5.82–5.84(2H,m), 6.74(1H,t,J=7.32 Hz), 6.92–6.97(2H,m), 7.47–7.49(1H,m), 7.51–7.58(2H,m), 7.67(1H,s) MASS (EI method, m/e): 462 (M$^+$) High resolution mass spectrum Calcd. (C$_{25}$H$_{25}$O$_5$F$_3$, M$^+$) 462.1641 Found (M$^+$) 462.1630

EXAMPLE 112 d-15-(m-trifluoromethylphenyl)-2,5,6,7,16,17,18,19,20-nonanor-4,8-inter-m-phenylene PGI$_2$ (196)

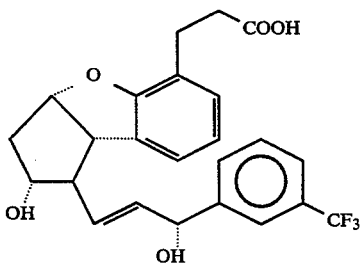
(196)

The same procedure as in Example 84 was repeated except that d-15-(m-trifluoromethylphenyl)-2,5,6,7,16,17,18,19,20-nonanor-4,8-inter-m-phenylene PGI$_2$ methyl ester (0.1873 g, 0.406 mmol) was employed as a reactant to obtain the captioned compound (0.1820 g, 0.407 mmol) having the following physical properties with a 100% yield.

$[\alpha]_D^{20} = +112.0°$ (C=0.200, MeOH) m.p. 147°–147.5° C. (Recrystallization Solvent:cyclohexane-ethyl acetate) IR (KBr method): 3380, 2930, 1710, 1600, 1480, 1450, 1410, 1390, 1335, 1310, 1280, 1270, 1250, 1190, 1165, 1120, 1100, 1088, 1020, 1002, 980, 960, 950, 920, 900, 870, 860, 835, 805, 780, 765, 742, 702 cm$^{-1}$ NMR (400 MHz, CDCl$_3$, δ): 1.98–2.05(1H,m), 2.50–2.72(5H,m), 2.83–2.95(2H,m), 3.47(1H,t,J=8.30 Hz), 3.96–4.01(1H,m), 5.10–5.15(1H,m), 5.30(1H,d,J=4.89 Hz), 5.76–5.86(2H,m), 6.71(1H,t,J=7.32 Hz), 6.88(1H,d,J=7.32 Hz), 6.95(1H,d,J=7.32 Hz), 7.46–7.50(1H,m), 7.55–7.59(1H,m), 7.66(1H,S) MASS (EI method, m/e): 448 (M$^+$) High resolution mass spectrum Calcd. (C$_{24}$H$_{23}$O$_5$F$_3$, M$^+$) 448.1485 Found (M$^+$) 448.1509

EXAMPLE 113 d-15-(m-trifluoromethylphenyl)-15-epi-2,5,6,7,16,17,18,19,20-nonanor-4,8-inter-m-phenylene PGI$_2$ (197)

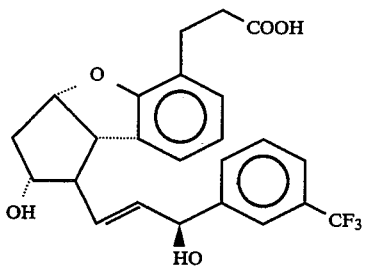
(197)

The same procedure as in Example 85 was repeated except that d-15-(m-trifluoromethylphenyl)-15-epi-2,5,6,7,16,17,18,19,20-nonanor-4,8-inter-m-phenylene PGI$_2$ methyl ester (0.1767 g, 0.381 mmol) was employed as a reactant to obtain the captioned compound (0.1695 g, 0.379 mmol) having the following physical properties with a 99% yield.

$[\alpha]_D^{20} = +97.39°$ (C=0.230, MeOH) m.p. 167.5°-168° C. (Recrystallization Solvent:cyclohexane-ethyl acetate) IR (KBr method): 3380, 2930, 2890, 1710, 1600, 1480, 1450, 1410, 1390, 1335, 1310, 1280, 1270, 1250, 1190, 1165, 1120, 1100, 1088, 1020, 1002, 980, 960, 950, 920, 900, 870, 860, 835, 805, 780, 765, 742 cm$^{-1}$ NMR (400 MHz, CDCl$_3$, δ): 1.99.-2.06(1H,m), 2.52-2.73(5H,m), 2.83-2.94(2H,m), 3.51(1H,t,J=8.05 Hz), 3.96-4.01(1H,m), 5.11-5.16(1H,m), 5.30(1H,d,J=4.40 Hz), 5.79-5.89(2H,m), 6.73(1H,t,J=7.33 Hz), 6.95(2H,t,J=7.33 Hz), 7.47(1H,t,J=7.81 Hz), 7.55-7.58(2H,m), 7.67(1H,S) MASS (EI method, m/e): 448 (M+) High resolution mass spectrum Calcd. (C$_{24}$H$_{23}$O$_5$F$_3$, M+) 448.1485 Found (M+) 448.1480

EXAMPLE 114 d-15-(o-chlorophenyl)-2,5,6,7,16,17,18,19,20-nonanor-4,8-inter-m-phenylene PGI$_2$ methyl ester (198) and 15-epimer thereof (199)

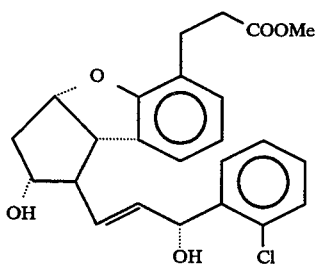
(198)

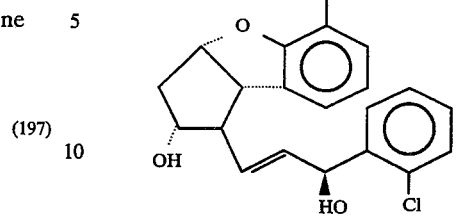
(199)

The same procedure as in Example 83 was repeated except that d-15-(o-chlorophenyl)-15-oxo-2,5,6,7,16,17,18,19,20-nonanor-4,8-inter-m-phenylene PGI$_2$ methyl ester, 11-acetate (0.925 g, 1.97 mmol) was employed as a reactant to obtain the captioned compounds (Compound (198) (0.293 g, 0.685 mmol) and Compound (199) (0.281 g, 0.656 mmol)) with a yield of 34.8% and 33.3%, respectively, which have the following physical properties.

d-15-(o-chlorophenyl)-2,5,6,7,16,17,18,19,20-nonanor-4,8-inter-m-phenylene PGI$_2$ methyl ester $[\alpha]_D^{20} = +144.78°$ (C=0.882, MeOH) m.p. 136.0°-137.8° C. (Recrystallization Solvent:ethyl acetate:n-hexane=3:5) IR (KBr method): 3500, 3450, 2950, 2880, 1685, 1450, 1430, 1405, 1305, 1240, 1185, 1150, 1095, 1070, 1030, 1005, 955, 855, 790, 750, 705 cm$^{-1}$ NMR (400 MHz, CDCl$_3$, δ): 1.9-2.t(1H,m), 2.30(1H,d,J=5.4 Hz), 2.46(1H,q,J=8.5 Hz), 2.5-2.8(4H,m), 2.8-3.0(2H,m), 3.46(1H,t,J=8.3 Hz), 3.64(3H,S), 3.9-4.1(1H,m), 5.0-5.2(1H,m), 5.6-5.7(1H,m), 5.71(1H,dd,J=15.0, 6.6 Hz), 5.84(1H,dd,J=15.0, 8.5 Hz), 6.69(1H,t,J=7.2 Hz), 6.88(1H,d,J=7.2 Hz), 6.94(1H,d,J=7.2 Hz), 7.2-7.3(1H,m), 7.31(1H,dt,J=7.7, 1.5 Hz), 7.37(1H,dd,J=7.7, 1.5 Hz), 7.57(1H,dd,J=7.7, 1.5 Hz) MASS (EI method, m/e): 428 (M+) High resolution mass spectrum Calcd. (C$_{24}$H$_{25}$O$_5$Cl, M+) 428.1390 Found (M+) 428.1389 d-15-(o-chlorophenyl)-15-epi-2,5,6,7,16,17,18,19,20-nonanor-4,8-inter-m-phenylenePGI$_2$ methyl ester $[\alpha]_D^{20} = +72.69°$ (C=0.912, MeOH) m.p. 95.0°-96.7° C. (Recrystallization Solvent:ethyl acetate:n-hexane=2:5) IR (KBr method): 3230, 2960, 1735, 1590, 1445, 1345, 1290, 1275, 1245, 1190, 1140, 1080, 1060, 1030, 970, 945, 860, 755, 745 cm$^{-1}$ NMR (400 MHz, CDCl$_3$, δ): 1.9-2.1(2H,m), 2.41(1H,d,J=3.9 Hz), 2.50(1H,q,J=8.0 Hz), 2.5-2.7(3H,m), 2.8-3.0(2H,m), 3.47(1H,t,J=8.0 Hz), 3.65(3H,S), 3.9-4.0(1H,m), 5.0-5.2(1H,m), 5.6-5.7(1H,m), 5.74(1H,dd,J=15.5, 8.0 Hz), 5.82(1H,dd,J=15.5, 6.8 Hz), 6.74(1H,t,J=7.5 Hz), 6.96(2H,d,J=7.5 Hz), 7.2-7.3(1H,m), 7.3-7.4(2H,m), 7.5-7.7(1H,m) MASS (EI method, m/e): 428 (M+) High resolution mass spectrum Calcd. (C$_{24}$H$_{25}$O$_5$Cl, M+) 428.1390 Found (M+) 428.1369

EXAMPLE 115 d-15-(o-chlorophenyl)-2,5,6,7,16,17,18,19,20-nonanor-4,8-inter-m-phenylene PGI$_2$ (200)

(200)

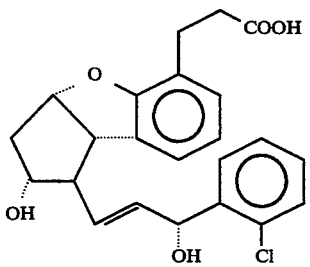

The same procedure as in Example 84 was repeated except that d-15-(o-chlorophenyl)-2,5,6,7,16,17,18,19,20-nonanor-4,8-inter-m-phenylene PGI$_2$ methyl ester (0.249 g, 0.58 mmol) was employed as a reactant to obtain the captioned compound (0.205 g, 0.495 mmol) having the following physical properties with a 85.4% yield.

$[\alpha]_D^{20} = +147.51°$ (C=0.564, MeOH) m.p. 161.2°–163.0° C. (Recrystallization Solvent:ethyl acetate:n-hexane=1:1) IR (KBr method): 3430, 2920, 1700, 1590, 1440, 1330, 1310, 1275, 1245, 1185, 1150, 1065, 1030, 995, 955, 940, 880, 855, 750, 740, 700 cm$^{-1}$ NMR (400 MHz, CDCl$_3$, δ): 1.9–2.0(1H,m), 2.35(1H,q,J=8.9 Hz), 2.5–2.8(3H,m), 2.8–3.0(2H,m), 3.43(1H,t,J=8.8 Hz), 3.3–3.7(1H,m), 3.8–4.2(2H,m), 5.0–5.2(1H,m), 5.58(1H,d,J=7.3 Hz), 5.63(1H,dd,14.5, 7.3 Hz), 5.84(1H,dd,J=14.5, 8.9 Hz), 6.67(1H,t,J=7.7 Hz), 6.88(1H,d,J=7.7 Hz), 6.95(1H,d,J=7.7 Hz), 7.22(1H,dt,J=7.8, 1.5 Hz), 7.2–7.4(1H,m), 7.36(1H,dd,J=7.8, 1.5 Hz), 7.65(1H,dd,J=7.8, 1.5 Hz), 10.4–12.0(1H,brs) MASS (EI method, m/e): 414 (M$^+$) High resolution mass spectrum Calcd. (C$_{23}$H$_{23}$O$_5$Cl, M$^+$) 414.1234 Found (M$^+$) 414.1259

EXAMPLE 116 d-15-(o-chlorophenyl)-15-epi-2,5,6,7,16,17,18,19,20-nonanor-4,8-inter-m-phenylene PGI$_2$ (201)

(201)

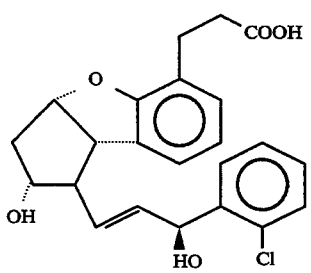

The same procedure as in Example 85 was repeated except that d-15-(o-chlorophenyl)-15-epi-2,5,6,7,16,17,18,19,20-nonanor-4,8-inter-m-phenylene PGI$_2$ methyl ester (0.226 g, 0.53 mmol) was employed as a reactant to obtain the captioned compound (0.211 g, 0.51 mmol) having the following physical properties with a 96.2% yield.

$[\alpha]_D^{20} = +70.97°$ (C=1.082, MeOH) IR {liquid film method): 3450, 2920, 1700, 1590, 1565, 1440, 1365, 1240, 1190, 1150, 1040, 960, 880, 850, 750, 700 cm$^{-1}$ NMR (400 MHz, CDCl$_3$, δ): 1.9–2.0(1H,m), 2.45(1H,q,J=7.9 Hz), 2.5–2.7(3H,m), 2.7–3.0(2H,m), 2.45(1H,t,J=7.8 Hz), 3.88(1H,q,J=7.9 Hz), 5.0–5.1(1H,m), 5.61(1H,d,J=5.9 Hz), 5.65(1H,dd,J=16.1, 7.9 Hz), 5.81(1H,dd,J=15.1, 5.9 Hz), 6.72(1H,d,J=7.7 Hz), 6.73(1H,t,J=7.7 Hz), 6.74(1H,d,J=7.7 Hz), 7.23(1H,dt,J=7.6, 1.6 Hz), 7.31(1H,dt,J=7.6, 1.6 Hz), 7.63(1H,dd,J=7.6, 1.56 Hz), 7.57(1H,dd,J=7.6, 1.6 Hz) MASS (EI method, m/e): 414 (M$^+$) High resolution mass spectrum Calcd. (C$_{23}$H$_{23}$O$_5$Cl, M$^+$) 414.1234 Found (M$^+$) 414.1259

EXAMPLE 117 d-15-(2,6-dichlorophenyl)-2,5,6,7,16,17,18,19,20-nonanor-4,8-inter-m-phenylene PGI$_2$ methyl ester (202)

(202)

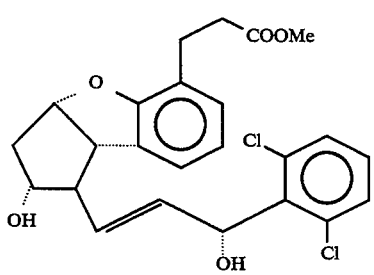

The same procedure as in Example 83 was repeated except that d-15-(2,6-dichlorophenyl)-15-oxo-2,5,6,7,16,17,18,19,20-nonanor-4,8-inter-m-phenylene PGI$_2$ methyl ester, 11-acetate (0.422g, 0.84 mmol) was employed as a reactant to obtain the captioned compound (0.0229 g, 0.05 mmol) having the following physical properties with a 5.95% yield.

$[\alpha]_D^{20} = +103.05°$ (C=0.458, MeOH) IR (liquid film method): 3350, 2925, 1730, 1595, 1580, 1560, 1445, 1430, 1340, 1250, 1190, 1150, 1080, 1060, 1030, 965, 855, 750 cm$^{-1}$ NMR (400 MHz, CDCl$_3$, δ): 1.8–1.9(1H,m), 1.9–2.1(1H,m), 2.52(1H,q,J=7.8 Hz), 2.5–2.7(3H,m), 2.8–3.0(2H,m), 3.0–3.3(1H,m), 3.4–3.6(1H,m), 3.65(3H,S), 3.96(1H,q,J=7.8 Hz), 5.0–5.2(1H,m), 5.71(1H,dd,J=13.9, 8.6 Hz), 5.9–6.1(2H,m), 6.71(1H,t,J=7.4 Hz), 6.92(1H,d,J=7.4 Hz), 6.96(1H,d,J=7.4 Hz), 7.1–7.3(1H,m), 7.34(2H,d,J=7.8 Hz) MASS (EI method, m/e): 462 (M$^+$) High resolution mass spectrum Calcd. (C$_{24}$H$_{24}$O$_5$Cl$_2$, M$^+$) 462.1001 Found (M$^+$) 462.0978

EXAMPLE 118 d-15-(2,6-dichlorophenyl)-2,5,6,7,16,17,18,19,20-nonanor-4,8-inter-m-phenylene PGI$_2$ (203)

(203)

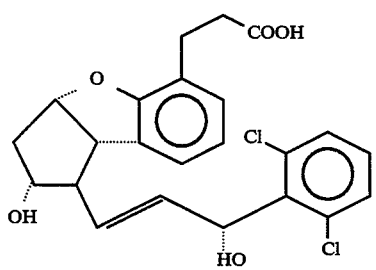

The same procedure as in Example 84 was repeated except that d-15-(2,6-dichlorophenyl)-2,5,6,7,16,17,18,19,20-nonanor-4,8-inter-m-phenylene PGI$_2$ methyl ester (0.0229 g, 0.05 mmol) was employed as a reactant to obtain the captioned compound (0.0221 g, 0.049 mmol) having the following physical properties with a 98.7% yield.

$[\alpha]_D^{20} = +98.86°$ (C=0.442, MeOH) IR (liquid film method): 3330, 2920, 1700, 1590, 1570, 1555, 1450, 1430, 1250, 1180, 1165, 1080, 1060, 1030, 995, 960, 890, 855, 750 cm$^{-1}$ NMR (400 MHz, CDCl$_3$, δ): 1.9–2.1(1H,m), 2.5–2.8(4H,m), 2.8–3.0(1H,m), 3.47(1H,t,J=8.1 Hz), 3.96(1H,q,J=7.2 Hz), 5.0–5.2(1H,m), 5.71(1H,dd,J=14.4, 8.5 Hz), 5.9–6.1(2H,m), 6.73(1H,t,J=7.3 Hz), 6.91(1H,d,J=7.3 Hz), 6.96(1H,d,J=7.3 Hz), 7.19(1H,t,J=8.1 Hz), 7.34(2H,d,J=8.1 Hz) MASS (EI method, m/e): 448 (M+) High resolution mass spectrum Calcd. (C$_{23}$H$_{22}$O$_5$Cl$_2$, M+) 448.0845 Found (M+) 448.0815

EXAMPLE 119 d-15-(p-nitrophenyl)-2,5,6,7,16,17,18,19,20-nonanor-4,8-inter-m-phenylene PGI$_2$ methyl ester (204) and 15-epimer thereof (205)

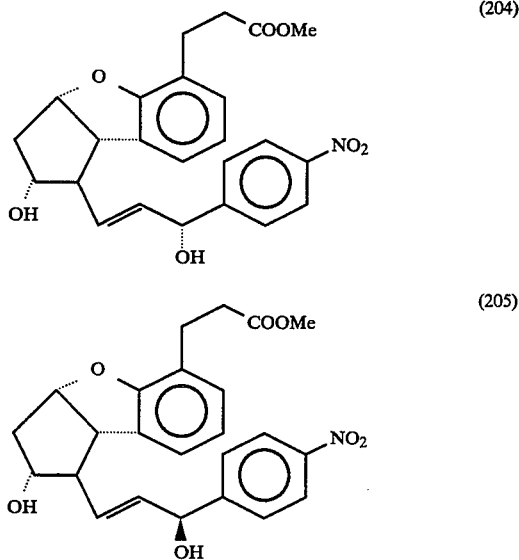

The same procedure as in Example 83 was repeated except that d-15-(p-nitrophenyl)-15-oxo-2,5,6,7,16,17,18,19,20-nonanor-4,8-inter-m-phenylene PGI$_2$ methyl ester, 11-acetate (820 mg, 1.71 mmol) was employed as a reactant to obtain the captioned compound (Compound (204) (235 mg, 0.54 mmol) Compound (205) (292 mg, 0.67 mmol)) with a yield of 31.3% and 38.9%, respectively, which have the following physical properties.

d-15-(p-nitrophenyl)-2,5,6,7,16,17,18,19,20-nonanor-4,8-inter-m-phenylene PGI$_2$ methyl ester

[α]$_D^{25}$ = +119.86° (C=0.720, MeOH) m.p. 140°–140.5° C. (Recrystallization Solvent:ethyl acetate:n-hexane) IR (KBr method): 3350, 2950, 1730, 1610, 1600, 1520, 1480, 1450, 1410, 1350, 1300, 1280, 1270, 1240, 1190, 1140, 1130, 1100, 1050, 1030, 1010, 990, 980, 950, 930, 910, 880, 860, 850, 840, 820, 790, 750, 700, 600, 580, 560, 520, 490, 440 cm$^{-1}$ NMR (400 MHz, CDCl$_3$, δ): 1.99(1H,ddd,J=5.4, 8.8, 13.7 Hz), 2.35–2.45(1H,m), 2.48(1H,q,J=8.6 Hz), 2.55–2.75(3H,m), 2.85–2.95(3H,m), 3.47(1H,t,J=8.6 Hz), 3.64(3H,S), 3.9–4.0(1H,m), 5.13(1H,ddd,J=5.4, 7.3, 8.6 Hz), 5.35(1H,d,J=6.8 Hz), 5.73(1H,dd,J=6.8, 15.1 Hz), 5.86(1H,dd,J=8.6, 15.1 Hz), 6.72(1H,t,J=7.3 Hz), 6.84(1H,d,J=7.3 Hz), 6.96(1H,d,J=7.3 Hz), 7.57(2H,d,J=8.5 Hz), 8.23(2H,d,J=8.5 Hz) MASS (EI method, m/e): 439 (M+) High resolution mass spectrum Calcd. (C$_{24}$H$_{25}$NO$_7$, M+) 439.1631 Found (M+) 439.1636 d-15-(p-nitrophenyl)-15-epi-2,5,6,7,16,17,18,19,20-nonanor-4,8-inter-m-phenylene PGI$_2$ methyl ester

[α]$_D^{25}$ = +98.71° (C=0.778, MeOH) IR (liquid film method): 3400, 3010, 2950, 1730, 1600, 1520, 1450, 1350, 1260, 1200, 1070, 1030, 970, 850, 840, 750, 700, 670 cm$^{-1}$ NMR (400 MHz, CDCl$_3$, δ): 1.9–2.1(2H,m), 2.4–2.7(5H,m), 2.8–2.95(2H,m), 3.49(1H,t,J=8.5 Hz), 3.65(3H,S), 3.9–4.0(1H,m), 5.14(1H,ddd,J=4.9, 7.3, 8.5 Hz), 5.35–5.4(1H,m), 5.75–5.9(2H,m), 6.75(1H,t,J=7.6 Hz), 6.91(1H,d,J=7.6 Hz), 6.97(1H,d,J=7.6 Hz), 7.57(2H,d,J=8.5 Hz), 8.24(2H,d,J=8.5 Hz) MASS (EI method, m/e): 439 (M+) High resolution mass spectrum Calcd. (C$_{24}$H$_{25}$NO$_7$, M+) 439.1631 Found (M+) 439.1638

EXAMPLE 120 d-15-(p-nitrophenyl)-2,5,6,7,16,17,18,19,20-nonanor-4,8-inter-m-phenylene PGI$_2$ (206)

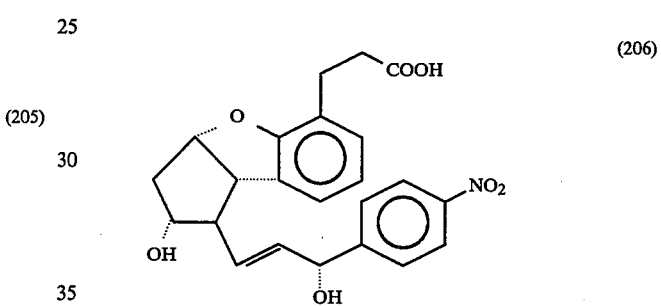

The same procedure as in Example 84 was repeated except that d-15-(p-nitrophenyl)-2,5,6,7,16,17,18,19,20-nonanor-4,8-inter-m-phenylene PGI$_2$ methyl ester (155 mg, 0.35 mmol) was employed as a reactant to obtain the captioned compound (133 mg, 0.31 mmol) having the following physical properties with a 88.7% yield.

[α]$_D^{25}$ = +118.13° (C=0.204, MeOH) m.p. 109°–110° C. (Recrystallization Solvent:acetone) IR (KBr method): 3350, 2930, 1700, 1600, 1520, 1450, 1350, 1190, 1070, 1040, 1000, 980, 960, 850, 840, 740, 700 cm$^{-1}$ NMR (400 MHz, CDCl$_3$, δ): 1.4–1.9(2H,m), 2.01(1H,ddd,J=4.9, 8.0, 13.4 Hz), 2.52(1H,q,J=8.0 Hz), 2.55–1.75(3H,m), 2.8–3.0(2H,m), 3.48(1H,t,J=8.0 Hz), 4.00(1H,q,J=8.0 Hz), 5.14(1H,ddd,J=4.9, 7.1, 8.0 Hz), 5.37(1H,d,J=6.8 Hz), 5.76(1H,dd,J=6.8, 15.4 Hz), 5.85(1H,dd,J=8.0, 15.4 Hz), 6.73(1H,t,J=7.2 Hz), 6.86(1H,d,J=7.2 Hz), 6.98(1H,d,J=7.2 Hz), 7.58(2H,d,J=8.5 Hz), 8.24(2H,d,J=8.5 Hz) MASS (FAB method, m/e): 424 (M+-H) High resolution mass spectrum Calcd. (C$_{23}$H$_{23}$NO$_7$, (M+-H)) 424.1396 Found (M+-H) 424.1394

EXAMPLE 122 d-15-(p-nitrophenyl)-15-epi-2,5,6,7,16,17,18,19,20-nonanor-4,8-inter-m-phenylene PGI$_2$ (207)

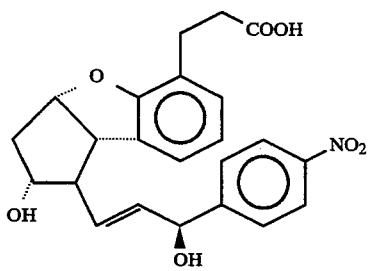
(207)

The same procedure as in Example 85 was repeated except that d-15-(p-nitrophenyl)-15-epi-2,5,6,7,16,17,18,19,20-nonanor-4,8-inter-m-phenylene PGI$_2$ methyl ester (175 mg, 0.40 mmol) was employed as a reactant to obtain the captioned compound (167 mg, 0.39 mmol) having the following physical properties with a 97.5% yield.

$[\alpha]_D^{25} = +98.21°$ (C=0.674, MeOH) IR (liquid film method): 3360, 3020, 2920, 1710, 1600, 1520, 1450, 1350, 1260, 1220, 1200, 1070, 1030, 970, 850, 840, 760, 700, 670 cm$^{-1}$ NMR (400 MHz, CDCl$_3$-DMSO-d$_6$, $\delta$): 1.79(1H,ddd,J=6.4, 9.8, 13.2 Hz), 2.28(1H,q,J=8.4 Hz), 2.49(2H,t,J=7.8 Hz), 2.5–2.65(1H,m), 2.76(2H,t,J=7.8 Hz), 3.42(1H,t,J=8.4 Hz), 3.75–3.9(1H,m), 4.75–4.8(1H,m), 5.0–5.1(1H,m), 5.2–5.3(1H,m), 5.67(1H,dd,J=6.6, 15.2 Hz), 5.7–5.8(1H,m), 5.85(1H,dd,J=8.4, 15.2 Hz), 6.67(1H,t,J=7.3 Hz), 6.9–7.0(2H,m), 7.65(2H,d,J=8.6 Hz), 8.19(2H,d,J=8.6 Hz) MASS (FAB method, m/e): 424 (M$^+$-H) High resolution mass spectrum Calcd. (C$_{23}$H$_{23}$NO$_7$, (M$^+$-H)) 424.1396 Found (M$^+$-H) 424.1422

INDUSTRIAL APPLICABILITY

The present invention provides novel PGI$_2$ derivatives which excell in the stability and the continuous of activity in vivo. Further, since the compound of the present invention exhibits gastric cytoprotection effect, gastric acid secretion-inhibiting effect, platelet aggregation-inhibiting effect and Hypotensive effect, the pharmaceutical compositions containing the compound at a dose of 0.1 μg to 100 mg are suitable as drugs such as antiulcer agent, antihypertensive agent and antithrombus agent.

We claim:

1. A 2,5,6,7-tetranor-4,8-inter-m-phenylene PGI$_2$ derivative having the formula:

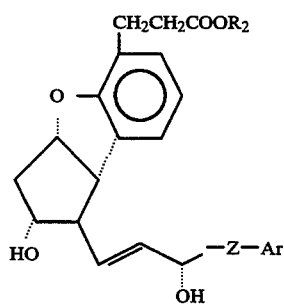

(wherein R$_2$ represents hydrogen atom, a pharmaceutically acceptable cation or an ester residue selected from the group consisting of (i) a normal alkyl group having 1 to 12 carbon atoms or a branched alkyl group having 3 to 12 carbon atoms;

(ii) —Z—R$_5$ (wherein Z represents a valence bond or a normal or branched alkylene group defined as the formula C$_t$H$_{2t}$ (t is an integer of 1 to 5 and R$_5$ represents a cycloalkyl group with 3 to 12 ring members which is unsubstituted or substituted by 1 to 4 normal alkyl substituents containing 1 to 4 carbon atoms), wherein R$_2$ and R$_4$ represented by the same formula may be the same or different;

(iii) —Z—Ar (wherein Z has the same meaning as in (ii) and Ar represents a phenyl group unsubstituted or substituted by 1 to 4 substituents selected from the group consisting of alkyl, methoxy, chloro, bromo, fluoro, iodo, trifluoromethyl, nitro, cyano, phenyl and phenoxy);

(iv) —(CH$_2$CH$_2$O)$_n$—CH$_3$ (wherein n is an integer of 1 to 5);

(v) —Z—R$_7$ (wherein Z has the same meaning as in (ii), R$_7$ represents α-naphthyl group, β-naphthyl group, 2-pyridyl group, 3-pyridyl group, 4-pyridyl group, α-furyl group, β-furyl group, α-thienyl group or β-thienyl group);

(vi) —C$_t$H$_{2t}$COOR$_8$ (wherein C$_t$H$_{2t}$ has the same meaning as in (ii); R$_8$ represents methyl group, ethyl group or propyl group) or (vii) 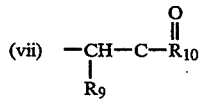

(wherein R$_9$ represents hydrogen atom or benzoyl group; R$_{10}$ represents phenyl group, p-bromophenyl group, p-chlorophenyl group, p-biphenyl group, p-nitrophenyl group, p-benzamidophenyl group or 2-naphthyl group); and R$_4$ represents (i) a normal alkyl group having 1 to 12 carbon atoms, or (ii) —Z—Ar (wherein Z represents a valance-bond or a normal or branched alkylene group defined as C$_t$H$_{2t}$ (wherein t is an integer of 1 to 5); Ar represents a phenyl group which is unsubstituted or substituted by 1 to 4 substituents selected from the group consisting of alkyl, methoxy, chloro, bromo, fluoro, iodo, trifluoromethyl, nitro, cyano, phenyl and phenoxy), or (iii) —Z—R$_5$ (wherein Z has the same meaning as in (ii); R$_5$ represents a cycloalkyl alkyl substituents containing 1 to 4 carbon atoms).

2. The PGI$_2$ derivative as claimed in claim 1 which is selected from the group consisting of 15-phenyl-2,5,6,7,16,17,18,19,20-nonanor-4,8-inter-m-phenylene PGI$_2$, 16-methyl-17-phenyl-2,5,6,7,18,19,20-heptanor-4,8-inter-m-phenylene PGI$_2$ and 16,16-dimethyl-17-phenyl-2,5,6,7,18,19,20-heptanor-4,8-inter-m-phenylene PGI$_2$.

3. A pharmaceutical composition comprising PGI$_2$ derivative as claimed in claim 1.

4. The pharmaceutical composition as claimed in claim 3, which is used as antihypertensive drug.

5. The pharmaceutical composition as claimed in claim 3, which is used as treatment for ischemic cerebral disease.

6. The pharmaceutical composition as claimed in claim 3, which is used as treatment for myocardial infarction.

7. The pharmaceutical composition as claimed in claim 3, which is used as treatment for angina pectoris.

8. The pharmaceutical composition as claimed in claim 3, which is used as treatment for TIA.

9. The pharmaceutical composition as claimed in claim 3, which is used as treatment for peripheral circulation disturbance.

10. The pharmaceutical composition as claimed in claim 3, which is used as antiarteriosclerosis drug.

11. The pharmaceutical composition as claimed in claim 3, which is used as antithrombus drug.

12. The pharmaceutical composition as claimed in claim 3, which is used as antiulcer drug.

* * * * *

UNITED STATES PATENT AND TRADEMARK OFFICE
CERTIFICATE OF CORRECTION

PATENT NO. : 5,401,768
DATED : March 28, 1995
INVENTOR(S) : Kiyotaka Ohno et al

It is certified that error appears in the above-indentified patent and that said Letters Patent is hereby corrected as shown below:

On the title page, at [60], please change "division" to --continuation--.

Column 2, line 1, delete "This"; and line 2, change "invention" to --This invention--.

Column 18, line 7, change "(3propylcyclohexyl)" to --(3-propylcyclohexyl)--.

Column 39, line 2 of text, after "Japanese Patent" insert --Disclosure (Kokai) No. 144277/82 by the present inventors.--

Column 70, line 60, after "1610," please insert --1580,--.

Column 91, line 36, change "2.0 ml" to --20 ml--.

Column 93, line 48, change "($C_{23}M32O_5^\bullet M^+$):" to --$C_{23}M_{32}O_5$, $M^+$):--.

Column 132, line 47, after "2870" insert --1730,--.

Column 144, line 48, change "3975," to --2975,--.

Column 177, line 49, change "131.8," to --1318--.

UNITED STATES PATENT AND TRADEMARK OFFICE
CERTIFICATE OF CORRECTION

PATENT NO. : 5,401,768
DATED     : March 28, 1995
INVENTOR(S) : Kiyotaka Ohno et al It is certified that error appears in the above-indentified patent and that said Letters Patent is hereby corrected as shown below:

Column 202, line 6, after "5" insert --)--;
    bridging lines 10 and 11, delete ", wherein $R_2$ and $R_4$ represented by the same formula may be the same or different";
    about line 32, please delete the formula and insert the following:

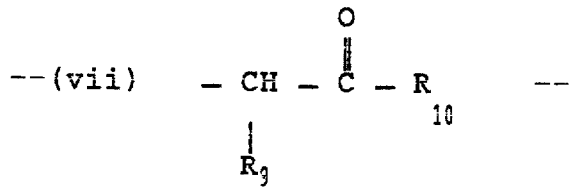

line 40, delete "and $R_4$ represents";
    lines 41 and 42, delete in their entirety;
    line 43, delete "(ii) — Z — Ar (wherein";
    line 50, delete "), or"; and
    lines 51-53, delete in their entirety, except for the period at the end of the sentence.

Signed and Sealed this

Sixteenth Day of September, 1997

BRUCE LEHMAN

*Attest:*

*Attesting Officer*  *Commissioner of Patents and Trademarks*